US008329186B2

(12) United States Patent
Kim et al.

(10) Patent No.: US 8,329,186 B2
(45) Date of Patent: Dec. 11, 2012

(54) TREATMENT OF INFLAMMATION USING BST2 INHIBITOR

(75) Inventors: Myung Kim, Bethesda, MD (US); Jay Chung, Bethesda, MD (US); June-Young Park, Seoul (KR); Hyouna Yoo, Kyunggi (KR); Sang-Min Lee, Kyunggi-do (KR); Yoon-Seok Lee, Kyunggi-do (KR); Mison Koo, Seoul (KR); Sang-Ho Park, Kyunggi-do (KR)

(73) Assignee: Isu Abxis Co., Ltd, Seoul (KR)

( * ) Notice: Subject to any disclaimer, the term of this patent is extended or adjusted under 35 U.S.C. 154(b) by 346 days.

(21) Appl. No.: 12/611,090

(22) Filed: Nov. 2, 2009

(65) Prior Publication Data

US 2010/0129365 A1 May 27, 2010

Related U.S. Application Data

(63) Continuation-in-part of application No. 11/757,329, filed on Jun. 1, 2007, now abandoned, which is a continuation-in-part of application No. 11/471,853, filed on Jun. 20, 2006, now Pat. No. 7,740,856, which is a continuation-in-part of application No. PCT/KR2005/004398, filed on Dec. 20, 2005.

(30) Foreign Application Priority Data

Dec. 20, 2004 (KR) ........................ 10-2004-0108909

(51) Int. Cl.
*A61K 39/00* (2006.01)
*A61K 38/00* (2006.01)

(52) U.S. Cl. ................................. 424/184.1; 424/185.1

(58) Field of Classification Search ........................ None
See application file for complete search history.

(56) References Cited

U.S. PATENT DOCUMENTS

| | | | |
|---|---|---|---|
| 5,367,056 | A | 11/1994 | Hession et al. |
| 5,821,336 | A | 10/1998 | Odink et al. |
| 5,863,540 | A | 1/1999 | Haynes et al. |
| 5,912,266 | A | 6/1999 | Perez |
| 6,689,869 | B2 | 2/2004 | Waldmann et al. |
| 7,317,091 | B2 | 1/2008 | Lazar et al. |
| 2002/0034507 | A1 | 3/2002 | Koishihara |
| 2003/0103970 | A1 | 6/2003 | Tsuchiya |
| 2004/0132101 | A1 | 7/2004 | Lazar et al. |
| 2008/0219974 | A1 | 9/2008 | Bernett et al. |
| 2010/0104557 | A1 | 4/2010 | Bernett et al. |

FOREIGN PATENT DOCUMENTS

| | | | |
|---|---|---|---|
| EP | 0 972 524 | A1 | 1/2000 |
| EP | 0997152 | | 5/2000 |
| EP | 1 059 533 | A1 | 12/2000 |
| EP | 1 304 379 | A2 | 4/2003 |
| EP | 1 394 274 | A2 | 4/2003 |
| EP | 1 394 274 | A2 | 3/2004 |
| JP | 10-298106 | | 11/1998 |
| JP | 2002-338599 | | 11/2002 |
| JP | 2003-219894 | | 8/2003 |
| WO | WO 03/026692 | A2 | 4/2003 |
| WO | WO2004/039398 | A1 | 5/2004 |
| WO | WO 2006/008886 | A1 | 1/2006 |
| WO | WO 2006/013923 | | 2/2006 |
| WO | WO 2006/068398 | A1 | 6/2006 |

OTHER PUBLICATIONS

The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock. see pp. 1-5.*
Standen et al. (N Engl J Med 2000, 343:447-448).*
Redl et al. (World J Surg 1996, 20:487-492).*
Goffinet et al., "HIV-1 antagonism of CD317/tetherin is species-specific and involves Vpu-mediated proteasomal degradation of the intrinsic immunity factor," Retrovirology, 6(Suppl 2):O10, Sep. 24, 2009.
Zhang et al., "Nef Proteins from Simian Immunodeficiency Viruses Are Tetherin Antagonists," Cell Hosts & Microbe 6:54-67, Jul. 23, 2009.
Cao et al., "Regulation of TLR7/9 responses in plasmacytoid dendritic cells by BST2 and ILT7 receptor interaction," J. of Experimental Medicine, 206(7):1603-1614, Jun. 29, 2009.
Ono, Koichiro, "The humanized anti-HM1.24 antibody effectively kills multiple myeloma cells by human effector cell-mediated cytotoxicity," Molecular Immunology, Pergamon, GB, 36(6):387-395, Apr. 1, 1999.
Kawai, Shigeto, "Antitumor activity of humanized monoclonal antibody against HM1.24 antigen in human myeloma xenograft models," Oncology Reports, 15(2):361-367, Feb. 2006.
Ohtomo et al., "Molecular Cloning and Characterization of a Surface Antigen Preferentially Overexpressed on Multiple Myeloma Cells," Biochemical and Biophysical Research Communications, 258:583-591, 1999.
Raw et al., Generation of Potent Antitumor CTL from Patients with Multiple Myeloma Directed against HM1.24, Clin. Cancer Res., 11:3377-3384, 2005.
PCT/KR2005004398, Feb. 6, 2009, Search Report.
Ohtomo, et al., "Molecular Cloning and Characterization of a Surface Antigen Preferentially Overexpressed on Multiple Myeloma Cells," Biochemical and Biophysical Research Communications, 1999, 258:583-591.
Strausberg, et al., "Generation and initial Analysis of more than 15,000 full-length human and mouse cDNA sequences," Proc. Natl. Acad. Sci. U.S.A., 2002, 99(26), 16899-16903.
Ishikawa, et al., "Molecular cloning and chromosomal mapping of a bone marrow stromal cell surface gene, BST2, that may be involved in pre-B-cell growth," Genomics, 1995, 26(3), 527-534.
NCBI Accession No. Q10589 (Mar. 15, 2004).
PCT/KR2005/004398 Search Report, 2009.
Ozaki S. et al., "Humanized Anti-HM1.24 Antibody Mediates Myeloma Cell Cytotoxicty That is Enhanced by Cytokine Stimulation of Effector Cells," Blood, 93:3922-3930, 1999.

* cited by examiner

*Primary Examiner* — Sharon Wen

(74) *Attorney, Agent, or Firm* — Joseph Hyosuk Kim; JHK Law

(57) ABSTRACT

The application discloses a method of preventing immune cells from binding to other cells, which includes contacting the immune cells and the other cells with a composition comprising Bst2 antagonist.

9 Claims, 51 Drawing Sheets

Figure 1

Human Bst2 & mouse Damp-1 genes

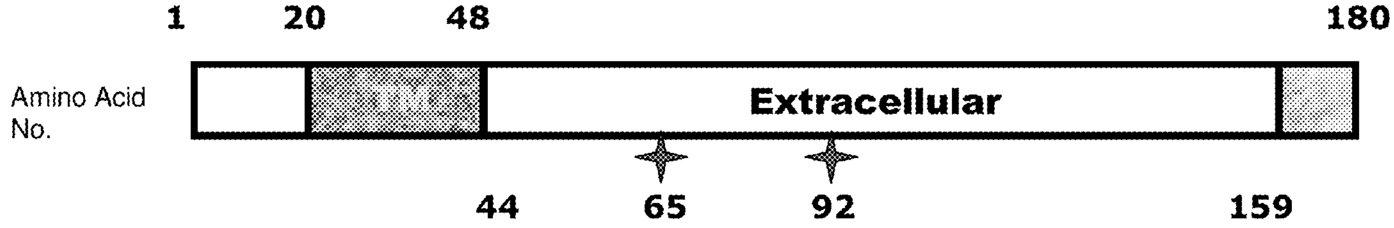

Identities = 70/180 (38.9%), Positives = 82/180 (45.6%), Gaps = 41/180 (22.8%)

Putative cytoplasmic (1-20 a.a.) T.M. (21-43 a.a.)

```
human_bst2    MASTSYDYCRVPMED-GDKR----CKLLLGIGILVLLIIVILGVPLIIFTIKANSEACRD 55
mouse_damp1   MAPSFYHYLPVPMDEMGGKQGWGSHRQWLGAAILVVLFGVTLVILTIYFAVTANSVACRD 60
              **.: *.*  ***:: *.*:    :  ** .***:*: * * :  * *::.*** ****

human_bst2    GLRAVMECRNVTHLLQQELTEAQKGFQDVEAQAATCNHTVMALMASLDAEKAQG---QKK 112
mouse_damp1   GLRAQAECRNTTHLLQRQLTRTQDSLLQAETQANSCNLTVVTLQESLEKKVSQALEQQAR 120
              ****  ****.*****::**.:*..: :.*:** :** **::*  **: : :*.   * :

human_bst2    VEELEGEITTLNHKLQDASAEVERLRRENQVLSVRIADKKYYPSSQDSSSAAAPQLLIVL 172
mouse_damp1   IKELENEVTKLN-------QELENLRIQKETSSTVQVN--------SGSSMVVSSLLVLK 165
              ::***.*:*.**       *:*.** :::. *.  .:         ..** ....**::

human_bst2    LGLSALLQ 180     SEQ ID NO: 73
mouse_damp1   VSLFLLF- 172     SEQ ID NO: 74
              :.*  *:
```

SM. Size marker
1. Bst2 decoy, non-reducing
2. Damp1 decoy, non-reducing
3. Bst2 decoy, reducing
4. Damp1 decoy, reducing SM. Size marker
1. Bst2 decoy, non-reducing
2. Bst2 decoy, reducing
3. Bst2 decoy, reducing, deglycosylation A: No treatment
B: untransfected cells treated with PMA and LPS
C: mock-transfected cells treated with PMA and LPS
D: Bst2-transfected cells treated with PMA and LPS A. No treatment
B. PMA + LPS
C. PMA + LPS + control media
D. PMA + LPS + Bst2 decoy media

| | challenge | sample |
|---|---|---|
| A. | Saline | saline |
| B. | Ovalbumin | saline |
| C. | Ovalbumin | vehicle |
| D. | Ovabumin | Bst2 decoy 0.4 mg/kg |
| E. | Ovalbumin | Bst2 decoy 2 mg/kg |
| F. | Ovalbumin | Bst2 decoy 10 mg/kg |

Figure 17
mPEG-Aldehyde (mPEG-propionaldehyde)
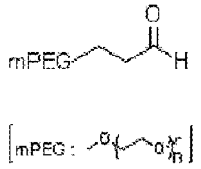
mPEG-SC (mPEG-succinimidyl carbonate)
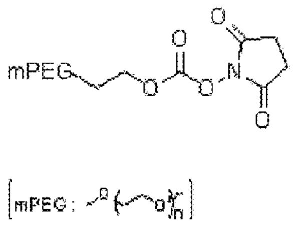

(A)

(B)

Figure 21
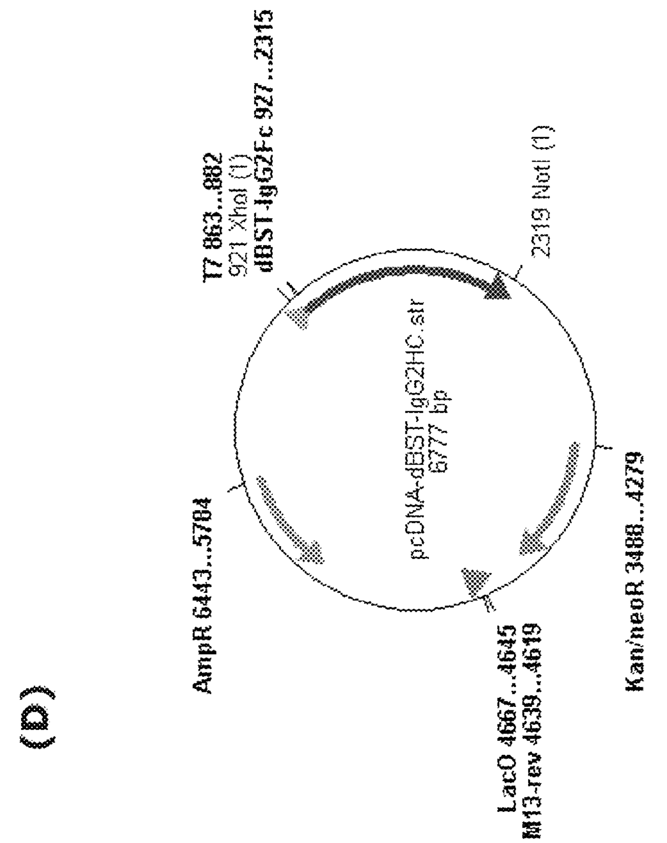
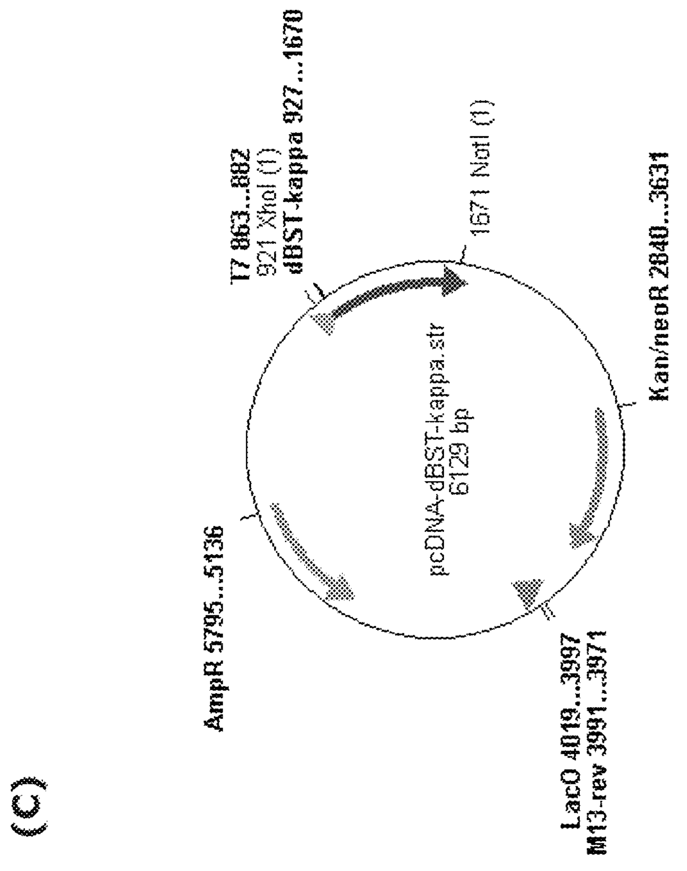

Creation of human-mouse chimeric BST2 mice

Figure 30

| | BST2 | | | GAPDH | | | | |
|---|---|---|---|---|---|---|---|---|
| | CT | ΔCT | Fold | CT | ΔCT | Fold | ΔΔCT | |
| Control | 32.0 | 0.0 | 1 | 26.3 | 0.0 | 1 | 1 | |
| IFN-g | 28.4 | 3.6 | 11.7 | 26.9 | -0.6 | 0.7 | 17.8 | |
| Con siRNA | 28.9 | 3.1 | 8.8 | 27.2 | -0.9 | 0.5 | 16.2 | |
| BST2 si | 29.1 | 2.9 | 7.5 | 26.8 | -0.5 | 0.7 | 10.2 | 57% |
| BST2 si | 29.2 | 2.8 | 7.1 | 26.9 | -0.6 | 0.7 | 10.4 | 58% |
| B+I siRNA | 29.3 | 2.7 | 6.6 | 26.9 | -0.6 | 0.7 | 10.0 | 56% |

| | ICAM-1 | | | GAPDH | | | | |
|---|---|---|---|---|---|---|---|---|
| Control | 33.0 | 0.0 | 1 | 26.9 | 0.0 | 1 | 1 | |
| IFN-g | 28.2 | 4.8 | 27.0 | 26.8 | 0.1 | 1.1 | 25.1 | |
| Con siRNA | 28.9 | 4.1 | 16.8 | 27.3 | -0.4 | 0.7 | 22.4 | |
| ICAM1si | 29.8 | 3.2 | 9.4 | 27.1 | -0.2 | 0.9 | 10.8 | 43% |
| ICAM1si | 29.4 | 3.6 | 11.8 | 27.0 | -0.1 | 0.9 | 12.6 | 50% |
| I+B siRNA | 29.9 | 3.1 | 8.8 | 27.1 | -0.2 | 0.8 | 10.3 | 41% |

Using bivalent Bst2-decoy to join two cell types

Figure 37A

```
            FR1                                          CDR1        FR2                          CDR2
                                                         *****       **************              ******************
2-15   MAQSVKESEGRLVTPGTPLTLTCTVSGFSLSNSGMSWVRQAPGKGLEWIGLINSYGTTYYASWAKG
2-14   MAQSVKESEGGLFKPTDTLTLTCTVSGFSLSNSGMSWVRQAPGKGLEYIGIIRSDGSTYYASWAKG
2-10   MAQSLEESGGGRLVKPDETLTLTCTVSGIDLSSYEMNWVRQAPGKGLEYIGFIYGSGDTYYATWAKG
2-4    MAQQLVESGGGRLVTPGGTLTLTCTASGIDLSSYHMQWVRQAPGKGLEYIGFDTVGSAYYASWAKG
2-5    MAQQLVESGGGGLVTPGTPLTLTCTVSGFSLSSYAMIWVRQAPGKGLEYIGIIRSSGNTYYASWAKG
2-7    MAQSVKESEGGLFKPTDTLTLTCTVSGFSLSSYHMSWVRQAPGNGLEYIGIINSYANTYYAGWAKS
2-9    MAQSLEESGGGRLVTPGTPLTLTCTVSGFSLSSYHMSWVRQAPGKGLEYIGFISTSGNTYYASWAKS
2-11   MAQEQLMESGGGGLVTPGGILSLTCTASGFSISSYRMGWVRQAPGKGLEWIGFINNYGSAYYASWAKS
2-13   MAQEQLVESGGGRLVTPGGSLTITCTVSGIDLSGYAMGWVRQAPGKGLEYIGIIGTSDTYYASWAKG
2-19   MAQSVKESEGGLFKPTDTLTLTCTVSGFSLSSYEMNWVRQAPGKGLEYIGIIRSDGSTYYASWAKS
2-24   MAQSVEESRGGLFKPTDTLTLTCTVSGFSLSTYEMNWVRQAPGSGLEYIGIINSAGTTYYASWAKS

          FR3                                       CDR3                 FR4
                                                    ******
2-15   RFTISKTSTTVELKITSPTTEDTATYFCAR    GAGSSYGL         WGQGTLVTVSSAS    SEQ ID NO: 77
2-14   RSTITRNTNLNTVTLKMTSLTAADTATYFCAR  SSGWGYGLDL       WGPGTLVTVSSAST   SEQ ID NO: 78
2-10   RFTISRPSTTVDLKITSPTTGDTATYFCAR    DSGYSIGIL        WGPGTLVTISSAST   SEQ ID NO: 79
2-4    RFTISRTSTTVDLKMTSLTAADTATYFCAG                    WGQGTLVTVSSAST   SEQ ID NO: 80
2-5    RFTISKTSTTVDLKITSPTTEDTATYFCAR    DSGYSFGL         WGQGTLVTVSSAST   SEQ ID NO: 81
2-7    RSTITRNTNENTVTLIMTSLTAADTATYFCVR  DLGYSSDI         WGPGTLVTISSAST   SEQ ID NO: 82
2-9    RFTISKTSTTVDLKITSPTIEDTAAYFCAR    GPAKSGYGTRLDLWGQGTLVTVSSAST       SEQ ID NO: 83
2-11   RSTITRNTNLNTVTLKMTSLTAADTATYFCARE SYSYGYAYDI       WGPGTLVTVSSAST   SEQ ID NO: 84
2-13   RFTISKTSSTTVDLKMTSLITTEDTATYFCVR  SPGGSADL         WGQGTLVTISSAST   SEQ ID NO: 85
2-19   RSTITRNTNLNTVTLKMTSLTAADTATYFCAR  DLGYSNDV         WGPGTLVTISSAST   SEQ ID NO: 86
2-24   RSTITRNTNENTVTLKMTSLTAADTATYFCAR  DLGYSSDI         WGPGTLVTVSSAST   SEQ ID NO: 87
```

Figure 37B

```
                              FR1                 CDR1       FR2          CDR2
             --------------------------***********----------------******
2-15         QAAELVMTQTPSSTSTAVGDTVTIKCQASQSIGSNLAWYQQKPGQPPKILIYSASNLAS
2-14         -----DL------------G----N-----N--I--------------L--WY--D---
2-10            --DL------------G----N-------NVW-S-----------L---Q--K---
2-4          ------L------V-A---G----N---T----I--------------L--WY--D---
2-5          -------------V-A---G----N----KN--I--------------Q--WY--D---
2-7          -------------------G----N-----N--I--------------L--WY--D---
2-9          -----DL------------G----N-----N--I----F---------L--WY--D---
2-11            --DL---------T--G----N-R---I--I--------------L--WY--D---
2-13         -----D-------------G---MN-----N--I--------------L--WY--D---
2-19         ------L------------G----N-----N--I--------------L--WYT-D---
2-24         -------------------G----N-----N--I--------------L--WY--D---

                                   FR3             CDR3      FR4
             --------------------------------**********-------------
2-15         GVPSRFKGSGSGTEYTLTISGVQREDAATYYCLGSDSSWDTVFGGGTELEILRTV   SEQ ID NO: 88
2-14         --S-------F--QF-------------------TYG-G-RA--A--NV--K---   SEQ ID NO: 89
2-10         -------------QF-----------V-------IYNDID-A------VVVK---   SEQ ID NO: 90
2-4          ----------F--QF----N---------------YG-G-RA--A--NV-IK---   SEQ ID NO: 91
2-5          ----------F--QF----N---------------YG-G-RA--A--NV--K---   SEQ ID NO: 92
2-7          ----------F--QF--------------------YG-G-RA--A--NV--K---   SEQ ID NO: 93
2-9          ----------F--QF-----N-E-----------TYG-G-RA--A--NV--K---   SEQ ID NO: 94
2-11         ------R-NV--SQF-------------------TYG-GVRA--A--NV--K---   SEQ ID NO: 95
2-13         ----------F--QF------M------------TYG-GVRA--A--NV--K---   SEQ ID NO: 96

2-19         ------R---F--QF-----AI------------TYG-GVRA--A--NV--K---   SEQ ID NO: 97
2-24         -A--------F--QF-------------------TYG-G-RA--T--NV--K---   SEQ ID NO: 98
```

Figure 47
A.
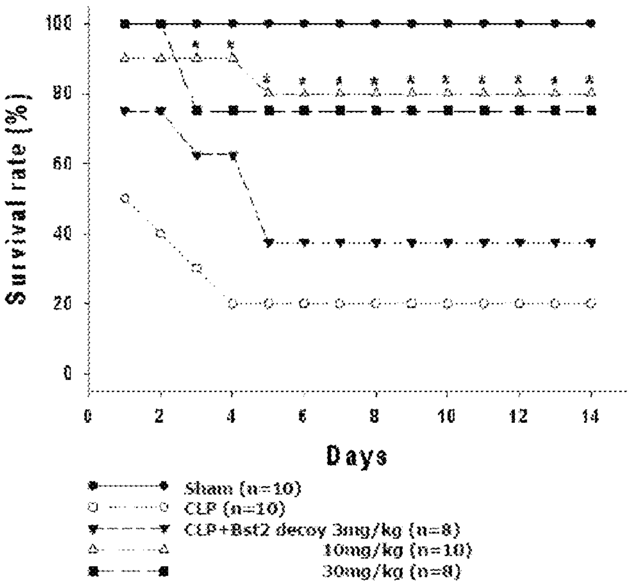
B.
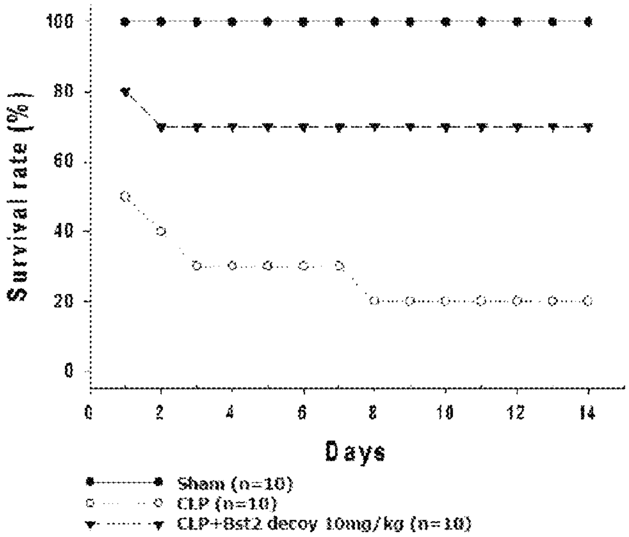

TREATMENT OF INFLAMMATION USING BST2 INHIBITOR

CROSS-REFERENCE TO RELATED APPLICATIONS

The present application is a continuation-in-part of U.S. patent application Ser. No. 11/757,329, filed Jun. 1, 2007, now abandoned which is a continuation-in-part of U.S. patent application Ser. No. 11/471,853, filed Jun. 20, 2006, now U.S. Pat. No. 7,740,856 which is a continuation-in-part of PCT/KR2005/004398, filed Dec. 20, 2005, which designates the U.S. and claims benefit of priority to Korean patent application 10-2004-0108909, filed Dec. 20, 2004, the contents of which are incorporated by reference herein in their entirety.

BACKGROUND OF THE INVENTION

1. Field of the Invention

The present invention relates to molecules inhibiting intercellular adhesion during inflammation and the use of the same. The present invention also relates to using Bst2 protein or fragments thereof as a decoy or Bst2-binding antibody in inhibiting intercellular adhesion and activation of cells participating in inflammation as well as small molecules. The present invention also relates to methods of discovering Bst2 ligand and inhibitor of Bst2 ligand. The present invention is also concerned with a composition comprising the same, and a method for preventing or treating inflammation-associated diseases.

2. General Background and State of the Art

Inflammation is a normal response of the body to protect tissues from infection, injury or diseases. The inflammatory response begins with the production and release of chemical agents by cells in the affected tissues. The chemical agents cause redness, swelling, pain, heat and loss of function. Cells in inflamed tissues generate signals that recruit leukocytes to the site of inflammation. Leukocytes must adhere to endothelial cells to migrate from the bloodstream into the site of inflammation. Also, leukocytes should adhere to antigen-presenting cells to allow normal specific immune responses, and should finally adhere to suitable target cells to lyse pathogen-infected cells, cancer cells, or the like. The recruited leukocytes eliminate any infective or injurious agent and remove debris of damaged cells from the injured tissue.

The infiltrating leukocytes play critical roles in tissue regeneration and immune response in normal inflammation by engulfing invading microorganisms or dead cells. However, the infiltrating leukocytes cause serious or lethal status in pathological chronic inflammation. The abnormal recognition of self cells as non-self (foreign) or excess inflammation by sustained inflammatory responses causes a variety of inflammatory diseases including diabetes mellitus, atherosclerosis, cataract, reperfusion injury, infectious meningitis, rheumatoid arthritis, asthma, sepsis, inflammatory bowel disease and multiple sclerosis.

The interaction between leukocytes and endothelial cells is as follows.

Leukocytes have dual functions to act in a form circulating in the bloodstream or adhering to specific cells. In particular, adherent leukocytes interact with endothelial cells, stabilize intercellular adhesion with antigen-presenting cells or act as effector cells to migrate into inflammatory or infected sites. For normal specific immune response, leukocytes should adhere to antigen-presenting cells and should finally adhere to suitable target cells to lyse pathogen-infected cells, cancer cells, or the like. A massive invasion of leukocytes occurs in an allograft rejection, skin infection or in an injured area, and is also observed in various diseases including degenerative joint diseases, such as osteoarthritis, psoriasis, multiple sclerosis, asthma, rheumatoid arthritis, contact dermatitis and inflammatory bowel disease In such diseases, greater than 95% of myeloid cells move to and accumulate at the site of inflammation. Leukocytes are crucial agents of the inflammatory response, which exert antimicrobial, secretory and phagocytic activity. They gather in tissues where inflammation is occurring or needs to occur by producing a water-soluble mediator or through specific adhesion to various cells. In fact, anti-inflammatory agents such as nonsteroidal anti-inflammatory drugs (NSAIDs) or glucocorticoid exert therapeutic efficacy by preventing the adhesion and influx of leukocytes. In animal models, the inhibition of intercellular adhesion improves or prevents diseases or allograft rejection in animal models of autoimmune diseases. Recent clinical studies have revealed that humanized monoclonal antibodies inhibiting LFA-1/ICAM-1 or VLA-4/VCAM-1 interaction have significant efficacy and good safety on autoimmue diseases including psoriasis, multiple sclerosis and inflammatory bowel disease.

The uncontrolled invasion of leukocytes into endothelial cells, which is a key feature in the pathogenesis of inflammation-associated diseases, occurs by a multi-step process, which begins with leukocyte adhesion and binding to the surface of endothelial cells. The binding of leukocytes to endothelial cell surface is mediated by cell surface molecules present on the surface of leukocytes and endothelial cells (Bevilacqua, *J. Clin. Invest.* 11:767-804, 1993). The cell surface molecules are overexpressed as a result of migration of leukocytes from the bloodstream.

The interaction between leukocytes and endothelial cells is a critical factor in many inflammatory diseases. For example, increased leukocyte-endothelial interaction leading to hepatic microperfusion disorders is proposed as a major contributor of hepatic failure (Croner et al., *Microvasc. Res.* 67:182-191, 2004). For example, atherosclerosis is a typical inflammatory disease in which a number of inflammatory cells including T lymphocytes and activated macrophages are concentrated in the site of atherosclerosis. The accumulation and adhesion of monocytes in discrete segments of arterial endothelium is among the earliest detectable events in atherogenesis and is a central feature of the pathogenesis of atherosclerosis (Ross, *Nature* 362:801-809, 1993). In this region, proinflammatory cytokines are abundant, which include interferon-gamma and tumor necrosis factor-alpha, regulating regional inflammatory response. A great number of adhesion molecules are expressed on the surface of monocytes (Valente et al., *Circulation* 86:III20-25, 1992), and endothelial cells overlying atherosclerotic lesions express a number of vascular ligands (Poston et al., *Am. J. Pathol,* 140:665-673, 1992).

The extravasation of leukocytes across the endothelial barrier is a critical event in the pathogenesis of inflammatory diseases such as rheumatoid arthritis. Endothelial cells participate in the basic mechanism of arthritis, by which various inflammation mediators, such as tumor necrosis factor-alpha and inflammation-inducing cytokines such as interleukin-1 beta, activate endothelial cells. This leads to elevated expression of endothelial cell adhesion molecules in rheumatoid arthritis, resulting in increased interaction between leukocytes and endothelial cells. The recruitment of leukocytes to vascular endothelial cells is also an important step of asthma.

In the airway of patients with asthma, there are increased numbers of activated eosinophils, CD25-positive T lymphocytes and immature macrophages with the phenotypic characteristics of blood monocytes. The expression of HLA class II increases in epithelial cells, macrophages, and other infiltrating cells (Arm et al., *Adv. Immunol.* 51:323-382, 1992).

An increased rate of leukocyte transmigration across the blood-brain barrier is a major symptom in multiple sclerosis. The interaction between tight junction proteins in leukocytes and those in endothelial cells contributes to the leukocyte extravasation to the central nervous system under physiological conditions, and the altered expression of tight junction proteins is a pathological prerequisite for multiple sclerosis (Worthylake et al., *Curr. Opin. Cell Biol.* 13:569-577, 2001).

As described above, since the adhesion of leukocytes to endothelial cells is important in a variety of diseases, the inhibition of intercellular adhesion may result in a therapeutic strategy for diverse inflammatory and immune diseases.

With respect to the molecular biology, the following molecules are known to participate in inflammation.

Cytokines: systemic inflammation, which is a general response to serious bacterial infections or traumatic injuries, may affect tissue systems distal to the early damage (Lush and Kvietys, *Microcirculation* 7:83-101, 2000). Bacterial products and other inflammation-inducing mediators, released from affected tissues, induce the formation of inflammation-inducing mediators including tumor necrosis factor-alpha (TNF-alpha), interleukin-1 beta, gamma-interferon and interleukin-6. In sepsis, vascular endothelial damage promotes the production of TNF-alpha and interleukin-1 beta. These cytokines directly act on endothelial cells and enhance leukocyte adhesion (Pober et al., *J. Immunol.* 137:1893-1896, 1986; Dustin and Springer, *J. Cell Biol.* 107:321-331, 1988; Cotran and Pober, *J. Am. Soc. Nephrol.* 1:225-235, 1988). These cytokines also activate blood neutrophils in blood and vascular endothelium (Arai et al., *Annu Rev Biochem,* 59:783-836, 1990). For example, TNF-alpha induces a series of cytokines, chemokines and proteases by an autocrine or paracrine pathway (Ghezzi and Cerami, *Methods Mol. Med.* 98:1-8. 2004). Interleukin-6 induces mononuclear-endothelial cell interaction and inflammatory damage through expression of adhesion molecules, thus initiating a process of atherosclerosis. Increased blood concentration of interleukin-6 involves vascular inflammation and development of atherosclerosis (Rader, *N. Engl. J. Med.* 343:1179-1182, 2000). Interleukin-17 induces the expression of many mediators of inflammation, and is involved in the differentiation, maturation and chemotaxis of neutrophil (Witowski et al., *Cell Mol Life Sci.* 61:567-579, 2004). Increased levels of interleukin-17 have been associated with several pathological conditions, including airway inflammation, rheumatoid arthritis, intraperitoneal abscesses and adhesions, inflammatory bowel disease, allograft rejection, psoriasis, cancer and multiple sclerosis.

Cell surface adhesion molecules: a plurality of inflammatory cytokines induce the expression of endothelial cell-lymphocyte adhesion molecules (ELAMs) on the cell surface (Nortamo et al., *Eur. J. Immunol.* 21:2629-2632, 1991). They are divided into two classes: intercellular adhesion molecule-1 (ICAM-1) and endothelial cell-lymphocyte adhesion molecule-1 (ELAM-1) (Staunton et al., *Cell* 52:925-933, 1988). In response to various mediators, vascular endothelium expresses specific cell surface glycoproteins. The binding and extravasation of blood leukocytes are achieved by interaction with a specific ligand or counter receptor (Bevilacqua et al., 1993, 1994). Molecules participating in this process include intercellular adhesion molecule-1 (ICAM-1) as a ligand for CD18, selectins recognizing glycoonjugates on the leukocyte surface, and members of the immunoglobulin superfamily interacting with other members of the same family, leukocyte integrin molecules (Panes et al., *J. Physiol.* 269:H1955-1964, 1995; Khan et al., *Microcirculation* 10:351-358, 2003; Nelson et al., *Blood* 82:3253-3258, 1993; Bevilacqua and Nelson, *J. Clin. Invest.* 91:379-387, 1993). Leukocyte rolling is regulated by selectins, and transmigration and adhesion of leukocytes on endothelial cells are triggered by the beta 2 integrin, Mac-1 (CD11b/CD18, aMb2, CR3), and LFA-1. Mac-1 and LFA-1 interact with a counter receptor expressed on the surface of endothelial cells, ICAM-1.

Prior art associated with inflammation therapy include the following.

The U.S. Pat. No. 5,367,056 patent describes the inhibition of the binding of polymorphonuclear leukocytes (PMNs) to endothelial cells by treatment of molecules or fragments thereof interrupting the binding to endothelial cell-leukocyte adhesion molecules (ELAMs) as receptors or ligands. This patent also describes antisense nucleotides and ribozymes for suppressing ELAM expression. This patent further describes a method for identifying molecules which inhibit the binding of ELAM to its ligand, and antibodies against ELAM and its ligands.

The U.S. Pat. No. 5,863,540 patent discloses a method of suppressing T cell activation by administering a CD44 protein peptide or a derivative thereof in an amount sufficient to suppress T cell activation. Also disclosed is a method of inhibiting CD44-mediated cell adhesion or CD44-mediated monocyte IL1 release by administering the CD44 protein peptide or derivative thereof in an amount sufficient to inhibit CD44-mediated cell adhesion or monocyte IL1 release. Further disclosed is a method of transporting a drug or cytotoxic agent to a site of inflammation by administering the CD44 protein peptide or derivative thereof linked to the drug or cytotoxic agent.

The U.S. Pat. No. 5,912,266 patent involves the inhibition of intercellular adhesion mediated by the beta 2 integrin family of cell surface molecules. The patent discloses a pharmaceutical composition useful for inhibiting or treating inflammatory and other pathological responses associated with cell adhesion. This patent also discloses a method of inhibiting or treating pathological conditions where leukocytes and lymphocytes cause cellular or tissue damage.

The WO03026692 patent relates to the therapeutic use of an antibody against CD3 antigen complexes in patients with chronic articular inflammation and rheumatoid arthritis.

The EP1304379 patent relates to a humanized anti-CD18 antibody comprising a portion or the whole of an antigen-determining region capable of binding to CD18 antigen.

The U.S. Pat. No. 6,689,869 patent describes the use of a humanized anti-CD18 antibody in inhibiting influx of leukocytes into the lung and other organs during sepsis, and other infectious or non-infectious traumas. The humanized anti-CD18 antibody can be used for inhibiting the ingress of leukocytes into the lung and other organs in patients having endotoxic shock or adult respiratory distress syndrome. The antibody can be administered to treat asthma or leukocyte-mediated reperfusion damage post thrombolytic therapy. Also, the antibody can be used to reduce or eliminate inflammation in a patient being administered with an anti-infective agent, or to assist in the administration of a therapeutic drug to a patient during anticancer chemotherapy.

The U.S. Pat. No. 5,821,336 patent describes polypeptides having a molecular weight of 160 kD, which are mediators or precursors for mediators of inflammation, derivatives thereof, such as mutants and fragments, and processes for their preparation. Nucleotide sequences coding for the polypeptides and derivatives, vectors comprising the nucleotide sequences, antibodies against the polypeptides or their derivatives and antibody derivatives are also disclosed in this patent. Also described are diagnostic and therapeutic methods for inflammatory conditions and Hodgkin's lymphomas using the antibodies and antibody derivatives.

WO2004/039398 discloses a cancer vaccine by generating cytotoxic T cells via utilization of dendritic cells as antigen-presenting cells for the HM1.24 antigen, which is a Bst2 protein. The WO '398 reference also discloses a cancer vaccine containing as an active ingredient an HM1.24 protein or peptide, or a DNA or an RNA encoding an HM1.24 protein or peptide. WO '398 also discloses the use of HM1.24 protein or peptide for cancer vaccine. However, WO '398 fails to disclose or suggest use of soluble HM1.24 protein itself as a therapeutic protein for treating inflammatory diseases such as, but not limited to, atherosclerosis, rheumatoid arthritis, asthma, sepsis, ulcerative colitis, multiple sclerosis, acute myocardial infarction, heart attack, psoriasis, contact dermatitis, osteoarthritis, rhinitis, Crohn's disease and autoimmune diseases. In addition, the mechanistic action of a cancer vaccine is substantially and significantly different from that of a therapeutic protein that inhibits inflammation.

Vaccines, including cancer treatment vaccines, stimulate antigen-specific immune responses directed against the specific protein or protein-containing particles. Protein-containing particles can be specific viruses, bacteria, or infected or otherwise pathogenic cells that express or incorporate the target protein. Inflammation is caused by active or, in the case of pathogenic inflammation, overly active immune cells, and anti-inflammatory therapeutics inhibit inflammation by suppressing the activity of certain immune cells involved in the inflammation.

A cancer vaccine works by activating immune cells to target the specific protein used, while a protein that functions as an anti-inflammatory therapeutic works by inhibiting the activity of immune cells involved in the inflammation. In the case of a cancer vaccine, Bst2 is shown to the immune system as the target that needs to be recognized and eradicated, while in the case of a therapeutic protein, soluble Bst2 protein (Bst2 decoy) itself would actively function to inhibit or suppress the function of certain immune cells. Thus, the use of soluble Bst2 protein as a therapeutic protein for inflammatory diseases is both conceptually and functionally distinct from the use of Bst2 as a cancer vaccine in WO '398.

SUMMARY OF THE INVENTION

Inflammation requires at least three sequential steps to attract immune cells that include leukocytes to the site of inflammation, as follows: (1) immune cells including leukocytes such as lymphocytes, polymorphonuclear leukocytes, natural killer cells and macrophages are activated by cytokines and/or intercellular interaction; (2) the aggregated immune cells migrate and are recruited to the site of inflammation, where they transduce related signals into endothelial cells through adhesion to endothelial cells; (3) T lymphocytes and macrophages are activated and secrete cytokines, such as interleukin-2, to amplify the inflammatory response.

The present inventors found that Bst2 protein mediates homotypic adhesion of immune cells or heterotypic adhesion between immune cells and endothelial cells, which play crucial roles in inflammation, and further found that an antagonist of the protein acts in the major three steps of inflammation and can thus be used in the prevention and treatment of inflammation-associated diseases, thereby leading to the present invention.

In one aspect, the present invention is directed to a method of preventing immune cells from binding to other cells, comprising contacting the immune cells and/or the other cells with a composition comprising Bst2 antagonist. The other cells may be immune cells, endothelial cells, smooth muscle cells, brain cells, spinal cord cells, peripheral nerve cells, heart cells, skeletal muscle cells, lung cells, liver cells, kidney cells, blood vessel cells, pancreatic cells, large and small intestinal cells, stomach cells, esophageal cells, nasoropharyngial cells, membraneous cells or connective tissue cells. The Bst2 antagonist may be a Bst2 decoy. And the Bst2 decoy may be a fragment of Bst2 or a variant thereof, having similar or improved binding compared to the Bst2 protein towards another molecule or protein. The Bst2 antagonist may be further a Bst2 decoy fused to a stabilizing protein, Bst2 decoy-Fc chimeric or fusion construct, Bst2-decoy-albumin chimeric or fusion construct, or pegylated Bst2-decoy. Further, the Bst2 antagonist may be a monoclonal antibody or an antibody-like protein domain which specifically binds to Bst2 and/or mouse Damp1 protein.

In another aspect of the invention, the Bst2 antagonist may be a chemical compound.

In yet another aspect, in the method described above, the immune cells and the other cells may be either located at a site of inflammation or at a site distant from inflammation but which is able to transmit inflammatory and immune cytokines or other inflammatory signals to the site of inflammation. Further, the composition may include a cell adhesion or signal transmission inhibiting compound or an immunosuppressive compound. In a preferred embodiment, the cell adhesion inhibiting compound may be ICAM1 antagonist, or LFA antagonist.

In still another embodiment, the invention is directed to a Bst2 decoy-Fc chimera. Preferably, the decoy may be fused to any domain of an immunoglobulin. In particular, the Bst2 decoy may be fused to the hinge-CH2-CH3 portion of an IgG heavy chain Fc; Bst2 fusion protein that is stabilized through IgG kappa chain-heavy chain disulfide bonding; or Bst2 decoy-IgG Fc without other Bst2 dimerization counterparts.

In another embodiment, the invention is directed to a monoclonal antibody specific for Bst2 and/or a homologue of Bst2. The homologue may be mouse Damp 1 protein. Further, the monoclonal antibody may comprise two arms one of which contains a region that specifically binds to a protein other than Bst2 or homologue thereof. In particular, a cell expressing Bst2 to which the monoclonal antibody is bound prevents Bst2 ligand-Bst2 interaction or Bst2-Bst2 interaction.

In a further alternative embodiment, the invention is directed to a method of isolating a ligand for Bst2, comprising:

(i) obtaining cells that bind to Bst2;

(ii) screening for ligand that binds to Bst2 from the cells that express the ligand, thereby isolating the ligand for Bst2.

In another embodiment, the invention is directed to a transgenic mouse whose somatic and germ cells comprise a functionally disrupted Damp or Bst2 gene, wherein the disrupted gene is introduced into the mouse or an ancestor of the mouse at an embryonic stage, wherein if homozygous for the disrupted gene exhibits an inflammation related disorder.

In yet another embodiment, the invention is directed to a transgenic mouse whose somatic and germ cells comprise a Damp gene which is fully or partially replaced with Bst2 gene, wherein the Bst2 gene is introduced into the mouse or an ancestor of the mouse at an embryonic stage.

In another aspect, the invention is directed to a method of reducing inflammation in a subject comprising administering a composition comprising Bst2 antagonist to a site of the inflammation.

In yet another aspect, the invention is directed to a method of treating a subject of symptoms of a disease associated with inflammation comprising administering a composition comprising Bst2 antagonist to the subject in need thereof. The composition may comprise another anti-inflammatory compound. And the indicated disease may be atherosclerosis, rheumatoid arthritis, asthma, sepsis, ulcerative colitis, type I diabetes, cataract, multiple sclerosis, acute myocardial infarction, heart attack, psoriasis, contact dermatitis, osteoarthritis, rhinitis, Crohn's disease, autoimmune diseases, cachexia, acute pancreatitis, autoimmune vasculitis, autoimmune and viral hepatitis, delayed-type hypersensitivity, congestive, coronary restenosis, glomerulonephritis, graft versus host disease, uveitis, inflammatory eye disease associated with corneal transplant, brain injury as a result of trauma, epilepsy, hemorrhage, stroke, sickle cell disease, type II diabetes, obesity, age-related macular degeneration (AMD), Eczema, dermatitis, learning/cognitive disability, neurodegenerative diseases, Parkinson's disease, Alzheimer disease, ulcerative colitis, radiation-induced injury, burn or electricity-induced injury, poisoning that causes tissue death and immune cell infiltration, drug-induced injuries, inhalation-induced injuries, radiation, aspiration-induced injury of the lung, inflammation resulting from chemotherapy or radiation therapy, autoimmune diseases, Lupus, Schogren disease, demyelinating diseases including multiple sclerosis, inflammatory myopathy including polymyositis, scleroderma, polyarteritis nodosa, sarcoidosis, localized and generalized myositis ossificans, amyloid-associated diseases including Alzheimer disease, herniated disc, spinal cord and nerve damage, Reye syndrome, bacterial and viral encephalitis and meningitis, Prion-related disease, Guillain-Barre syndrome, rabies, poliomyelitis, cerebral hemorrhage, intracranial hemorrhage-related damage, chronic fatigue syndrome, thrombophlebitis, gout, granulomatosis, nephritis including glomerulonephritis and interstitial nephritis, insect-sting allergy, anaphylaxis, asplastic anaemia, bone marrow failure, multiple organ failure, thyroiditis, insulitis, cirrhosis (chronic and acute hepatitis), pulmonary embolism, toxin and drug-induced liver disease, pancreatitis, ischemic intestinal diseases, acute respiratory distress syndrome, or pericarditis.

In still another aspect, the invention is directed to a method of assaying for chemical compound that is effective to inhibit Bst2 mediated cell-cell binding, comprising determining a compound that binds to Bst2. Further, the Bst2 decoy may be recombinantly expressed in a host cell.

In one aspect, the invention is directed to a method of reducing inflammation in a subject comprising administering a composition comprising an effective amount of isolated Bst2 (bone marrow stromal cell antigen 2) protein polypeptide as an active ingredient, wherein said isolated Bst2 protein polypeptide comprises a soluble portion of Bst2, which comprises an extracellular portion of Bst2 or a fragment of the extracellular portion, wherein the extracellular portion is shown in amino acid positions 44 to 180 of SEQ ID NO:73 or 49-172 of SEQ ID NO:74. In one aspect, the inflammatory disease or disorder is not related to cancer. Optionally, the inflammation sought to be treated is not the site of injection inflammation side effect of vaccines, in particular cancer vaccines. Rather, the inflammation sought to be treated by the inventive compound are nonspecific, innate inflammatory responses. The inflammatory disease sought to be treated by the inventive compound may include without limitation, asthma, atopic dermatitis or sepsis and so forth. The isolated Bst2 protein polypeptide may be optionally a Fc chimeric or fusion construct, an albumin chimeric or fusion construct, or linked to a non-proteinaceous polymer. The polypeptide may also be as shown in SEQ ID NO:1, which is a fragment of the Bst2 protein or SEQ ID NO:2, which is a fragment of the Damp1 protein, or a fragment thereof. In the above described method, the composition may include another anti-inflammatory compound.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein FIG. 1 is an amino acid sequence alignment showing sequence similarity between full length human Bst2:

```
                                   (SEQ ID NO: 73)
MASTSYDYCRVPMEDGDKRCKLLLGIGILVVLIIVILGVPLIIFTIKANS

EACRDGLRAVMECRNVTHLLQQELTEAQKGFQDVEAQAATCNHTVMALMA

SLDAEKAQGQKKVEELEGEITTLNHKLQDASAEVERLRRENQVLSVRIAD

KKYYPSSQDSSSAAAPQLLIVLLGLSALLQ
and mouse Damp1:

                                   (SEQ ID NO: 74)
MAPSFYHYLPVPMDEMGGKQGWGSHRQWLGAAILVVLFGVTLVILTIYFA

VTANSVACRDGLRAQAECRNTTHLLQRQLTRTQDSLLQAETQANSCNLTV

VTLQESLEKKVSQALEQQARIKELENEVTKLNQELENLRIQKETSSTVQV

NSGSSMVVSSLLVLKVSLFLLF;
```

Figure 4:
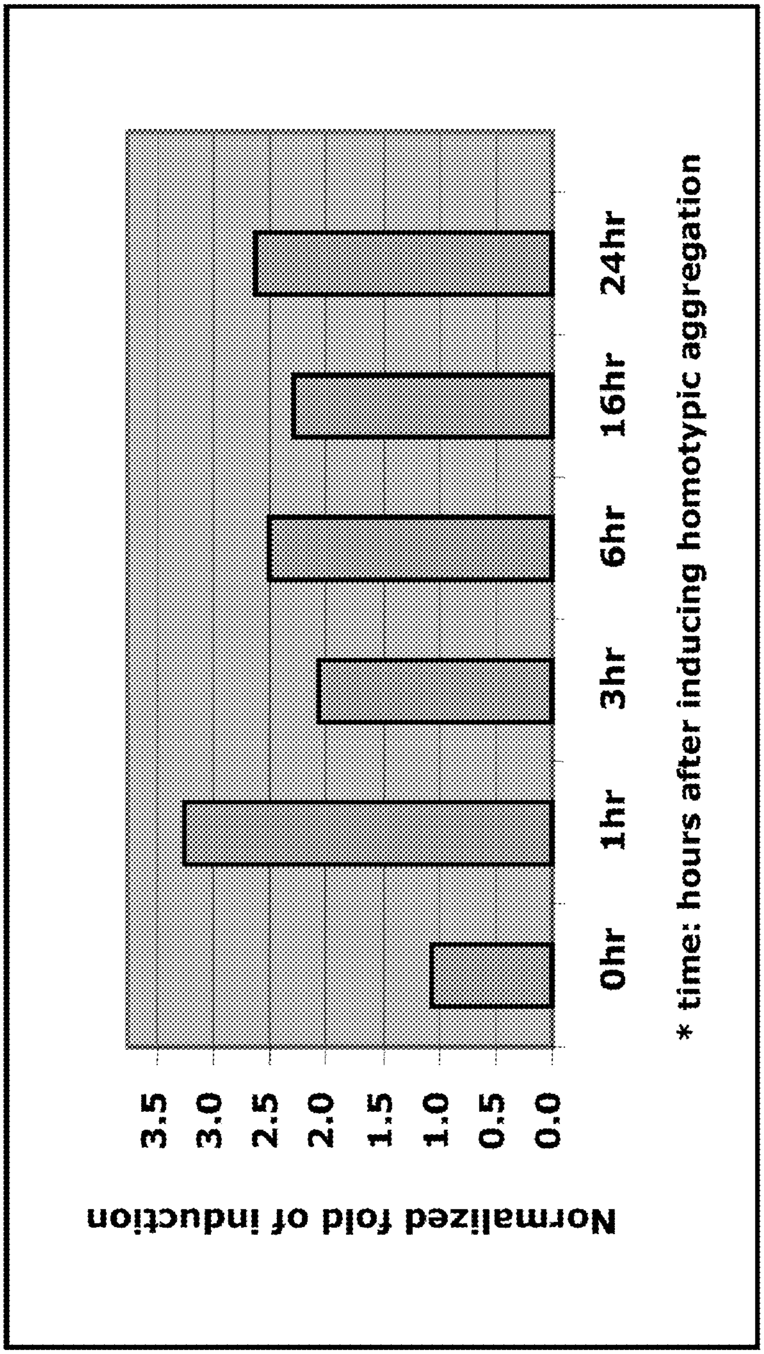
Figure 5:
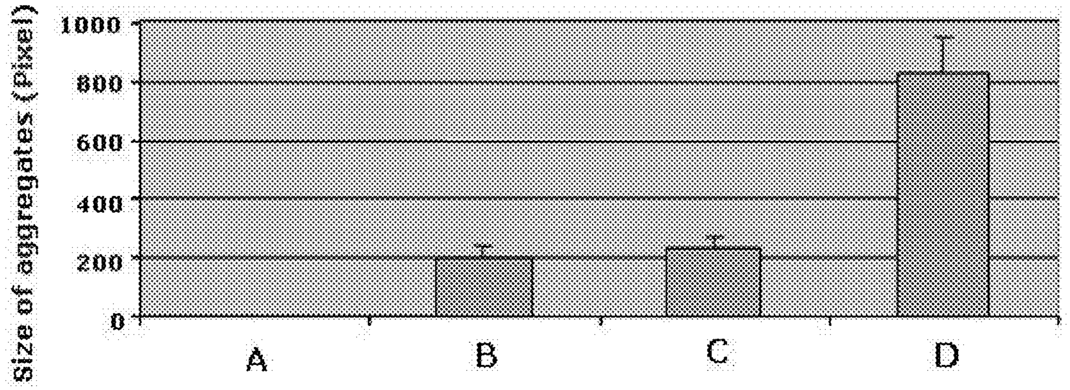
Figure 13:
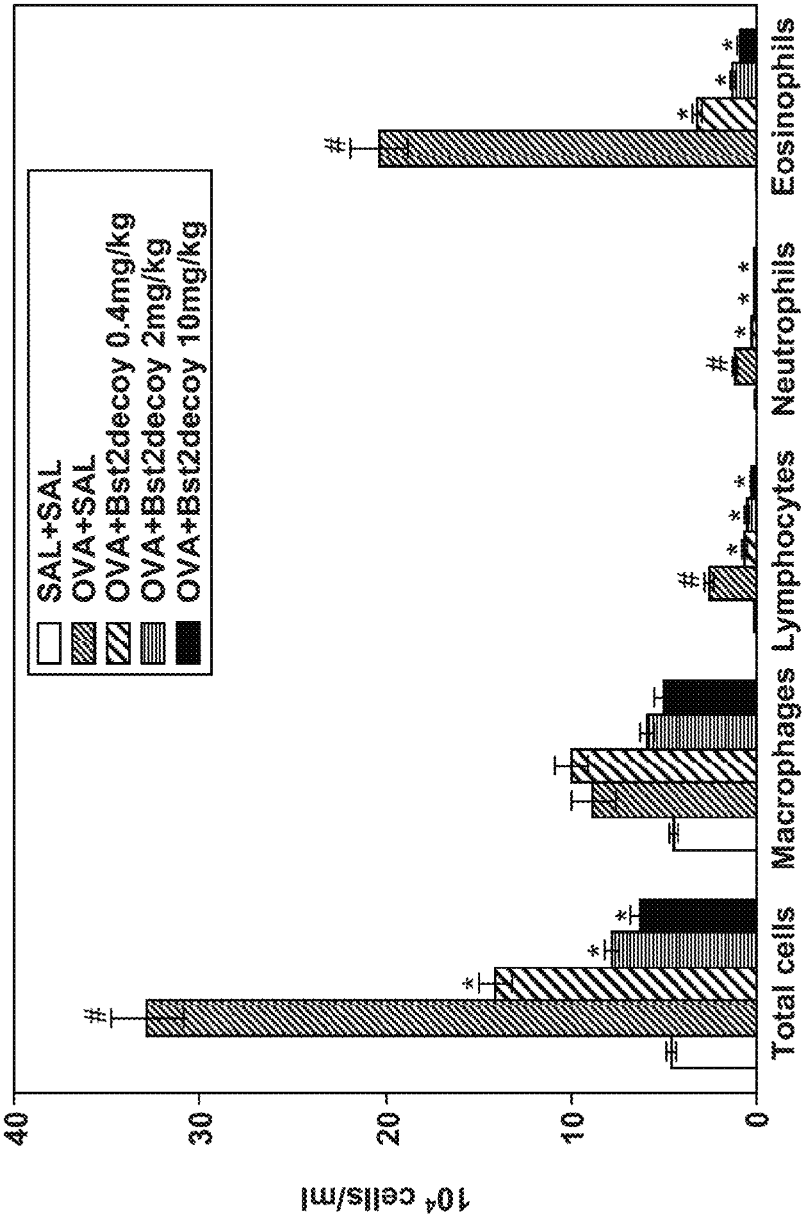
Figure 14:
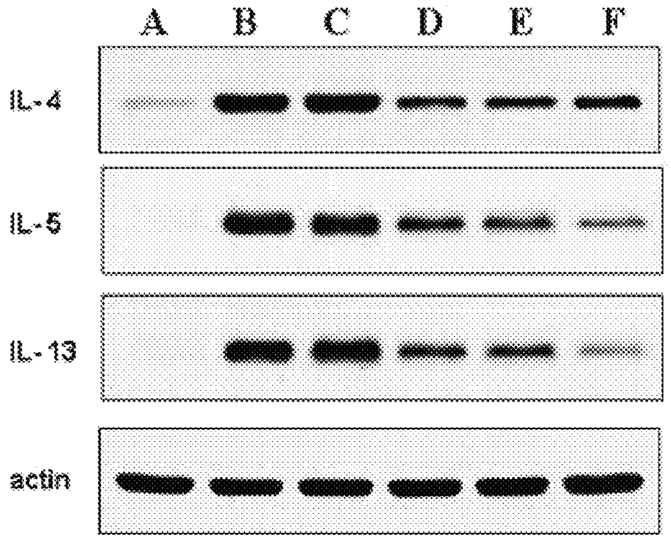
Figure 18:
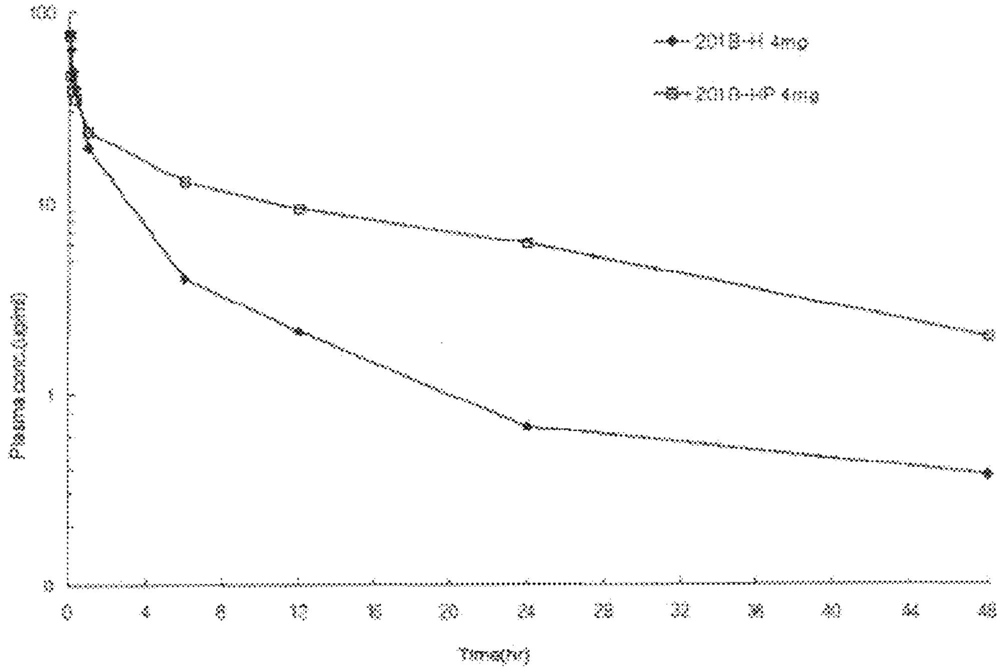
Figure 19:
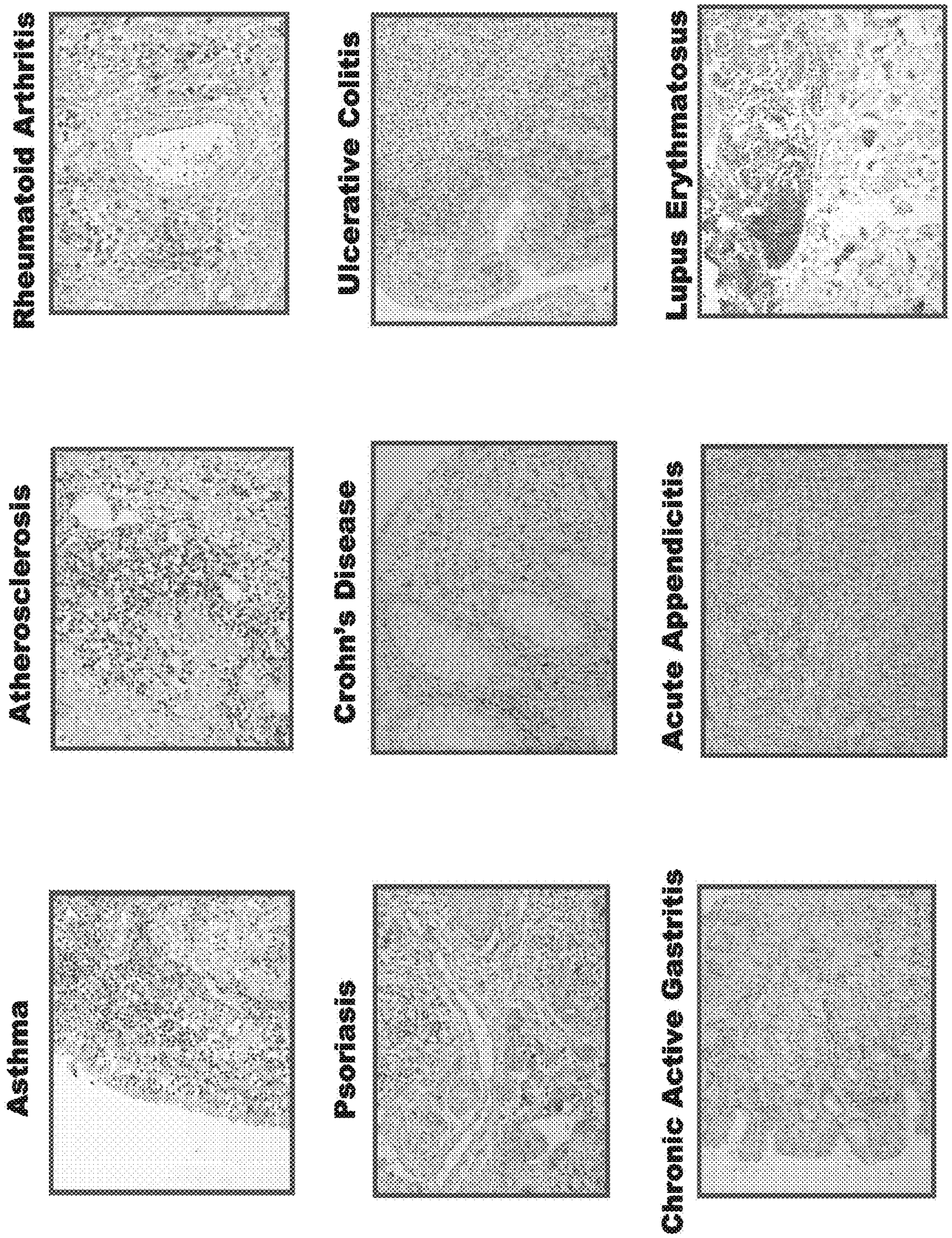
Figure 20:
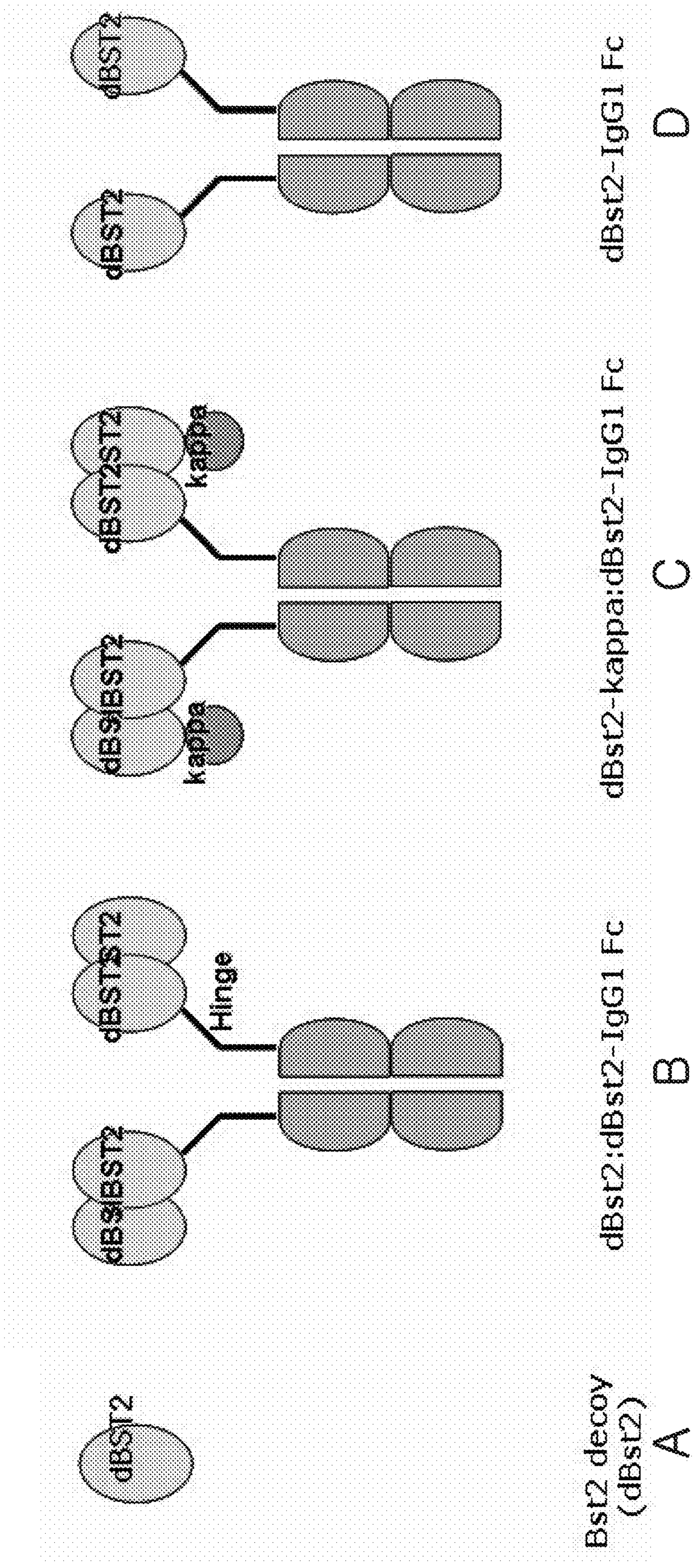
Figure 22:
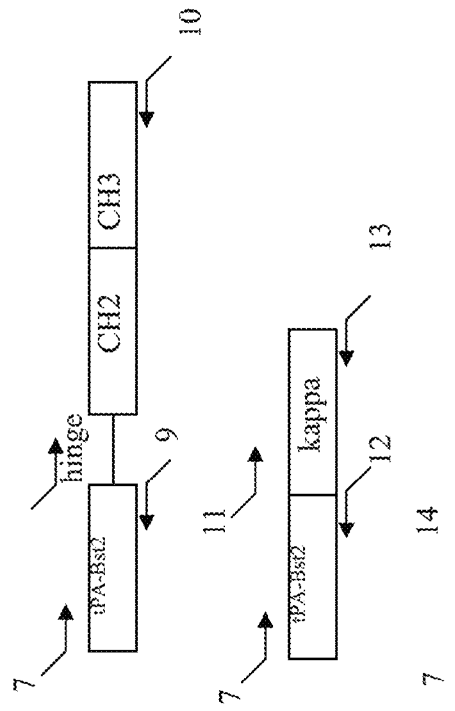
Figure 25:
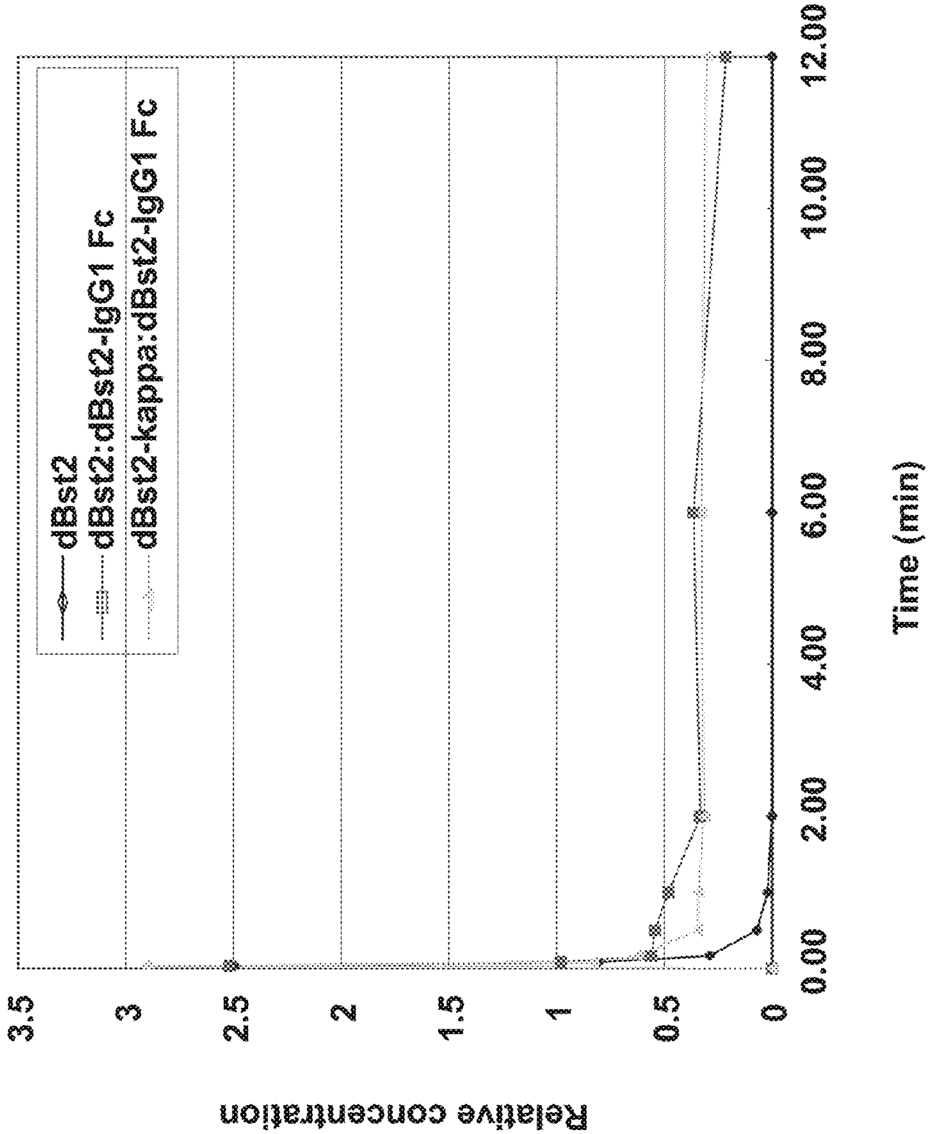
Figure 26:
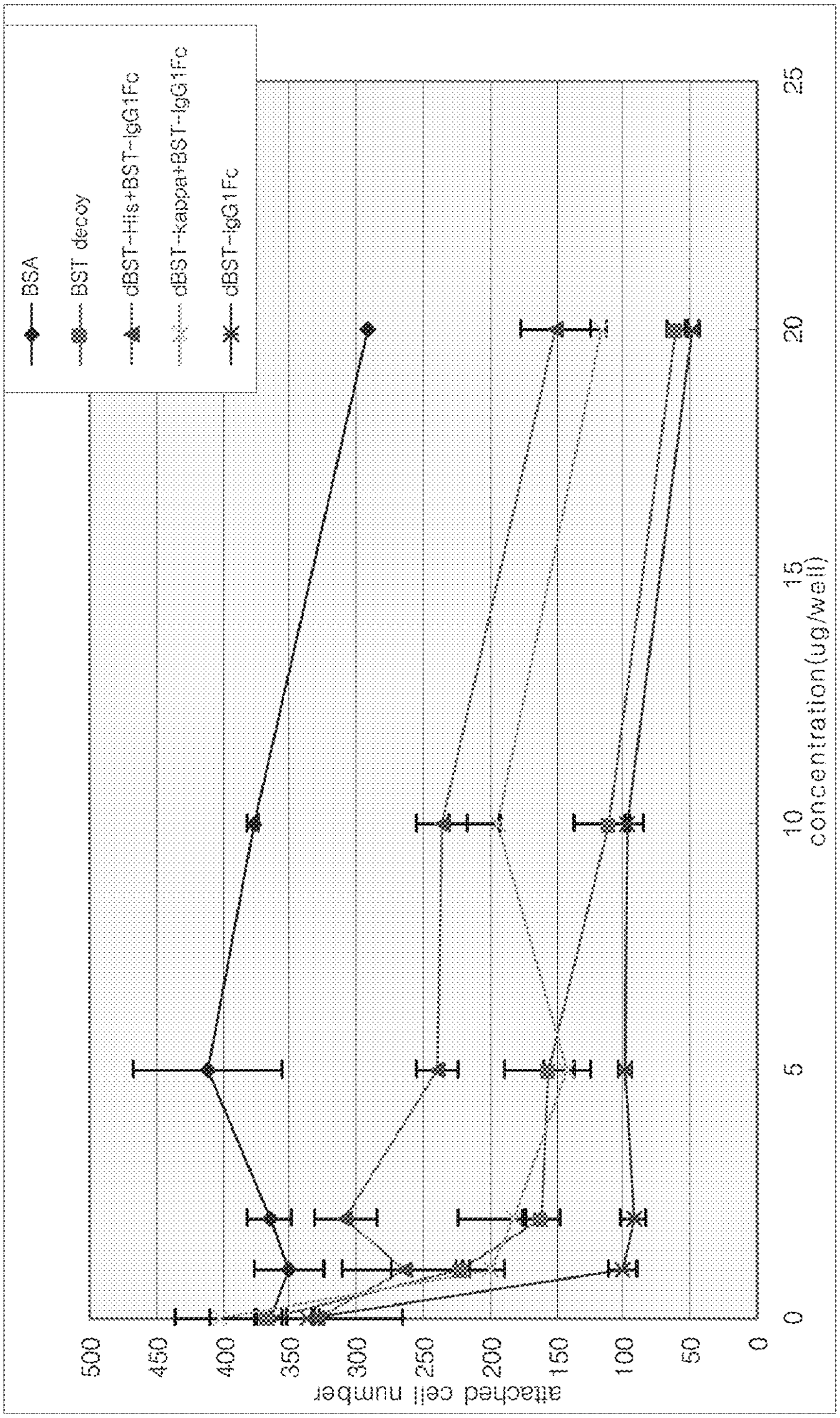
Figure 34:
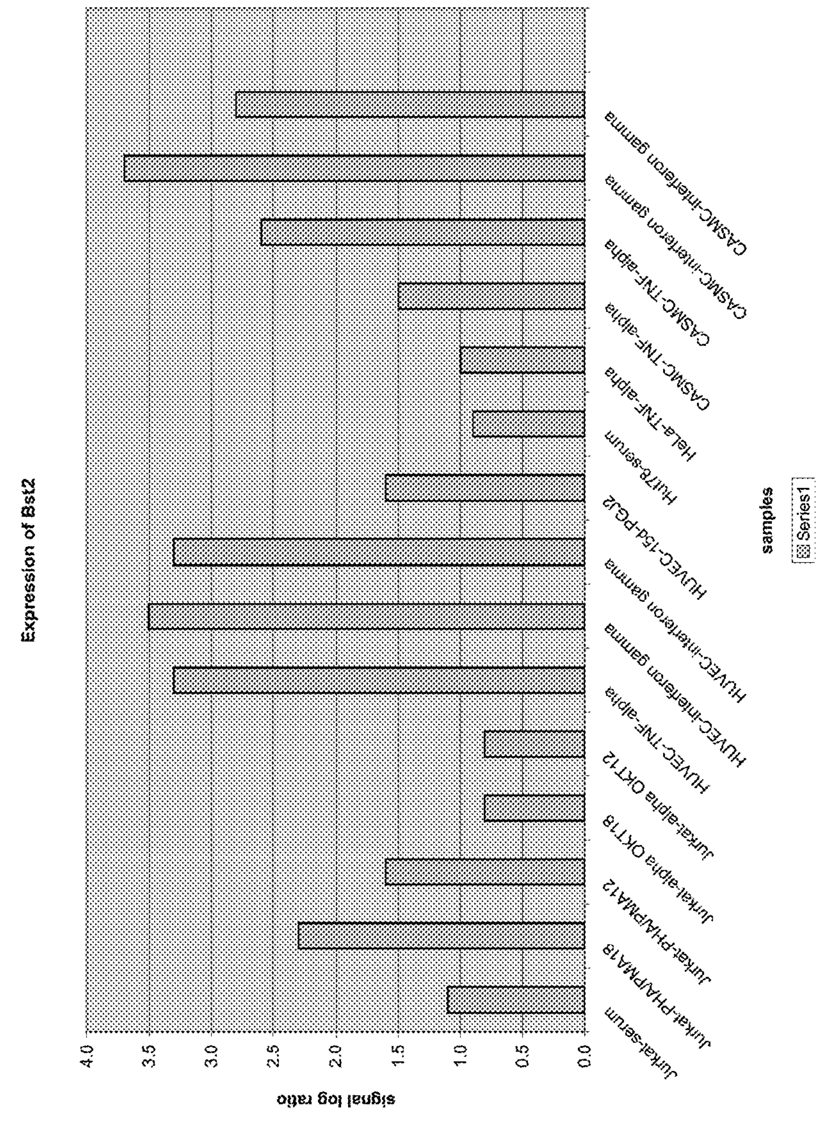
Figure 35:
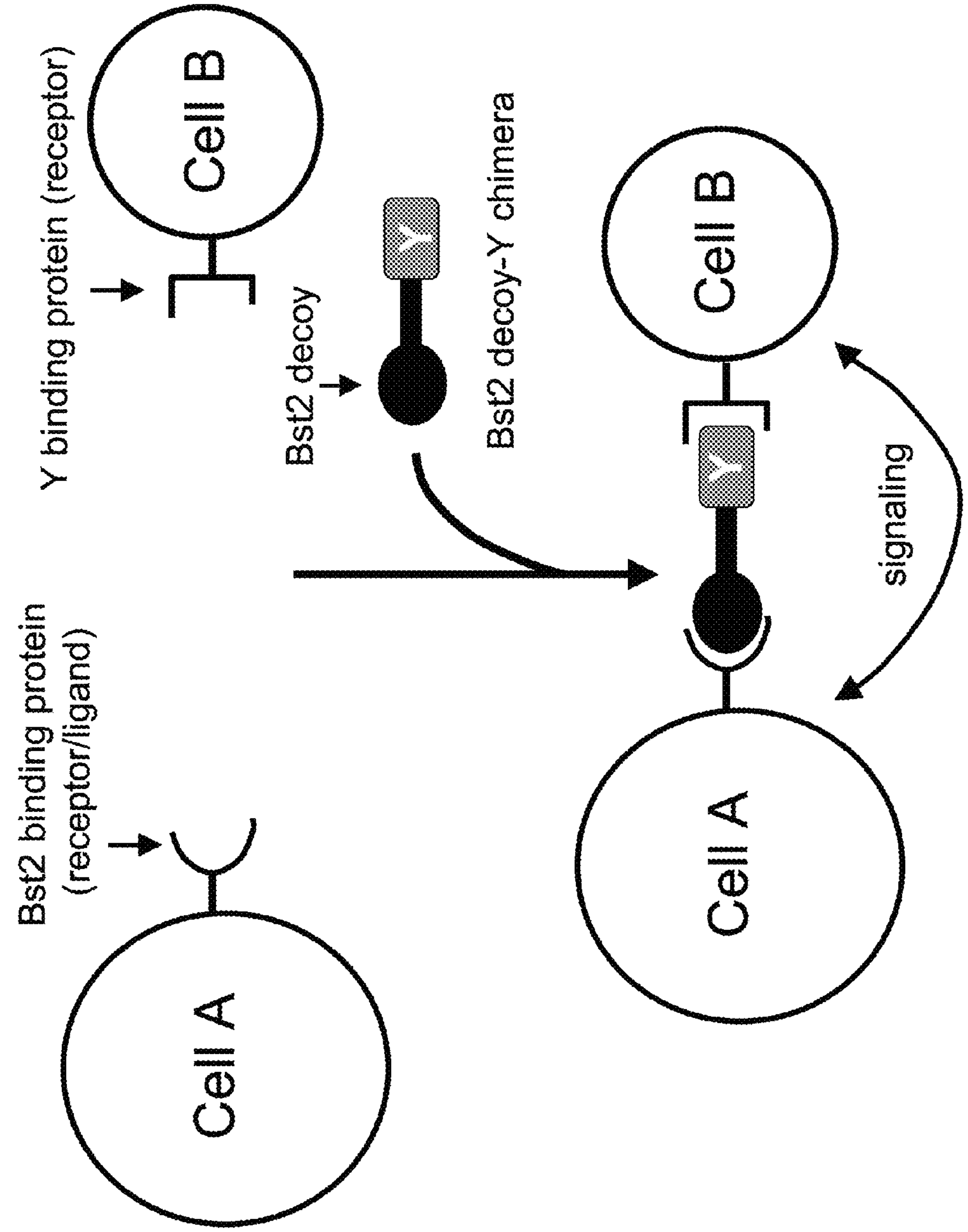
Figure 36:
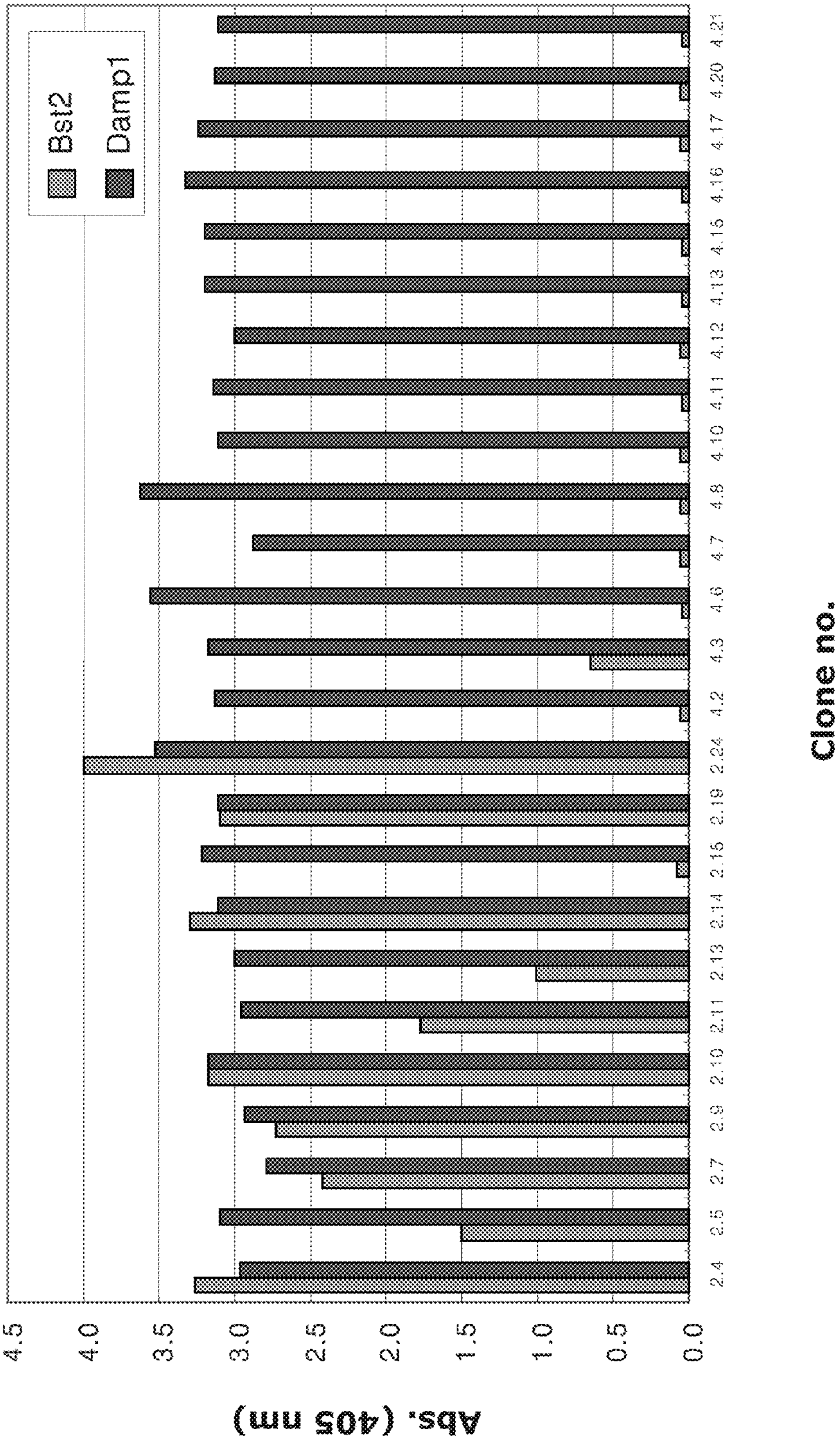
Figure 38:
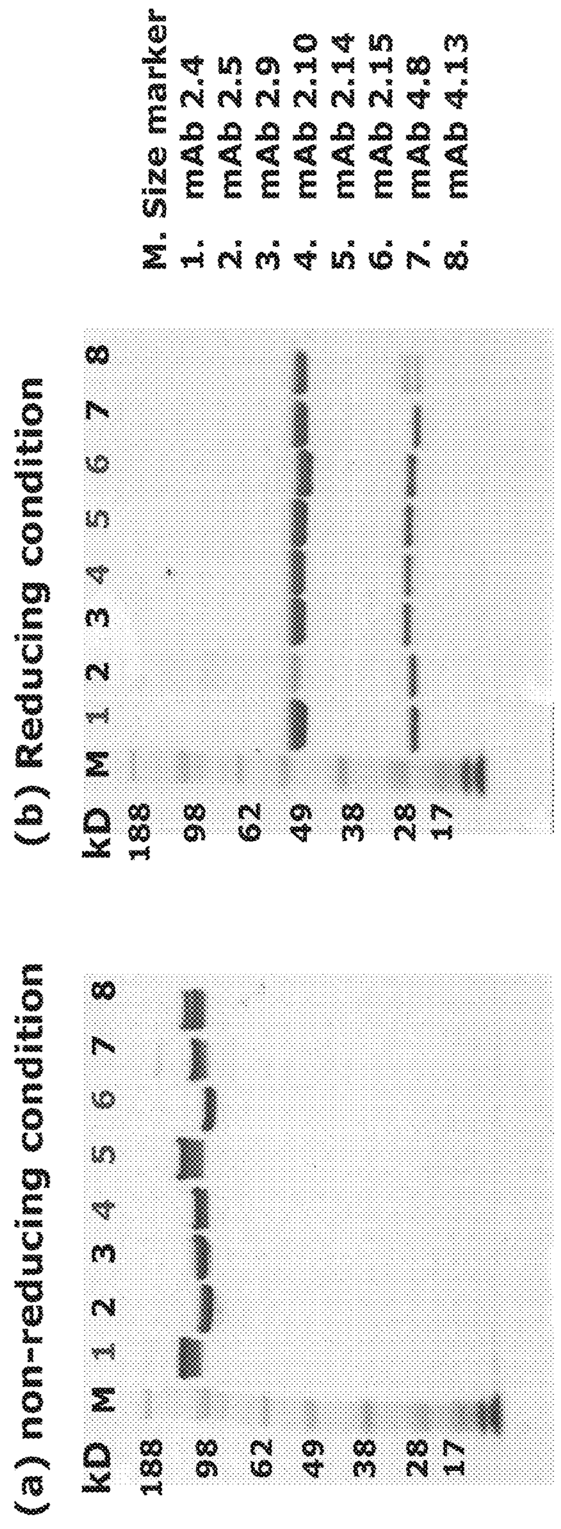

FIGS. 2A-2B show the locations of PCR primers used in a process for cloning a human Bst2 decoy and a mouse Damp1 decoy into an expression vector;

FIGS. 3A-3B show the results of electrophoresis analysis of a human Bst2 decoy and a mouse Damp1 decoy;

FIG. 4 shows the expression pattern of Bst2 gene during homotypic aggregation of U937 cells;

FIG. 5 shows the promoting effect of Bst2 overexpression on homotypic aggregation of U937 cells;

FIGS. 6A-6E show the effect of a Bst2 decoy on homotypic aggregation of U937 cells;

FIGS. 7A-7G show the effect of a Bst2 decoy on intercellular adhesion between human vascular endothelial (HUVEC) cells and U937 cells;

FIGS. 8A-8F show the dose-dependent effect of a Bst2 decoy on intercellular adhesion between HUVECs and U937 cells;

FIGS. 9A-9G show the effect of Bst2 siRNA on intercellular adhesion between HUVECs and U937 cells;

FIGS. 10A-10B show the effect of Bst2 overexpression on aggregation of Jurkat cells and interleukin-2 (IL-2) production in Jurkat cells;

FIGS. 11A-11I show the effect of a Bst2 decoy and Bst2 siRNA on aggregation of Jurkat cells;

FIGS. 12A-12B are graphs showing the effect of a Bst2 decoy on aggregation of Jurkat cells and IL-2 production;

FIG. 13 shows the change in the number of sedimented immune cells upon treatment of a Bst2 decoy;

FIG. 14 shows the decreased levels of cytokines upon treatment of a Bst2 decoy;

FIGS. 15A-15D show the functional similarity between human Bst2 and mouse Damp1;

FIGS. 16A-16D show the inhibitory effect of a Bst2 decoy and mouse Damp1 decoy on ovalbumin-induced asthma in mice;

FIG. 17 shows PEG moieties used in preparation of PEG-conjugated forms of a Bst2 decoy;

FIG. 18 shows the improved metabolic degradation of PEG-conjugated Bst2 decoy;

FIG. 19 shows the expression and distribution of Bst2 in inflammation-associated diseases;

FIGS. 20A-20D show schematics of Bst2 decoy fused to Fc region. A, the Bst2 decoy itself; B, the Bst2 decoy fused to the hinge-CH2-CH3 portion of an IgG heavy chain Fc; C, Bst2 fusion protein that is stabilized through the naturally-occurring IgG kappa chain-heavy chain disulfide bonding; D, Bst2 decoy-IgG Fc is expressed without other Bst2 dimerization counterparts;

FIGS. 21A-21D show representative vector maps of Bst2 decoy-IgG Fc fusion proteins of FIG. 20;

FIG. 22 shows PCR-cloning and fusion strategy;

FIGS. 23A-23B show PAGE of purified Bst2 decoy and other Fc fusions. A, representative PAGE gel (4~12% gradient gel, Invitrogen) stained with Coomassie depicting various Bst2 fusion proteins following affinity purification. B. Page after size-exclusion chromatography;

FIGS. 24A-24B show direct binding of Bst2 decoy to immune cells on A, Bst2 coated plate; and B, BSA coated plate;

FIG. 25 shows plasma half-life of Bst2 decoy or Fc fusions;

FIG. 26 shows inhibitory effect of Bst2 decoy-Fc fusions in the binding between Bst2 decoy and cells;

FIGS. 27A-27D show the effect of Bst2 decoy-Fc fusions on a mouse model of asthma;

FIGS. 28A-28B show creation of human-mouse chimeric Bst2 mice. A. The genomic locus for murine (top, black) and human (bottom, gray). Exons are shown as rectangular boxes. The end of the trans-membrane domain is indicated with an arrow and the location of the initiating methionine (ATG) is indicated with an asterisk. The approximate physical distance spanning coding exons are indicated below the genomic locus. The diagram is not drawn to scale. B. Strategy for making chimeric human-mouse BST2;

FIGS. 29A-29E show that endogenous Bst2 is required for heterotypic aggregation between endothelial cells (HUVEC) and monocytic cells (U937) after stimulation with IFNγ. A, Control; B, IFNγ stimulation of inflammation; C, IFNγ stimulation of inflammation+control siRNA; D, IFNγ stimulation of inflammation+Bst2 siRNA; E, Quantitative analysis of the Bst2 siRNA results from A-D;

FIG. 30 shows that Bst2 siRNA treatment or ICAM1 siRNA treatment does not affect ICAM1 expression or Bst2 expression in IFNγ-treated HUVEC, respectively. RT-PCR analyses were performed;

FIGS. 31A-31G show combination treatment of Bst2 siRNA and ICAM1 siRNA, and shows additive effects in heterotypic adhesion assay. A, Control; B, IFNγ stimulation of inflammation; C, IFNγ stimulation of inflammation+control siRNA; D, IFNγ stimulation of inflammation+Bst2 siRNA; E, IFNγ stimulation of inflammation+ICAM1 siRNA; F, IFNγ stimulation of inflammation+ICAM1 siRNA+Bst2 siRNA; G, Quantitative analysis of Bst2 siRNA and ICAM 1 siRNA results from A-F;

FIGS. 32A-32M show dose-dependent response of anti-ICAM1 or Bst2 decoy in heterotypic adhesion assay. A shows Control; B, C, D, E, and F show IFNγ stimulation of inflammation+increasing dosage of ICAM-1 Ab; G shows IFNγ stimulation of inflammation+control BSA; H shows IFNγ stimulation of inflammation+control IgG; I, J, K, and L show IFNγ stimulation of inflammation+increasing dosage of BST2 decoy; M shows quantitative analysis of the dose-dependent response of anti-ICAM1 and Bst2 decoy results from A-L;

FIG. 33A-33C show that combination treatment of Bst2 decoy and anti-ICAM results in additive effects in cell adhesion. Suboptimal doses of Bst2 decoy (100 ng/ml) and anti-ICAM1 (1 ug/ml) were used. Cell adhesion was completely inhibited to the control level when both Bst2 decoy and anti-ICAM1 were used;

FIG. 34 shows relative expression level of Bst2 mRNA after cytokine treatment. Bst2 mRNA level (in log ratio) is shown after Jurkat, HUVEC (human vascular endothelial cells), HeLa or CASMC (coronary artery smooth muscle cells) were treated with serum, PMA (12 or 18 hours), OKT (12 or 18 hours), TNF-alpha, interferon gamma or PGD2, as indicated. Bst2 mRNA level was measured by real-time PCR;

FIG. 35 shows a schematic for a method to force interaction and signaling between cell A, which expresses the ligand for Bst2, and cell B, which expresses the receptor for protein or compound Y. The bivalent fusion protein composed of Bst2 decoy and protein or compound Y may function as an adaptor to force interaction between cells A and B. In doing so, signaling between cell A and cell B may be improved;

FIG. 36 shows binding of phage clones to Bst2/Damp1 decoy;

FIGS. 37A-37B show anti-Bst2/Damp1 monoclonal antibody (A) Heavy chain variable regions; and (B) kappa chain variable regions; and FIGS. 38A-38B show anti-Bst2 monoclonal antibodies transiently expressed and purified on a PAGE gel. (A) under non-reducing conditions; (B) under reducing conditions.

Figure 39:
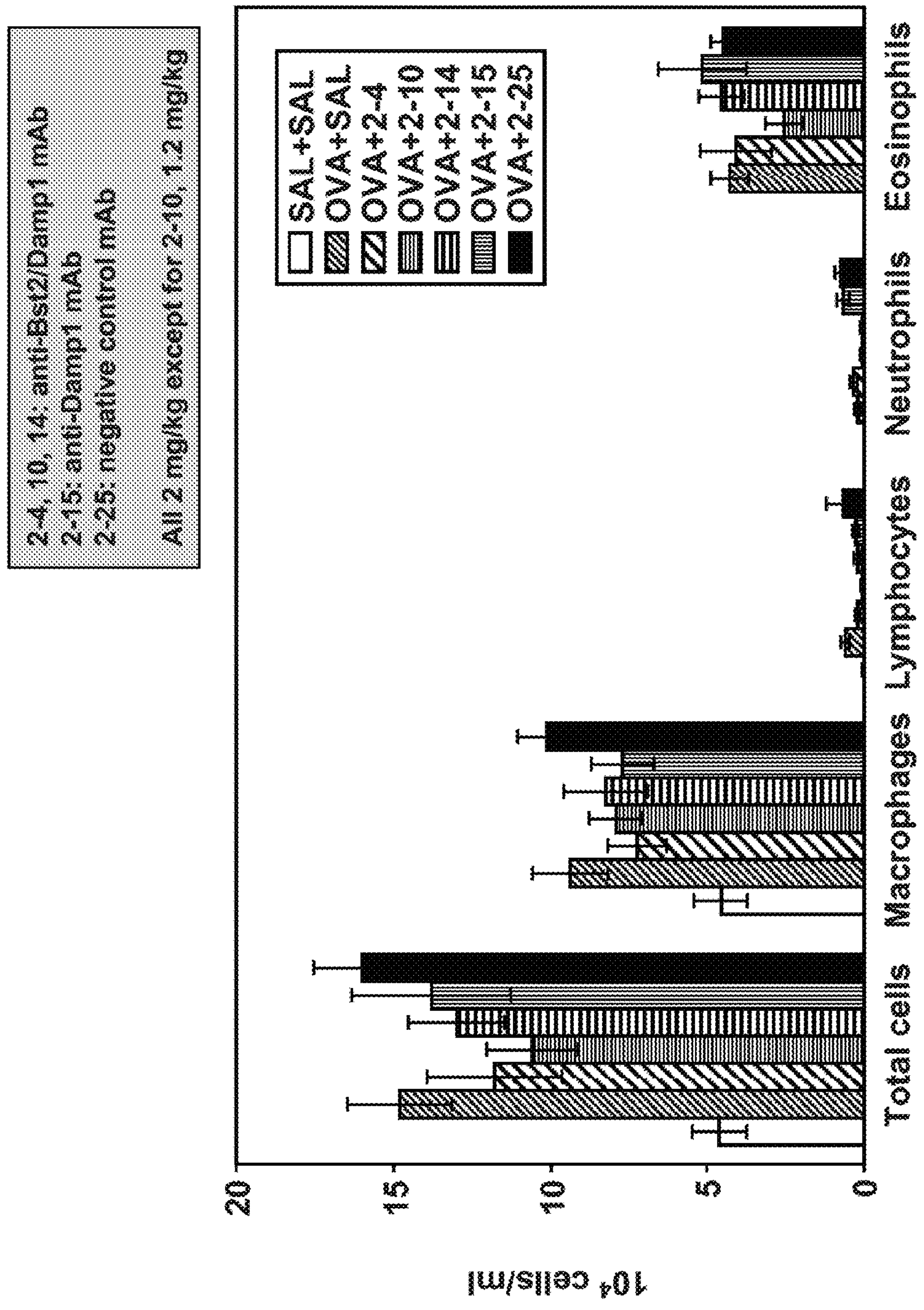

FIG. 39 shows the change in the number of sedimented immune cells upon treatment of anti-Bst2/Damp1 monoclonal antibody in ovalbumin-induced asthma in mice.

Figure 40:
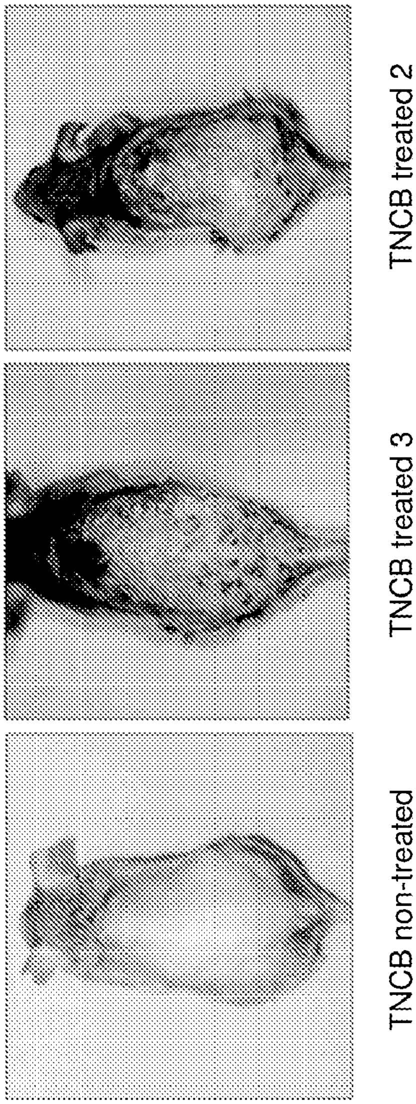

FIGS. 40A-40C show contact hypersensitivity induced by TNCB treatment.

Figure 41:
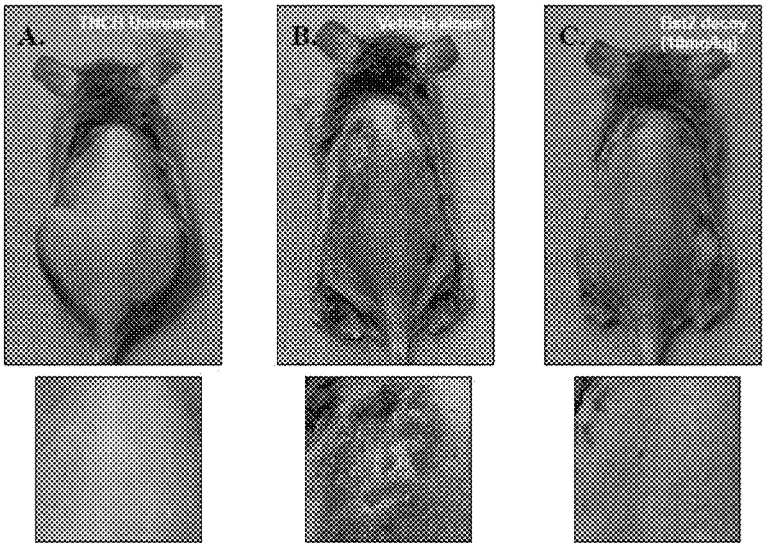
Figure 42:
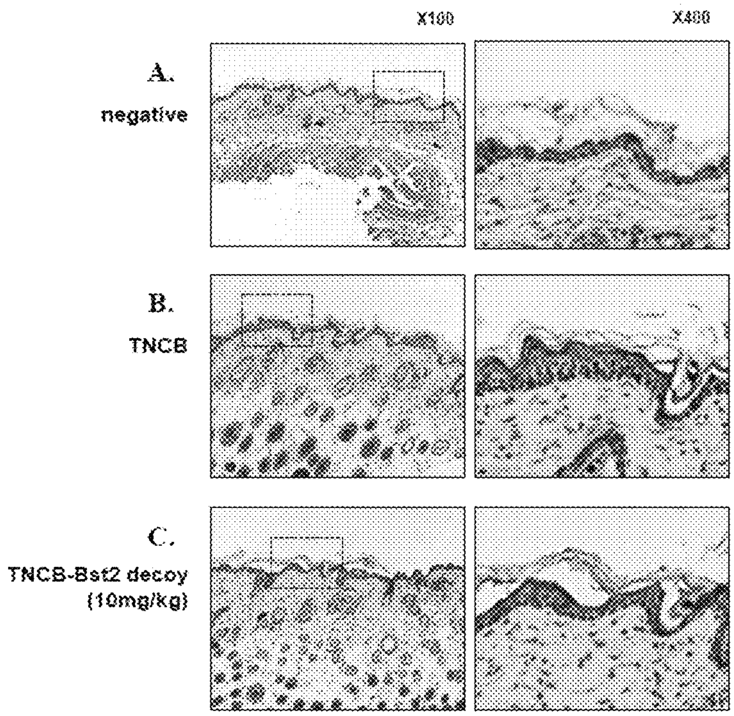

FIGS. 41A-41C show effects of a Bst2 decoy on TNCB-induced contact hypersensitivity in mice. (A) negative control, (B) vehicle alone and (C) Bst2 decoy treated mice FIGS. 42A-42C show H&E staining sections of dorsal skin in dermatitis models induced by repeated application of TNCB. (A) negative control, (B) positive control and (C) Bst2 decoy treated mice.

Figure 43:
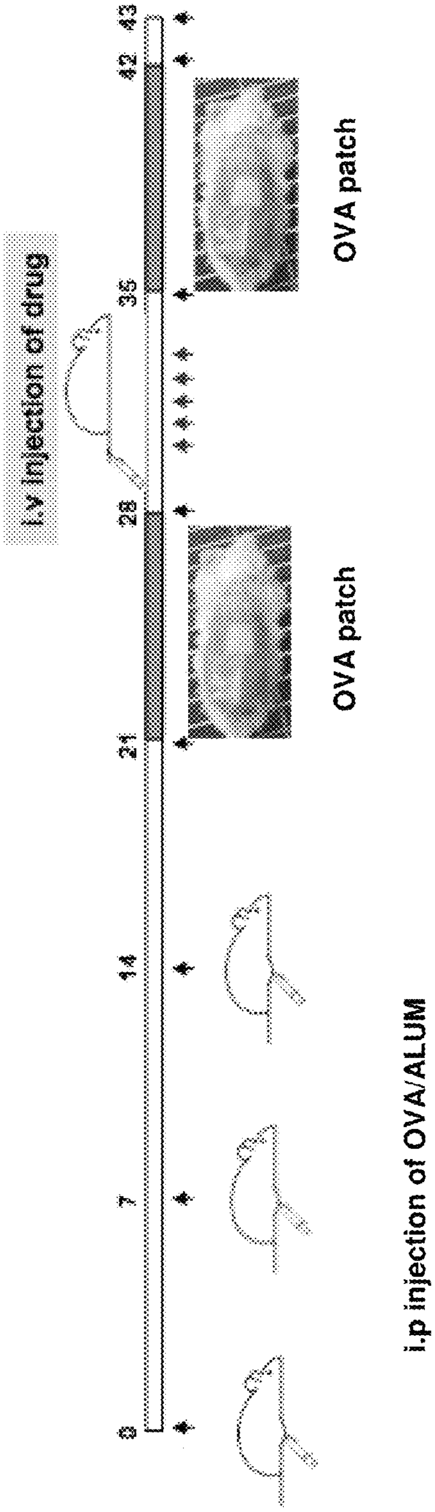

FIG. 43 shows a schematic of experimental model of OVA-induced dermatitis.

Figure 44:
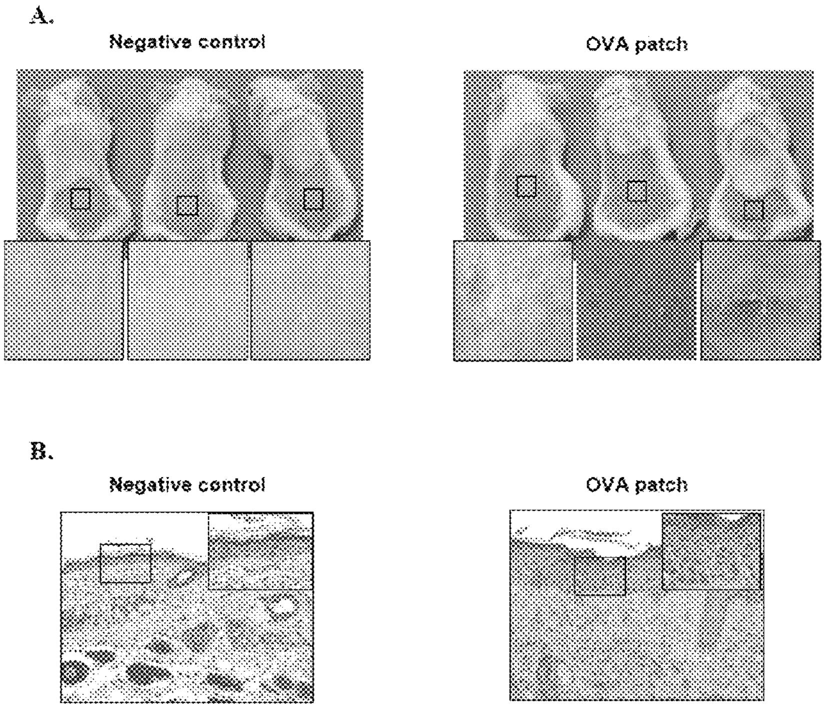

FIGS. 44A-44B shows induction of allergic dermatitis following OVA challenge A. Non-sensitized negative control group (left) show no lesion formation, while the positive control group (right) show lesion formation upon challenge with OVA; B. Representative H&E stained sections of dorsal skin. Negative control group (left), positive control group (right). Magnification 100×, inset in upper right corner 400×.

Figure 45:
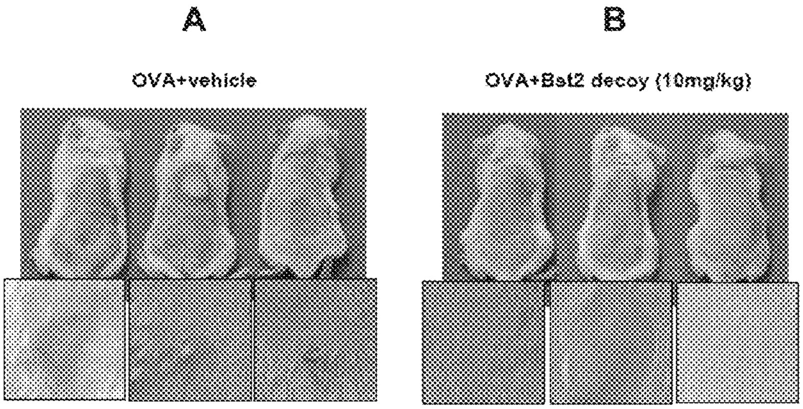

FIGS. 45A-45B show effects of Bst2 decoy on OVA-induced atopic dermatitis in mice.

Figure 46:
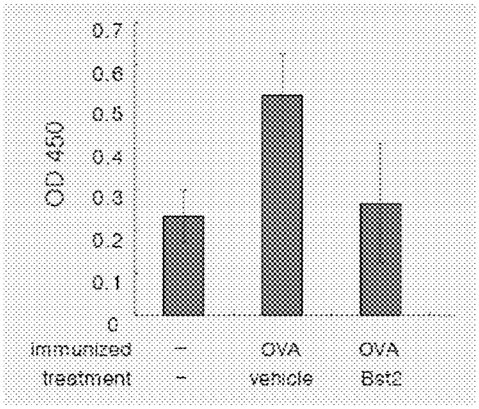

FIG. 46 shows serum levels of OVA-specific IgE as measured by ELISA.

FIGS. 47A-47B show survival curve demonstrating survival of vehicle or Bst2 decoy treated rats after CLP. A. Vehicle or Bst2 decoy was treated immediately (A) or 6 hours after the CLP procedure (B) by intravenous injection.

Figure 48:
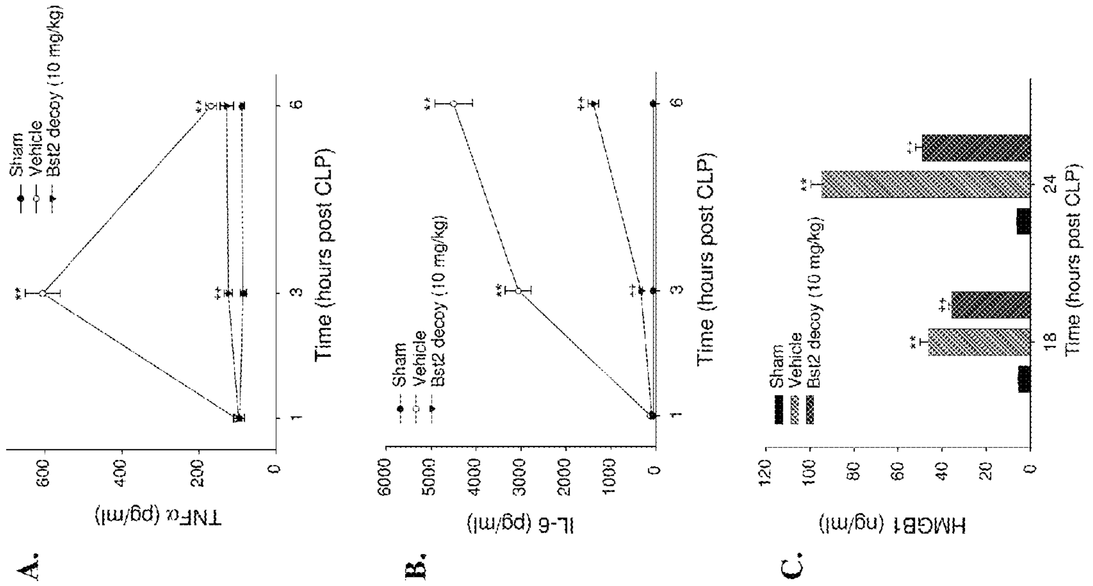
Figure 49:
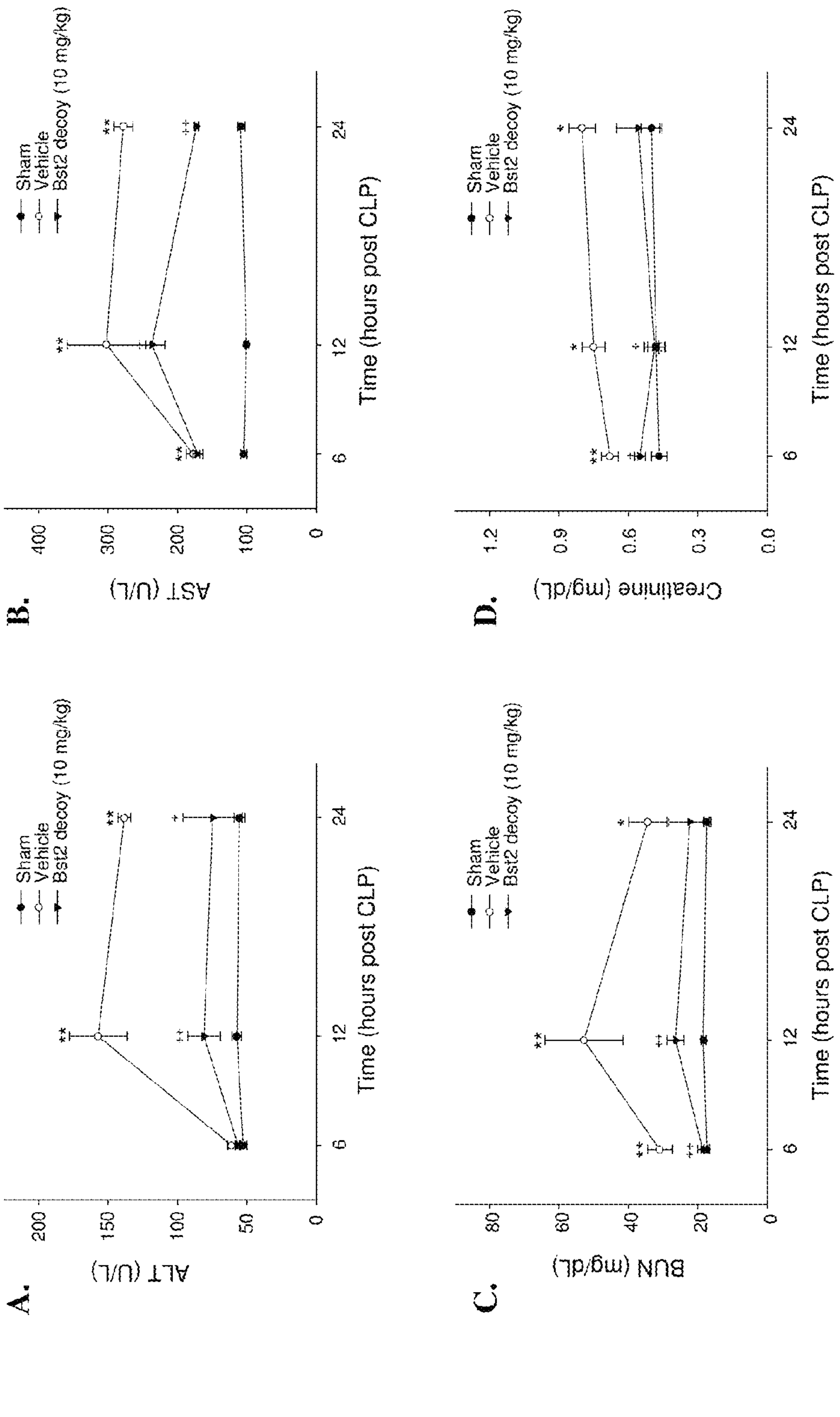

FIGS. 48A-48C show the effect of Bst2 decoy on cytokine production after CLP. A. TNF-α level, B. IL-6 level, and C. HMGB1 level. The results were presented as mean±S.E.M of 8-10 animals per group. ** denotes significant differences from the sham group (P<0.01); ++ denotes significant differences from the vehicle-treated CLP group (P<0.01).

FIG. 49A-49D show the effect of Bst2 decoy on tissue and organ damage. Serum levels of ALT (A), AST (B), BUN(C), and cratinine (D) were measured at 6, 12, and 24 hours post-CLP. The results were presented as mean±S.E.M of 8-10 animals per group. ** denotes significant differences from the sham group (P<0.01); +, ++ denotes significant differences from the vehicle-treated CLP group (P<0.05 and P<0.01).

Figure 50:
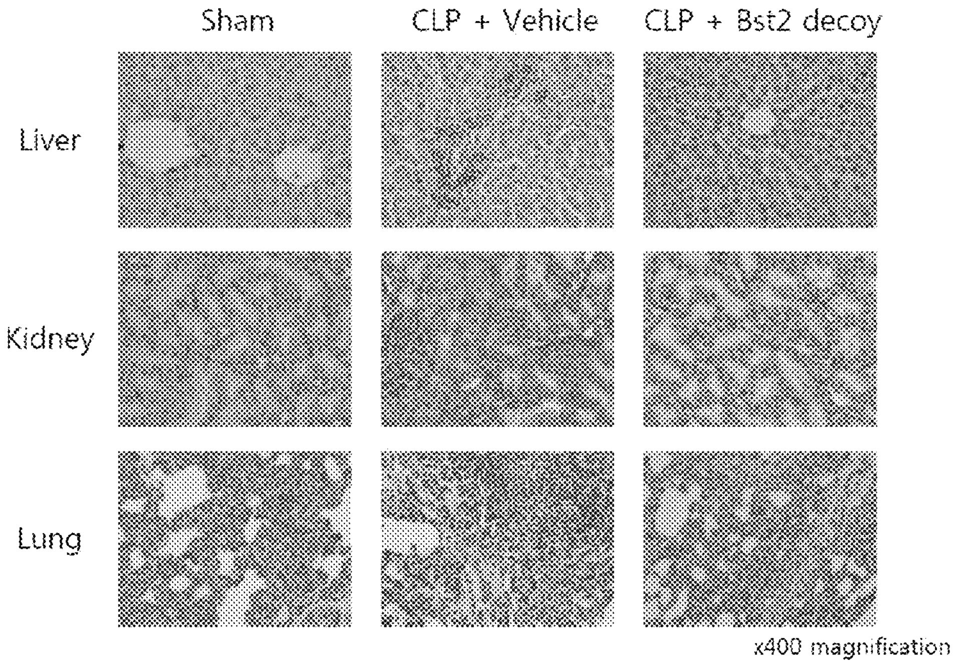

FIG. 50 shows histological analysis of liver, kidney, and lung samples after CLP.

DETAILED DESCRIPTION OF THE PREFERRED EMBODIMENTS

In the present application, "a" and "an" are used to refer to both single and a plurality of objects.

As used herein, "antagonist" or "blocker" refers to a substance that inhibits, blocks or reduces the activity of a protein that induces inflammation. The action mechanism of the antagonist is not specifically limited. Examples of the antagonist include organic or inorganic compounds; polymeric compounds, such as proteins, carbohydrates and lipids; and composites of multiple compounds. For example, a "Bst2 antagonist" or "Bst2 blocker" may include a substance that inhibits, blocks or reduces the activity of Bst2 protein in its activity in inducing inflammation.

As used herein, "Bst2 ligand" or "Bst2 L" refers to the molecule that specifically binds to Bst2.

As used herein, a "homologue" of a protein is one which is considered to possess similar activity or similar specific activity to the reference protein, regardless of its level of general sequence similarity to the reference protein.

The term "inflammatory diseases", as used herein, refers to all diseases that result from the body's defense responses or infectious responses against harmful influences, which results in states (physical, chemical and biological states) of having symptoms such as redness, swelling, tenderness, pain, fever and dysfunction.

The term "modification", as used herein, indicates a process in which a non-peptide polymer is linked to Bst2 protein, or a fragment thereof.

The term "non-peptide polymer", as used herein, refers to a biocompatible polymer in which two or more repeating units are linked to each other. Examples of the non-peptide polymer include polyethylene glycol, polypropylene glycol (PPG), co-poly(ethylene/propylene) glycol, polyoxyethylene (POE), polyurethane, polyphosphazene, polysaccharide, dextran, polyvinyl alcohol, polyvinyl pyrrolidone, polyvinyl ethyl ether, polyacryl amide, polyacrylate, polycyanoacrylate, lipid polymer, chitins, hyaluronic acid, and heparin. A preferred non-peptide polymer is polyethylene glycol.

The term "operably linked", as used herein, refers to a functional linkage between a nucleic acid expression control sequence and a second nucleic acid sequence coding for a target protein in such a manner as to allow general function to occur. For example, a promoter may be operably linked to a nucleic acid sequence coding for a protein and affect the expression of the coding sequence. The operable linkage to a vector may be prepared using a genetic recombinant technique well known in the art, and site-specific DNA cleavage and ligation may be achieved using enzymes generally known in the art.

The term "prevention", as used herein, means all activities that inhibit inflammatory diseases or delay incidence of inflammatory diseases through administration of the composition. The term "treatment" "treating" and "therapy", as used herein, refers to all activities (curative therapy, prophylactic therapy and preventative therapy) that alleviate and beneficially affect humans suffering from inflammatory diseases.

The term "siRNA", as used herein, refers to a short double-stranded RNA molecule that is able to induce RNA interference (RNAi) through cleavage of the target mRNA. The term "specific" or "specific to", as used herein, means an ability to suppress only a target gene while not affecting other genes in cells. In the present invention, siRNA molecules specific to Bst2 are provided.

As used herein, "similar" activity to a reference activity is considered to be greater than about 80% as measured through objectively defined parameters of the indicated activity.

As used herein, "small molecular weight compound or modulator" or "chemical compound" refers to a chemical compound that is distinguished from biological molecules such as carbohydrates, polypeptides, nucleic acids, or lipids. The small molecular compound or modulator may include without limitation antagonists, agonists, peptide mimetics, inhibitors, ligands, and binding factors for Bst2/Bst2 L binding.

As used herein, "variant" refers to a protein or a fragment thereof, which has a sequence different from a native amino acid sequence of a protein, by a deletion, an insertion, a non-conservative or conservative substitution or a combination thereof. For example, amino acid exchanges in proteins and peptides which do not generally alter the activity of the proteins or peptides are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly, in both directions.

The term "vector", as used herein, which describes a vector capable of expressing a protein of interest in a suitable host cell, refers to a genetic construct that comprises essential regulatory elements to which a gene insert is operably linked in such a manner as to be expressed in a host cell.

Bst2 Protein

Bst2 participates in intercellular adhesion during inflammation. In one aspect, the present invention provides antagonists of Bst2 (Bone Marrow Stromal Antigen-2) protein so as to prevent intercellular adhesion and activation of immune cells to the endothelial cells or with each other during inflammation.

The present inventors, through studies using (1) a homotypic aggregation model of human U937 monocytic cells to investigate the effect of Bst2 on aggregation of immune cells, (2) a heterotypic aggregation model between U937 cells and HUVECs to investigate the effect of Bst2 on intercellular adhesion between immune cells and endothelial cells, (3) a Jurkat T-cell model to investigate the effect of Bst2 on T lymphocyte activation, found that Bst2 protein participates in an inflammation process in which leukocytes migrate to the site of inflammation, recognize extracellular matrix components to interact with cells, and adhere to the cells. The present inventors further found that an antagonist of Bst2 protein effectively inhibits such intercellular adhesion and is thus able to effectively treat inflammatory diseases.

The Bst2 protein was initially identified in bone marrow stromal cells and is considered to be involved in the differentiation and proliferation of cells. A cDNA encoding Bst2 was cloned in 1995, and the BST-2 gene was found to be located on human chromosome 19p13.2 (Ishikawa et al., *Genomics* 26:527-534, 1995). The Bst2 gene consists of five exons and four introns. Bst2 is a 30-to 36-kD type II transmembrane protein consisting of 180 amino acids (Ohtomo et al., *Bio-*

*chem. Biophys. Res. Commun.* 258:583-591, 1999). Damp 1 gene, a mouse homologue of human Bst2 gene, has 45% DNA sequence identity to the human Bst2 gene, and as shown in FIG. 1, has less than 40% amino acid sequence similarity to human Bst2. The Bst2 protein is predominantly expressed in the liver, lung, heart and placenta, and in lower levels in the pancreas, kidneys, skeletal muscle and brain. BST-2 surface expression on fibroblast cells accelerates the stromal cell-dependent growth of murine bone marrow-derived pre-B cells. This result suggests that Bst2 regulates pre-B-cell growth or plays a critical role in B cell activation in rheumatoid arthritis. Bst2 is also overexpressed in some types of cancer, including oral cancer, breast cancer, adenoma and cervical cancer. It is to be noted that in referring to FIG. 1, the edges of the transmembrane domain are not limited to the sequence as shown. The transmembrane regions may be plus or minus 5 amino acids in either the N-or C-termini of the region.

With respect to Bst2 protein, the isolation and expression of a gene encoding Bst2 protein (EP1033401), and the use of the Bst2 protein in cancer diagnosis (WO01/57207 and WO01/51513) have been reported. The Bst2 protein is divided into three domains: cytoplasmic, transmembrane and extracellular domains, and an intracellular domain contains cytoplasmic and transmembrane domains.

Inflammatory Diseases

The present inventive composition may be used for preventing or treating all types of inflammatory diseases that involve Bst2 overexpression. In fact, Bst2 was overexpressed in various inflammatory diseases including asthma, atherosclerosis, rheumatoid arthritis, psoriasis, Crohn's disease, ulcerative colitis, chronic active gastritis, acute appendicitis, and Lupus erythmatosus (FIG. 19). Thus, diseases which may be prevented or treated by the present composition include without limitation, atherosclerosis, rheumatoid arthritis, asthma, sepsis, ulcerative colitis, multiple sclerosis, acute myocardial infarction, heart attack, psoriasis, contact dermatitis, osteoarthritis, rhinitis, Crohn's disease, type II diabetes, diabetic neuropathy, chronic obstructive pulmonary disease, cachexia, acute pancreatitis, autoimmune vasculitis, autoimmune and viral hepatitis, delayed-type hypersensitivity, congestive, coronary restenosis, glomerulonephritis, graft versus host disease, uveitis, inflammatory eye disease that may be associated with corneal transplant, brain injury as a result of trauma, epilepsy, hemorrhage or stroke. Bst2 blockers may be also useful for treatment of sickle cell disease. Recurrent inflammation and vasculopathy occur in sickle cell disease. Adhesion of leukocytes to other blood cells and endothelium has been shown to contribute to vaso-occlusion in sickle cell disease (Okpala I. Curr Opin Hematol. 2006, January; 13(1): 40-4). In addition, the concept that activation of the proinflammatory pathway can be a mechanism for obesity-associated insulin resistance has emerged in recent years (Roytblat et al., Obes Res. 2000, 8(9):673-5; Straczkowski et al., Science. 1996, 271(5249):665-8; Hirosumi et al., Nature. 2002, 420(6913):333-6). Bst2 blockers may be also beneficial for insulin-resistance, type II diabetes and obesity.

Other inflammation associated diseases include age-related macular degeneration (AMD), Eczema, dermatitis, learning/cognitive disability, neurodegenerative diseases, Parkinson's disease, Alzheimer disease, ulcerative colitis, radiation-induced injury, burn or electricity-induced injury, poisoning that causes tissue death and immune cell infiltration, drug induced injuries, inhalation-induced injuries, radiation, aspiration-induced injury of the lung, inflammation resulting from chemotherapy or radiation therapy, autoimmune diseases including Lupus, Schogren disease, demyelinating diseases including multiple sclerosis, inflammatory myopathy including, polymyositis, scleroderma, polyarteritis nodosa, sarcoidosis, localized and generalized myositis ossificans, amyloid-associated diseases including Alzheimer disease, herniated disc, spinal cord and nerve damage, Reye syndrome, bacterial and viral encephalitis and meningitis, Prion-related disease, Guillain-Barre syndrome, rabies, poliomyelitis, cerebral hemorrhage, intracranial hemorrhage-related damage, chronic fatigue syndrome, thrombophlebitis, gout, granulomatosis, nephritis including glomerulonephritis and interstitial nephritis, insect-sting allergy, anaphylaxis, asplastic anaemia, bone marrow failure, multiple organ failure, thyroiditis, insulitis, cirrhosis (chronic and acute hepatitis), pulmonary embolism, toxin and drug-induced liver disease, pancreatitis, ischemic intestinal diseases, acute respiratory distress syndrome, and pericarditis.

Atopic Dermatitis

Atopic dermatitis is a type of eczema and is an inflammatory, chronically relapsing, non-contagious and pruritic skin disease.

The skin of a patient with atopic dermatitis reacts abnormally and easily to irritants, food, and environmental allergens and becomes red, flaky and very itchy. It also becomes vulnerable to surface infections caused by bacteria. The skin on the flexural surfaces of the joints (for example inner sides of elbows and knees) are the most commonly affected regions in people.

Atopic dermatitis often occurs together with other atopic diseases like hay fever, asthma and conjunctivitis. It is a familial and chronic disease and its symptoms can increase or disappear over time. Atopic dermatitis in older children and adults is often confused with psoriasis. Atopic dermatitis afflicts humans, particularly young children; it is also a well-characterized disease in domestic dogs.

Although there is no cure for atopic eczema, and its causes not well understood, it can be conventionally treated in the short term through a combination of prevention (learning what triggers the allergic reactions) and drug therapy.

Sepsis

Sepsis is a spectrum of clinical conditions caused by the immune response of a host to infection or trauma and characterized by systemic inflammation (called a systemic inflammatory response syndrome or SIRS) and coagulation. It ranges from a systemic inflammatory response to organ dysfunction, to multiple organ failure leading to death.

Initial sepsis is characterized by evidence of acute inflammation present throughout the entire body, and is, therefore, frequently associated with fever and elevated white blood cell count (leukocytosis) or low white blood cell count and lower-than-average temperature. It is likely that the host's immune response to the infection causes most of the symptoms of sepsis, resulting in hemodynamic consequences and damage to organs. Outward physical symptoms of this response frequently include a high heart rate (above 90 beats per minute), high respiratory rate (above 20 breaths per minute), elevated or lowered WBC count (above 12,000/$mm^3$ or under 4,000/$mm^3$) and elevated or lowered body temperature (under 36° C. or over 38° C.). Visible symptoms resulting from these conditions are fever, chills, severe shaking, tachycardia, confusion, disorientation and agitation, rash on the skin and pain in the joints.

This systemic inflammatory response causes widespread activation of acute-phase proteins, affecting the complement system and the coagulation pathways, which then cause damage to the vasculature as well as to the organs. Various neuroendocrine counter-regulatory systems are then activated as well, often compounding the problem. Even with immediate and aggressive treatment, this may progress to multiple organ dysfunction syndrome and eventually death.

Severe sepsis is defined as sepsis with organ dysfunction, hypoperfusion, or hypotension. Sepsis can turn into severe sepsis within a few hours.

Septic shock is defined as sepsis with refractory arterial hypotension or hypoperfusion abnormalities in spite of adequate fluid resuscitation. Signs of systemic hypoperfusion may be either end-organ dysfunction or serum lactate greater than 4 mmol/dL. Other signs include oliguria and altered mental status. Patients are defined as having septic shock if they have sepsis plus hypotension after aggressive fluid resuscitation (typically upwards of 6 liters or 40 ml/kg of crystalloid).

Multiple organ dysfunction syndrome (MODS) is characterized by the presence of altered organ function in an acutely-ill patient such that homeostasis cannot be maintained without intervention. MODS leads to multi-organ failure. Organs most commonly affected by sepsis are the brain, heart, lungs, kidneys and liver.

Bst2 antagonist can be administered in one or more of the following periods: (i) prior to the onset of sepsis, (ii) during initial sepsis but before the onset of severe-sepsis, (iii) during severe sepsis but before the onset of septic shock, or (iv) after the onset of septic shock.

Bst2 or Damp1 Decoy

Any soluble form of Bst2 or Damp1 protein or a fragment or variant thereof can be used as a decoy that binds competitively to a molecule or a site to which an immune cell expressing Bst2 or Damp1 would bind to induce inflammation. The Bst2 or Damp1 fragment used as a decoy is not specifically limited so long as it has an inflammation-suppressing effect by inhibiting intercellular adhesion, but is preferably a Bst2 or Damp1 protein having a deletion of the whole or a portion of the intracellular domain. The Bst2 decoy may be a fragment of the full length Bst2 protein. In one aspect, the Bst2 decoy may be a fragment of the 44-180 amino acid region of the full length Bst2 protein of SEQ ID NO:73, or a fragment of the 44 to 159 amino acid region of the full length Bst2 protein. The Damp1 fragment may be a fragment of the full length Damp 1 protein. In one aspect, the Damp 1 fragment may be a fragment of the 49-172 amino acid region of the full length Damp1 protein of SEQ ID NO:74, or a fragment of the 49 to 152 amino acid region of the full length Bst2 protein.

In an exemplified embodiment, the Bst2 protein fragment may be a Bst2 protein fragment comprising the amino acid sequence of: FTIKANSEACRDGLRAVMECRNVTHLLQQELTEAQKGFQDVEAQAATCNHTVMALMASLDAEKAQGQKKVEELEGEITTLNHKLQDASAEVERLRRENQVLSVRIADKKYYPSSQD (SEQ ID NO:1). The Damp1 protein fragment may be a Damp1 protein fragment comprising the amino acid sequence of: FAVTANSVACRDGLRAQAECRNTTHLLQRQLTRTQDSLLQAETQANSCNLTVVTLQESLEKKVSQALEQQARIKELENEVTKLNQELENLRIQKETSSTVQVNS (SEQ ID NO:2). The Bst2 protein fragment and Damp1 protein fragment were found to effectively inhibit the intercellular adhesion induced by Bst2.

It is to be understood that in certain aspects of the invention, mouse Damp1 may be used in place of Bst2 and they may be used interchangeably. For instance, when Bst2 decoy is used, it is also contemplated that Damp1 decoy may be used, including any chimera of Damp1 decoy. It is also comtemplated that Damp 1 and its variants may be used for treatment or reduction of inflammation in a subject along with Bst2. Accordingly, it is understood that any specific usage of Bst2 indicated in this application applies to Damp1 as well and may be claimed in the same manner.

The scope of the present invention includes protein having a native amino acid sequence of the Bst2 protein or a fragment or variant thereof, and DNA and RNA capable of encoding such protein that has an inflammation-suppressing effect by inhibiting intercellular adhesion and signaling.

In addition, the protein or fragment thereof provided in the present invention, may be in the form of having native sugar chains, increased sugar chains compared to a native form or decreased sugar chains compared to the native form, or may be in a deglycosylated form. The increase, decrease or removal of sugar chains of the protein may be achieved by an ordinary method, such as a chemical method, an enzymatic method, or a genetic engineering method using a microorganism. Genetic engineering method includes deleting one or more carbohydrate moieties found in native sequence of Bst2, Bst2 decoy, Bst2 decoy Fc, and/or adding one or more glycosylation sites that are not present in the native proteins.

Bst2 Decoy/Bst2 Decoy-Fc Variants

Overly rapid clearance, particularly of small proteins, can limit therapeutic efficacy. Injected protein therapeutics may be processed by plasma proteases, bind to plasma proteins or receptors on the endothelial cells or blood cells, which may result in uptake of the protein. Proteins that escape from the vascular capture may then be cleared in the liver or the renal glomeruli. In the renal system, the protein will enter the urine and leave the body. The glomerular barrier discriminates proteins both on the basis of molecular size and molecular charge (Brenner et al., Am J. Physiol., 1978, 234:F455). Thus, increases in molecular size or negative charge can reduce renal clearance (Wilson et al., J. Gen. Physiol., 1970, 74:495).

General strategies to improve in vivo activity and duration of action of the Bst2 decoy include PEGylation, chemical modifications aiming to decrease clearance, protein cross-linking to albumin, multimerization, direct fusion to albumin using recombinant DNA technology, fusion to Fc and so forth. In addition, glycoengineering is also applicable as a strategy for increasing the in vivo activity and prolonging the duration of action of the Bst2 decoy or Bst2 decoy-Fc. Extra N-linked oligosaccharides are attached to consensus sequences (Asn-X/Ser/Thr, where X is any amino acid except proline) (Imperiali B and Shannon K L. Biochemistry, 1991, 30: 4374). N-linked carbohydrates have been added to proteins such as Epo, Mp1 ligand or even leptin which normally lacks carbohydrates entirely. Glycoengineered proteins showed substantially increased in vivo activity and duration of action (Elliott S. et al., Nat. Biotechnol. 2003, 21:414).

Bst2 decoy (Bst2 decoy-Fc) variants with higher affinity binding to Bst2 L can be generated. Dimerization domain of Bst2 may be involved in controlling ligand-binding affinity of Bst2. Dimerization of Bst2 is thought to play a role in Bst2 signal transduction. The receptors for interleukins 2, 3, 5, and 6 and granulocyte macrophage colony stimulating factor, contain two different subunits (Hatakeyama M, et al., Science. 1989, 244(4904):551-6; Kitamura T, et al., Cell. 1991, 66(6):1165-74). The ligand binding subunits of the granulocyte colony stimulating factor receptor, prolactin receptor and growth hormone receptor form homodimers (Larsen A, et al., J Exp Med. 1990, 172(6):1559-70, Kelly P A, et al., Recent Prog Horm Res. 1993, 48:123-64). Dimerization has been indicated to yield high-affinity receptors and to provide the first step in the signal transduction pathway (Cunningham B C, et al. Science. 1991, 254(5033):821-5; Nicola N A, Metcalf D, Cell. 1991, 67(1):1-4).

Because homodimerization of Bst2 is likely to play a role in Bst2 L (ligand)-induced signal transduction, it is contemplated that Bst2 decoy (Bst2decoy-Fc) variants with higher affinity binding may be made by mutating amino acid residues within the potential dimerization domain.

SMART analysis of Bst2 predicts a coiled coil domain in the amino acid regions of 96-153 (human Bst2) (or 102-149, rat Bst2) or in the corresponding region in the mouse Damp1. Coiled-coil domain of Bst2 may be involved in Bst2 dimerization.

Determination of the Dimerization Domain of Bst2

Cytokine-induced dimerization of Bst2 can be demonstrated in stable cells transfected with two differently-tagged Bst2 (such as HA-Bst2 and Bst2-Flag) or after transient transfection with expression vectors for tagged-Bst2. Dimerization of Bst2 is demonstrated by co-immunoprecipitation of the tagged Bst2 proteins. Dimerization of the wild-type Bst2 receptor may be shown. When dimerization of Bst2 is confirmed, information on critical residues for dimerization can be obtained after deletion analysis, alanine scanning mutation analysis, and/or site-directed mutagenesis. The mutations may be made in the entire extracellular domain or the coiled coil domain. While dimerization of the wild-type receptor may be shown, mutants containing a deletion or substitution in important residues for dimerization would not coimmunoprecipitate. Bst2 mutants containing a deletion or substitution in the dimerization domain may function as a dominant-negative mutant to block inflammatory responses and inhibit cell-cell adhesion after cytokine stimulation when transiently transfected into Bst2-containing cells. When stably expressed in Damp 1−/− cells (for example, Damp 1−/− mouse embryonic fibroblasts), these mutants may not be able to manifest inflammatory responses or cell-cell adhesion efficiently.

Many deletion variants, insertion variants or substitution variants are screened for use as high-affinity Bst2 decoy or Bst2 decoy-Fc. Deletion, insertion or substitution may be introduced to the target mutation sites in the entire extracellular domain, coiled coil domain or dimerization domain identified as described above. The location of the mutation sites may be, for example, in the regions of low homology in the human Bst2, rat Bst2 and mouse Damp 1. Deletion of the target amino acid residue, insertion of one or more amino acid residues adjacent to the target amino acid residue, or substitution of the target amino acid residue may be made. The target amino acid residues may be single or multiple amino acid residues. Amino acid sequence deletions or insertions may be made from 1-5 contiguous residues, because radical deletions/insertions may result in complete loss of the biological activity.

The target amino acid residues for deletion, insertion or substitution include the critical residues for Bst2 dimerization identified as described above. Other sites of interest include those in which the amino acid residues are similar or identical in human Bst2, rat Bst2 and mouse Damp1. For substitutional mutagenesis, random mutagenesis may be conducted.

Screening for Bst2 Decoy-or Bst2 Decoy-Fc Variants

1. The Bst2 decoy-or Bst2 decoy-Fc variants are screened using the cell-cell adhesion assay. Variants with higher affinity inhibit the cell-cell adhesion more efficiently than the parent Bst2 decoy or Bst2 decoy-Fc protein.

2. The variants of Bst2 decoy-Fc are screened using the solid-phase assay as described here. Plates are coated with anti-Fc antibody and incubated with the Bst2 decoy-Fc variants. The source cell line for Bst2 L (see Example 29-1, under Identification of an abundant in vitro cell source for Bst2 L) or U937 cells (see Example 20) is then radiolabeled with 3H-thymidine and added to the well. After isolation and validation of Bst2 L (see Examples 28-34), COST cells transfected with the expression vector for Bst2 L may be radiolabeled and also used for the assay. After fixation, the adherence of radiolabeled cells is measured.

3. The methods described herein enable a person of ordinary skill in the art to identify mutants with higher binding affinity without the need for protein purification. Mutagenic Bst2 PCR primers are designed for random mutagenesis of selected amino acid residues or any random amino acid in the extracellular domain, coiled-coil domain or dimerization domain. PCR products encoding mutations are subcloned into the digested Bst2 expression vector. COST cells are transiently transfected with mutant Bst2 cDNAs. In this method, Bst2 variants containing mutations in the extracellular domain, coiled coil domain or dimerization domain are expressed on the surface of the transfected cells for panning. Cells are added to panning plates coated with purified Bst2 L. Cells expressing Bst2 decoy with higher affinity for Bst2 L are then screened by indirect immunofluorescence or FACS analysis with FITC-labeled human Bst2 L-Fc, followed by secondary antibody staining. Plasmid DNA is recovered from the cells attached to the plate and used for the next cycle of enrichment. Bst2 decoy or Bst2 decoy-Fc is modified to contain the selected mutated sequences. The variant Bst2 decoy or Bst2 decoy-Fc containing the selected mutations is tested in the cell-cell adhesion assay for functional validation.

Production of Bst2, Bst2 Decoy, Bst2 Decoy Fc Proteins, Bst2 L, a Portion of These Proteins or Mutants of These Proteins The scope of the present invention includes methods of constructing the expression vectors for Bst2, Bst2 decoy, Bst2 decoy Fc proteins, Bst2 L, a portion of these proteins or mutants of these proteins for expression in host cells of mammalian, insect, fungal, plant or bacterial origin and methods of purifying these proteins. Bst2, Bst2 decoy, Bst2 decoy Fc or Bst2 L include those derived from Bst2 and Bst2 L homologues from mice, rats, rabbits, dogs, primates and other animals. For the construction of expression vectors for recombinant protein production, it would be necessary to chemically synthesize the corresponding genes or fragments of Bst2, Bst2 decoy, Bst2 decoy Fc, Bst2 L or their mutants with codon-optimized nucleotide sequences for each expression system.

Expression vectors designed for Bst2, Bst2 decoy, Bst2 decoy Fc or Bst2 L expression in mammalian, insect (baculovirus, Schneider cells), fungal, plant or bacterial cells are constructed by inserting the DNA fragment encoding Bst2, Bst2 decoy, Bst2 decoy Fc or Bst2 L adjacent to the host cell-specific promoter in a host cell-specific vector, which can be in a plasmid or viral form. These proteins may be expressed as a tagged fusion protein in mammalian, insect, fungal, plant or bacterial cells. Tags are short protein sequence, which has high binding affinity to antibodies or specially modified solid supports. The tag may include but not necessarily limited to Histidine, Flag, V5, GST and HA tags. Tagged Bst2 decoy is purified based on the affinity of the tag to the solid support such as columns or beads. Additional steps including liquid chromatography may be used to increase the purity of all of the Bst2-related proteins.

The protein or fragment of Bst2, Bst2 decoy, if desired, may be modified by acetylation of the N-terminal amine, amidation of C-terminal carboxyl group, phosphorylation of serine, threonine or tyrosine residues, methylation of the alpha-amino groups of lysine, arginine and histidine residues, deamidation of glutaminyl and asparaginyl residues, hydroxylation of proline and lysine, biotinylation, palmitylation, sulfation, farnesylation, and the like.

The Bst2 or Bst2 L protein, Bst2 decoy, a fragment thereof, or a variant thereof, which has an inflammation-suppressing effect by inhibiting intercellular adhesion, may be naturally isolated or synthesized (Merrifield, J. Amer. Chem. Soc., 85:2149-2156, 1963), or may be prepared by a recombination method based on DNA sequence (Sambrook et. al., Molecular Cloning, Cold Spring Harbour Laboratory Press, New York, USA, 2nd Ed., 1989). When a genetic recombination technique is used, a desired protein may be obtained by inserting a nucleic acid encoding the Bst2 or Bst2 L protein, a fragment thereof or a variant thereof into a suitable expression vector, transforming a host cell with the expression vector, culturing the host cell to express the desired protein, and recovering the produced protein from the culture.

1. Preparation of Recombinant Bst2, Bst2 Decoy, Bst2 Decoy Fc, Bst2 L, a Portion of These Proteins or Mutants Successful recombinant protein-based approaches require the ability to produce biologically active protein that can be easily scaled up for mass production. The compatibility of codon usage between the native gene sequence of the above Bst2-related proteins and that of the expression host is an important consideration.

In addition to the therapeutic utilities of the Bst2 decoy and Bst2 decoy Fc proteins, recombinant proteins of Bst2, Bst2 decoy, Bst2 decoy Fc, Bst2 L, a portion of these proteins or mutants of these proteins are required for screening variants of anti-Bst2 antibody or anti-Bst2 L antibody.

Recombinant Bst2, Bst2 decoy, and Bst2 decoy Fc proteins are also used in assays to identify Bst2 L involved in the binding interaction. Bst2 L can be Bst2 itself, or other proteins, peptides or molecules.

Bst2, Bst2 decoy, Bst2 decoy Fc and Bst2 L, portions of them and mutants can be used to screen for peptides or small molecule inhibitors or agonists of the Bst2-Bst2 L interaction. Such screening assays include high-throughput protein-protein binding assays, cell-based assays, immunoassays or biochemical screening assays of chemical libraries, suitable for identifying small molecule drug candidates.

Recombinant Bst2, Bst2 decoy, Bst2 L, portions and mutants thereof may be also useful for recombinant protein-based vaccine approaches.

1-1. Expression of Bst2, Bst2 Decoy, Bst2 Decoy Fc, Bst2 L, a Portion of these Proteins or Mutants of these Proteins (Various Bst2-related Proteins) in Mammalian Cells Many mammalian expression vectors and host cell systems are commercially available. Mammalian expression system has been described in Example 4.

1-2. Expression of the Various Bst2-related Proteins in Baculovirus

In addition to the mammalian cells, glycosylated Bst2, Bst2 decoy, Bst2 L and other Bst2-related proteins can be derived from invertebrate cells including insect cells such as *Drosophila* S2, Sf9 as well as plant cells. For baculovirus expression, the corresponding Bst2 or Bst2 L sequences are fused upstream of an epitope tagged, for example, poly-his tagged baculovirus expression vector. Bst2 decoy Fc may be used without other tag. Many baculovirus expression vectors are commercially available. Viral infection and protein expression is performed as described by O'Reilley et al., Baculovirus expression vectors: A laboratory Manual, Oxford: Oxford University Press (1994). Recombinant baculovirus is generated by cotransfecting the Bst2, Bst2 decoy baculovirus vectors and BaculoGold virus DNA (Pharmingen) into Sf9 cells (ATCC) using lipofectin. After 4-5 days of incubation at 28° C., the released viruses are harvested and used for amplification.

Poly-his tagged Bst2, Bst2 decoy or Bst2 L are purified by $Ni^{2+}$-chelate affinity chromatography (Rupert et al. Nature, 362:175, 1993). Purification of Bst2 decoy Fc can be performed using protein A column chromatography.

1-3. Expression of the Various Bst2-related Proteins in *Pichia pastoris*

*Pichia pastoris* is a unicellular eukaryote that has many similarities to *E. coli* in terms of ease of cloning foreign genes, as well as having a tightly controlled inducible expression in cultures that are easy to handle (Kocken, C. H. et al., Infect. Immun. 67:43-49. 1999). Being a eukaryote, *P. pastoris* is capable of several posttranslational modifications, for instance, the ability to form disulfide bonds that enable proper folding of proteins, and *Pichia* is also known to potentially glycosylate proteins (Yadava A and Ockenhouse, Infect. Immun. 71:4961, 2003).

The genes of the various Bst2-related proteins are chemically synthesized using nucleotide sequences optimized for *Pichia* codon usage. *P. pastoris* constructs, for example, PicZα (Invitrogen), a zeocin-selectable plasmid, is used for cloning and expression of the Bst2-related proteins in *P. pastoris*. The plasmid contains an alcohol oxidase 1 promoter from *P. pastoris* fused to the α-mating factor from *Saccharomyces cerevisiae* for directing the protein to the secretory pathway. Upon induction with methanol, the protein is expressed under control of the alcohol oxidase 1 promoter and secreted into the culture medium.

After constructing PicZα expression vectors of various Bst2-related proteins, *E. coli* XL-1 blue cells are transformed with the constructs, and zeocin-resistant clones are screened for the insert by PCR and restriction digestion. Positive clones are used to transform *P. pastoris*. The transformation mixture is plated on yeast-peptone-dextrose-sorbitol plates containing zeocin. For expression, the positive clones are grown in buffered glycerol medium for about 24 h. The cells are pelleted and induced with fresh medium containing 1% methanol for another 24 h. Supernatants are tested for expression by ELISA or Western blotting to detect various Bst2-related proteins. The *Pichia*-expressed protein is purified from culture supernatant.

1-4. Expression of the Various Bst2-related Proteins in Yeast

Yeast expression vectors are constructed for intracellular production or secretion using codon-optimized sequences. For secretion, DNAs encoding Bst2, Bst2 decoy, Bst2 L, portions or mutants of these proteins, can be cloned into the selected plasmid with DNA encoding the ADH2/GAPDH promoter, the yeast alpha factor secretory signal/leader sequence. Yeast cells can be transformed with the expression plasmids and cultured in selected fermentation media (Hsiao et al. Proc. Natl. Acad. Sci. USA, 76:3829, 1979). The yeast supernatants are analyzed by TCA precipitation, SDS-PAGE and Coomassie blue staining. Recombinant Bst2-related proteins can be isolated from concentrated supernatant using selected column chromatography methods.

1-5. Expression of Bst2, Bst2 Decoy in *E. coli*

Under certain conditions, some of the above Bst2-related proteins may be produced in *E. coli*. However, it is known that not all soluble proteins produced in *E. coli* may be correctly folded, and incorrectly folded proteins may form insoluble aggregates in the form of inclusion bodies (Curio, M. M., and A. Villayerde. 2002. J. Biotechnol. 96:3-12).

The DNA sequence encoding the Bst2-related proteins selected for expression in *E. coli* system is amplified using PCR primers containing suitable restriction enzyme sites. A variety of expression vectors are commercially available. The vector is digested with restriction enzyme and dephosphorylated. The PCR amplified sequences are then ligated into the vector. The ligation mixture is then used to transform *E. coli* strain. Transformants are selected and plasmid DNA is isolated. Selected clones are grown in liquid culture medium and then used for a larger scale culture, during which the expression promoter is turned on. The cell pellet can be solubilized and the solubilized Bst2-related proteins may then be purified using, for example, a metal chelating column, if the protein is expressed from a vector containing a poly-his sequence and enterokinase cleavage site.

2. Preparation of Bst2, Bst2 Decoy, Bst2 Decoy Fc, Bst2 L, a Portion of these Proteins or Mutants by Peptide Synthesis Bst2, Bst2 decoy, Bst2 decoy Fc, Bst2 L, various portions thereof or mutants may be produced by direct peptide synthesis using solid phase technique or by a combination of solid phase and solution phase methods (Stewart et al., Solid Phase peptide Synthesis, W.H. Freeman Co., San Francisco, Calif., (1969); Barbs K et al. Int J Pept Protein Res. 1991; 37: 513-520; Babiker E et al. J Org. Chem. 1978; 43: 4196-4199). Various portions of these Bst2-related proteins may be chemically synthesized separately and combined using chemical or enzymatic methods to produce the full length Bst2, Bst2 decoy, Bst2 L or mutants.

Peptide synthesis method may be also useful to produce modified versions of these proteins (for instance, phosphorylated version).

Peptides can be synthesized using L form or D form amino acids. In particular, mammalian proteases and peptidases cannot degrade peptides synthesized from D-amino acids. D form Bst2 decoy or various portions of D form Bst2 decoy would be very stable in vivo despite their small sizes and may be administered in drinking water or mixed with food, air spray and/or patches.

The Bst2 protein or a fragment thereof, provided in the present invention, which has an inflammation-suppressing effect by inhibiting intercellular adhesion or interaction and immune cell activation, may be in a monomeric or multimeric form. A multimer may be formed by various methods commonly known in the art, and the method for forming a multimer is not specifically limited.

The multimer may be a dimer, trimer, tetramer, pentamer, hexamer, and so on without limitation. For example, a multimer may be prepared using a sequence inducing multimer formation, for example, isoleucine zipper (ILZ) sequence inducing trimer formation, or surfactant protein-D (SP-D) inducing dodecamer formation. Otherwise, a multimer may be prepared by conjugating two or more polypeptides, which each have been produced in a monomeric form, for example, using a linker.

The multimer may form parallel or anti-parallel structure, or a combination of parallel and anti-parallel structures of the Bst2 protein or a fragment thereof. While Bst2 is thought to function as a homodimer, the orientation of each monomer in the homodimers is not known. For construction of the expression vectors for the multimer that contains anti-parallel structure of the Bst2 protein or a fragment thereof, the coding sequences for the anti-parallel structured Bst2 protein or a fragment thereof should be chemically synthesized with codon-optimized nucleotide sequences. In the expression vector, each Bst2 protein (or a fragment) unit may be linked by a synthetic linker. A synthetic linker includes a Gly/Ser-rich synthetic linker (Berezov A et al., 2001, J Med Chem 44:2565) or a flexible Gly linker (Kim et al. Proc. Natl. Acad. Sci. USA 96:10092, 1999).

When the Bst2 fragment unit is small enough to be directly synthesized through peptide synthesis, both L form-and D form multimers may be produced.

The Bst2 protein, or fragment thereof, which has an inflammation-suppressing effect by inhibiting intercellular adhesion, or interaction and immune cell activation, may be modified by a non-peptide polymer.

In a further detailed aspect, the antagonist includes non-peptide polymer-modified Bst2 protein or a fragment thereof, which has an inflammation-suppressing effect by inhibiting intercellular adhesion or interaction and immune cell activation.

The linkage of the Bst2 protein, or fragments thereof with a non-peptide polymer include covalent bonds and all types of non-covalent bonds, such as hydrogen bonds, ionic interactions, van der Waals forces and hydrophobic interactions. Preferably, the polymer is linked with a protein through a specific reactive group. Examples of reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. The non-peptide polymer reacts with reactive groups of a polypeptide, for example, an N-terminus, a C-terminus and/or side chain of amino acid residues (e.g., side chain of a lysine residue, a histidine residue or a cysteine residue).

The Bst2 protein, which has an inflammation-suppressing effect by inhibiting intercellular adhesion, or interaction and immune cell activation, may be linked with a non-peptide polymer in a molar ratio of 1:1 to 1:10, preferably 1:1 to 1:2. When the Bst2 protein, or fragment thereof, is modified by two or more non-peptide polymers, the non-peptide polymers are identical or different. The proteins may have improved in vivo stability and metabolism through modification with non-peptide polymers.

In still another aspect, the present invention provides a composition for preventing or treating inflammatory diseases, comprising one or more selected from among, as described above, Bst2 protein or a fragment thereof having an inflammation-suppressing effect by inhibiting intercellular adhesion or interaction and immune cell activation; non-peptide polymer-modified Bst2 protein or a fragment thereof having an inflammation-suppressing effect by inhibiting intercellular adhesion.

The present composition may be applied to humans, as well as to livestock whose inflammatory diseases can be inhibited or reduced by administration of Bst2, such as bovine, horses, sheep, swine, goats, camels, antelopes, dogs and cats. In this context, the present inventors found that human Bst2 and mouse Damp1 have functional similarity and act on cells having the same origin as well as a different origin.

In still another detailed aspect, the present invention relates to a method of preventing or treating inflammatory diseases, comprising administering to a patient one or more proteins selected from among Bst2 protein or a fragment thereof having an inflammation-suppressing effect by inhibiting intercellular adhesion or interaction and immune cell activation.

Decoy Protein Stabilization by Fc Fusion

Fusion of the decoy Bst2 to the Fc portion of an antibody is described. The resulting fusion was able to prolong the therapeutic effect of the decoy Bst2 protein allowing for a more favorable dosing schedule. Fusion to albumin has also been shown to extend serum half life of small proteins Like fusion of Bst2 decoy to the Fc portion of an antibody, fusion of Bst2 decoy to albumin may increase the serum half-life of Bst2 decoy.

Many potential therapeutic proteins including the Bst2 decoy are smaller than 40 kDa and therefore susceptible to renal clearance by glomerular filtration. These small proteins rarely make perfect pharmaceuticals. The redesign of proteins to promote longer serum half-life is an important medical and commercial goal. Since proteins must generally be administered by injection, it is preferable to have therapeutic proteins that minimize the frequency of protein administration.

In general, a protein's effective molecular weight may be increased by fusion to a heterologous carrier protein, such as to albumin or the Fc region of an antibody which may aid in purification of the protein (Capon et al. Nature. 1989 Feb. 9; 337(6207):525-31; Yeh P. et al. Proc. Natl. Acad. Sci. USA, 89:1904-1908, 1992). The heterologous sequence could be any sequence as long as it allows the resulting chimeric protein to retain at least one of the biological activities of the Bst2 decoy.

Bst2 is thought to exist as a homodimer on the cell surface (Ohtomo et al., Biochem Biophys Res Commun. 1999, 258 (3):583-91). It is also thought that Bst2 requires dimerization for its activity. Thus, heterologous sequences which promote association of the Bst2 decoy monomers to form dimers, trimers and higher multimeric forms are preferred. The construction of an Fc chimeric protein using a small protein with a molecular weight of less than 40 kDa results in a dramatic extension of serum half-life (Lo et al., PCT WO00/40615, 2000). Bst2 decoy-Fc is a recombinant chimeric fusion protein consisting of the extracellualr domain of human Bst2 and the Fc region of human IgG. Bst2 decoy-Fc was produced as a dimer and to some extent as a higher multimer.

Rat Bst2 Decoy-Fc

Rat Bst2 has 44% and 70% amino acid similarity to human Bst2 and mouse Damp1, respectively (Kupzig t al., 2003, Traffic 4(10): 694). Putative coiled coil domain is present in the region of amino acids 96-153 (or 102-149) in human Bst2 protein, and in the corresponding regions of the rat Bst2 protein and mouse Damp1 protein.

The observation that mouse Damp1 decoy inhibits cell-cell interaction between human endothelial cells and human monocytic U937 cells, and that, human Bst2 decoy functions in the mouse asthma model indicates that Bst2 decoy and Bst2 decoy-Fc function in a cross-species manner. The efficacy of mouse Damp1 decoy (Fc fusion), rat Bst2 decoy (Fc fusion) or human Bst2 decoy (Fc fusion) proteins may be investigated in any animal disease model including mouse, rat, rabbit, dog or primate, interchangeably without species barrier. Alternatively, Fc fusion of decoys derived from Bst2 homologues from rabbits, dogs or primates can be used. For antibody treatment in mice, anti-mouse Damp1 antibodies or rat anti-Damp 1 antibodies could be used. For antibody treatment in rats, rabbits, dogs or primates, antibody specific for the Bst2 homologues from these animals can be used. One method to generate panels of monoclonal antibodies against mouse Damp1 is to use Damp1−/− mice. Damp1−/− (knockout) mice are generated by well-known homologous recombination methods.

Rat anti-Damp 1 monoclonal antibodies can be produced using rat hybridoma technology (Lebacq-Verheyden et al., Hybridoma. 1983, 2(3):355-8.). Similarly, antibody treatment in rats can be performed using mouse anti-rat Bst2 monoclonal antibodies.

Constitutive Damp 1−/− (Knock-Out) Mice

Damp1−/− mice are generated by homologous recombination methods. As indicated above, mouse anti-Damp 1 monoclonal antibodies can be obtained using Damp1−/− mice. In addition, Damp1−/− mice are useful to generate information on which disease models may be pursued with the Bst2 blockers (Bst2(Damp1) decoy, anti-Bst2(Damp1)). Because it is quite expensive to produce purified protein drugs for preclinical studies, it is difficult to try numerous disease models. On the other hand, most of the disease-inducible treatments used for the animal models, for example, collagen or adjuvant treatment for arthritis models, ovalbumin treatment for asthma models, or any other treatments commonly used in animal models, can be easily implemented without much cost. By comparing the severity of the symptoms and disease progression in Damp1−/− and wild-type mice after various disease-inducible treatments, valuable information can be obtained regarding which disease models may be pursued with the Bst2 blockers. In this manner, more treatment options using Bst2 blockers may be generated.

Tissue Specific Damp1−/− (Knock-Out) Mice

Although transgenic expression of a dominant negative protein of Damp1 or Bst2, or simple Damp1−/− (knock-out) as described above may be relevant to human disease or the inflammatory/autoimmune pathways, deletion of Damp 1 in a specific cell-type would be also valuable to study gene function of Damp1/Bst2 and deduce the gene function of Bst2.

Site-specific recombinase-systems such as the widely used CreloxP system (Lasko M et al. Proc. Natl. Acad. Sci. USA, 93:5860, 1996; Orban P et al., Proc. Natl. Acad. Sci. USA, 89:6861, 1992) may be used. In this system, two transgenic mouse lines are required to facilitate tissue-specific Damp 1 knockout. The first mouse line expresses Cre recombinase under the control of a tissue-specific promoter of choice. Currently, nearly forty~fifty Cre lines are available, and the availability and variety of Cre lines increase. The second line carries loxP sites around Damp1. After intercrossing, the Damp1 gene is removed from cells expressing Cre recombinase. One or both copies of the Damp1 gene can be targeted, for example, to examine dosage-sensitivity of the Damp1 gene.

Tissue Specific, Inducible Damp1−/− (Knock-Out) Mice

Physiological relevance of the Damp1 gene function in disease may further require temporal control in addition to tissue-specificity. One way to achieve inducible expression of tissue-specific Cre recombinase is the use of steroid receptor ligand-regulated forms of Cre by fusing a mutant estrogen receptor (ER) ligand-binding domain to the C-terminus of Cre. These fusion proteins are induced by the synthetic estrogen antagonist 4-OH tamoxifen but are insensitive to endogenous beta-estradiol. Three different mutant estrogen receptors, mouse ERTM (Danielian P S, Cum Biol. 8:1323, 1998), human ERT (Logie and Stewart, Proc. Natl. Acad. Sci. USA, 92:5940, 1995) and human ERT2 (Feil R et al., Biochem. Biophys. Res. Commun. 237:752, 1997), are available. By placing CreER under the control of a tissue-specific promoter, one can generate a Damp1 knock-out system in a tissue-specific, tamoxifen-inducible manner. The second transgenic line carries loxP sites around Damp1. After intercrossing, the Damp1 gene is removed from cells expressing Cre recombinase in tamoxifen-inducible manner.

In another approach, tetracycline-sensitive systems may be used. Tetracycline binds to the tetracycline transactivator protein, tTA, or "reverse tetracycline transactivator protein, rtTA. These complexes repress or activate the Damp1 expression by binding to the Tet operator (tetO). To achieve Tet-inducible knockout of Damp1 in a tissue-specific manner, triple transgenic mice are required. In the first line, tTA or rtTA protein is expressed under the control of a tissue-specific promoter/ enhancer. Second line carries Tet-operator promoter (tetO) and Cre-recombinase. Only in the presence of tTA or rtTA, and tetracycline delivered in the drinking water, the tetO promoter is activated and Cre recombinase is expressed.

Third line carries loxP sites flanking Damp1. Then, the Cre recombinase excises the Damp1 gene in a tissue-specific, Tet-inducible manner.

Transgenic Damp1 or Bst2 Knockdown Animals Via RNAi (RNA Interference) Using shRNA Given the difficulty of applying gene knockout technology to species other than mice, RNA interference (RNAi) may be used in silencing the expression of Damp1 or Bst2 in mice or other animals, respectively. It would be possible to silence Damp1 gene in mice or Bst2 homologues in other animals using short pieces of Damp1 or Bst2 siRNA in transgenic animals. Tissue-specific Damp1 or Bst2 knockdown using RNA interference could be an alternative approach for generating loss of function models.

RNA interference is the sequence-specific, posttranscriptional gene silencing mediated by small double-stranded RNA (dsRNA) homologous to the sequences of the silenced gene. The mediators of sequence-specific messenger RNA degradation are 21-and 22-nucleotide small interfering RNAs (siRNAs) generated by cleavage from longer dsRNAs (Bernstein E et al. Nature 409:363, 2001; Elbashir S M et al. Nature 411:494, 2001). These siRNAs are incorporated into a multiprotein RNA-inducing silencing complex. The antisense strand guides the silencing complex to its homologous target mRNA resulting in cleavage. It has been shown that double strand-specific RNase inside the cell called Dicer can process small hairpin RNA structures (shRNA) resulting in the generation of micro RNAs. By inhibition of translation, micro RNA can effectively silence gene expression making it possible to target genes using only one vector. The shRNA systems can be used to generate transgenic animals that silence gene expression stably.

Damp1 or Bst2 siRNA: Damp1 or Bst2 siRNA may be designed by incorporating corresponding sequences of the human Bst2 siRNA used in FIG. 9, or siRNAs may be newly designed. In order to select potential Damp1(Bst2)-siRNA sequences for the generation of Damp1(Bst2) shRNAs, mammalian cells such as Cos-7 cells are cotransfected with a green fluorescent protein (GFP)-Damp1(Bst2) fusion construct plus different siRNAs directed against Damp1(Bst2). Expression and knockdown of the Damp1(Bst2)-GFP fusion protein is analyzed by immunoblotting.

Construction of the Damp1(Bst2)-shRNA expression vector: Both pol III and pol II promoters are used to synthesize short hairpin RNA (shRNA) for knockdown of gene expression in mammalian cells and animals. For construction of the shRNA expression vector, the most efficient of the siRNAs as screened above is then cloned into an shRNA expression plasmid in which sense and antisense strands of short Damp1 (Bst2) sequences are transcribed into hairpin structures under the control of, for example, a U6 promoter, as a DNA sequence encoding the Damp1(Bst2)-shRNA, and then processed into functional siRNAs by double strand-specific RNase, Dicer, inside the cells. An shRNA expression vector is generated by cloning the corresponding DNA oligonucleotides into an shRNA expression plasmid such as pSilencer 1.0-U6 from Ambion (Austin, Tex., USA). The oligonucleotides cover the sense and antisense sequence of Damp1 (Bst2) and a 7 by loop, and the annealed product contains appropriate restriction enzyme sites. This duplex is ligated into pSilencer 1.0-U6. This vector is then used to endogenously express shRNA in mammalian cells. The control RNAi vector is constructed by insertion of a sequence that expresses a siRNA with limited homology to any known sequences in the mouse or human genomes.

Generation of transgenic animals expressing Damp1 or Bst2-shRNA: Using pronuclear injection method, Xia et al. (PLoS Genet. 2006; 2(1): e10) were able to show that shRNAs transcribed from the human Pol II promoter such as human ubiquitin C promoter could mediate gene silencing in mice. The transgenic mice were made by pronuclear injection of the linearized construct into the fertilized eggs. Similarly, one may use any kind of tissue-specific promoter coupled to Damp1-or Bst2 shRNA for generation of transgenic mice by simple pronuclear injection.

Alternatively, adeno-associated viral (AAV) vectors (A. Auricchio et al., Hum. Mol. Genet. 10 (2001), pp. 3075-3081) or lentiviral vectors (Golding M C et al. Proc. Natl. Acad. Sci. USA 2006 Apr. 4; 103(14):5285-90) expressing the Damp 1-or Bst2 shRNA may be used to deliver the transgene into animals.

Transgenic Animals Expressing Bst2, Bst2 L, Portions or Mutants of Bst2 or Bst2 L Transgenic animals (a mouse or rat) overexpressing the entire Bst2 or Bst2 L (or any portion of it), are useful in the development and screening of therapeutically useful reagents such as anti-Bst2, Bst2 decoy, Bst2 decoy Fc and anti-Bst2 L. The transgenic lines can be designed to express the Bst2 or Bst2 L proteins constitutively, in an inducible-manner, a tissue-specific manner, or a tissue-specific/inducible manner.

Transgenic animals expressing Bst2 or Bst2 L (or any portion of it) could show pathological conditions associated with overexpression of Bst2 or Bst2 L. These animals can be treated with the Bst2 blocker and a reduced incidence of the pathological condition, compared to untreated animals bearing the Bst2 or Bst2 L transgene, would indicate a potential therapeutic benefit. When a dominant-negative version of Bst2 (Damp 1) or Bst2 L (Damp 1 L) is identified (one which interferes with the function of the wild type protein), transgenic animals expressing the dominant negative forms of these proteins may be generated to test whether the disease process is inhibited. Transgenic animals expressing the dominant negative protein of human Bst2 can be bred with Bst2 knock-in mice prior to testing the disease process.

Transgene expression cassettes contain the transcription unit including the Kozak consensus sequence, coding exons of the Bst2 or Bst2 L, portions or mutants of these proteins, a termination signal (poly-A-tail) and regulatory elements controlling the expression of the transgene. Numerous tissue-specific promoter/enhancers are available in the literature. Inducible systems including tetracycline-or tamoxifen-inducible systems to control the temporal expression are commercially available (see above, under Tissue Specific, Inducible Damp1−/− (Knock-Out) Mice). Methods for generating transgenic mice or rats have become conventional (U.S. Pat. Nos. 4,736,866 and 4,870,009).

Transgenic Animals Expressing Bst2 Decoy, Bst2 Decoy-Fc and Bst2 Decoy-Albumin Fusion Transgenic animals expressing the extracellular domain of Bst2 or Damp1 (or any portion of it), or extracellular domain of Bst2, or Damp1 (or any portion of it) fused to the Fc fragment or albumin, can be used to assess therapeutic effects of the Bst2 decoy (Fc) under the pathological conditions. Transgenic mice expressing these proteins may be bred with knock-in mice expressing Bst2 to assess the therapeutic effects of the Bst2 decoy (Fc) protein, in monotherapy or in combination therapy, under any pathological condition. The transgenic lines can be designed to express these proteins constitutively, in an inducible-manner, a tissue-specific manner, or a tissue-specific/inducible manner.

Knock-In Mouse—Creation of Human-Mouse Chimeric Bst2 Mice

Figure 28:
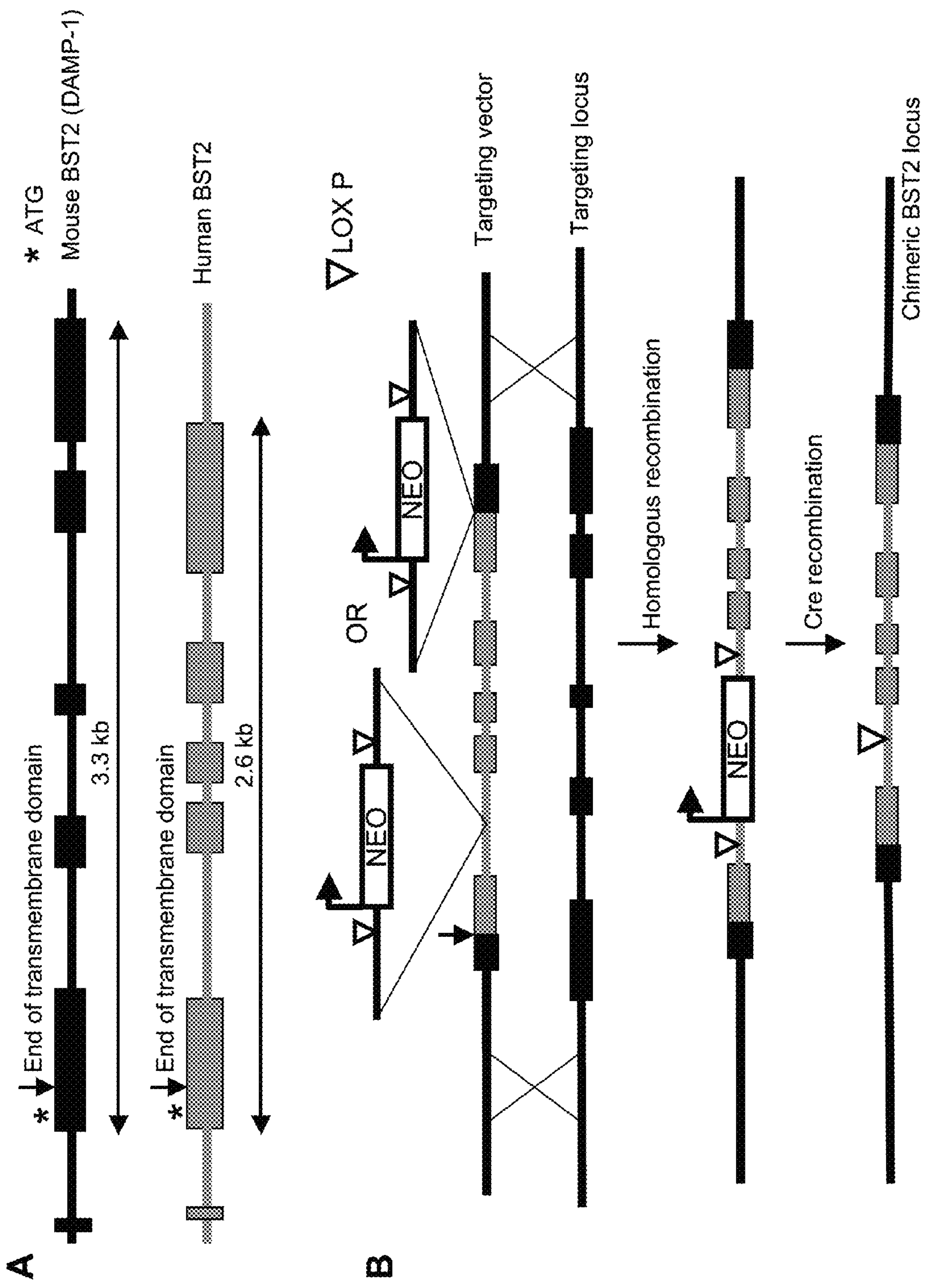

Because the amino acid sequence homology between human Bst2 and mouse Damp1/rat Bst2 is not extensive, it is not possible to test the efficacy of the panels of the anti-human Bst2 antibodies in murine or rat immune, inflammatory disease models. One way to overcome this problem is to generate knock-in mice expressing human Bst2, in this case, the human-mouse chimeric Bst2. The knock-in mice may have the entire coding region of Damp1 replaced by human or just the extracellular domain of Damp1 replaced by the extracellular domain of human Bst2 resulting in a chimeric protein. Although transgenic mice expressing human Bst2 may be used for this purpose, an overexpression system is not an ideal system to test the efficacy of the Bst2 blockers. A knock-in approach that allows the human-mouse chimeric Bst2 expression at the physiological level supercedes the transgenic approach. A knock-in mouse expressing human-mouse chimeric Bst2 may be produced according to standard knock-in homologous recombination protocol, and may be carried out using an exemplified construct such as shown in FIG. 28. The knock-in mice are treated to induce immune-inflammatory conditions. Anti-human Bst2 antibodies are administered.

These mice are also useful for testing the efficacy of combination therapy with anti-human Bst2 antibody or Bst2 decoy-Fc with various rat antibodies against mouse protein target. For example, knock-in mice expressing human Bst2 may be treated with collagen to induce arthritis (Andren et al., J. Immunol. 2006, 63(4):282-9) and then treated with human Bst2 decoy-Fc or anti-human Bst2 in combination with any single agent, two agents, three agents or four agents of rat anti-mouse TNFR (TNF alpha receptor I or II) (Abcam), rat anti-mouse IL-6 receptor (Genzyme), rat anti-mouse IL-1 receptor (Abcam) or murine CTLA4-Ig (in-house). Murine CTLA4-Ig has been shown to inhibit T cell responses in rat (Shiraishi T et al. 2002, Am J Transplant 2:223).

Animal Disease Models to Test Efficacy of the Bst2 Blockers

Useful animal models to test efficacy of the Bst2 blockers include but are not limited to; rat or mouse collagen-induced arthritis model (Webb et al., Eur J. Immunol. 1996, 26(10):2320-8; Andren et al., Scand J. Immunol. 2006, 63:282), rat or mouse adjuvant induced arthritis model (Haruna et al., Arthritis Rheum. 2006, 54(6):1847-1855; Hida et al., J. Autoimmun. 2005 September; 25(2):93-101), ovalbumin-induced asthma model (Sy et al., Int Immunopharmacol. 2006, 6(7):1053-60), osteoarthritis model (Averbeck et al., J. Rheumatol. 2004 October; 31(10):2013-20), graft versus-host disease (GvHD) model (Zhang et al., Blood, 2006, 107:2993-3001; Baliga et al., Transplantation. 1994, 58(10):1082-90), type 1 diabetes model in NOD (non-obese diabetic) mice or BB (BioBreeding) rat (Yang Y, Santamaria P. Clin Sci. 2006, 110(6):627-39), ischemia/reperfusion model (Arumugam et al. Nat. Med. 2006 June; 12(6):621-3), septic shock model (Motobu et al. Phytother Res. 2006, 20(5):359-63), autoimmune uveitis model (Yilmaz et al. Curr Eye Res. 2005, 30(9):755-62), experimental allergic encephalomyelitis (EAE) in mice that is an animal model for multiple sclerosis (Mujtaba et al., J. Immunol. 2005, 175(8):5077-86), brain embolism model in rabbit (Chapman D F, Stroke. 2001, 32(3):748-52), mouse colitis model for Crohn's disease and inflammatory bowel disease (Yen D et al. J Clin Invest. 2006, 116(5):1310-6), concanavalin A-induced liver damage model for autoimmune or viral hepatitis (Li et al., Hepatology. 2006 June; 43(6):1211-9), psoriasis model (Gudjonsson J E, Elder J T. Eur J Hum Genet. 2006, 14(1):2-4), and corneal allograft rejection model in rabbit (Shirao E, Deschenes J, Char D H. Curr Eye Res. 1986, 5(11):817-22). The animal models to study AMD have been described (Dithmar et al., Arch Opthalmol 2001, 119(11):1643-9; Cousins et al., Exp Eye Res. 2002, 75(5):543-53).

Blockage of Bst2 may suppress early acceleration of atherosclerosis by stabilizing established atherosclerosis. This hypothesis can be tested in streptozotocin-treated (diabetic) apoE-null mice or LDL-receptor knock-out mice (Jackson laboratories) (Bucciarelli et al., Circulation, 2002, 106(22):2827). Csaky K. Exp Eye Res. 2002, 75(5):543-53). Many patients with type II diabetes develop atherosclerosis. The effect of Bst2 blockers in type II diabetes and atherosclerosis can be tested in db/db apoE-null double mutant mice.

The concept of whether interference with the Bst2 action is beneficial for treatment of antibody-mediated autoimmune disease is initially tested by measuring antibody responses to sheep red blood cells and key hole limpet hemocyanin as described in Linsley P S, Wallace P M, Johnson J, Gibson M G, Greene J L, Ledbetter J A, Singh C, Tepper M A. Science. 1992, 257(5071):792-5.

Other autoimmune disease models include lupus-like illness (Finck et al., Science. 1994, 265(5176):1225-7) and glomerulonephritis model in rats (Nishikawa et al., Eur J. Immunol. 1994, 24(6):1249-54.). Donor specific transplantation tolerance can be tested using diabetic mice which has received pancreatic islet cell xenografts (Lenschow et al., Science, 1992, 257(5071):751). Tolerance can also be demonstrated in a vascularized murine cardiac allograft model (Larsen et al., Nature, 1996, 381(6581):434-8; Pearson et al., Transplantation, 1995, 59(3):450) and skin allograft rejection model in mice (Tepper et al., Transplant Proc. 1994, 26(6):3151-4) and renal transplantation model (Laskowski I A. J Am Soc Nephrol. 2002, 13(2):519-27).

Combination Therapy

Immune, inflammatory diseases are complex disorders mediated by complex net work of immune, inflammatory signaling. These events may be closely linked to each other, however, the underlying cellular and molecular processes may differ considerably. Therefore, complete remission of immuno-inflammatory diseases may require combined therapies. Usually, combined therapies that may vary in their ability to affect various proinflammatory processes have been shown to be superior to monotherapy.

The concept for combination therapy with the Bst2 blockers has been tested in vitro with cell-cell adhesion assay using ICAM1 (intercellular adhesion molecule) as an example (Example 25 and Example 26). ICAM1 was chosen because ICAM1 has been shown to regulate many genes critical for immune, inflammatory pathways and extensively studied for its involvement in many inflammatory, immune diseases.

ICAM1 is the target cell counter-receptor of the lymphocyte function-related antigen, LFA-1 (CD11c/CD18), a member of the integrin subfamily expressed in leukocytes. The interaction between these two molecules is crucial for triggering the cellular immune reaction. ICAM-1 is also thought to play a role in acute rejection of allografted tissues. ICAM1 and LFA1 are involved in cell-cell interaction between antigen presenting cells and T cells. ICAM1 on APCs can bind its receptor LFA1 on T cells and ICAM1 on T cells can bind LFA1 on APC (Mackay C R, Imhof B A, Immunol Today, 1993, 14:99). Increasing evidence supports the notion that several molecules previously considered to be adhesion molecules are also capable of delivering costimulatory signals for T cell activation (e.g., LFA3, LFA1 and ICAM1) (Mackay C R Imhof B A, Immunol Today, 1993, 14:99). Costimulatory molecules provide T cells with additional signals that result in the initiation and enhancement of proliferation (Steinman R M Young J W. 1991, Cum Opin Immunol 3:361).

Combination Therapy for Cardiovascular Diseases

Combination therapy for cardiovascular diseases may be accomplished with statin, ACE inhibitors, beta blockers, calcium channel blockers, ReoPro, Clopidogrel, and renin-angiotensin inhibitors. Endothelial cell dysfunction is associated with cardiovascular disorders such as atherosclerosis, hypertension, and vascular smooth muscle cell proliferation. Bst2 expression is induced by inflammatory cytokines such as TNF alpha, interferon gamma and histamine which indicates that Bst2 may be involved in cardiovascular disease. Therefore, blocking Bst2, either as a monotherapy or in combination with conventional therapies including statin, ACE inhibitors, beta blockers, calcium channel blockers, ReoPro, Clopidogrel, and renin-angiotensin inhibitors may improve treatment of cardiovascular diseases.

Moreover, Bst2 is induced by inflammatory cytokines in smooth muscle cells. Proliferation of smooth muscle cells can reduce the success rate of angioplasty, a procedure that increases the diameter of the atherosclerotic artery, typically coronary artery. Blocking Bst2 may decrease smooth muscle cell proliferation and increase the success rate of angioplasty.

Combination Therapy for Rheumatoid Arthritis

Combination therapy for rheumatoid arthritis with CTLA4-Ig or blockers of TNF alpha, IL6 or IL1. Rheumatoid arthritis (RA) is a complex inflammatory disorder characterized by chronic synovial inflammation, bone erosion and cartilage destruction. Blockage of a single proinflammatory cytokine, tumor necrosis factor (TNF alpha) effectively inhibited the arthritic process in clinical trials. However, complete remission of signs and symptoms of RA is rarely achieved by the TNF alpha blockers alone suggesting that several proinflammatory pathways may act independently of TNF alpha. TNF alpha blockade has been shown to arrest bone erosion in a large number of patients whose clinical signs of inflammation show no response. The effects of TNF alpha on bone are independent from a clinical response in the signs and symptoms of disease. The relative role of TNF alpha in joint inflammation, bone erosion and cartilage destruction may therefore differ.

Blockage of a major target molecule of TNF alpha, interleukin-1 (IL-1), has been shown to have some effects on RA. IL-1 has shown its effects on cartilage damage, although monotherapy of IL-1 receptor antagonist did not eliminate the clinical signs and symptoms of arthritis in a majority of patients. Although complete remission of signs and symptoms of RA is rarely achieved by any of the monotherapies, not even by TNF inhibition, preliminary results of combined inhibition of TNF alpha/IL-1, TNF alpha/RANKL or TNF alpha/IL-1/RANKL in experimental models suggested that such treatment may have additive effects. These results strengthen the rationale for using combined blockade of more than one proinflammatory pathway for treatment of rheumatoid arthritis.

Recently, anti-IL6 or cytotoxic T lymphocyte associated-antigen 4-Ig (CTLA4-Ig) has also shown to be beneficial for the treatment of arthritis. The promoter region of the Bst2 gene has binding sites for STAT3, which mediates interleukin-6 (IL-6) response gene expression suggesting that the expression of Bst2 may be regulated by the IL6-STAT3 pathway (Ohtomo et al., Biochem Biophys Res Commun. 1999, 258(3):583-91). Blockade of Bst2 that is a downstream target of IL6 may be beneficial for treatment of RA.

Cytotoxic T lymphocyte associated antigen 4 (CTLA4) is a T cell receptor upregulated after T cell activation. In most cases, signals from the T-cell receptor (TCR) alone are insufficient to result in optimal immune responses and a second, costimulatory signal is required to overcome a threshold for T cells to respond. This enhancement of TCR signals is provided primarily by CD28 on the T cells, which can be triggered by B7 expressed on the antigen-bearing cells. Once activated, T cells express a second receptor, CTLA-4, that can also bind the same B7 molecules. In contrast to CD28, CTLA-4 inhibits T-cell responses.

CTLA4-Ig is a recombinant chimeric fusion protein consisting of the extracellular domain of human CTLA4 and the Fc region of human IgG (Abatacept, Bristol-Myers Squibb). CTLA4-Ig binds to the APC (antigen presenting cell) B7 molecule, blocking its interaction with the CD28 receptor on the T cell, thus blocking the costimulatory interaction with CD28 on T cells (Linsley et al., J Exp Med. 1991, 174(3): 561-9). CTLA4-Ig has been shown to be effective in the treatment of rheumatoid arthritis (Moreland et al., Nat Rev Drug Discov. 2006, 5(3):185-6). Thus, combined treatment of the Bst2 blockers with CTLA4-Ig, or blockers of TNF alpha, IL6 or IL1 may be beneficial for treatment of arthritis.

Rat collagen-induced arthritis model or rat adjuvant-induced model may be used. Mouse anti-rat Bst2 antibody, human Bst2 decoy-Fc, rat Bst2 decoy-Fc or mouse Damp1 decoy-Fc may be tested in combination with mouse anti-rat TNFR, -rat IL6 receptor or -rat IL1 receptor monoclonal antibodies, or with murine CTLA4-Ig. Murine CTLA4-Ig produced as reported in Lane et al. (Lane et al., Immunology, 1993, 80(1):56-61) can be used in rat models as shown by other studies (Shiraishi et al., Am J. Transplant. 2002, 2(3): 223-8). Mouse CTLA4-Ig can be made from the chimeric gene of the extracellular portion of the mouse CTLA-4 gene and the constant region of human IgG1. Human CTLA4-Ig (Abatacept, Bristol Squibb) may be used in rat model of collagen-induced arthritis as well.

The knock-in mice expressing human Bst2 may also be used. Knock-in mice are treated with collagen or adjuvant to induce arthritic condition and then treated with anti-human Bst2 antibody or human Bst2 decoy-Fc in combination with rat anti-mouse TNF alpha receptor (Abcam),—mouse IL6 receptor (Genzyme) or—mouse IL1 receptor (Abcam) monoclonal antibodies, or with mouse CTLA4-Ig. Anti-Bst2 treatment may also be used for treatment of more common form of arthritis, osteoarthritis, which also has an inflammatory component.

Combination Therapy for Asthma

Combination therapy for asthma, in particular with theophiline, glucocorticoid, TNF alpha blockers or anti-ICAM1, is described. Most descriptions of the pathologic features of asthma include bronchial smooth muscle hypertrophy/contraction, mucosal edema and thickening of the epithelial basement membrane and inflammatory cells, particularly eosinophils, in submucosal tissue. These events are thought to occur in a sequential manner leading to the pathologic features of asthma. Current treatment for asthma include: anticholinergics, steroids, competitive agonist of adenosine and long and short acting beta 2 agonists. A combined therapy of the Bst2 blockers with these conventional treatments may be beneficial for asthma. Furthermore, our gene expression profile data indicate that Bst2 is highly inducible in smooth muscle cells after inflammatory stimulation such as interferon gamma (FIG. 34). These data indicate the possibility that Bst2 may be involved in smooth muscle cell physiology, and that, the Bst2 blockers might manifest some additional beneficial effects, in addition to the previously characterized anti-inflammatory responses, during the course of asthma treatment. For these reasons, combination therapy of the Bst2 blockers with conventional asthma therapies may have additive effects.

When asthma becomes progressively more severe or the patient does not respond to theophylline therapy, the patients are treated with corticosteroids. Combination therapy of the Bst2 blockers and corticosteroids may allow a decrease in the dose of corticosteroids, thus reducing their side effects.

Roles of ICAM1, alpha 4 integrin and TNF alpha in ovalbumin-induced asthma model in rats or primates have been demonstrated (Taylor et al., Am J Respir Cell Mol. Biol. 1997, 17(6):757-66). Combined inhibition of Bst2 with blockers of ICAM1, TNF alpha and/or alpha 4 integrin may be effective in treatment of asthma. Mouse anti-rat ICAM1 antibodies, rat anti-mouse ICAM1 antibodies, mouse anti-rat TNFR antibodies, rat anti-mouse TNFR antibodies, mouse anti-rat alpha 4 integrin antibodies and rat anti-mouse alpha 4 integrin antibodies are commercially available for preclinical studies using murine or rat models. Mouse anti-rat ICAM1 antibodies, rat anti-mouse ICAM1 antibodies, mouse anti-rat TNFR antibodies, rat anti-mouse TNFR antibodies, mouse or rat anti TNF alpha antibodies, mouse anti-rat alpha 4 integrin antibodies and rat anti-mouse alpha 4 integrin antibodies are commercially available for preclinical studies using murine or rat models.

Combination Therapy for Autoimmune Hepatitis

Combination therapy for autoimmune hepatitis (AIH), in particular, with corticosteroid, is described. Autoimmune hepatitis is a chronic, progressive liver disease. Possible triggering factors include viruses, other autoimmune disorders and drugs. The natural history of autoimmune hepatitis shows a poor prognosis, with frequent progression to cirrhosis and hepatic insufficiency in untreated patients. AIH rarely undergoes spontaneous regression.

The molecular mechanisms contributing to the pathogenesis include: reactions of autoantibodies against autoantigens, cell adhesion molecules and cytokines; and the occurrence of angiogenesis (Medina et al., Aliment Pharmacol Ther. 2003, 17(1):1-16). Elevated serum levels of intercellular adhesion molecule-1 (sICAM-1), vascular cell adhesion molecule-1 (sVCAM-1), (s)E-selectin, (s)P-selectin and soluble interleukin-2 receptor (sIL-2R), IL4, LFA1, LFA3, TGF beta occur in patients with AIH (Simpson et al., Eur J Gastroenterol Hepatol. 1995, 7(5):455-60). In chronic viral hepatitis, autoimmune hepatitis, T cell mediated immune mechanisms play a major role in the pathogenesis of tissue damage (Bruck et al., Isr Med Assoc J. 2000, 2 Suppl:74-80).

The treatment of choice for AIH patients is glucocorticoids, as monotherapy or in combination with azathioprine (Czaja A J, Drugs 57:49-68, 1999, Cook et al., Q J. Med. 1972, 40:159; Murray-Lyon et al., Lancet, 1973, I:735-7). Although corticosteroids reduce the incidence of cirrhosis during initial therapy, cirrhosis develops despite therapy in more than 90% of patients within 5-10 years (Davis et al., 1984, Gastroenterology 87:1222-7).

Treatment with corticosteroids is associated with well-known, dose-dependent side-effects (Summerskill et al. Gut 16:876-83, 1975, Czaja A J, In: Krawitt E L, Wiesner R H, eds. Autoimmune Liver Disease. New York; Raven Press, 1991:143-66). Hyperglycemic effects and hypertension are also frequent. Therefore, special attention must be paid to diabetic patients, as well as to patients with metabolic bone disease triggered by the liver disease.

Combination therapy of anti-Bst2 or Bst2 decoy with corticosteroids could be beneficial to maintain remission of the disease. This combination may allow a decrease in the dose of corticosteroids, thus reducing their side-effects and achieving better results than with corticosteroids at high doses.

The use of anti-Bst2 or Bst2 decoy can be investigated using the models such as the concanavalin A-induced liver damage model in mice (Kaneko et al., Biochem Biophys Res Commun. 2006, 345(1):85-92) using mouse anti-Damp1 antibody that can be generated using Damp1−/− mice, rat anti-mouse Damp1 or human-, rat-or mouse Bst2 (Damp1) decoy-Fc or in thioacetamide-induced liver cirrhosis model in rats (Zimmermann et al., Gastroenterol Hepatol. 2006, 21(2): 358-66) using mouse anti-rat Bst2 or human-, rat-or mouse Bst2 (Damp1) decoy-Fc.

Combination Therapy for Transplantation

Combination therapy for transplantation, in particular with cyclosporine, rapamycin, or anti-LFA1 antibody, is described. Adhesion molecules have been demonstrated to be critically involved in graft rejection and are obvious molecular candidates for targeted intervention therapy. Adhesion molecules affect the cellular mechanisms of allograft rejection by controlling trafficking of host leukocytes into the allograft. Trafficking of cells into the allograft is mediated by binding of adhesion molecule receptor ligand pairs between circulating leukocytes and vascular endothelium. Within the allograft, adhesion molecules can also participate in T-cell recognition of target cells.

Immuno-suppressant cyclosporine or rapamycin is used in transplantation medicine as a potent calcineurin inhibitor. However, patients treated with calcineurin inhibitors are associated with nephrotoxic effects that can lead to renal failure (Miller et al., J Heart Lung Transplant, 1995, 14:S227; Vitko S, Viklicky 0. Transplant Proc. 2004, 36(2 Suppl): 243S-247S). Other side effects include neurotoxicity, hyperkalemia and hypertension.

Combination therapy of Bst2 decoy or anti-Bst2 with either subthreshold or a moderate dose of cyclosporine or rapamycin may have a beneficial synergistic immunosuppressive effect with a decreased nephrotoxic potential.

The transplantation animal models to test efficacy of the Bst2 blockers include skin allograft rejection model in mice (Tepper et al., Transplant Proc. 1994, 26(6):3151-4), graft versus-host disease (GvHD) model (Zhang et al., Blood, 2006, 107:2993-3001; Baliga et al., Transplantation. 1994, 58(10):1082-90), corneal allograft rejection model in rabbit (Shirao et al., Curr Eye Res. 1986, 5(11):817-22), pancreatic islet cell xenograft model (Lenschow et al., Science, 1992, 257(5071):751), murine cardiac allograft model (Larsen et al., Nature, 1996, 381(6581):434-8; Pearson et al., Transplantation, 1995, 59(3):450) and renal transplantation model.

For preclinical studies, mouse anti-Damp1, rat anti-mouse Damp1, mouse anti-rat Bst2, human-, rat-, mouse Bst2(Damp 1) decoy-Fc are used depending on the models in combination with different doses of cyclosporine or rapamycin. Graft survival and T cell activation/proliferation are examined.

Combination Therapy for Multiple Sclerosis

Combination therapy for multiple sclerosis, in particular with blockers of alpha 4 integrin, is described. Multiple sclerosis (MS) is a common demyelinating and inflammatory disease of the central nervous system (CNS) with a presumed autoimmune inflammatory etiology. Antibodies to block the adhesion of activated T cells to endothelial cells can reduce the inflammatory feature of the multiple sclerosis plaque. Current treatments include monoclonal antibody against alpha 4 integrins (Natalizumab), interferon beta and glatiramer (Ropper A H, 2006, N Engl J. Med. 354:965; Rudick R A, et al., N Engl J. Med. 2006, 354(9):899-910.)

Combination therapy of anti-Bst2 or Bst2 decoy with monoclonal antibody against alpha 4 integrins may be beneficial. The use of anti-Bst2 or Bst2 decoy can be investigated using experimental allergic encephalomyelitis (EAE) model in mice using anti-Damp 1 antibody, mouse anti-mouse Damp1 that can be generated using Damp1−/− mice, rat anti-mouse Damp1 or human-, rat-or mouse Bst2 (Damp1) decoy-Fc with rat anti-mouse alpha 4 integrin (Abcam).

Combination Therapy to Minimize Tissury Injury

Tissue injury can occur as a result of ischemia, hemorrhage, trauma, swelling, burns or exposure to chemicals, toxins or drugs. Cell deaths as a result of inflammatory reactions to tissue injury often increase tissue damage. By blocking Bst2, tissue injury may be minimized. For example, steroids such as glucocorticoids are used to minimize brain damage after stroke. Blocking Bst2 either during or immediately after stroke, in combination with steroids, may minimize the extent of final brain damage. Similarly, blocking Bst2 during or immediately after myocardial infarction, may decrease the extent of heart damage.

Combination Therapy for Crohn's Disease

Combination therapy for Crohn's disease, in particular with anti alpha 4 integrin antibodies is described. Crohn's is a chronic debilitating disease characterized by severe T helper cell (Th)1-driven inflammation of the colon. The role of Bst2 antagonist can be tested using mouse model of colitis (Gonzalez-Rey et al., Gastroenterology. 2006 June; 130(6): 1707-20). For inflammatory bowel disease, combination therapy with anti alpha 4 integrin antibodies may be beneficial.

Combination Therapy for Metabolic Syndrome

Combination therapy for metabolic syndrome, in particular with metformin, TZD, statin, NSAID, ACE inhibitors and angiotensin receptor blockers is described.

In recent years, the concept that activation of the proinflammatory pathway can be a mechanism for obesity-associated insulin resistance has emerged. Tumor necrosis factor alpha (TNF)-is elevated in adipose tissue and blood from obese rodents, and blockade of TNF alpha improves insulin sensitivity. Interleukin (IL)-6 and monocyte chemoattractant protein (MCP-1) can also cause insulin resistance and elevated levels of TNF alpha, IL-6 and IL-8 have been reported in diabetic and insulin-resistant patients (Roytblat et al., Obes Res. 2000, 8(9):673-5; Straczkowski et al., J Clin Endocrinol Metab. 2002, 87(10):4602-6; Hotamisligil et al., Science. 1996, 271(5249):665-8; Sartipy P, Loskutoff D J. Proc Natl Acad Sci USA. 2003, 100(12):7265-70; Hotamisligil et al., J Clin Invest. 1995, 95(5):2409-15). In addition, elevated levels of the inflammatory marker C-reactive protein (CRP) are observed in patients with insulin-resistance (Visser et al., JAMA. 1999, 282(22):2131-5). Furthermore, treatment with high-dose salicylate can inhibit Ikappa B kinase (IKK), a major kinase in the inflammatory pathway, and reverse glucose intolerance and insulin resistance in obese rodents (Yuan et al., Science. 2001, 293(5535): 1673-7).

Insulin resistance can promote endothelial dysfunction, and anti-TNF-alpha blockade yields a rapid improvement of endothelial function. Systemic inflammation, insulin resistance, and endothelial dysfunction have been implicated in the development of cardiovascular disease. The endothelium is responsible for the maintenance of vascular homeostasis. In physiological conditions, it acts by keeping vascular tone, blood flow and membrane fluidity. Endothelial dysfunction occurring in the metabolic syndrome is the result of effects of the inflammatory cytokines such as TNF-alpha. Thus, the metabolic syndrome is considered to be a state of chronic inflammation accompanied by endothelial dysfunction, for example, causing an increased incidence of ischemic cardiovascular events, insulin resistance and high mortality. Therefore, therapies capable of blocking inflammatory condition are thought to consequently minimize the cardiovascular risk, type II diabetes and dyslipidemia due to metabolic syndrome.

The following medication is widely used to treat the metabolic syndrome: oral anti-diabetics such as metformin and thiazolidinediones (TZD), anti-hypertensives such as angiotensin-converting enzyme (ACE) inhibitors and angiotensin receptor blockers (ARBs) and lipid-lowering statin drugs, and non-steroidal anti-inflammatory drug (NSAID). These drugs that have been shown to reduce the incidence and/or delay the onset of type 2 diabetes and athrosclerosis were shown to have apparent anti-inflammatory properties.

Metformin has been shown to activate AMPK that plays a central role in regulation of energy homeostasis and metabolic stress. Metformin also dose-dependently inhibited tumor necrosis factor (TNF)-alpha-induced NF-kappaB activation and TNF-alpha-induced IkappaB kinase activity (IKK). Furthermore, metformin attenuated the TNF-alpha-induced gene expression of various proinflammatory and cell adhesion molecules, such as vascular cell adhesion molecule-1 (VCAM1), E-selectin, intercellular adhesion molecule-1 (ICAM1), and monocyte chemoattractant protein-1 (MCP1). Angiotensin-converting enzyme (ACE) inhibitors and angiotensin receptor blockers (ARBs) reduce markers of inflammation, and reduce risk of developing type 2 diabetes. Insulin-sensitizing drugs, Thiazolidinediones (TZDs), are selective ligands of peroxisome-proliferator-activated receptor gamma (PPAR gamma) widely used in the treatment of type 2 diabetes. PPARs are members of the nuclear hormone receptor superfamily of transcription factors and are key regulators in various pathophysiological processes related to energy metabolism including lipid and carbohydrate metabolism and inflammation. PPAR gamma is abundantly expressed in adipose tissue and PPAR gamma signaling pathways are reported to exert anti-inflammatory effects by inhibition of NF-kappaB. Consistent with these results, both in vitro and in vivo studies provide evidence that TZDs have anti-inflammatory properties. TZDs inhibit macrophage activation and decrease inflammatory cytokine expression and release in macrophage and monocyte. In vivo, treatment with TZDs decreases circulating mononuclear cells nuclear NF-kB content while increasing, in the same cells, expression of IkB, an NK-kB inhibitor, inhibiting inflammatory mediators such as interleukin-1 beta (IL-1 beta), IL 6, adhesion molecules, VCAM-1 and P-selectin and monocyte.

Bst2 Ligand (Bst2 L)

The Bst2 decoy that consists of the extracellular domain of the receptor protein, Bst2, inhibits both homotypic-and heterotypic cell-cell interactions in vitro. Because the extracellular domain of any given receptor is the domain that interacts with its ligand, the Bst2 decoy-mediated inhibition of the cell-cell interaction indicates that 1) a naturally-occurring ligand for Bst2 (Bst2 L) exists, 2) interaction between Bst2 and Bst2 L is required for cell-cell adhesion, and 3) the Bst2 decoy must interact with naturally occurring Bst2 L and inhibit the cell-cell interaction in the adhesion assay by neutralizing Bst2 L, thereby negatively regulating immune inflammatory reactions.

The observation that the Bst2 decoy inhibits U937 attachment to HUVEC indicates that Bst2 L is present on cell surface of unstimulated U937 cells. Another observation that the Bst2 decoy inhibits homotypic aggregation of activated T cells or activated U937 cells suggest that Bst2 L may be expressed on the surface of T cells and/or U937 cells both before and after activation. Bst2 L expression may be upregulated after activation of T cells or U937 cells. Therefore, Bst2 L may be expressed in U937 cells (or other monocytic cell lines), T cells, or primary hematopoietic cells either before or after activation, for example, T cell activation conditions or LPS stimulation conditions. Bst2 L may be also expressed in B cells, dendritic cells, endothelial cells or fibroblasts.

Bst2 L may be proteins or molecules. Bst2 L may be membrane proteins or soluble proteins. It is possible that many different Bst2 L proteins or molecules may exist that show the different binding specificities and functional characteristics of the Bst2 receptor. It is also contemplated that Bst2 itself could be the potential functional ligand of Bst2, as Bst2 is known to form a homodimer. Bst2 on the inflamed cell may recognize Bst2 on the infiltrated leukocytes and immune cells. It is possible that all Bst2 L proteins or molecules could be completely unrelated with respect to the functional or binding characteristics of each other. Therefore, the functional characteristics whether they mediate rate-limiting steps in the inflammatory or immune responses should be tested thoroughly in order to establish the therapeutic target for the Bst2 decoy (Bst2 decoy-Fc) and the subsequent development for therapeutic material for prevention and/or treatment of the inflammatory conditions. Other Bst2 L proteins or molecules that may not be in the rate-limiting steps in the inflammatory pathways may mediate other important pathways in different disease processes.

Demonstration of the existence Bst2 L is a significant feature of the present invention, because Bst2 L may be a target for interaction with anti-inflammatory molecules. Antibodies against Bst2 L may become a therapeutic antibody for treatment of various immune and inflammatory diseases. Chimeric molecules of the extracellular domain of Bst2 L to Fc may be beneficial as well. It is possible that Bst2 L may be involved in, for example, T cell co-stimulatory (or inhibitory) signaling for T cell activation. Although Bst2 L would bind to Bst2, Bst2 L may interact with many other receptors on T cells or antigen presenting cells that mediate co-stimulatory or co-inhibitory signal. Agonistic or antagonistic antibodies or Fc fusion proteins of these new sets of receptors may become protein therapeutic drugs for treatment of various immune, inflammatory diseases.

In addition, by using Bst2 L, a direct binding assay or binding competition assay may be set up for screening Bst2 decoy-(Fc) variants or small molecule modulators of Bst2. These assays enable inventors to screen Bst2 decoy variants or small molecule modulators of Bst2 to inhibit or augment the Bst2-Bst2 L interaction.

Anti-Bst2 L Antibody

If administration of Bst2 L (mouse Damp1 L) enhances immune, inflammatory responses, it is logical to generate anti-Bst2 L to treat various immune, inflammatory diseases. Combination therapy of anti-Bst2 antibody and anti-Bst2 L antibody is also contemplated.

Anti-Bst2 Antibody

Conventional IgG antibodies are bivalent with the ability to bind to two antigens. This ability greatly increases their functional affinity and confers high retention time on many cell surface receptors and antigens. Anti-Bst2 antibodies could be antagonistic or agonistic antibodies, that inhibit or augment immune, inflammatory responses, respectively. Both antagonistic and agonistic anti-Bst2 antibodies may be obtained in the following examples of many different anti-Bst2 antibody formats.

1. The anti-Bst2 antibodies of the invention may be humanized monoclonal antibodies or human monoclonal antibodies. An entirely antigenic murine mAb becomes human friendly when small parts of the murine antibodies are engrafted onto human immunoglobulin molecules creating either chimeric antibodies where only the Fc part of the immunoglobulin molecule is human, or humanized antibodies where only the complementarity determining regions (CDR) of the immunoglobulin are murine and 90 to 95% of the molecule is human. In one respect, fully human monoclonal antibodies may be generated in transgenic mice by employing conventional methods such as HuMAb-Mouse (GenPharm-Medarex) or XenoMouse (Abgenix, Inc.) technology. Humanized antibodies include human immunoglobulins in which residues from a CDR of the recipient are replaced by residues from a CDR of a non-human species such as mouse, rat or rabbit having the desired specificity, affinity and biological function.

Human antibodies also can be produced using techniques such as phage display libraries (Hoogenboom and Winter, J. Mol. Biol, 1991, 227:381, Marks et al., J. Mol. Biol. 1991, 222:581). Methods for humanizing non-human antibodies are well known. Humanization can be performed following the method of Winter et al. as disclosed in Jones et al., Nature, 1986, 321:522; Riechmann et al., Nature, 1988, 332:323; and Verhoeyen et al., Science, 1988, 239:1534 by substituting rodent CDR sequences or CDRs for the corresponding sequences of a human antibody. Such humanized antibodies are chimeric antibodies (U.S. Pat. No. 4,816,567). Typically, humanized antibodies are antibodies where CDR residues are substituted by residues from analogous sites in rodent antibodies.

2. The anti-Bst2 antibodies of the invention may be Nanobodies. Heavy chain antibodies that function without light chains are naturally occurring in nurse sharks, wobbegong sharks and Camelidae (Greenberg A S. et al. 1995, Nature 374:168; Nuttall S D. et al. Mol. Immunol. 2001, 38:313; Hamers-Casterman C. et al. 1993, Nature 363:446). Their antigen-binding site is reduced to a single domain, the VhH domain. Because the variable domain of the heavy chain antibodies is the smallest fully functional antigen-binding fragment with a molecular mass of only 15 kDa, this entity is referred to as Nanobody.

Nanobody may become a new class of therapeutic antibodies. Nanobodies have superior properties compared with classical antibodies in that they are small, very stable, easy to produce in large quantities and easy to reformat into multivalent or multi-specific proteins. Nanobodies may be administered through non-injectable means. Thus, Nanobodies offer the binding affinity and specificity of antibodies, with the small size, stability and pharmacokinetics of small molecules.

The small size of Nanobodies make them particularly suitable for targeting antigens in obstructed locations such as tumors where penetration is critical, or in the regions that are inaccessible to conventional antibodies. Anti-Bst2 Nanobodies could be useful for in vitro diagnostic immunoassays and in vivo imaging applications. Anti-Bst2 Nanobodies may cross the Blood-Brain barrier and thus may deliver the therapeutic Nanobody into the brain.

Anti-Bst2 Nanobody can be obtained using phage display technique. Nanobody library is constructed from the immunized dromedary as described (Conrath K E. et al. Antimicrob Agents Chemother. 2001, 45:2807). The phage display library is then used for panning on human Bst2 coated on microtiter plates. Selection of enriched clones is performed by ELISA, and clones are sequenced. Proteins are purified from positive clones.

3. The anti-Bst2 antibodies of the invention may be bispecific antibodies. Bispecific antibodies are monoclonal antibodies, preferably human or humanized antibodies that have dual-targeting specificities. Bispecific antibodies are derived from the recombination of variable domains of two antibodies with different specificities; Bispecific antibodies are thus capable of binding both antigens of their parental antibodies. In the case of anti-Bst2, one of the binding specificities could be for Bst2 and the other may be for Bst2 L, or any other cell surface protein, for example, receptors on T cells or other inflammatory proteins on the surface of the same cells that express Bst2 under inflammatory or autoimmune conditions. These bispecific anti-Bst2 antibodies may function as antagonistic or agonistic antibodies.

Methods for making bispecific antibodies are well known (Traunecker et al., EMBO J, 1991, 10:3655; WO 93/08829; Suresh et al., Methods in Enzmology, 1986, 121:210; Milstein and Cuello, 1983, Nature, 305:537). Briefly, antibody variable domains with the desired binding specificities are fused to immunoglobulin constant domain. This fusion contains an immunoglobulin heavy-chain constant domain (part of the hinge, CH2 and CH3 regions) and preferably contains the first heavy chain constant region (CH1). DNAs encoding the immunoglobulin heavy chain fusions and the immunoglobulin light chain are inserted into separate expression vectors and are cotransfected.

4. The anti-Bst2 antibodies of the invention may be single-chain variable fragment antibody (scFV). Recombinant approaches have led to the development of single chain variable fragment antibody (scFv). A monomeric scFv has a molecular mass of only about 30 kDa, which is expressed in a variety of systems as a single VL-VH pair linked by a Gly/Ser-rich synthetic linker (Berezov A. et al., 2001, J Med Chem 44:2565). When expressed in bacteria or eukaryotic cells, the scFv folds into a conformation similar to the corresponding region of the parental antibody. It was shown to retain comparable affinity to that of a Fab (Kortt et al., 1994, Eur J Biochem 221:151). ScFvs are amenable to various genetic modifications such as humanization and the production of fusion proteins to enhance their potential as therapeutic agents. For example, Pexelizumab, a humanized scFv that binds to the C5 component of complement has been shown to reduce myocardial infarctions during coronary artery bypass graft surgery (Varrier et al., 2004, JAMA 291:2319).

ScFvs of different specificity can also be linked together to produce bispecific antibodies that bind two different receptors on single or different cells. In the case of anti-Bst2, it could be bispecific antibody-like molecules with an anti-Bst2 scFv and anti-Bst2 L scFv, or with anti-Bst2 scFv and any other cell surface proteins, for example, receptors on T cells or other inflammatory proteins on the surface of the same cells that express Bst2 under inflammatory or autoimmune conditions.

Phage display method may be used to produce anti-Bst2 scFv. In this method, large repertoires of antibody variable region cDNAs are collected from the B cells and combinations of VHs and VLs are expressed in the form of scFvs on the surface of filamentous bacteriophage. The phages that express scFvs are to be panned from antigen-coated plates. The affinity of the anti-Bst2 scFv may be improved by mutating the CDRs of the construct and then repeating the panning procedure.

5. The anti-Bst2 antibodies of the invention may be Fab, Fab2 bispecific antibodies, Fab3 trispecific antibodies, bivalent minibody, trivalent triabody, or tetravalent tetrabodies.

6. The anti-Bst2 antibodies of the invention may be monoclonal antibodies. Monoclonal antibodies are prepared using hybridoma methods, such as those described by Kohler and Milstein (Nature, 1975, 256:495). Mouse, rat, hamster or other host animals, is immunized with an immunizing agent to generate lymphocytes that produce antibodies with binding specificity to the immunizing antigen. In an alternative approach, the lymphocytes may be immunized in vitro.

Monoclonal Antibody to Bst2

The use of immune therapy has become popular recently in case where the protein target of a disease has been determined. The highly specific targeting allowed by therapeutic antibodies results in virtually no side effects, even at relatively high doses. This also makes use of the antibodies' naturally inherent serum stability, providing the basis for a long-acting therapeutic molecule.

Antibody therapeutics generally falls into one of two categories that are not mutually exclusive. The first category is dependent on the variable region (target protein recognition portion) of the antibody. The specific epitope recognized by the antibody will allow the antibody to inhibit the binding of the target protein with other proteins (inhibitory or antagonistic effect) interfering with cell-cell interactions or terminating signal transduction through the target protein, or generate an artificial signal as a result of its binding with the target protein in the absence of a required secondary protein (activation or agonistic effect) as is the case of dimerization-dependent receptor signaling or receptor-dependent ligand mimicking. The second category depends on the constant region (Fc portion) of the antibody, that determines which, if any, immune effector functions will become activated as a result of the binding of the Fc portion of the antibody with its cognate Fc receptor present on the immune effector cells. The presence of a specific target protein on the surface of a target cell targets that cell for destruction by an effector function.

By developing an antibody that is highly specific for Bst2, we have been able to create a therapeutic antibody that shares many of the characteristics of the decoy Bst2 molecule, in that it is capable of interfering with cell-cell adhesion and acting as a therapeutic protein in inhibiting disease-specific inflammatory response.

In certain cases that deal with the pathogenic mechanisms of the mucosal immune system, antibodies may be administered orally or nasally. The mucosal immune system is unique, as tolerance is preferentially induced after exposure to antigen, and induction of regulatory T cells is a primary mechanism of oral tolerance. Orally administered antibody can be rapidly taken up by the gut-associated lymphoid tissue (GALT), where it exerts its immunologic effects. Oral administration of antibody can signal T cells in the gut in a fashion that delivers a weak but effective signal in enhancing the regulatory function of T cells. Oral administration of CD3 specific antibody has been demonstrated in experimental autoimmune encephalitis (EAE) model. These studies showed that the Fc portion of the CD3-specific antibody was not required. An orally administered $F(ab')_2$ fragment of CD3-specific antibody suppressed EAE.

Antibody Engineering

1. Antibody Engineering

Once therapeutic anti-Bst2 antibodies are available, the next step is to engineer the antigen-binding domains (affinity maturation, stability) and alter the effector functions (antibody-dependent cellular cytotoxicity (ADCC), complement-dependent cellular cytotoxicity (CDC), and clearance rate). Another way to improve the potency of anti-Bst2 antibodies is to pursue antibody-toxin conjugate, bispecific antibody and/or to explore FcR (Fc receptor) polymorphism.

Anti-Bst2 antibodies block interaction between Bst2 and Bst2 L after binding to the cell bound Bst2 to result in intervention of a cellular signal. For antibody engineering, it is important to characterize the anti-Bst2 antibodies if they cross-link to elicit intracellular signal for apoptosis, deliver toxins to a cell after internalization, or use effector functions to kill cells. All these parameters of anti-Bst2 may be important in treatment of autoimmune/inflammatory conditions.

1-1. Improvement of Anti-Bst2 Antibodies Via Engineering of the Antigen Binding Domains 1-1-1. F(ab) Fragment of Anti-Bst2

F(ab) fragments of anti-Bst2 may be used when rapid clearance or a short-half life is required such as in the case of ReoPro (Centocor). Because of their smaller size, F(ab) fragments may better penetrate solid tissues. F(ab) fragments can be made in *E. coli* rather than in mammalian cells. Cross-linking of Bst2 by a bivalent, full-length anti Bst2 antibodies may cause apoptosis of the target cells. Depending on the diseases to be treated, such apoptosis may be either advantageous or deleterious. Use of an F(ab) may be beneficial if cross-linking of Bst2 by a full-length anti-Bst2 antibody is deleterious.

1-1-2. Affinity Maturation

Somatic hypermutation of immunoglobulin genes is critical in the generation of high-affinity antibodies in vivo but occurs only after immunization. Thus, in phage display libraries from nonimmunized donors, high-affinity antibodies are rarely found. In vitro affinity maturation is often needed to improve antibodies from such libraries. Regardless of whether anti-Bst2 antibody is derived from phage library, hybridoma or other technologies, the antibody affinity may need improvement. Affinity may not only be important for efficient blockage of the Bst2-Bst2 L interaction, but also for a reduced dosage and cost-effectiveness.

With regard to antibody affinity, however, it may not be always the case that anti-Bst2 antibodies with the strongest binding would be the best selection. One antibody may bind strongly to Bst2 but cover only part of the Bst2 L binding site on Bst2, whereas another antibody may bind to Bst2 less strongly but accurately cover the Bst2 L binding site. The latter may be the better choice. In studies by Adams et al. using anti-Her2 antibodies (Cancer Res. 61:4750, 2001), the highest affinity antibody did not exhibit optimal penetrance to a solid tissue/tumor. High affinity scFv fragments were retained in the periphery of the tumor, whereas the medium affinity antibodies penetrated throughout the tumor. Depending on the diseases to treat, impaired tissue penetrance may be a potential concern for affinity maturation of anti-Bst2 antibodies.

1-1-2-1. General Methods for Affinity Maturation

In affinity maturation (Levin and Weiss, Mol. BioSyst. 2:49, 2006), residues in the CDRs are varied using mutagenesis, and the resulting mutated antibodies are screened for improved binding and efficacy. Several methods of affinity maturation have been published. These include affinity maturation via phage (Gram et al. PNAS 89:3576, 1992; Lowman et al., J. Mol. Biol., 1993, 234, 564), ribosome-display (Lipovsek et al. J. Immunol. Methods 290 (2004), pp. 51-67), yeast surface-display (Graff et al. Protein Eng. Des. Sel. 17 (2004), pp. 293-304), error-prone PCR (Schlapschy et al. Protein Eng. Des. Sel. 17 (2004), pp. 847-860), mutator bacterial strains (Low et al. J. Mol. Biol. 260:359, 1996), stepwise focused mutagenesis (Wu et al. PNAS 95:6037, 1998) and saturation mutagenesis (Nishimiya et al. J. Biol. Chem. 275:12813, 2000; Yang et al. J. Mol. Biol. 254:392, 1995; Chowdhury and Pastan Nat. Biotechnol. 17:568, 1999). Other techniques often use alanine-scanning or site-directed mutagenesis to generate limited collections of specific variants.

1-1-2-2. Affinity Maturation Via Look-Through Mutagenesis (LTM) Method

Recently, Rajpal et al. (Bioren, San Carlos, Calif.) has developed Look-Through Mutagenesis (LTM) technology to optimize antibodies using the yeast display system. LTM may be applicable to the affinity maturation of anti-Bst2 antibodies. LTM may be also useful for screening high-affinity variants of Bst2 decoy (or Bst2 decoy-Fc). A brief description of the method according to Rajpal et al. is illustrated below for affinity maturation of anti-Bst2 antibodies.

LTM is a multidimensional mutagenesis method that allows a single amino acid mutation in all positions for each CDR for rapid affinity enhancement. In LTM, targeted positions are substituted with either the wild-type residue or one of nine amino acids representing the major side chain chemistries-small (A), nucleophilic (S, H), hydrophobic (L, P), aromatic (Y), acidic (D), amide (O), or basic (K). LTM generates a series of single mutations within a CDR where each wild type residue is substituted by one of nine selected amino acids.

First, the anti-Bst2 scFv construct is assembled by overlap PCR using codons optimized for both *S. cerevisiae* and *E. coli*, and subcloned into yeast display vector. This original construct serves as the template for subsequent anti-Bst2 LTM libraries. For anti-Bst2 LTM library construction, individual CDR oligonucleotides are synthesized to encode a mutagenized CDR with one target amino acid substitution for each CDR position. PCRs containing LTM oligonucleotide mixtures are used to amplify LTM-substituted CDR fragments. In the triple CDR library, oligonucleotides for CDR1, CDR2 and CDR3 are combined to produce libraries with three mutagenized CDRs (both for VH and VL domains). Corresponding antibody libraries are then displayed on the cell surface of yeast.

After positive selection, clones that result in higher affinity binding to Bst2 are sequenced, and those beneficial mutations are mapped. To identify synergistic mutations for improved binding, libraries of combinatorial beneficial mutations are generated by mixed degenerate DNA probes. Degenerate oligonucleotides encoding the selected amino acid mutations and the wild-type amino acid are synthesized and assembled to produce these libraries. For positive clone selection, Bst2 (or Bst2 decoy) is biotinylated. Cells are incubated with biotinylated Bst2 and bound to Streptavidin beads. A pulse-chase strategy to label the yeast cells with biotinylated Bst2 (or Bst2 decoy) and chase with unlabeled Bst2 (or Bst2 decoy) is used to select for clones that display greater binding to biotinylated Bst2 (or Bst2 decoy). These clones can be sorted by FACS. After several rounds of selections, mutations conferring higher affinity could be obtained. All scFvs are then subcloned into expression vectors and secreted into the *E. coli*. Binding affinities of the scFv antibodies are measured by using a BIAcore surface plasmon resonance system (BIAcore, Switzerland).

1-1-3. High Affinity Antibodies without Affinity Maturation

Hoet et al. at Dyax has constructed human F(ab) libraries having a combination of naturally occurring heavy chain CDR3 and light chain sequences obtained from human donors, and synthetic diversity in antigen contact sites in heavy CDR1 and CDR2. F(ab)s selected for binding to four human drug targets using the Dyax F(ab) library showed higher affinities than approved therapeutic antibodies (Hoet et al. Nature Biotechnol. 23:344, 2005). Such F(ab) libraries may provide an efficient means to generate high-affinity anti-Bst2 antibodies circumventing the need for affinity maturation.

1-1-4. Elimination of the Asn-linked Glycosylation in the Variable Domain

The Asn-linked glycosylation in the antibody variable domain could affect antigen binding (Leibiger et al. Biochem J. 338:529, 1999). If the Asn-linked glycosylation is observed in the variable domain of the anti-Bst2 antibodies and the carbohydrate is not required for binding or biological activity of the antibodies, the Asn in the variable region may be removed by altering the Asn to Ala, Gln or other amino acids.

An Asn-Gly or Asp-Gly sequence in CDR has been reported to undergo spontaneous isomerization to form isoaspartic acid (Cacia et al. Biochemistry 35:1897, 1996). Formation of isoaspartate may debilitate or abrogate the binding of the antibody. If CDRs in the anti-Bst2 antibodies contain these sequences, substitution of the Asn or Asp with Ala, Gln, or Glu may be beneficial. One can determine if these substitutions can maintain the antibody binding and efficacy.

The presence of methionine in a CDR could be problematic as well if the methionine is oxidized and this interferes with binding. If this is the case with anti-Bst2 antibodies, one can investigate substituting methionine with other amino acids.

1-1-5. Increase in Stability of Anti-Bst2 through Mutagenesis of the Antigen Binding Domains Stability of anti-Bst2 may be obtained by altering specific residues that influence stability, grafting of the CDRs from an unstable scFv onto a more stable framework as has been shown by Angal et al. (Mol. Immunol. 30:105, 1993), or altering the VH-VL interface via introduction of disulfide bonds as shown by Schuurman et al. (Mol. Immunol. 38:1, 2001).

1-2. Improvement of Anti-Bst2 Antibodies Via Fc Engineering

Unlike small molecular weight drugs, which must be able to both bind a target and affect its function, therapeutic antibodies can bind a target and direct the immune system to attack it through effector functions: antibody-dependent cellular cytotoxicity (ADCC), complement-dependent cytotoxicity (CDC) and phagocytosis. However, monoclonal antibodies that function by blocking a ligand-receptor interaction, which may be the case of anti-Bst2 antibodies, can function without utilizing effector mechanisms (Agus et al. J. Clin. Oncol. 23 (2005), pp. 2534-2543; Wang et al. Angiogenesis 7 (2004), pp. 335-345).

Nevertheless, enhanced effector function could be beneficial in the action of anti-Bst2 antibodies. For example, all CD20-directed monoclonal antibody therapies result in temporary B cell depletion for the treatment of autoimmune, inflammatory conditions, specifically rheumatoid arthritis, due to the effector functions. Infliximab (anti-TNF alpha) is also known to result in CDC and ADCC following binding to TNF alpha in vivo (Scallon et al. Cytokine, 1995).

For anti-Bst2 antibodies, it is important to decide whether activation of ADCC, CDC and/or subsequent destruction of the target cell are beneficial or deleterious for the treatment of diseases. One way to assess the effect of ADCC and CDC on the therapeutic function of anti-Bst2 is to test the efficacy of anti-Bst2 antibodies in FcγR knock-out mice.

1-2-1. Use of Bst2 Knock-in FcγR Knock-out (Double Mutants) to Determine Whether the Effector Functions are Advantageous or Deleterious.

ADCC and phagocytosis are mediated through interaction with a set of closely related Fc gamma receptors (FcγR) with both activating and inhibitory activities; CDC through interaction with proteins in the complement system (e.g. C1q, C3, C4, etc.); and half-life/clearance rate through binding of antibodies to the neonatal Fc receptor (FcRn). The role of FcγR (and potentially ADCC) in the mechanism of action of anti-Bst2 antibodies can be investigated by using mice deficient in the common gamma chain (FcγR−/−) (Takai et al. Cell 76:519, 1994), lacking the activation Fc receptors FcγRI and FcγRIII, and mice deficient in FcγRIIB (Takai et al. Nature 379:346, 1996).

Bst2 knock-in mice crossed with FcγR knock-out would be used. When Bst2 knock-in is generated in C57Bl/6 mice, for example, an FcγR-deficient strain is crossed to C57Bl/6 and back-crossed to establish a syngenic strain. This syngenic strain is then mated with Bst2 knock-in mice to generate FcγR−/−/Bst2/Bst2 and FcγRIIB−/−/Bst2/Bst2 mice. These double mutant mice are subject to disease-inducible treatments. Mice are then treated with anti-Bst2 antibodies.

1-2-2. Improvement of Anti-Bst2 Activity through Enhancement of Effector Functions and/or Stability If anti-Bst2 antibodies use ADCC for therapeutic action, engineering the IgG Fc to improve effector function (via improved binding to FcγR and/or complement) could be a valuable enhancement to the therapeutic antibody. Improved binding has been achieved by mutating residues in the Fc (Shields et al. J. Biol. Chem. 276:6591, 2001), removal of the fucose moiety from the conserved carbohydrate in the Fc (Shields et al. J. Biol. Chem. 277:26733, 2002; Shinkawa et al. J. Biol. Chem. 276:3466, 2003) and multiple Fc (Scallon et al., Mol. Immunol. 41:73, 2004).

1-2-2-1. Via Amino Acid Changes in the Fc

Alteration of amino acid residues in the human IgG has been shown to enhance FcγR binding and effector function. Much of such work focused on the hinge (residues 216-230) and lower hinge region (residues 231-236). In recent years, a comprehensive map of the binding site on human IgG1 for human FcRI, FcRIIA, FcRIIB, FcRIIIA, and FcRn receptors has been published (Shields et al., J. Biol. Chem. 276:6591, 2001 and references therein). In this study, select IgG1 variants with improved binding to FcRIIIA exhibited significant enhancement in ADCC. It has been also reported that it may be possible to improve C1q binding by alteration of specific IgG1 residues (Idusogie et al., J. Immunol. 166 (2001), pp. 2571-2575).

The neonatal Fc receptor (FcRn) plays a role in clearance rate of therapeutic monoclonal antibodies (Lencer and Blumberg, Trends Cell Biol. 15 (2005), pp. 5-9). In contrast to the FcγRs which are immunoglobulin superfamily members, FcRn is structurally related to MHC class I, comprising a γ-chain that non-covalently associates with α2-microglobulin (Martin et al. Mol. Cell. 7 (2001), pp. 867-877).

The information generated by Shields et al. would be helpful to design anti-Bst2 variants with improved binding to FcγR to enhance effector functions. Increase of the half-life of anti-Bst2 may be obtained by changing their affinity for FcRn.

1-2-2-2. Defucosylation of Anti-Bst2 Antibodies for Enhanced Effector Function

Another way to improve effector functions of anti Bst2 antibodies may be by changing glycosylation (fucosylation or sialylation) at Asn297 in the Fc domain.

Glycosylation of IgG is essential for binding to all Fc gamma receptors (Jefferis and Lund, Immunol. Lett. 82:57, 2002). On human IgG, the Asn297-linked carbohydrate is found in the Fc domain. This complex carbohydrate is composed of a core oligosaccharide that contains GlcNAc (N-acetylglucosamine) and mannose. The core also contains various additional monosaccharides attached such as galactose, fucose, GlcNAc, and/or galactose-sialic acid at one or both of the terminal N-acetylglucosamine. Over 30 different covalently attached glycans have been detected at this single glycosylation site (Routier et al., J. Immunol. Methods 213: 113, 1998).

The presence or absence of the fucose moiety has been shown to play a significant role in binding to FcγR. Defucosylated monoclonal antibodies exhibited significantly increased binding to FcγR and showed enhanced ADCC in vitro (Shields et al., J. Biol. Chem. 277 (2002), pp. 26733-26740; Shinkawa et al. J. Biol. Chem. 276 (2003), pp. 3466-3473; Nimmerjahn and Ravetch, Science 310:1510, 2005; Niwa et al. Cancer Res. 64 (2004), pp. 2127-2133).

Subsequently, an engineered Chinese hamster ovary cell line in which α-1,6-fucosyltransferase was knocked out has been established (Yamane-Ohnuki et al. Biotechnol. Bioeng. 67 (2004), pp. 614-622). GlyArt (Zurich) and BioWa (Princeton, N.J.) developed technology that engineers cell lines to make antibodies with decreased fucosylation. Antibodies produced with this cell line lacked fucose and the defucosylated antibodies showed enhanced ADCC in vitro (Niwa et al. Cancer Res 64:2127, 2004).

1-2-2-3. Fc Sialylation Change in Anti Bst2 Antibodies for Enhanced Effector Function Fc receptors sense the presence on IgG of both fucose and sialic acid residues. Recent studies showed that Fc sialic acids at the Asn297 site are critical in determining the interaction of IgG and Fc receptors for antibody activity (Kaneko et al. Science 313:670, 2006) further supporting a role of glycosylation in immune response. Sialylation of the Asn297-linked glycan of IgG resulted in reduced binding affinities to the FcγRs and reduced in vivo cytotoxicity.

The sialylation change in anti-Bst2 antibodies might be beneficial in improving the potency of anti-Bst2 antibodies. The influence of sialic acids on anti-Bst2 activity can be investigated by performing surface plasmon resonance binding analysis (BIAcore analysis) with neuraminidase-treated, asialylated anti-Bst2 antibodies and the sialic acid-containing anti-Bst2 antibodies. Anti-Bst2 antibodies enriched in sialic acid content may be obtainable by lectin affinity chromatography. Binding affinity of asialylated-and sialic acid-containing anti-Bst2 antibodies to activating or inhibitory FcγRs should be compared first. These antibodies may show differences in binding affinity for the FcγRs, while they would not show any differences in binding affinity for Bst2. The in vivo efficacy of asialylated (neuraminidase-treated) anti-Bst2 antibodies is then tested using animal models and compared with that of sialylated anti-Bst2 antibodies or normal, untreated anti-Bst2 antibodies. Because the sequences of IgG oligosaccharides are determined by the level of glycosyltransferases or glycosidases, sialylation change in anti-Bst2 antibodies may be achieved by cell engineering.

1-2-2-4 Attachment of Xencor's Fc Variants to Anti-Bst2 F(ab)

Attachment of new Fc variants such as Xencor's to anti-Bst2 F(ab) may enhance anti-Bst2 potency.

Lazar et al. at Xencor (Monrovia, Calif.) used a combination of computational design algorithms and high throughput protein screening to change amino acids in the Fc region, either enhancing or decreasing the response by the immune system (Lazar et al. PNAS 103:4005, 2006). Xencor has engineered a series of Fc variants with optimized FcγR affinity and specificity. When the Xencor's new Fc was attached to trastuzumab (Herceptin; Genentech, S. San Francisco, Calif., USA) and rituximab (Rituxan; Genentech), it improved the antibodies' potency by about 500-fold in an in vitro assay; altered rituximab was also more potent in a monkey model.

1-2-3. Improvement of Anti-Bst2 Activity through Elimination of Effector Functions In different cases, depending on the diseases to treat, effector functions of anti-Bst2 antibodies may be unnecessary or even detrimental. For example, anti-CD3 (Xu, M. L. et al. Cell. Immunol. 200 (2000), pp. 16-26; Carpenter et al. J. Immunol. 165 (2000), pp. 6205-6213; Bolt et al. Eur. J. Immunol. 23 (1993), pp. 403-411) and anti-CD4 (Newman et al. Clin. Immunol. 98 (2001), pp. 164-174) targeted to T cells showed deleterious side-effects due to binding of the monoclonal antibodies to FcγR-bearing cells, effecting T cell depletion or activation. In the case of anti-CD3, engineered variants with reduced FcγR binding alleviated the problem (Herold et al. Diabetes 54 (2005), pp. 1763-1769; Carpenter et al. Biol. Blood Marrow Transplant. 11 (2005), pp. 465-471).

1-2-3-1. Use of IgG4 or IgG2 for Anti-Bst2

When effector functions of anti-Bst2 are not warranted, one could use either human IgG2 or IgG4, since these two subclasses are inefficient at or lack complement fixation (Presta L G, J Allergy Clin Immunol. 2005, 116(4):731). Because lack of complement activation by IgG4 has been consistently reported, given the choice between using IgG2 or IgG4, IgG4 is thought to be the better choice. However, antibodies of a specific subclass may not be equivalent in the efficacy of their effector function (Chan et al. Mol. Immunol. 41 (2004), pp. 527-538).

1-2-3-2. Removal of Asn297-linked Glycosylation from the Anti-Bst2 Antibodies

Absence of the carbohydrate attached to Asn297 of the Fc was reported to result in reduced effector functions in some cases (Leatherbarrow et al. Mol. Immunol. 22 (1985), pp. 407-415). Furthermore, a recent report of a phase II clinical trial of aglycosylated anti-CD3 (Keymeulen et al. N. Engl. J. Med. 352 (2005), pp. 2598-2608) in type 1 diabetes showed some promise.

1-2-3-3. Mutagenesis of Residues in the Anti-Bst2 Fc for Decreased Binding to FcR Using the comprehensive map of the binding site on human IgG1 disclosed by Shields et al. (Shields et al., J. Biol. Chem. 276:6591, 2001 and references therein), it may be possible to design anti-Bst2 variants with decreased binding to FcγR or FcRN.

1-2-3-4. Fc Hinge Variants of Anti-Bst2 for Decreased Effector Function

When the effector functions are not advantageous for anti-Bst2 antibodies, hinge variants of anti-Bst2 may be pursued. Exchanging hinge regions between IgG subclasses showed that the hinge is important for FcγR and C1q binding. Specific mutations in the hinge (Leu235Glu) or outside the hinge (Asp265Ala) showed reduced binding to FcγR (Shields et al. J. Biol. Chem. 276 (2001), pp. 6591-6604; Lund et al. FASEB J. 9 (1995), pp. 115-119; Morgan et al. Immunology 86 (1995), pp. 318-324; Clynes et al. Nat. Med. 6 (2000), pp. 443-446). Hinge variant anti-CD3 monoclonal antibodies with debilitated effector function are now in clinical trials (Herold et al. Diabetes 54 (2005), pp. 1763-1769; Carpenter et al. Biol. Blood Marrow Transplant. 11 (2005), pp. 465-471).

1-3. Improvement of Anti-Bst2 by Generating Bispecific Antibodies

Bispecific antibody that targets Bst2 and another drug target for inflammatory diseases that are expressed on the same cell may elicit ADCC and CDC more efficiently. Such bispecific Bst2 antibodies may be more potent than antibodies targeting a single antigen. Bispecific antibodies that target epidermal growth factor receptor and insulin like growth factor receptor were reported to be more potent than antibodies targeting a single antigen (Lu D. J. Biol. Chem. 279:2856, 2004).

1-4. Improvement of Anti Bst2 by Generating Antibody Conjugates with Toxic Materials Another way to improve the power of antibodies is by linking them to toxins or radioactive ligands. The antibody binds the target on the cells, internalizes, delivers the toxin and kills the cell. These toxins are attached to antibodies by using a linker that is cleaved by intracellular enzymes such as cathepsins. The choice of both the drug and the linker are crucial. If the linker is cleaved outside the cell, toxins are released in the bloodstream. Anti-Bst2 antibodies that internalize after binding to Bst2 are required for targeted delivery of toxins. Some anti-Bst2 antibodies may bind strongly to Bst2 but not at an epitope that is optimal for internalization. For this reason, development of screening techniques to select for anti-Bst2 antibodies which are most efficiently internalized is required. Methods for screening antibodies with enhanced internalization have been developed (Marks J D, Methods Mol. Biol. 248:201, 2004; Neve et al. Biochem. Biophys. Res. Commun. 280 (2001), pp. 274-279; Heitner et al. J. Immunol. Methods 248 (2001), pp. 17-30).

1-5. Improvement of Anti Bst2 Antibodies Via FcR Polymorphism

FcR polymorphism appears to play a significant role in many diseases including autoimmune diseases, infectious diseases, cardiovascular diseases, atherosclerosis and transplantation biology (van Sorge et al. Tissue Antigens 61 (2003), pp. 189-202; Karassa et al. Biomed. Pharmacother. 58 (2004), pp. 286-291; Kastbom et al. Rheumatology 44 (2005), pp. 1294-1298; van Sorge et al. J. Neuroimmunol. 162 (2005), pp. 157-164; Brouwer et al. J. Infect. Dis. 190 (2004), pp. 1192-1198; Gruel et al. Blood 104 (2004), pp. 2791-2793; Gavasso et al. Atherosclerosis 180 (2005), pp. 277-282; van der Meer et al. Thromb. Haemost. 92 (2004), pp. 1273-1276; Pawlik et al. Transplant. Proc. 36 (2004), pp. 1311-1313).

It has been also reported that FcγR polymorphic forms of patients affect response to therapeutic monoclonal antibodies such as rituximab (anti-CD20) for cancers (Cartron et al. Blood 99 (2002), pp. 754-758; Carton et al. Blood 104 (2004), pp. 2635-2642; Treon et al. J. Clin. Oncol. 23 (2005), pp. 474-481; Ghielmini et al. Ann. Oncol. 16 (2005), pp. 1675-1682), rituximab for systemic lupus erythematosus (Anolik et al. Arthritis Rheum. 48 (2003), pp. 455-459), and alemtuzumab (anti-CD52) for chronic lymphocytic leukemia (Lin et al., Blood 105 (2005), pp. 289-291).

Thus, in diseases where FcγR polymorphism may play a role, engineering of anti-Bst2 antibodies with enhanced or reduced binding to FcγR may provide a new class of therapeutic anti-Bst2 monoclonal antibodies.

Stem Cell Expansion

Bst2 is also thought to play a role in cell growth and proliferation to promote growth and differentiation of hematopoietic cells. As a bone marrow stromal cell antigen and an adhesion protein, Bst2 may play a major role for critical cell-cell interaction in hematopoiesis and differentiation of other stem cells.

The growth and differentiation of many hematopoietic cells in vivo require direct contact with stromal cells that produce a variety of growth factors and, in some systems, direct contact between stromal cells and hematopoietic cells is required for cell growth and differentiation (Daniel et al., Haematol. Blood Transfus. 32:172, 1989). Thus, bone marrow stromal cells and bone marrow stromal cell antigens are important regulators of cell survival and apoptosis.

The bone marrow contains various types of stem cells. Among them are hematopoietic stem cells, which are the precursors of all blood cells, and mesenchymal stem cells. Mesenchymal stem cells transdifferentiate into many different cell types; bone cells, adipocytes, chondrocytes, tendocytes, neural cells and stromal cells of the bone marrow. Bst2 may also regulate differentiation of mesenchymal stem cells.

The importance of stromal cells in regulating the proliferation and apoptosis is further exemplified in the regulation of cell survival and apoptosis of cancer cells including leukemia cells. For instance, AML leukemia cells were shown to be protected from chemotherapy-induced apoptosis when the leukemia cells are incubated with bone marrow stromal cells (Gamido et al., Exp. Hematol 29:448, 2001; Konopleva M et al. Leukemia 16:1713, 2002). Recent study showed that Bst2 directly mediates the regulatory effects of bone marrow stromal cells on the leukemia cells, leading to leukemia-cell protection from chemotherapy-induced apoptosis (Ge et al., Blood 107:1570, 2006). Consistent with such role of Bst2 in chemosensitivity, Bst2 has also been reported to be up-regulated in tamoxifen-resistant breast cancer cells (Becker et al., Mol. Cancer. Ther. 4:151, 2005) suggesting potential multiple functions of Bst2 in different cancers. All of these studies suggest that Bst2 is a pleiotropic protein that mediates multiple functions.

Bst2 agonists, Bst2 peptide mimetics and Bst2 ligands may be used to stimulate stem cell growth/proliferation in vitro for a large preparation of stem cells. Ex vivo expanded stem cells may be used for transplantation. For example, mesenchymal stem cells cultured in vitro may be used for the enhancement of hematopoietic stem cell transplantation by rebuilding the bone marrow microenvironment which is damaged after radiation-and/or chemotherapy.

Bst2 agonists, Bst2 peptide mimetics and Bst2 ligands may be used for ex vivo expansion of mesenchymal stem cells for gene therapy. It is thought that mesenchymal stem cells are promising as vehicles for gene transfer and therapy. Cultured mesenchymal cells may home to the bone marrow after transplantation, differentiate and produce the intact protein.

Small Molecular Weight Modulators of Bst2

It is another aspect of the present invention to provide small molecular weight (m.w.) modulators of Bst2 for treatment of prevention of various immune/inflammatory diseases. Bst2 modulators can affect the function or activity of Bst2 in a cell and modulate or affect Bst2-Bst2 L interaction and signal transduction. In addition, Bst2 modulators can affect downstream targets and molecules that are regulated by, or that interact with, Bst2 in the cell.

The major factor for small m.w. compounds is whether the interaction interface between Bst2 and Bst2 L is small enough so that a small molecule could disrupt or augment enough of the Bst2/Bst2 L interactions to produce an inhibitor or activator with high affinity. Protein-protein interaction of the receptor and ligand usually requires a large interaction interface. Of these many residues, however, it is possible that only few residues in a very small area may contribute to the binding activity. Mutational studies suggest that protein-protein interactions in many cases are driven by a small set of the contact residues, termed "hot spots," whose footprints are not significantly larger than those covered by small molecules (Clackson T, Wells J A. Science. 1995; 267:383-386; DeLano W L. Curr Opin Struct Biol. 2002; 12:14-20. Wells J A. Proc Natl Acad Sci USA. 1996; 93:1-6).

If Bst2 binds to Bst2 L through small epitopes, the potential for finding small molecule ligands may be good.

Antagonist and Agonist Modulators of Bst2

Bst2 modulators include antagonists, agonists, peptide mimetics, inhibitors, ligands, and binding factors. Antagonists include compounds, materials, or drugs that antagonize, inhibit, reduce, block, suppress, diminish, decrease, or eliminate Bst2 protein function and/or activity in a cell's Bst2-Bst2 L interaction and/or Bst2 downstream signaling pathways. Agonist modulators of Bst2 include compounds or drugs that agonize, enhance, stimulate, increase, augment, or amplify Bst2 protein function and/or activity in a cell's Bst2-Bst2 L interaction and/or Bst2 downstream signaling pathways.

Utility of Bst2 Modulators

While anti-Bst2 antibodies and Bst2 decoy (Fc) could have a therapeutic role in immune/inflammatory diseases, small m.w. inhibitors with sufficient affinity to block Bst2 binding to Bst2 ligand would be also therapeutically valuable for the treatment of various immune/inflammatory diseases.

In addition to immune/inflammatory diseases, antagonist modulators of Bst2 could be also valuable for the treatment of some types of cancer. Bst2 may be involved in interaction between bone marrow stromal cells and cancer cells such as leukemic cells, leading to leukemic cell survival, as exemplified in recent studies by Ge Y et al. (Blood 107:1570, 2006). Bst2 may also play an important role for stromal cell interaction with cancer cells for tumor progression and invasion in some cancer such as prostate cancer or breast cancer.

Bst2 agonists, Bst2 peptide mimetics and Bst2 ligands may be therapeutically valuable for the treatment of patients with immune deficiency including HIV patients or immune compromised patients. Bst2 peptide mimetics synthesized with D form amino acids would be stable in vivo. These stable peptides may have greater therapeutic potential compared to the L form mimetics.

Bst2 agonists, Bst2 peptide mimetics and Bst2 ligands may also play a role in the treatment of anemia or bone diseases including osteoporosis. The hematopoietic system requires nurturing from a supportive stromal environment allowing maintenance and differentiation of hematopoietic stem cells (HSC). However, only a limited number of these stromal cell clones support hematopoiesis in the absence of cytokine supplementation. Bst2 agonists, Bst2 peptide mimetics and Bst2 ligands may be useful to promote hematopoiesis.

Bst2 agonists, Bst2 peptide mimetics and Bst2 ligands may be used for the treatment of bone marrow cells which have been damaged after radiation-and or chemotherapy. By restoring the bone marrow microenvironment, these Bst2 modulators may be useful for the treatment of cancer patients under chemotherapy or radiation therapy.

1. High Throughput Screening (HTS) Methods for Bst2 Modulators.

Several high throughput screening (HTS) methods are designed below based on the known properties of Bst2 and/or Bst2 L for screening of Bst2 modulators. Hit compounds identified by HTS methods are further evaluated by several secondary assay methods as indicated below.

1-1. High Throughput Screening of Bst2 Inhibitors by Detecting Direct Binding to Bst2 with Fluorescence Thermal Shift Assay.

Most small molecules that bind to Bst2 may modulate Bst2 activity in some manner, due to preferential or higher affinity binding to functional areas or sites on Bst2, for example, the Bst2 L binding site or the dimerization site important for the Bst2-Bst2 dimer formation. Screening and small molecule detection assays for identification of small molecules that can bind to Bst2 or Bst2 peptides can be designed using thermal shift assays. For thermal shift assays, all that is needed is the purified Bst2 protein and a chemical library. Fluorescence-based thermal shift assays would be particularly useful when the in vivo Bst2 ligands are unknown.

The drugs or binding molecules determined by this technique can be further assayed by methods, such as those described herein under Secondary screening assays, to determine if the molecules affect or modulate function or activity of Bst2.

1-1-1. Thermal Shift Assay

The fluorescence-based thermal shift assay (3-Dimensional Pharmaceuticals, Inc., 3DP, Exton, Pa.) as described in U.S. Pat. Nos. 6,020,141 and 6,036,920 to Pantoliano et al.; J. Zimmerman, 2000, Gen. Eng. News, 20(8); Pantoliano et al. J. Bioimol Screen 6:429, 2001; Lo M C et al. Anal Biochem. 332:153, 2004) is a general method for identification of inhibitors of target proteins from compound libraries. Pantoliano et al. described their fluorescence-based thermal shift assay apparatus for high-throughput drug screening.

In this assay, using an environmentally sensitive fluorescent dye to monitor protein thermal unfolding, the ligand-binding affinity is assessed from the shift of the unfolding temperature (Delta Tm) obtained in the presence of the compounds relative to that obtained in the absence of the compounds.

To monitor protein unfolding, the fluorescent dye such as Sypro orange is used. Sypro orange is an environmentally sensitive dye. The unfolding process exposes the hydrophobic region of proteins and results in a large increase in fluorescence, which is used to monitor the protein-unfolding transition.

Fully automated instrumentation has been designed and implemented by Pantoliano et al. to perform miniaturized fluorescence-based thermal shift assays in a microplate format for the high throughput screening of compound libraries (J. Biomol. Screen 6:429, 2001).

The thermal shift assay may be also conducted in the iCycler iQ Real Time Detection System (Bio-Rad, Hercules, Calif.), originally designed for PCR, as described by Lo et al. (Anal Biochem. 332:153, 2004). The system contains a heating/cooling device for accurate temperature control and a charge-coupled device (CCD) detector for simultaneous imaging of the fluorescence changes in the wells of the microplate. The reaction contains Bst2 (approximately 1 uM), Sypro orange, compound (0, 10, 50, 100 uM), and the buffer. The plate is heated from 25 to 89° C. with a heating rate of 0.5° C./min. The fluorescence intensity is measured with Ex/Em:490/530 nm. The fluorescence imaging data are analyzed according to Equations disclosed by Pantoliano et al. (J. Biomol. Screen 6:429, 2001). By fitting the fluorescence intensity to the equation, the midpoint temperature of transition, Tm, is obtained for each well.

1-2. High Throughput Screening of Bst2 Modulators by Detecting the Bst2-NFkB Pathway Using Dual Luciferase Reporter Assays Bst2 overexpression results in NFkB activation in mammalian cells (Matsuda et al., Oncogene 22:3307, 2003). Although the detailed signaling mechanism of Bst2 in the inflammatory pathways remains unknown, previous report by Matsuda et al. suggests that Bst2 overexpression and activation lead to the activation of NFkB-mediated transcription via NFkB response element.

Using this property of Bst2, high-throughput dual luciferase reporter assays (Promega, Madison, Wis., Paguio et al., Cell Notes 16:22, 2006) have been designed for the screening of Bst2 modulators by coupling Bst2 inhibition or activation to the regulation of luciferase reporter gene transcription.

1-2-1. DNA Constructs for HTS Dual Luciferase Assays and Stable Cell Lines

In this assay, the first plasmid is constructed to express, for instance, firefly luciferase coupled to tandem NFkB response elements upstream of firefly luciferase and a selection marker such as hygromycin (Promega). The second plasmid expresses Bst2 and another luciferase such as *Renilla* luciferase as an internal control—a selection marker (such as neomycin) fusion (Promega). The dual reporter luciferase Bst2 assay method has a built-in control using *Renilla* luciferase. The firefly luciferase activity for each sample is normalized using the *Renilla* luciferase activity.

Mammalian cells and cells transfected with the reporter constructs and the doubly transfected stable cell lines are then obtained for the high throughput screening assays. Control stable cell lines expressing an empty vector are also obtained. Bst2 expressing stable cells would show higher luciferase activity as reported in studies by Matsuda et al. (Oncogene 22:3307, 2003) compared to the control stable cells that contain an empty vector of the *Renilla* luciferase-neomycin fusion.

1-2-2. HTS Dual Reporter Luciferase Bst2 Assay

The screening assay is performed in a 384 well format using each compound (usually 10 uM or higher concentrations). Ten thousand cells/well are plated. Half of the wells are stimulated with compounds and half are mock stimulated. Cells are harvested after several hours. Luciferase activity is determined using the Dual Glo Luciferase Assay System (Promega) and quantified using the luminomitor. Results from a sample plate of NFkB-fire fly luciferase/Bst2 screen are obtained. Hits may be defined as reporter expression greater than three-to four-fold inhibition or activation above the average of the uninduced control. The control luciferase value obtained from the control stable cells would indicate the highest level of inhibition. All assays are performed in quadruplicates. Induction or inhibition is calculated as the average firefly (NFkB)-stimulated LU/average mock stimulated RLU.

1-2-3. Titration Experiments to Validate Hits

The doubly transfected stable NFkB response elements/Bst2 cell line is plated at 10,000 cells/well in a 96-well plate. Each compound is serially diluted 1:2, and added to wells in quadruplicates. Cells are incubated with antagonists or agonists for several hours, harvested and analyzed using the Dual Glo Assay System (Promega). Luciferase activity is measured on the GloMax 96 Microplate Luminometer (Promega).

1-3. High Throughput Screening of Bst2 Expression Modulators by Monitoring the Expression of the Bst2 Promoter/luc Using Dual Luciferase Assay There are many precedents of using the promoter containing reporter constructs for identifying small molecular weight therapeutics. For example, the promoters of BMP-2, BMP-4 and BMP-7 have been fused with the reporter molecule either beta galactosidase or luciferase to screen for the small molecules which can bind to the promoter and increase the expression of the reporter gene.

From the experiments using microarray it is evident that there are number of therapeutically important molecules which can induce BST2 (interferon gamma, TNF alpha, histamine, etc). In addition, from the literature search, it is evident that some other molecules could also do the same. In addition, (Blood 107:1570, 2006; Matsuda et al. Oncogene 22:3307, 2003; Goto et al. Blood 84:1922, 1994) the promoter region of the Bst2 gene has been analyzed. A number of important sites were found including that for AML, GATA1, STAT and AP1. All of these studies indicate that transcription regulation of Bst2 is an important regulatory mechanism of Bst2 function or activity in a cell.

HTS assays can be designed to identify compounds that bind to the regulatory sequences in the Bst2 gene. Bst2 promoter region (approximately 1 kb or more) is fused to upstream of the luciferase gene. Compounds screened after this assay may modulate the level of Bst2 gene expression. In the secondary screening assays, compounds are screened for inhibitory or stimulatory activity with respect to the cell-cell adhesion and inflammatory function of Bst2.

1-3-1. DNA Constructs and Stable Cell Lines

The Bst2 promoter region spanning 759 by upstream of the translation start site and 211 by of exon 1 is PCR amplified using forward (5'-ttcacgctagcccccctttgcagatgaa-gaaacaggctcaga-3' (SEQ ID NO:75)) and reverse (5'-ttcacctc-gaggcaggagatgggtgacattgcgacactc-3' (SEQ ID NO:76)) primers containing restriction enzyme sites for NheI and XhoI as reported by Ge et al. (Blood 107:1570, 2006). For constructing DNA vectors containing longer fragments of the Bst2 promoter, Bst2 promoter region spanning 1 kb or more is PCR amplified. The amplified product is digested with NheI and XhoI and ligated to the corresponding sites of the reporter gene vector expressing fire fly luciferase. This construct is used for high throughput screening using luciferase assay.

1-3-2. HTS Dual Reporter Luciferase Assay using the Bst2 Promoter/Luciferase Fusion Construct In the HTS format, mammalian cells are added to the wells of the 384 well plates, and cotransfected with the Bst2 reporter gene construct and an internal control *Renilla* luciferase reporter gene using Fugene 6 reagent (Roche). Luciferase activities are assayed using the Dual luciferase assay system (Promega) and normalized.

1-4. High Throughput Screening of Bst2 Modulators by Detecting Bst2-Bst2 Interaction using Fluorescence Polarization Technology Bst2 is thought to exist as a homodimer on the cell surface (Ohtomo et al., Biochem Biophys Res Commun. 1999, 258 (3):583-91). It is also thought that Bst2 requires dimerization for its activity. To be consistent with this, the Bst2 decoy protein (extracellular domain of Bst2) was expressed and secreted as a dimer (See FIG. 3, panel B).

Furthermore, the extracellular domain of Bst2 contains a predicted coiled coil region which may play a role in Bst2 dimerization. All these results suggest that Bst2 interacts with Bst2.

Using this property of homodimerization of Bst2, a high throughput competitive Bst2 binding assay for the Bst2 modulators with the ability to block Bst2-Bst2 interaction is devised as indicated below.

This screening method utilizes the technique of fluorescence polarization (Roehrl et al. Biochemistry 43:16056, 2004), which is one of the most sensitive high throughput methods for the study of protein-protein interactions, and HyperCyt flow cytometry platform. In this method, a fluorescently labeled Bst2, Bst2 decoy, Bst2 coiled coil (Bst2 CC) or any fragment of these proteins is excited by polarized light. Dissociation of Bst2 from fluorescently labeled Bst2, Bst2 decoy, Bst2 CC or any fragment of these proteins in the presence of small molecules can be detected by binding competition assay in the HTS format.

1-4-1. HyperCyt

HyperCyt is a conventionally used automated high-throughput flow cytometry (HTFC) analysis platform by which cell samples are rapidly aspirated from microplate wells and delivered to the flow cytometer (Edwards BS Molecular Pharmacology 68:1301, 2005; Young S M et al. (2005) J Biomol Screen 10: 374-382; Arnold L A et al. Science STKE (2006) 2006:p13). This screening approach allows high throughput protein-protein interaction assays to be performed in a no-wash homogeneous format that would not be feasible with conventional fluorescence plate-readers. The HyperCyt platform for HTFC screening has been shown to be a robust, sensitive, and highly quantitative method with which to screen lead compound libraries (Ramirez et al., (2003) Cytometry 53A: 55-65; Kuckuck et al., (2001) Cytometry 44: 83-90).

1-4-2. Fluorescein-labelled Bst2 Reagents, Recombinant Bst2 Proteins and Stable Cell Lines Fluorescein-labelled Bst2, Bst2 decoy, Bst2 CC or any fragment of these proteins is prepared. Bst2, Bst2 decoy or Bst2 decoy Fc recombinant protein is expressed and purified. Stable cell lines expressing Bst2 are generated. If the Bst2 mutant that does not internalize after binding to Bst2 can be identified, this Bst2 mutant, instead of the wild type Bst2, may be used to generate stable cell lines to screen the Bst2 modulators.

1-4-3. HTS Fluorescence Polarization Assay by Detecting Bst2-Bst2 Interaction

The fluorescence polarization assay measures the ability of test compounds to compete with a fluorescent Bst2, Bst2 decoy, Bst2 CC or any fragment of these proteins, for binding to cell membrane Bst2 or purified Bst2, Bst2 decoy or Bst2 decoy Fc.

For the high-throughput assay, a chemical library is screened in 384 well format. Control wells contain unlabeled Bst2 proteins or buffer alone. Unlabeled Bst2 decoy, Bst2 CC or any fragment of these proteins is added at a 100-fold higher concentration that completely blocks binding of the fluorescently labeled Bst2 decoy, Bst2 CC or any fragment of these proteins. Another control that contains buffer alone is also set up. Fluorescence polarization values of these positive and negative controls determine 0% and 100% inhibition of recruitment of Bst2, Bst2 decoy, Bst2 CC or any fragment of these proteins.

Additions to wells are in sequence as follows: 1) test compounds and control reagents (usually 10 uM and up); 2) Bst2 stable cells ($10^7$ cells/ml); 3) (after incubation at 4° C.) fluorescein labeled Bst2 decoy, Bst2 CC or any fragment of these proteins. After an additional incubation at 4° C., plates are analyzed by flow cytometry with the HyperCyt platform.

In another format, the high-throughput assays can be performed using purified Bst2, Bst2 decoy or Bst2 decoy Fc. Prior to setting up HTS, the binding constant of Bst2 and the screening concentrations are determined. Kd value is determined after binding of the serial dilutions of Bst2, Bst2 decoy or Bst2 decoy Fc protein to the fluorescently labeled Bst2, Bst2 decoy, Bst2 CC or -any fragment of these proteins. Binding is measured using fluorescence polarization (excitation at 485 nm, emission at 530 nm) with plate reader. The data are analyzed using programs such as SigmaPlot and the Kd value is determined. After the Kd value determination, test compounds are added to the wells. Bst2, Bst2 decoy or Bst2 decoy Fc protein is added and fluorescently labeled Bst2, Bst2 decoy, Bst2 CC or any fragment of these proteins, is added. Positive and negative controls with excess amount of unlabeled Bst2, Bst2 decoy, Bst2 CC or any fragment of these proteins, or buffer alone, are set up. Fluorescence polarization and fluorescence intensity are measured with a plate reader.

Test compound inhibition of fluorescent peptide binding is calculated as described in studies by Edwards B S et al. Molecular Pharmacology 68:1301, 2005) as 100×[1−(MFITest−MFIBlocked)/(MFIUnblocked−MFIBlocked)], in which MFI is the median fluorescence intensity of cells in wells containing test compounds, blocked control wells and unblocked control wells.

After the initial screening, the dose response analysis using a competition binding assay determines the $IC_{50}$ value of the compounds.

Figure 6:
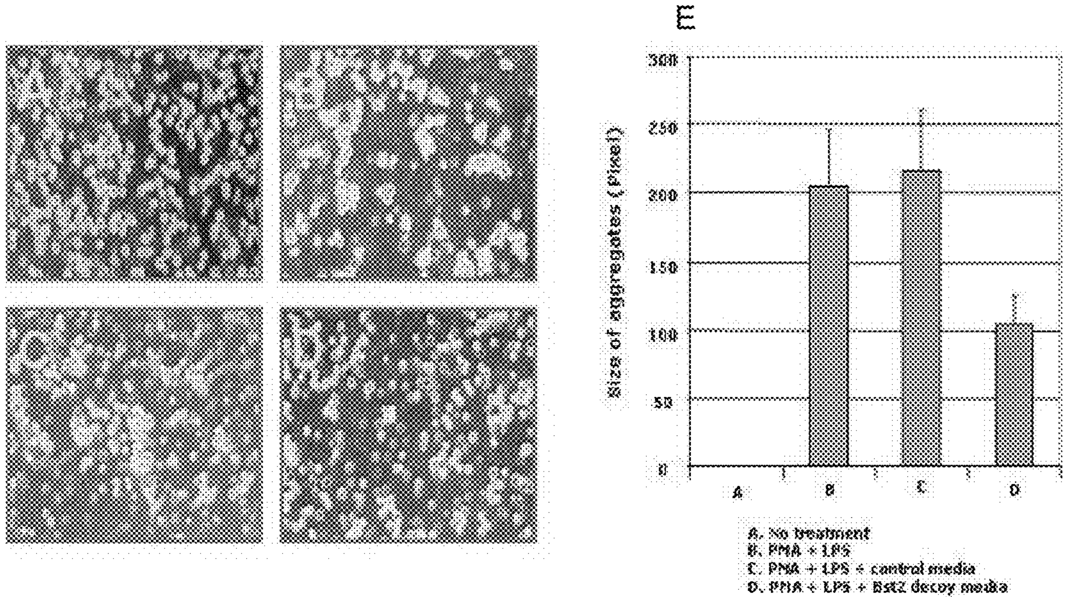
Figure 7:
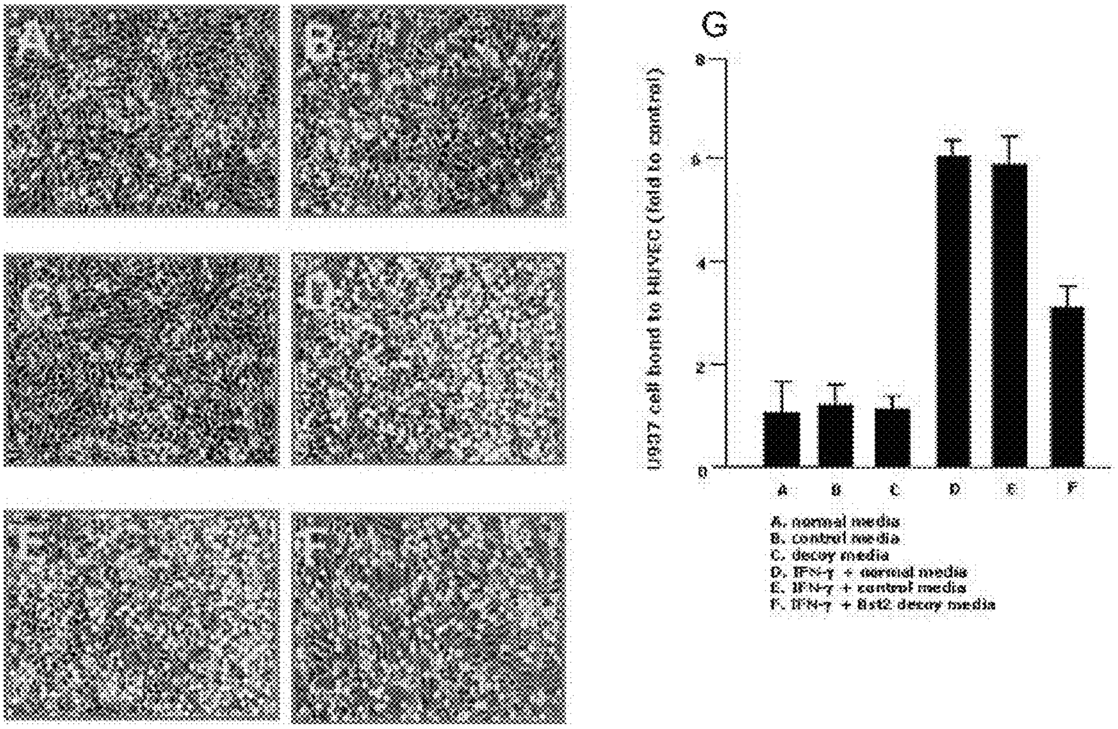
Figure 24:
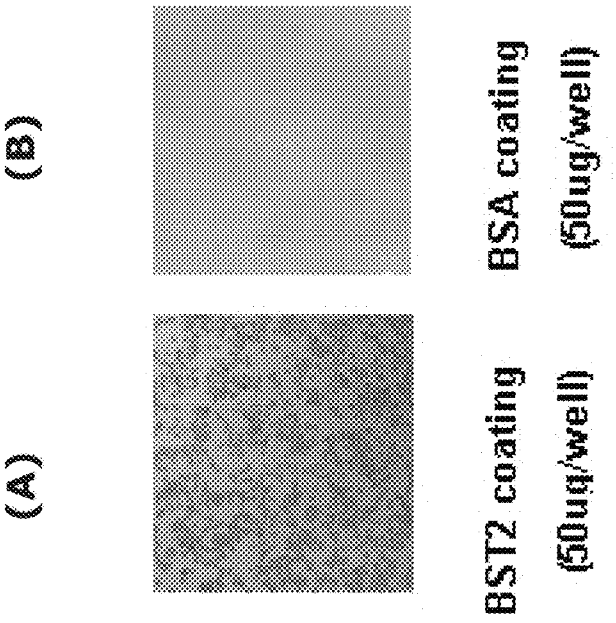

1-5. High Throughput Screening of Bst2 Modulators by Detecting Bst2-Bst2L Interaction using Fluorescence Polarization Technology 1-5-1. Bst2 L Expressing Cell The HTS assay described below requires Bst2 L expressing cells or purified Bst2 L or Bst2 L fragments. One of the Bst2 L expressing cells is U937 cells as shown in our experiments (FIGS. 6, 7 and 24). The observation that the Bst2 decoy inhibits U937 attachment to interferon gamma-treated HUVEC indicates that Bst2 L is present on cell surface of unstimulated U937 cells (FIG. 7). Another observation that the Bst2 decoy inhibits homotypic aggregation of activated T cells (FIG. 12) or activated U937 cells (FIG. 6) suggest that Bst2 L may be expressed on the surface of T cells and/or U937 cells both before and after activation. In support of these results, direct binding of U937 cells to the purified Bst2 decoy protein has been shown (FIG. 24).

When the Bst2 L protein and nucleotide sequence are identified, the purified Bst2 L or fragments thereof, or CHO cells or COS cells stably transfected with Bst2 L can be used in replacement of U937 cells.

1-5-2. HTS Fluorescence Polarization Assay by Detecting Bst2-Bst2 L Interaction

Using the interaction of the purified Bst2 decoy (or Bst2) and the Bst2 L expressing U937 cells (or any Bst2 L expressing cells), the high throughput binding competition assay for screening Bst2 modulators is designed as indicated below.

This HTS assay is based on displacement of the fluorescently labeled Bst2 or Bst2 decoy from membrane Bst2 L on the Bst2 L-expressing cells such as U937 cells. The fluorescence polarization assay measures the ability of test compounds to compete with a fluorescent Bst2 or Bst2 decoy for binding to the membrane Bst2 L or purified Bst2 L (or fragments).

For the high-throughput assay, additions to wells are in sequence as follows:

Test compounds are added to the well first and then U937 cells are added. After incubation, fluorescent labeled Bst2, Bst2 decoy or fragments thereof are added. After an additional incubation at 4° C., plates are analyzed by flow cytometry with the HyperCyt platform.

In another format, this HTS assay can be performed using purified Bst2 L or fragments thereof, and fluorescently labeled Bst2, Bst2 decoy or fragments thereof. Test compounds are added to the wells, Bst2 L or Bst2L fragment is added and fluorescently labeled Bst2, Bst2 decoy or fragments thereof is then added. Positive and negative controls are set up as described above in HTS fluorescence polarization assay for the detection of Bst2-Bst2L interaction. Fluorescence polarization and fluorescence intensity are measured with a plate reader.

In another format, this high-throughput assay can be performed using purified Bst2 or Bst2 decoy and fluorescently labeled Bst2 L peptide. Test compounds are added to the wells, Bst2 or Bst2 decoy protein is added and fluorescently labeled Bst2 L peptide is added. Positive control and negative control are set up. Fluorescence polarization and fluorescence intensity are measured with a plate reader.

1-6. High Throughput Screening of Bst2 Modulators by Detecting the Interactions Between Bst2-Bst2 Peptide Mimetics using Fluorescence Polarization Technology 1-6-1. Bst2 Peptide Mimetics Small peptides that bind to Bst2 with high affinity can serve as peptide mimetics of Bst2. Such peptides can be identified via phage display as described below. High throughput binding competition assay for Bst2 modulators is devised by detecting the interaction between Bst2 and Bst2 peptide mimetics using fluorescence polarization technology.

1-6-2. Isolation of Bst2 Peptide Mimetics that Bind to Bst2 with High Affinity via Phage Display Bst2 peptide mimetics that bind to the extracellular domain of Bst2 with high affinity may be screened via phage display. Vast libraries of peptides can be created through cloning complex mixtures of combinatorially synthesized oligonucleotides into phage display vectors. The filamentous phage display system, whereby the expressed peptides are displayed as fusions to phage coat proteins has been effective in the discovery of peptide ligands (Devlin et al. Science 249:404, 1990; Greenwood et al. J. Mol. Biol. 220:821, 1991; Scott and Smith Science 249:386, 1990).

Phage pools are incubated with beads coated with the Bst2 decoy protein or the control beads, and the positive pools are selected by magnetic separation method. Affinity purification of the population of phage particles on Bst2 decoy beads is used to recover peptides with binding activity. Sequencing the appropriate segment of the DNA of each captured phage provides the primary sequence of peptides that bind Bst2 decoy. Bst2 peptide mimetics are further screened in functional assays to select those with activity to stimulate inflammatory responses.

1-6-3. Confirmation of the Ability of the Bst2 Peptide Mimetics to Bind Bst2

Whether the selected peptide has the ability to bind Bst2 is confirmed in the binding assay of the labeled Bst2 L expressing cells such as U937 cells to immobilized Bst2 decoy or Bst2 decoy Fc protein. Different concentrations of the Bst2 peptide mimetics is added to this binding assay to measure binding competition.

In another format, the binding assay can be set up with immobilized Bst2 L expressing cells such as U937 cells, and Bst2 decoy Fc or biotinylated Bst2 decoy as a probe.

In another format, when the Bst2 L protein is identified, the binding assay of $^{125}$I-labeled Bst2 L to immobilized Bst2 decoy or Bst2 decoy Fc can be performed.

1-6-4. Confirmation of the Bst2 Peptide Mimetic Activity in Biological Assays

Biological function of the Bst2 peptide mimetics can be assessed in many different assays. One of such assays is as follows: HUVECs are transfected with the expression vector for Bst2 or an empty vector. After 48 hours of transfection, cells are treated with Bst2 peptide mimetics or control peptides. Gene expression for inflammatory mediators and adhesion molecules is analyzed by RT-PCR and the protein expression of these genes is determined by immunoblotting. Bst2 peptide mimetics stimulate inflammatory responses in the Bst2-expressing HUVECs.

1-6-5. High Throughput Screening of Bst2 Modulators with Fluorescence Polarization Technology using the Bst2 Peptide Mimetics The HTS assay is performed in a similar manner as described above. Briefly, Bst2 peptide mimetic is fluorescently labeled. Mammalian cells are stably transfected with the expression vector for Bst2. If Bst2 mutant that does not internalize after binding to Bst2 is known, this Bst2 mutant is transfected into mammalian cells to screen the Bst2 modulators.

For the HTS assay, test compounds are added to the wells. Bst2 expressing stable cells are added and then the fluorescently labeled Bst2 peptide mimetics are added. Fluorescence polarization and fluorescence intensity are measured with a plate reader as above.

In another format, purified Bst2 or Bst2 decoy can be used in place of Bst2 expressing stable cells. Dose-dependent response of the compounds is assessed to validate the hits.

2. Secondary Assays to Validate Hits after High Throughput Screening

The initial hits must be verified using a series of profiling assays in any drug discovery process. The hit verification by secondary assays is to determine if the inhibition or activation by the small molecular weight compounds has biological relevance. The secondary assays described herein are only a few examples of possible alternative assays that can be used to validate hit compounds.

2-1. Hit Validation by Bst2-Bst2 L Binding Assay

Activity of the small m.w. compound is measured by the Bst2-Bst2 L interaction as a function of compound concentration in an ELISA format. Biotinylated Bst2 decoy (or Bst2 decoy Fc) is immobilized in the wells of a streptavidin-coated (or anti-Fc antibody-coated) 96-well plate. Serial dilutions of the selected lead compounds are added to a solution of Bst2 L and the Bst2 L mutant (if available) that does not bind to Bst2 decoy as a control, and incubated with the immobilized Bst2 decoy. Unbound Bst2 L is washed from the plate. Bound Bst2 L is measured with anti-Bst2 L antibody labeled with horseradish peroxidase followed by colorimetric reaction for horseradish peroxidase.

2-2. Hit Validation by Bst2-Bst2 L Binding Assay using Biacore Surface Plasmon Resonance Technology The Bst2-Bst2 L binding may be analyzed with Biacore's surface plasmon resonance technology in a solution competition format. A concentration series of each compound is incubated with recombinant Bst2 L and then injected onto a chip surface with captured recombinant Bst2 decoy. Binding is measured at equilibrium and calculated as the percentage of maximum binding.

2-3. Hit Validation by Glutathione S Transferase Pull-down Assay

GST-Bst2 decoy protein is expressed in *E. coli* and purified. Radiolabeled ($^{35}$S)-Bst2 L can be obtained by using a TNT T7 transcription/translation system. A serial dilution of hit compound is prepared in DMSO. 1 ul of hit compound of each concentration is added to tubes. Beads containing GST-Bst2 decoy protein is added. Radiolabeled-Bst2 L is then added and incubated. Pull-down assay is performed following manufacturer's instructions.

2-4. Hit Validation by Cell—Cell Adhesion Assay Using Fluorescently Labeled Cells Cell adhesion assays are performed as described by Edwards et al. (Molecular Pharmacology 68:1301, 2005). Bst2 cells (stable cells expressing Bst2) are labeled with red-fluorescent Fura-Red (Invitrogen) and Bst2 L cells (stable cells expressing Bst2 L or U937 cells may be used) with green-fluorescent 5,6-carboxyfluorescein diacetate succinimidyl ester (Invitrogen) and maintained on ice until the experiment. Three hundred microliters of Bst2 cells ($1\times10^6$ cells/ml) and 300 μl of Bst2 L cells ($3\times10^6$ cells/ml) are incubated separately for 5 min at 37° C. in the presence or absence of test compounds (100 μM final). Cells are then combined and analyzed in the flow cytometer, during which time the cell suspension is continuously stirred at 300 rpm and 37° C. with a magnetic microstirbar. After 90 s of stirring to determine basal levels of cell adhesion, compounds are added at different concentrations. Bst2 cells are resolved into two fractions in the flow cytometer: singlets that are uniformly red fluorescent and conjugates containing red/green co-fluorescence (red fluorescent Bst2 cells adhered to green fluorescent Bst2 L cells). At each indicated time point, the percentage of adherent Bst2 cells is calculated as 100×(number of conjugates)/(number of conjugates+number of singlets).

2-5. Hit Validation by Luciferase Reporter Assay

Bst2 antagonist or agonist activity may be confirmed with luciferase reporter assay using (NFkB)n-luc, a plasmid containing multiple NFkB sites upstream of a luciferase reporter. 293T cells are transfected with the (NFkB)n-luc and a mammalian expression vector for Bst2. After 48 h, cells are treated with varying concentrations of the selected compounds. After 6 hours of incubation, luciferase assay is performed and luminescence is measured using luminometer.

2-6. Hit Validation by Transcription Assay

The transcription assay determines if the small molecules inhibit or augment Bst2-mediated signal transduction in the inflammatory pathways in the cellular environment. One such assay is as follows. HUVECs are transfected with the expression vector for Bst2 or an empty vector. After 48 hours of transfection, cells are treated with various concentrations of hit compounds. Gene expression for inflammatory mediators and adhesion molecules is analyzed by RT-PCR and the protein expression of these genes is determined by immunoblotting or ELISA.

Bst2 and Angiogenesis

Angiogenesis is the growth of new capillary blood vessels. Inflammation can promote angiogenesis and new vessels also enhance tissue inflammation. Thus, angiogenesis and inflammation are codependent processes (Jackson et al. FASEB J 11:457, 1997), while angiogenesis and inflammation can also occur independently of each other. Especially, chronic inflammation can stimulate vessel growth. Angiogenesis is required for embryogenesis, tissue repair after injury, growth and the female reproductive cycle. Angiogenesis also contributes to the pathology of cancer and a variety of chronic inflammatory diseases including psoriasis, diabetic retinopathy, rheumatoid arthritis, osteoarthritis, asthma and pulmonary fibrosis. For example, angiogenesis is required to support the growth of most solid tumors beyond a diameter of 2-3 mm. Recent studies show that angiogenesis inhibitors block tumor progression. Moreover, cancer is not the only disease in which the use of angiogenesis inhibitors can make a difference. Angiogenesis plays a critical role in age-related macular degeneration and diabetic retinopathy. These conditions cause sight loss when blood vessels infiltrate the retina, cloud it, and eventually destroy it. Indeed, the blood vessel blockers (antibodies, small molecular weight compounds) are the newest and most effective treatment for age-related macular degeneration, the leading cause of blindness in people over 65. Angiogenesis inhibitors may reduce inflammation and inhibitors of chronic inflammation may be expected to inhibit angiogenesis where the stimulus for vascular growth is derived from inflammatory cells (Stogard et al. J Clin Invest 103:47, 1999). It is possible that Bst2 induces angiogenesis and that the Bst2 blockers may have anti angiogenic activities inhibiting neovascularisation.

Delivery

Regarding delivery, in addition to conventional routes of administration such as subcutaneous, intravenous, intramuscular and intraperitoneal injections, Bst2 blockers may be administered by transdermal patches and controlled-release methods. Controlled-release of Bst2 blocking reagents such as Bst2 decoy or Bst2-binding antibody can be accomplished locally or systemically by implanting Bst2 blocking reagents that has been encapsulated or bound to solid matrix that can degrade or empty over time to release the Bst2 blocking reagent over longer period of time than injections. Bst2 blocking reagents may also be applied topically in a cream or ointment form to treat skin disease or injury.

The present composition may be administered in a pharmaceutically effective amount. The term “pharmaceutically effective amount”, as used herein, refers to an amount sufficient for treatment of diseases, which is commensurate with a reasonable benefit/risk ratio applicable for medical treatment. An effective dosage amount of the composition may be determined depending on the type of disease, severity of the illness, the patient’s age and gender, drug activity, drug sensitivity, administration time, administration routes, excretion rates of a drug, duration of treatment, drugs used in combination with the composition; and other factors known in medical fields. The present composition may be administered as individual therapeutic agents or in combination with other therapeutic agents, and may be administered sequentially or simultaneously with conventional therapeutic agents. This administration may be single or multiple dosing. Taking all factors into consideration, it is important to conduct administration with a minimum of doses capable of giving the greatest effects with no adverse effects, and the doses may be readily determined by those skilled in the art.

Therapeutic Composition

In one embodiment, the present invention relates to treatment for various inflammatory diseases or disorders that are characterized by being treatable with a Bst2 antagonist. In this way, the inventive therapeutic compound may be administered to human patients who are either suffering from, or prone to suffer from the disease by providing compounds that antagonizing Bst2.

The formulation of therapeutic compounds is generally known in the art and reference can conveniently be made to Remington’s Pharmaceutical Sciences, 17th ed., Mack Publishing Co., Easton, Pa., USA. For example, from about 0.05 μg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide compound may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 μg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Cell Culture

A human monocytic cell line U937 (ATCC, U.S; Cat. CRL-1593.2) was suspension-cultured in RPMI-1640 (Gibco-BRL) supplemented with 10% fetal bovine serum (FBS; Gibco-BRL), 100 U/ml of penicillin (Gibco-BRL) and 100 μg/ml of streptomycin (Gibo-BRL) at 37° C. under a 5% $CO_2$ atmosphere.

Human umbilical vein endothelium cell line HUVEC (Cambrex, U.S.; Cat. CC-2517A) was subcultured in EGM-2 medium (Cambrex, U.S.) supplemented with 10% FBS at 37° C. under a 5% $CO_2$ atmosphere. In the following examples, cells were pretreated with 0.5% FBS, instead of 10% FBS, for 16 hrs. According to given conditions, cells were pretreated with human recombinant interferon-gamma (10 ng/ml, Calbiochem, U.S.) and PMA (1 ng/ml, Cambiochem) or a medium for a predetermined period of time.

A mouse monocytic cell line WEHI-274.1 (ATCC, Cat. CRL-1679), and a mouse endothelial cell line, SVEC 4-10 (ATCC, Cat. CRL-2181), were cultured and pretreated according to the same method as in the human cell lines.

A human T-lymphocyte cell line Jurkat (ATCC, TIB152 clone) was suspension-cultured in RPMI-1640 (Gibco-BRL) supplemented with 10% FBS, 100 U/ml of penicillin and 100 μg/ml of streptomycin at 37° C. under a 5% $CO_2$ atmosphere.

Protein expression and purification were carried out using CHO-S cells (Invitrogen, Cat. 11619-012). CHO-S cells were suspension-cultured in F12/HAM (Gibco-BRL) medium supplemented with 10% FBS, 100 U/ml of penicillin and 100 μg/ml of streptomycin at 37° C. under 5% $CO_2$ atmosphere.

Example 2

Cloning of Human Bst2 Gene and Mouse Damp1 Gene

An expression vector of histidine-tagged Bst2 was constructed as follows. Full-length cDNA (NM004335) of human Bst2 gene was synthesized by Origene Technologies (USA), and amplified by PCR using Pfu ultra HF DNA polymerase (Stratagene) in a volume of 50 μl. A PCR product was cloned into a pCMV HA vector (Clontech) using SalI and NotI.

Figure 2:
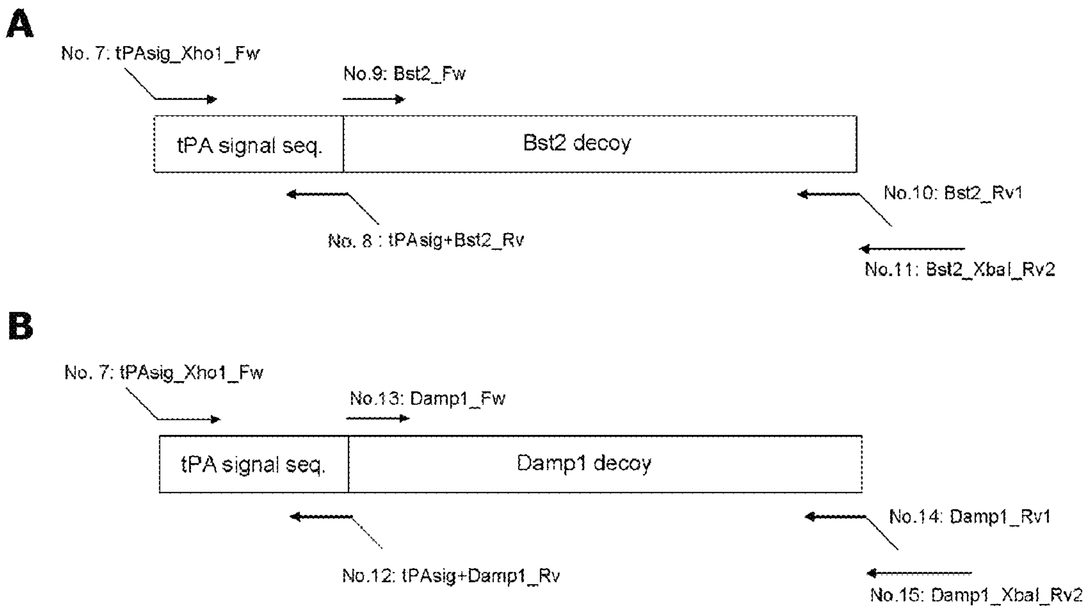

Vectors for expressing decoys of Bst2 and Damp1 were constructed as follows. FIG. 2 shows the locations of PCR primers used in cloning the decoys. The following primers were used.

```
Sequence 7
                                        (SEQ ID NO: 14)
tPAsig_XhoI_Fw: 5'-cgctcgagacagccatcATGgatg-3'

Sequence 8
                                        (SEQ ID NO: 75)
tPAsig + Bst2_Rv: 5'-ggccttgatggtgaagctgggcgaaa
c-3'

Sequence 9
                                        (SEQ ID NO: 76)
Bst2_Fw: 5'-agcttcaccatcaaggccaacag-3'

Sequence 10
                                        (SEQ ID NO: 77)
Bst2_Rv1: 5'-gtgatgatggtcctgggagctggggtag-3'

Sequence 11
                                        (SEQ ID NO: 78)
Bst2_XbaI_Rv2: 5'-gcagatcttcaatggtgatggtgatgatgg
tc-3'

Sequence 12
                                        (SEQ ID NO: 79)
tPAsig + Damp1_Rv: 5'-cgctgtgacggcgaagctgggcgaaa
c-3'

Sequence 13
                                        (SEQ ID NO: 80)
Damp1_Fw: 5'-agcttcgccgtcacagcgaacagc-3'
```

-continued

```
Sequence 14
                                        (SEQ ID NO: 81)
Damp1_Rv1: 5'-gtgatgatgagagttcacctgcactgtgc-3'

Sequence 15
                                        (SEQ ID NO: 82)
Damp1_Xba1_Rv2: 5'-gcagatcttcaatggtgatggtgatgatga
g-3'
```

A DNA fragment coding for the extracellular region of human Bst2 protein was obtained by PCR, and was fused at the N-terminus to a signal sequence P of tPA (tissue Plasminogen activator) to promote extracellular secretion after being expressed. The DNA fragment was also fused at the C-terminus to a six-histidine tag to facilitate determination of protein expression levels and protein purification. The Bst2 decoy did not contain 21 amino acid residues at the C-terminus and also did not contain the transmembrane and cytoplasmic domains. The PCR product was treated with a final concentration of 0.8% dimethyl sulfoxide (DMSO; Sigma), digested with BamHI and XbaI, and cloned into a pCDNA 3.1 vector (Invitrogen). In other experiments, the nucleotide sequences of the human Bst2 decoy were codon-optimized for the mammalian expression system and the DNA fragments were chemically synthesized.

Full-length cDNA (NM 198095) of mouse Damp1 gene was obtained by RT-PCR using mRNA isolated from mouse liver. A RT-PCR product was digested with BamHI and XbaI and cloned into pCDNA 3.1 (Invitrogen). A decoy region was determined by amino acid sequence homology analysis between human Bst2 and mouse Damp1. As a result, a vector expressing the soluble Bst2 fragment (SEQ ID NO:1) and another vector expressing the soluble Damp1 fragment of (SEQ ID NO:2) were obtained.

Example 3

Real-time Quantitative RT-PCR

Intracellular expression levels of specific genes were analyzed by real-time quantitative RT-PCR using ABI Prism 7900HT (Applied Biosystems, Foster City, Calif.) and a SYBR-Green assay kit. Primers and probes used were designed using Primer Express software (Applied Biosystems).

10 ng of single-stranded cDNA was placed in a reaction tube and subjected to multiplex TaqMan PCR (50 μl) using the TaqMan Universal PCR Master Mix. The relative amount of target cDNA was calculated using the comparative cycle threshold (CT) method. PCR products were analyzed by agarose gel electrophoresis.

The relative levels of a specific gene A were expressed as a change compared to a control sample (untransfected cells). All values were obtained using a 2-CT ($C_{t1}-C_{t0}$, $C_{t1}=C_{t1A}-C_{t1B}$, $C_{t0}=C_{t0A}$-Ct0B) calculation method relative to a normalization gene B (human GAPDH gene) in transfected cells. Each value was obtained from each sample in triplicate. The above experiments were carried out to quantify the expression of the Bst2 gene and interleukin-2.

Example 4

Expression and Purification of Soluble Bst2 Protein Fragment or Damp1 Protein Fragment In order to express the above-prepared soluble Bst2 protein fragment or Damp1 protein fragment, a vector DNA was transiently or permanently introduced into specific animal cells. Transient transfection was performed by calcium phosphate ($CaPO_4$) precipitation, as follows. 24 hrs before transfection, $7\times10^6$ 293T cells (ATCC) were seeded onto a 150-mm cell culture plate and cultured. One hour before transfection, the culture medium was exchanged with IMDM medium (Cambrex) supplemented with 2% fetal bovine serum (FBS; GIBCO-BRL). 1.5 ml of TE buffer (1 mM Tris, 0.1 mM EDTA, pH 8.0) containing 75 μg of DNA and 250 mM calcium was mixed with 1.5 ml of HEPES buffer (50 mM HEPES, 140 mM NaCl, 1.4 mM $Na_2HPO_4$, pH 7.05), was incubated for about 1 min at room temperature, and was applied to the pre-cultured cells. The cells were incubated in a $CO_2$ incubator at 37° C. for 6 hrs. After the DNA/calcium solution was removed, the cells were refed with serum-free medium and further cultured for 72 hrs or longer, and the culture medium was then recovered. Separately, a permanent cell line was established using lipofectamine and dihydrofolate reductase as a selectable marker, as follows. 48 hrs before transfection, $1.35\times10^6$ CHO-DUKX-B11 ($dhfr^-$) cells (ATCC) were seeded onto a 100-mm cell culture plate and cultured in IMDM medium complemented with 10% FBS. 0.6 ml of serum-free IMDM medium containing 18 μg of DNA was mixed with 0.6 ml of serum-free IMDM medium containing 54 μl of Lipofectamine 2000 (Invitrogen), and was incubated at room temperature for 45 min. The DNA/lipofectamine mixture was supplemented with 8.8 ml of serum-free IMDM medium and applied to the pre-cultured cells. The cells were incubated in a $CO_2$ incubator at 37° C. for 6 hrs. The medium was exchanged with a selection medium, 10% dialyzed FBS-containing IMDM medium. To analyze the transiently expressed protein, the cells were further cultured for 72 hrs or longer. The medium was then recovered and passed through a 0.2-μm filter (Millipore). The produced Bst2 decoy protein was analyzed by immunoblotting using anti-Bst2 polyclonal antibody (Roche) or anti-histidine antibody (Roche).

For large-scale expression and purification of the soluble Bst2 protein fragment or Damp1 protein fragment, host cell lines into which a Bst2 or Damp1 expression vector was stably introduced were selected as production cell lines, as follows. CHO cells deleted in dihydrofolate reductase (DHFR) gene were transfected with an expression vector. Since the expression vector carried a dhfr gene, dihydrofolate reductase was used as a selectable marker. After 48 hrs, the transfected CHO cells were seeded onto a 96-well cell culture plate in a density of $1\times10^3$ cells/well and cultured in a medium containing 20 nM methotrexate (MTX) to amplify the DHFR gene. After two weeks, the medium was recovered and subjected to ELISA using anti-Bst2 antibody to compare clones for the expression levels of Bst2 decoy protein. Clones exhibiting high expression levels were selected and exposed to gradually increased concentrations of MTX up to 300 nM to complete gene amplification. Thereafter, the medium was collected from each clone and subjected to ELISA and immunoblotting in order to finally select a production cell line exhibiting the highest protein expression levels. Since the Bst2 decoy protein was produced in the culture medium under serum-free conditions, the expressed protein was purified from the collected medium using the six-histidine tag added to the C-terminus. Protein purification was performed by NTA chelating chromatography using a column, NTA chelating agarose CL-6B (Peptron Inc.). The purity of the purified protein was analyzed by electrophoresis and ELISA, and the amount of the purified protein was determined by a BCA method (Biorad, USA) and UV spectrophotometry.

Figure 3:
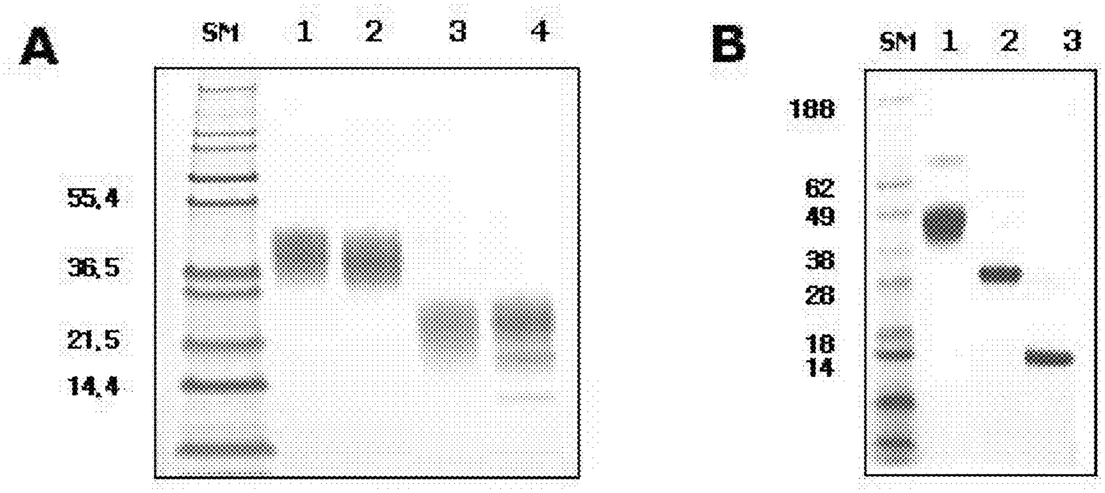

The human Bst2 decoy and the mouse Damp1 decoy, purified as described above, were analyzed by 4-20% SDS-PAGE (FIG. 3, panel A). The treatment of 1% dithiothreitol (DTT) and N-glycosidase F (Sigma) resulted in the Bst2 decoy being a dimeric glycoprotein (FIG. 3, panel B). The results of the following examples were obtained using, among the prepared decoys, a soluble Bst2 protein fragment having the amino acid sequence of SEQ ID NO:1 and a soluble Damp1 protein fragment having the amino acid sequence of SEQ ID NO:2.

Example 5

Evaluation of the Effect of Bst2 Protein on Homotypic Aggregation of U937 Cells

Example 5-1

Change in Expression Levels of Bst2 During Aggregation of U937 Cells

Expression levels of Bst2 protein were examined during aggregation of human U937 monocytic cells. $1\times10^6$ U937 cells were treated with PMA (2 ng/ml) and LPS (10 μg/ml) for 24 hrs to induce homotypic cell aggregation of U937 cells, and were observed for the degree of homotypic cell aggregation under a phase-contrast inverted microscope (Olympus 1×71, state, USA). To determine the degree of cell aggregation, the size of formed cell aggregates was measured as pixel intensity, using Adobe's Photoshop software, version 7.0. The standard deviation values shown in drawings were calculated from mean values of six randomly selected aggregates. Thereafter, all used cells were recovered, and total RNA was isolated and subjected to RT-PCR using a set of primers of SEQ ID NOS:3 and 4 to assess Bst2 expression levels.

```
                                        (SEQ ID NO: 3)
Sense oligomer: 5'-TTTTCTCTTCTCAGTCTC-3'

                                        (SEQ ID NO: 4)
Antisense oligomer: 5'-GCATCTACTTCGTATGAC-3'
```

One hour after U937 cells were treated with PMA and LPS to induce homotypic aggregation, intracellular Bst2 expression increased by about three times. This increased level was maintained for 24 hrs. These results indicate that Bst2 gene expression increases during homotypic aggregation of U937 cells (FIG. 4).

Example 5-2

The Effect of Bst2 Protein on Homotypic Aggregation of U937 Cells

In order to determine whether the increased expression of Bst2 gene is essential for the homotypic aggregation of U937 cells, cell aggregation was assessed when Bst2 protein was overexpressed.

$1\times10^6$ U937 cells, which had been cultured under the aforementioned conditions, were seeded onto a 96-well cell culture plate (NUNC) and treated with PMA (2 ng/ml, Calbiochem) and LPS (10 μg/ml, Calbiochem) for 24 hrs. The cells were then observed for the degree of homotypic cell aggregation under a phase-contrast inverted microscope (Olympus 1X71, state, USA).

Bst2 protein itself did not induce aggregation of U937 cells, whereas the PMA/LPS treatment stimulated homotypic aggregation of U937 cells. Transient overexpression of Bst2 increased homotypic aggregation of the PMA/LPS-stimulated U937 cells by about four times (FIG. 5). These results indicate that Bst2 expression promotes homotypic aggregation of the activated monocytic leukocytes.

Example 5-3

Inhibition of Homotypic Aggregation of U937 Cells using Bst2 Decoy

In order to confirm whether the increased expression of Bst2 gene is essential for homotypic aggregation of U937 cells, cell aggregation was assessed when the action of Bst2 protein was suppressed.

U937 cells were pretreated with PMA and LPS to induce cell aggregation, and were treated with serial dilutions of medium (decoy medium) containing a Bst2 decoy transiently expressed in CHO-S cells. The Bst2 decoy was found to decrease U937 cell aggregation induced by PMA and LPS by 50% in comparison with the culture (control medium) of CHO-S cells not expressing the Bst2 decoy (FIG. 6). These results indicate that the Bst2 decoy inhibits homotypic aggregation of U937 cells.

Example 6

Evaluation of the Effect of Bst2 Protein on Heterotypic Aggregation Between Two Different Cell Types

Example 6-1

Inhibition of Aggregation Between U937 and HUVECs using Bst2 Decoy

HUVECs ($1-5\times10^4$ cells/ml) were seeded onto a 12-well cell culture plate. After one day, the medium was exchanged with a low-serum medium containing 0.5% FBS, and the cells were pretreated with interferon-gamma (IFN-γ; Calbiochem) in a final concentration 10 ng/ml for 24 hrs. Then, the pretreated HUVECs were co-cultured with U937 cells ($2\times10^6$ cells/ml, 500 μl) at 37° C. for 4 hrs. The co-culture was washed with phosphate buffer three or four times, and the remaining cells were fixed with 4% paraformaldehyde and microscopically observed.

Figure 8:
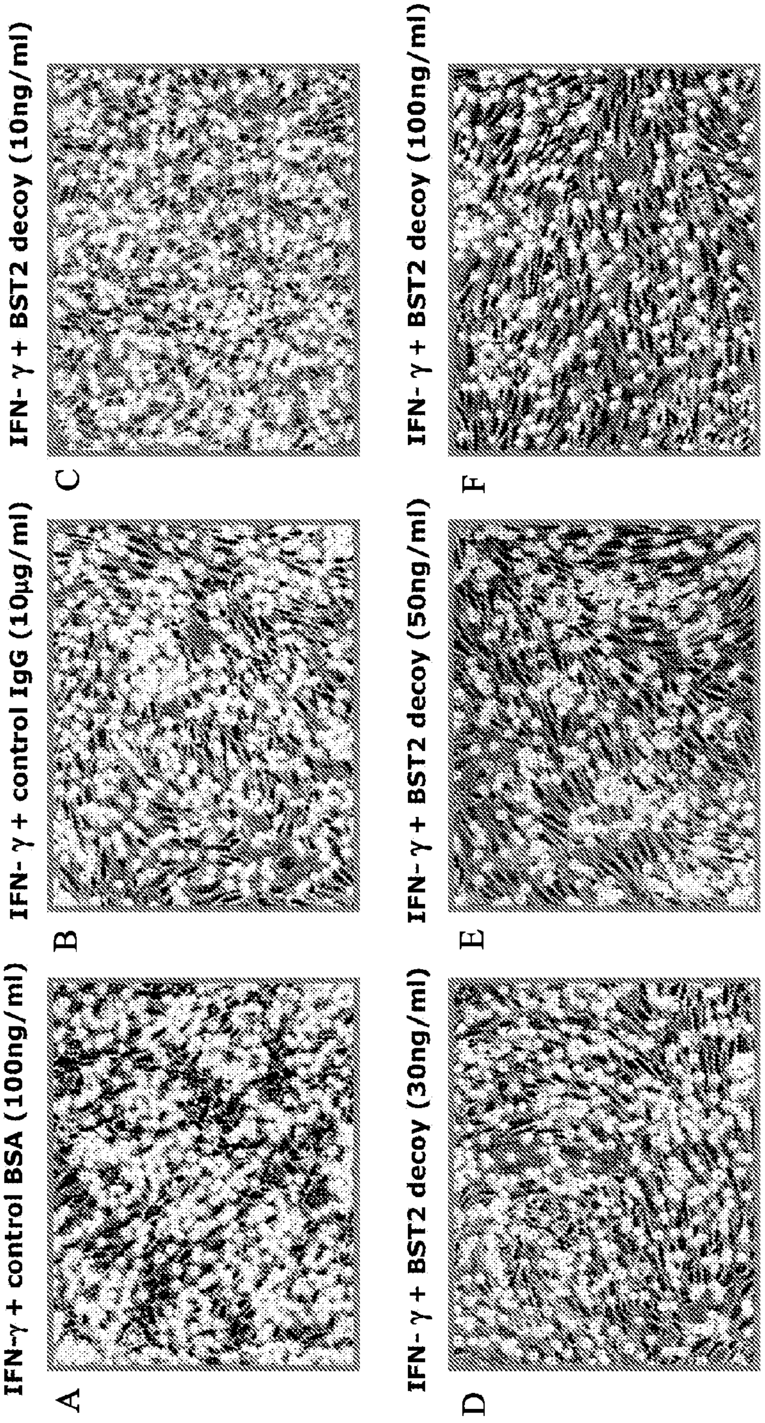

U937 cells showed a decreased binding to IFNγ-treated HUVECs when the Bst2 decoy-containing medium was added to the culture. In the control medium that does not contain the Bst2 decoy, U937 cells bound to IFNγ-treated HUVECs efficiently and formed heterotypic cell aggregates. The treatment of a control medium or albumin did not affect cell aggregation (FIG. 7). In FIG. 7, a "normal medium" HUVECs not pretreated with IFN-γ did not bind to U937 cells. In contrast, IFN-γ-treated HUVECs bound to U937 cells and formed heterotypic cell aggregation. HUVECs treated with a Bst2 decoy protein-containing medium, obtained from the culture pretreated with IFN-γ, exhibited decreased aggregation with U937 cells. The treatment of a basic medium or albumin did not affect cell aggregation (FIG. 7). In FIG. 7, a "normal medium" indicates a FBS-containing general medium, and a "control medium" indicates a culture fluid of cells not expressing a Bst2 decoy protein. In addition, the heterotypic cell aggregation was inhibited in such a manner of being dependent on concentrations of the Bst2 decoy (FIG. 8).

Example 6-2

Inhibition of Aggregation Between U937 and HUVECs using Bst2 siRNA

Various siRNA molecules acting in a Bst2-specific manner were constructed (QIAGEN). A total of 23 siRNA molecules specific to Bst2 were constructed.

The test results below were obtained using siRNA consisting of an antisense RNA strand, complementary to Bst2 mRNA encoded by the sequence of SEQ ID NO:5, and a sense RNA strand complementary to the antisense RNA strand.

HUVECs were transfected with an expression vector for Bst2, treated with or without IFN-γ and then transfected with Bst2 siRNA. These cells were assessed for U937 cell adhesion.

```
                                        (SEQ ID NO: 5)
Target sequence: 5'-AAGCGTGAGAATCGCGGACAA-3'

                                        (SEQ ID NO: 6)
Sense oligomer: 5'-r(UUGUCCGCGAUUCUCACGC)d(TT)-3'

                                        (SEQ ID NO: 7)
Antisense oligomer:
5'-r(GCGUGAGAAUCGCGGACAA)d(TT)-3'
```

Figure 9:
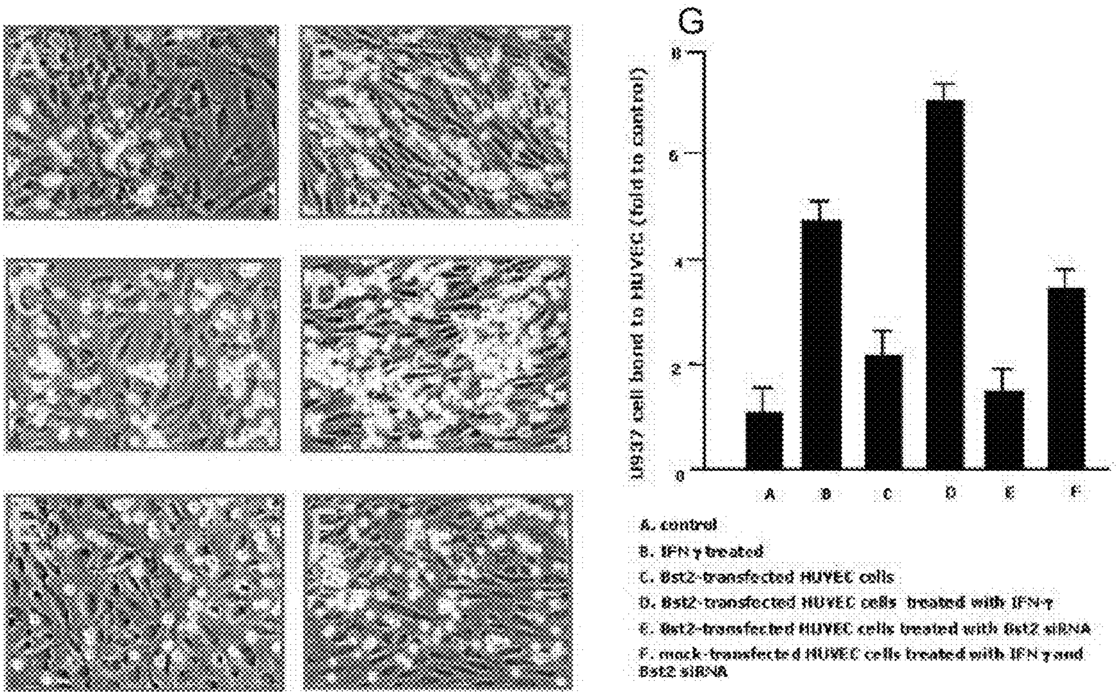

Exogenously expressed Bst2 promoted U937 cell binding to HUVECs treated with or without INF-γ. Bst2 siRNA treatment resulted in decreased U937 cell adhesion (FIG. 9). Together with the data shown in FIG. 29 demonstrating the inhibitory effect of Bst2 siRNA on cell adhesion between untransfected HUVEC and U937 cells, these results suggest that Bst2 plays a role in the HUVEC-U937 adhesion.

Example 7

Evaluation of the Effect of Bst2 Protein on Homotypic Aggregation of T Lymphocytes and Activity of the Aggregation

Example 7-1

The Effect of Bst2 Overexpression on Homotypic Aggregation of T Lymphocytes and IL-2 Production Human Jurkat T cells were induced to form homotypic cell aggregation and activated, as follows.

Figure 10:
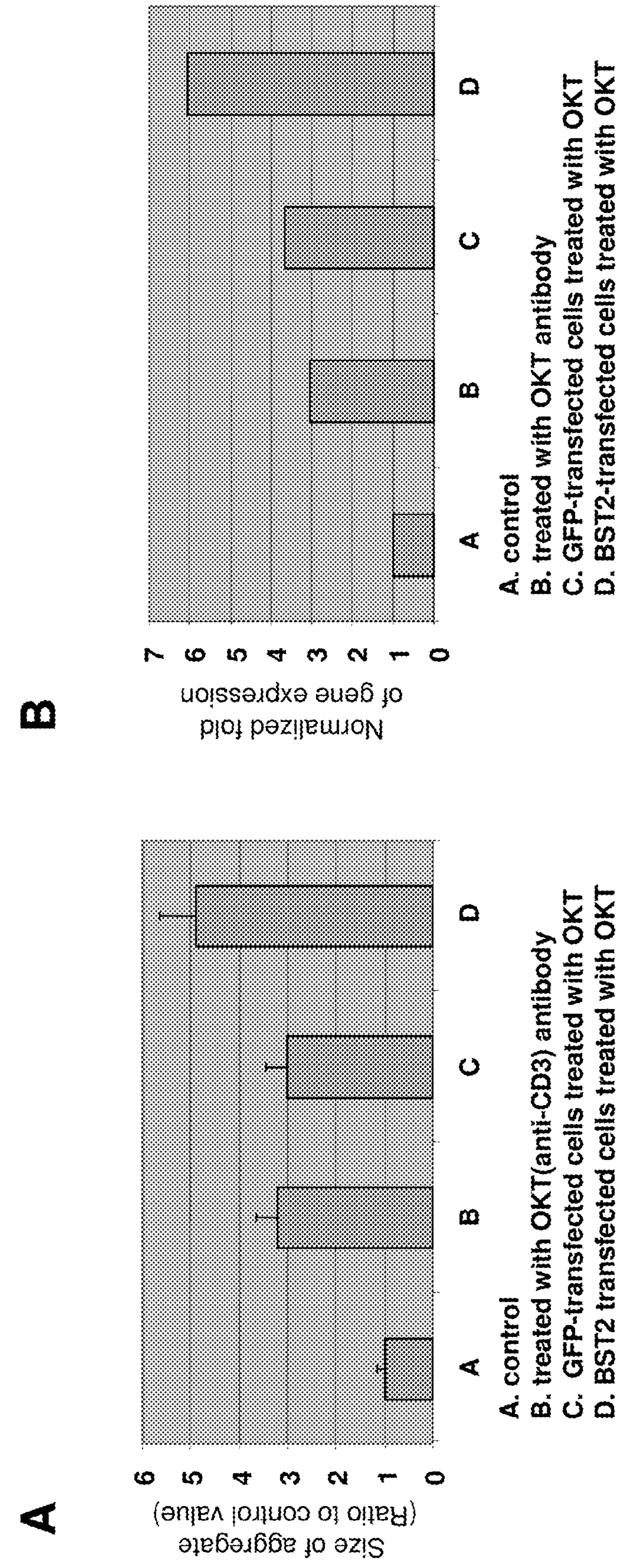
Figure 11:
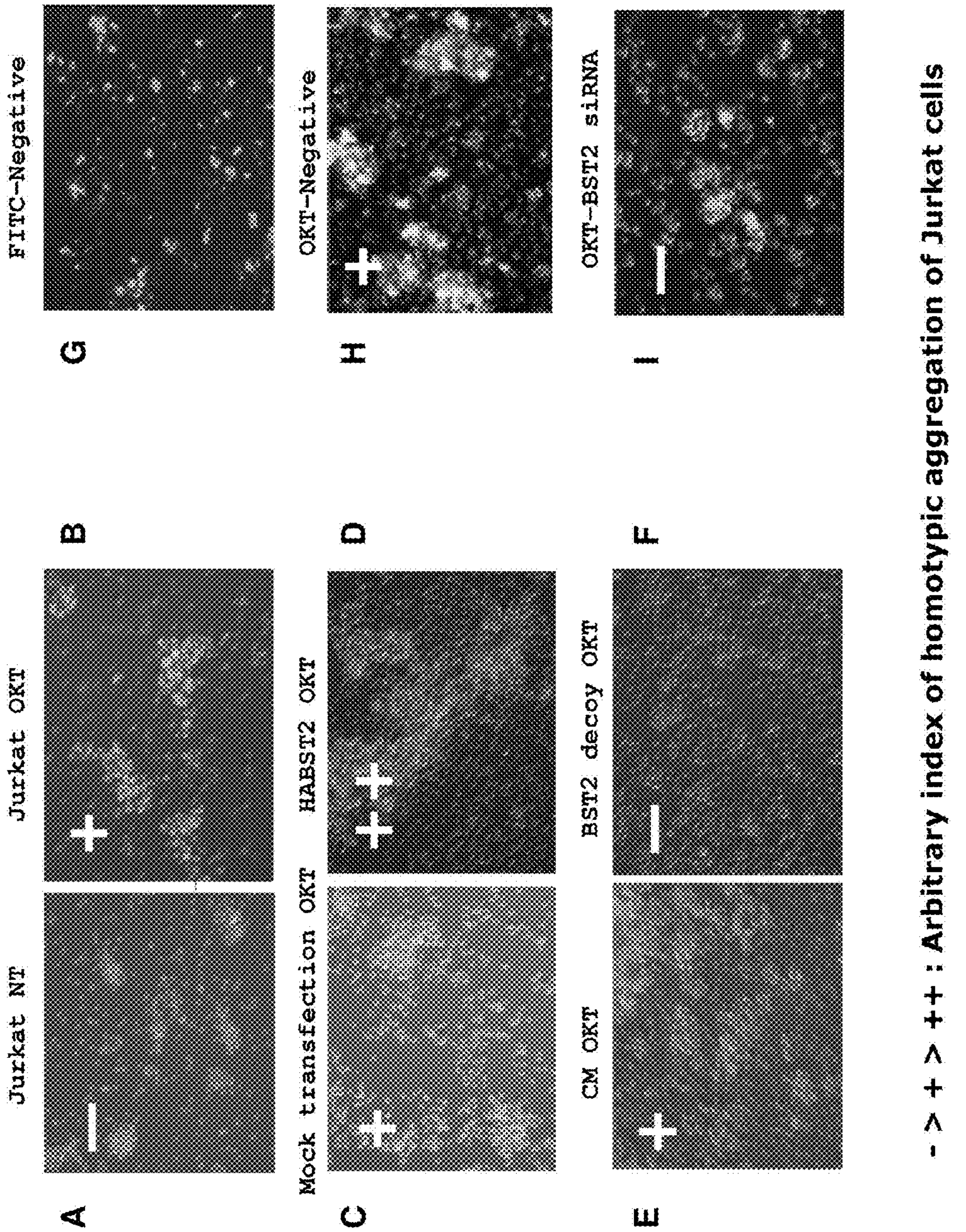

When Jurkat cells ($5\times10^5$ cells/ml) were incubated with anti-CD3 monoclonal antibody (OKT3: 10 μg/ml, BD Pharmingen) at 4° C. for 20 min and then with anti-mouse immunoglobulin polyclonal antibody (25 μg/ml, Zymed) 37° C. for 1 hr, cell aggregation occurred, and the cells were activated and induced to produce interleukin-2 (IL-2) (FIGS. 10 and 11). According to the same method, when green fluorescent protein (GFP) overexpression was induced, there was no effect. In contrast, when Jurkat cells were transfected with a Bst2-overexpressing vector and were induced to activate, homotypic cell aggregation increased (FIG. 10, panel A). IL-2 mRNA levels upon T cell activation were measured by real-time RT-PCR (Example 3). IL-2 mRNA expression was elevated by about two times under Bst2 overexpression in comparison with GFP overexpression (FIG. 10, panel B).

Example 7-2

The Effect of Bst2 Decoy and Bst2 siRNA on Homotypic Aggregation of T Lymphocytes and IL-2 Production Jurkat cells were pretreated with a Bst2 decoy 30 min before activation, were activated using anti-CD3 monoclonal antibody, and were evaluated for inhibition of cell aggregation. The cells were treated with a relative amount of serial dilutions of an animal cell culture fluid containing a Bst2 decoy. The size of aggregates was represented as a ratio to the size of aggregates of a non-treatment group.

Figure 12:
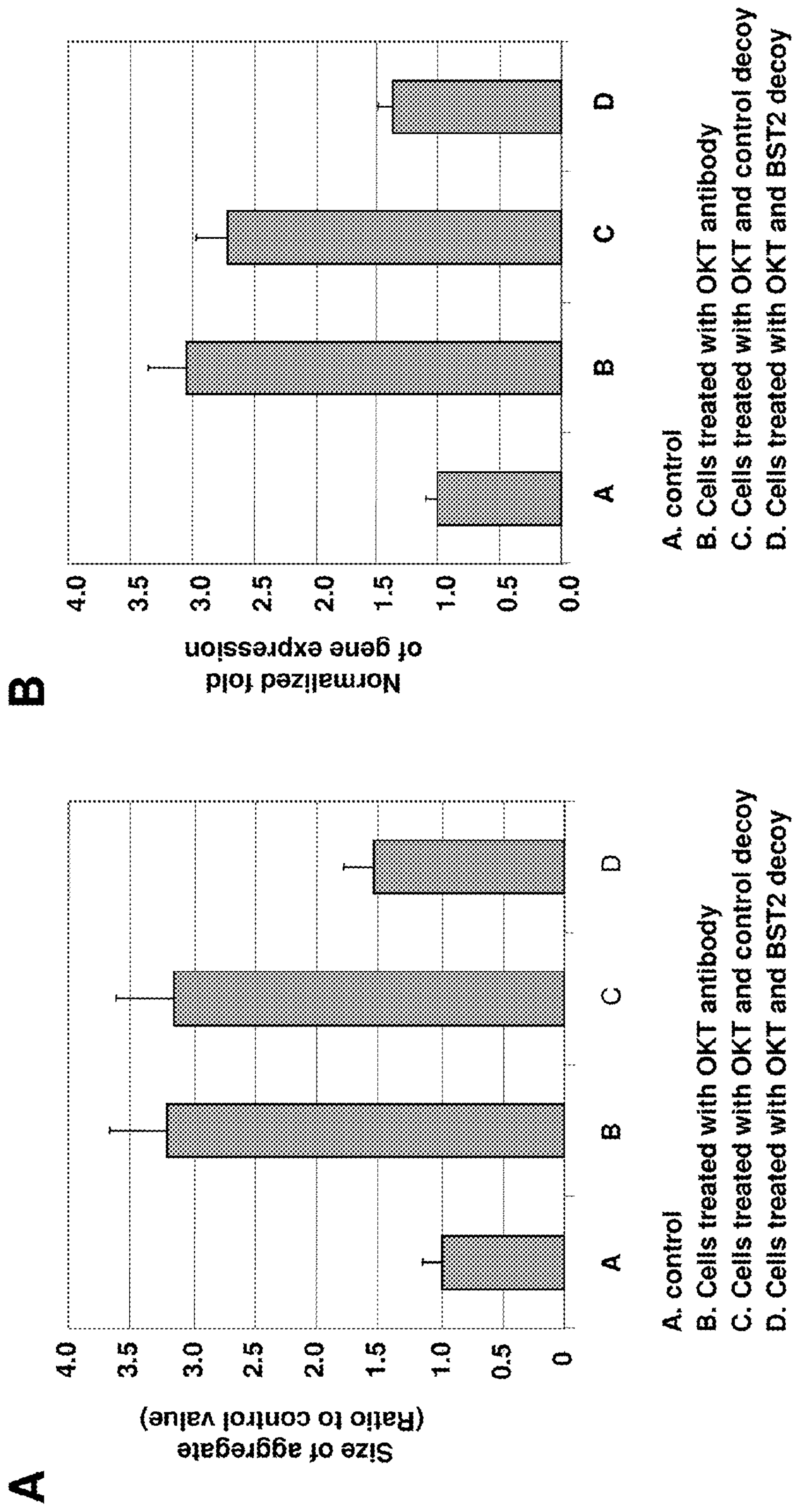

The Bst2 decoy pretreatment under the activation condition resulted in a significant decrease in aggregation of Jurkat cells. In addition, the 3-fold increased expression of IL-2 by Jurkat cell activation was decreased again to the basal level by the Bst2 decoy treatment (FIGS. 11 and 12).

The data presented herein indicate that Bst2 is important for inflammation and immunity. Blocking Bst2 function may reduce inflammation-induced diseases. In immunocompromised subjects such as AIDS patients and patients with immune deficiency, increasing immune signaling may benefit them. A bivalent fusion protein composed of Bst2 decoy and another molecule Y, which may be a protein or a compound, can act as an adaptor forcing interaction and signaling between the cell that expresses Bst2 ligand, and another cell which expresses the receptor for Y. See FIG. 35.

Example 8

Evaluation of the Action of Bst2 decoy in a Mouse Model of Asthma

Example 8-1

Asthma Induction in Mice

A mouse model of asthma was prepared by sensitizing mice (C57B6, 8 weeks) with ovalbumin. In detail, mice were initially sensitized for five continuous days by intranasal injection of ovalbumin. After three weeks, mice were intranasally sensitized again with ovalbumin for five continuous days. One week after the secondary sensitization, mice were challenged intranasally with ovalbumin three times every 24 hrs to induce asthma. Herein, a Bst2 decoy was intravenously injected into mice 30 min before sensitization with ovalbumin, and was injected into mice 30 min before the first sensitization and the last injection of ovalbumin. Three days after the last injection, serum samples, lung tissues, and the like were collected from mice.

Example 8-2

Bst2 Decoy-induced Changes in the Number of Sedimented Immune Cells

In mice sensitized with ovalbumin and treated with a Bst2 decoy, the total number of infiltrating cells and the number of each cell type (neutrophils, eosinophils and lymphocytes) were remarkably decreased in bronchoalvelar lavage fluid (FIG. 13).

Example 8-3

The Effect of Bst2 Decoy on Cytokine Production

When a Bst2 or Damp1 decoy was injected into a mouse model of asthma which was induced by sensitization and challenge with ovalbumin, expression levels of cytokines (interleukin-4 (IL-4), interleukin-5 (IL-5) and interleukin-13 (IL-13)) were measured as follows. After bronchoalveolar lavage, lung tissues were excised from mice, and proteins were isolated from the lung tissues. Cytosolic proteins were isolated using lysis buffer containing NP-40. The isolated proteins were separated on a SDS-PAGE gel, and were transferred onto a PVDF membrane by a wet transfer method. The blot was incubated in a 1:1000 dilution of each several primary antibodies (anti-IL-4 antibody (Setotec Inc.), anti-IL-5 antibody (Santa Cruz Inc.), anti-IL-13 antibody (R&D Inc.), and anti-actin antibody (Sigma Inc.)). The bound primary antibodies were detected with a HRP-conjugated secondary antibody (anti-rabbit HRP-conjugated IgG) using ECL reagent. The levels of cytokines, such as IL-4, IL-5 and IL-13, were found to increase in the lung tissue of mice with asthma induced by sensitization and challenge with ovalbumin. Also, when ovalbumin-sensitized asthmatic mice were injected with a Bst2 decoy protein, cytokine levels decreased with increasing doses of the decoy protein. These results indicate that the Bst2 decoy protein has a therapeutic effect on asthma (FIG. 14).

Example 9

Evaluation of Functional Similarity between Human Bst2 Protein and Mouse Damp1 Protein There is about 35% amino acid sequence similarity between human Bst2 protein and mouse Damp1 protein. In this regard, it was examined whether the two proteins would exhibit functional similarity in cell-cell adhesion assays in vitro and in the murine asthma model in vivo. Human Bst2 and mouse Damp1 proteins were examined for an inhibitory effect on adhesion between IFN-γ-treated HUVECs and U937 cells according to the same method as in Example 6.

Example 10

Preparation of Anti-Bst2 Polyclonal Antibody

The purified Bst2 and Damp1 decoy proteins expressed in CHO-S cells were mixed with a Ribi adjuvant at a ratio of 1:1, and were injected into rabbits with time intervals of two weeks. During immunization, blood samples were collected and examined for antibody production. After three immunizations, serum samples were obtained from rabbits. Anti-Bst2 polyclonal antibody was purified by affinity chromatography using a column in which Bst2 protein was bound to an immobilized support.

Example 11

Preparation of PEG-conjugated Forms for Improvement of Metabolism of Bst2 Decoy

Example 11-1

Preparation of PEG-conjugated Forms

PEG conjugation was carried out by two types of PEG: (1) aldehyde PEG and (2) succinimidyl carbonate PEG (FIG. 17). First, aldehyde PEG conjugation was carried out as follows. 1 mg of Bst2 decoy protein was dialyzed in 0.1 M phosphate buffer (pH 7.5), and was mixed with a 30-fold molar ratio of (mPEG12000-OCH2COGly-Gly)$_2$(2,4-diamino butylic acid)-PEG'-NHS, followed by incubation at room temperature of 2 hrs with agitation. Separately, for carbonate PEG conjugation, 1 mg of Bst2 decoy protein was dialyzed in 0.1 M phosphate buffer (pH 5.0), and was mixed with a 20-fold molar ratio of succinimidyl carbonate PEG, followed by incubation at room temperature of 2 hrs with agitation. After the reaction was completed, PEG-conjugated Bst2 decoys were isolated and purified using a size exclusion column (Superdex-200, Pharmacia), and were dialyzed in 50 mM phosphate buffer (pH 7.4).

Example 11-2

The Enhancing Effect of PEG-conjugated Forms on in vivo Stability of Bst2 Decoy

The PEG-conjugated forms of Bst2 decoy, prepared in Example 11-1, were injected into the tail vein of 7 week-old male Sprague-Dawley rats in a dose of 0.4 to 2 mg/kg. A negative control group was injected with an equal dose of physiological saline. Also, an equal dose of Bst2 decoy protein was used as a positive control. Blood samples were collected before drug administration, and 2 min, 5 min, 10 min, 30 min, 1 hr, 2 hrs, 6 hrs, 12 hrs and 24 hrs after drug administration from the jugular vein using a cannula. The collected blood samples were analyzed by ELISA. A 96-well plate was coated with an anti-Bst2 decoy antibody (100 ng/ml in PBS) at 4° C. for 8 hrs or longer, and was blocked with albumin in PBS at 37° C. for 2 hrs. The plate was reacted with a proper dilution of rat serum or Bst2 decoy (standard sample) at 37° C. for 2 hrs. The plate was then reacted with a monoclonal antibody (mAb conjugated with horseradish peroxidase, Roche Inc.) recognizing the histidine tag added to the C-terminus of Bst2 decoy at 37° C. for 2 hrs. After being well washed, the plate was treated with a substance of peroxidase, and absorbance was measured at 450 nm. Quantitation of the PEG-conjugated Bst2 decoys present in blood was performed using the standard samples (FIG. 18). In FIG. 18, "201B-H" indicates a human Bst2 decoy sample, and "201B-HP" indicates an aldehyde PEG-conjugated human Bst2 decoy sample.

Example 12

Expression and Distribution of Bst2 in Inflammation-associated Diseases

Tissues of patients with various inflammatory diseases were obtained for investigating expression and distribution of Bst2. Obtained tissues include: lung tissue of asthma patient, arterial blood vessel of atherosclerosis patient, skin lesions of psoriasis patient, intestine tissue of Crohn's disease patient, intestine/colon tissue of ulcerative patient, stomach tissue of chronic active gastritis patient, and cecum tissue of acute appendicitis patient. Each tissue was selected as a representative lesion showing typical inflammation phenotype.

For asthma, a paraffin block of the lung tissue, prepared by fixing the lung tissue in 10% formaldehyde and embedding the tissue in paraffin, was sectioned into a thickness of 1.5 μm, and was mounted onto glass slides. The slides were stained with hematoxylin and eosin to investigate the changes in the lung tissue according to allergen and drug administration. Histostaining was performed with the polyclonal antibody prepared in Example 10. Other tissues were prepared in a similar manner. Compared to the normal tissue, Bst2 protein was overexpressed in inflammation-associated diseases. Bst2 was detected in immune cells leukocytes, vascular endothelial cells and other cell types (FIG. 19).

Example 13

Cell Culture

Cell culture was performed as described in Example 1.

Example 14

Construction of the Expression Vectors for the Human Bst2 Decoy and Bst2 Decoy Fc Fusions Fusion constructs are prepared based on expression vector pCDNA 3.1 or other dhfr vectors commercially available.

FIG. 20 shows a schematic of Bst2 decoy and other Fc fusions. These are schematic representations of possible fusion proteins. Referring to FIG. 20, FIG. 20A shows the Bst2 decoy itself, FIG. 20B shows the Bst2 decoy fused to the hinge-CH2-CH3 portion of an IgG heavy chain Fc with separate expression of Bst2 decoy to form a Bst2 decoy dimer on the head of each fusion protein. FIG. 20C shows a form in which Bst2-kappa fusion is expressed in concert with the Bst2-IgG Fc fusion to allow the stable formation of Bst2 decoy dimer on the head of each fusion protein that is stabilized through the naturally-occurring IgG kappa chain-heavy chain disulfide bonding. FIG. 20D shows a form in which the Bst2 decoy-IgG Fc is expressed without other Bst2 dimerization counterparts. Dimerization of the hinge-CH2-CH3 portion of the fusion occurs in each case where the IgG Fc portion is expressed due to the naturally-occurring disulfide bonding between these chains.

Figure 21:
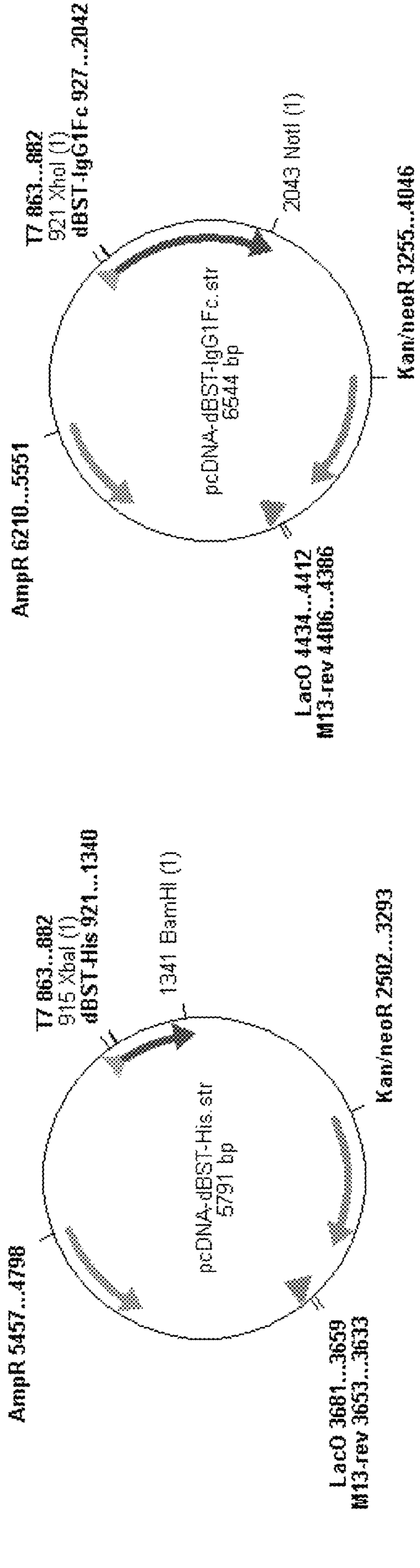

FIG. 21 shows vector maps of Bst2 decoy-IgG Fc fusion proteins described above. Representative expression vectors depicting the expression vectors for the IgG1 and IgG2 Fc fusions are illustrated. FIG. 21A shows Bst2 decoy (dBst2). The Bst2 decoy expression vector was constructed by PCR-cloning an XbaI site 5' of the start of the decoy protein with an N-terminal tPA signal peptide and C-terminal His-tag followed by a BamH1 site on the 3' end; this insert was cloned into pCDNA3.1 cut with XbaI and BamH1. FIG. 21B shows dBst2-IgG1Fc fusion. The hinge-CH2-CH3 region of IgG1 heavy chain was PCR-cloned and fused to the C-terminal end of Bst2 decoy with a 5' XhoI and 3' NotI site; this insert was cloned into pCDNA3.1 cut with XhoI and NotI. FIG. 21C shows dBST-kappa fusion. The constant region of the IgG kappa light chain was PCR-cloned and fused to the C-terminal end of Bst2 decoy with a 5' XhoI and 3' NotI site; this insert was cloned into pCDNA3.1 cut with XhoI and NotI. (d) dBST2-IgG2HC fusion. The hinge-CH2-CH3 region of IgG2 heavy chain was PCR-cloned and fused to the C-terminal end of Bst2 decoy with a 5' XhoI and 3' NotI site; this insert was cloned into pCDNA3.1 cut with XhoI and NotI.

Example 15

Vector Construction

An expression vector of histidine-tagged Bst2 decoy was constructed as described in Example 2.

Immunoglobulin gene fragments were cloned from a human blood cell cDNA library (Clontech) by PCR: the Fc region (hinge, CH1 and CH2 region) of human IgG1 heavy chain (Genbank No: BC089417., primers 1, 2), the constant region of human immunoglobulin kappa chain (Genbank No: BC067092, primers 3, 4), and the constant region (CH1- hinge-CH2-CH3) of human IgG2 heavy chain (Genbank No: AJ294731, primers 5, 6). The sequence of PCR primers used in cloning the fragment are as follows.

```
Sequence 1
                                        (SEQ ID NO: 8)
201-H-5': 5'-ctc cca gga cga gcc caa atc ttg-3'

Sequence 2
                                        (SEQ ID NO: 9)
201-IgG1-3': 5'-ggcggccgc TCA ttt acc cgg gga-3'

Sequence 3
                                       (SEQ ID NO: 10)
201-L-5': 5'-ctc cca gga ccg tac ggt ggc tgc-3'

Sequence 4
                                       (SEQ ID NO: 11)
201-kappa-3': 5'-ggcggccgc TTA aca ctc tcc cct-3'

Sequence 5
                                       (SEQ ID NO: 12)
201-H2-5': 5'-ctc cca gga cgc ctc cac caa ggg-3'

Sequence 6
                                       (SEQ ID NO: 13)
201-IgG2-3': 5'-ggcggccgc TCA ttt acc cag aga-3'
```

Example 16

Human Bst2 Decoy-Fc Fusion Constructs (IgG1, 2, and 4)

Three different constructions of human Bst2 decoy-Fc fusion were cloned into the expression vector pCDNA3.1 (Invitrogen). A DNA fragment coding for the extracellular region of human Bst2 protein was obtained by PCR, and was fused at the N-terminus to the signal peptide sequence of tPA to promote extracellular secretion after being expressed. The BST2 extracellular fragment was also fused at the C-terminus to IgG1 Fc region of IgG1, IgG2 and IgG4 or the constant region of kappa chain. The overlapped PCR product was digested with XhoI and NotI, and cloned into the vector pCDNA3.1 (Invitrogen). These fused fragments were produced by overlap PCR and primers were as follows and designated "pCDNA-dBST2-IgG1Fc", "pCDNA-dBST2-kappa", and "pCDNA-dBST2-IgG2HC" or pCDNA-dBST2-IgG4Fc.

Example 17

PCR Cloning and Fusion Strategy

PCR cloning and fusion strategy is set forth in FIG. 22. The following primers were used.

```
Sequence 7
                                       (SEQ ID NO: 14)
tPAsig_XhoI_Fw: 5'-cgctcgagacagccatcATGgatg-3'

Sequence 8
                                       (SEQ ID NO: 15)
201-H-5': 5'-ctc cca gga cga gcc caa atc ttg-3'

Sequence 9
                                       (SEQ ID NO: 16)
201-H-3': 5'-ttg ggc tcg tcc tgg gag ctg ggg-3'

Sequence 10
                                       (SEQ ID NO: 17)
201-IgG1-3': 5'-ggcggccgc TCA ttt acc cgg gga-3'
```

-continued

```
Sequence 11
                                       (SEQ ID NO: 18)
201-L-5': 5'-ctc cca gga ccg tac ggt ggc tgc-3'

Sequence 12
                                       (SEQ ID NO: 19)
201-L-3': 5'-acc gta cgg tcc tgg gag ctg ggg-3'

Sequence 13
                                       (SEQ ID NO: 20)
201-kappa-3': 5'-ggcggccgc TTA aca ctc tcc cct-3'

Sequence 14
                                       (SEQ ID NO: 21)
201-H2-5': 5'-ctc cca gga cgc ctc cac caa ggg-3'

Sequence 15
                                       (SEQ ID NO: 22)
201-H2-3': 5'-gtg gag gcg tcc tgg gag ctg ggg-3'

Sequence 16
                                       (SEQ ID NO: 23)
201-IgG2-3': 5'-ggcggccgc TCA ttt acc cag aga-3'

Sequence 17
                                       (SEQ ID NO: 24)
201-H4-3'; 5'-cat att tgg act cgt cct ggg agc-3'

Sequence 18
                                       (SEQ ID NO: 25)
201-H4-5'; 5'-ctc cca gga cga gtc caa ata tgg tcc
c-3'

Sequence 19
                                       (SEQ ID NO: 26)
201-IgG4-3'; 5'-ggc ggc cgc TCA ttt acc cag aga
cag g-3'
```

Example 18

Expression of Soluble Decoy-Fc Fusion Proteins

Soluble Bst2 decoy-Fc fusion proteins were prepared after transient transfection as described in Example 4. Stable cell lines expressing Bst2 decoy and Bst2 decoy Fc fusion proteins were established as described in Example 4. Large-scale expression and purification were performed as described in Example 4.

Example 19

PAGE of Purified Bst2 Decoy and Other Fc Fusions

Fc fusion proteins were purified from the culture media. After concentration by ultra-filtration, a two-step chromatography process was used, including Protein A affinity chromatography (Amersham Biosciences, MabSelect) and size-exclusion chromatography (Amersham Biosciences, Superdex 200).

Fc fusion proteins were loaded on protein A-packed column previously equilibrated with PBS buffer (1.06 mM potassium phosphate monobasic, 155.17 mM sodium chloride, 2.97 mM sodium phosphate dibasic, pH 7.4). The column was washed with excess amount of PBS to remove contaminants. Bound antibodies were eluted by low pH buffer, such as 50 mM glycine-HCl using a step gradient and neutralized with the equal volume of 1M Tris (pH 8.0).

An additional size-exclusion chromatography step was employed to remove immunoglobulin multimers. The purified antibody multimer mixture was loaded onto a Superdex 200 column previously equilibrated with PBS (pH 7.4). The linear flow rate of the buffer was selected from rates within the range of 50 cm/h to 150 cm/h.

Figure 23:
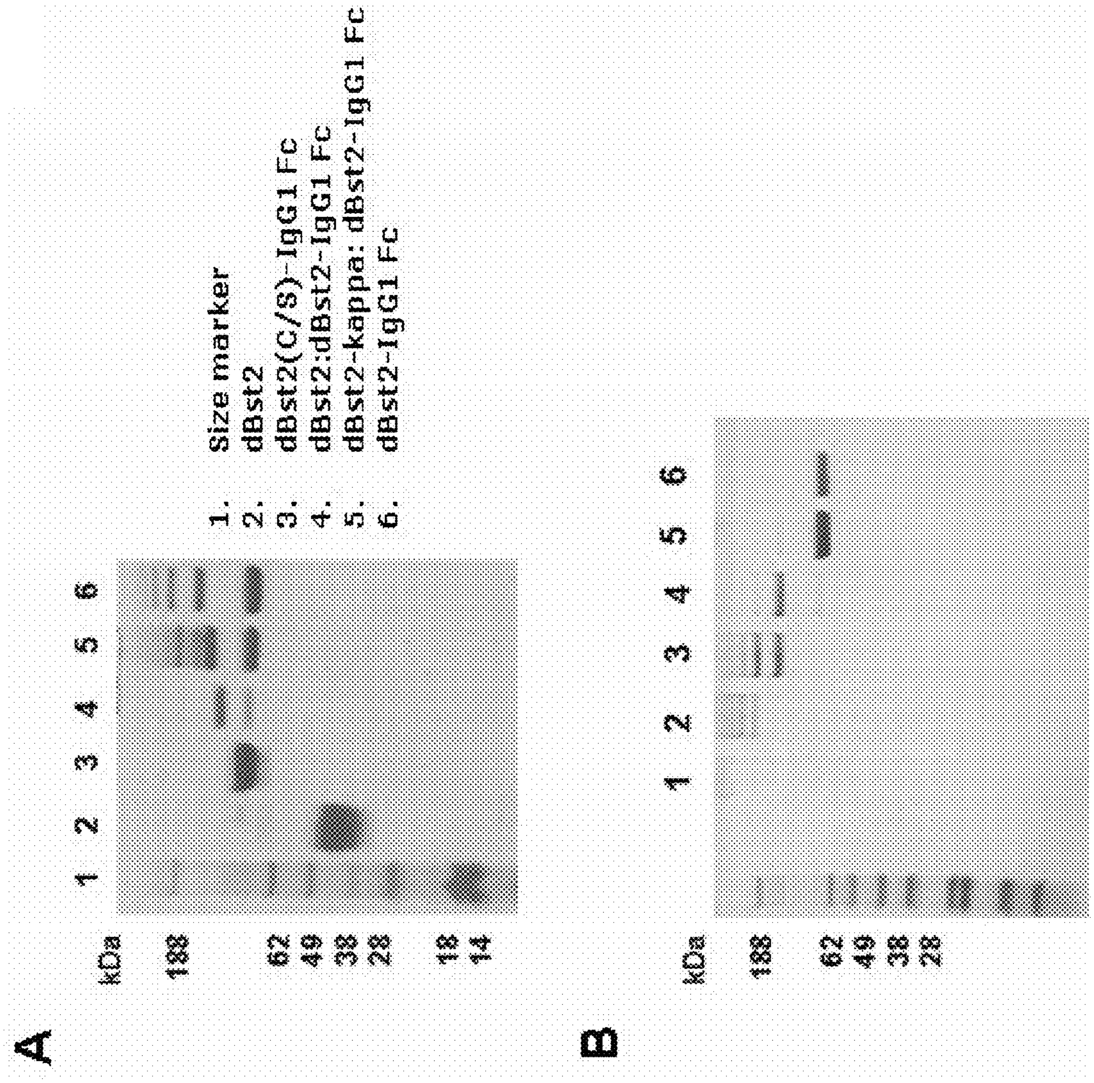

FIG. 23 shows a representative PAGE gel (4~12% gradient gel, Invitrogen) stained with Coomassie depicting various Bst2 fusion proteins following affinity purification. FIG. 23B shows that high molecular weight, multimeric forms can be removed by appropriate size-exclusion chromatography.

Example 20

Direct Binding of Bst2 Decoy to Immune Cells

Flat-bottomed 96-well plates were coated with Bst2 decoy with sodium bicarbonate (100 mM, pH 9.5) for 2 hrs at 37° C. The plates were washed with PBS (pH 7.4) and incubated with 1% bovine serum albumin (BSA) at 25° C. After a rinse with PBS (pH 7.4) containing 1 mM $CaCl_2$ and 0.5 mM $MgCl_2$, U937 cells ($1\times10^6$/ml) were added to each dBst2-coated well. After 2 hrs of incubation at 37° C., unbound cells were removed by two gentle washes with RPMI1640 media (Gibco-BRL) and bound cells were fixed with 2% paraformaldehyde for 20 minutes, washed, and stained with 0.5% crystal violet. After 30 minutes at 25° C., the plates were washed with PBS and bound cells were counted.

FIG. 24 shows direct binding of Bst2 decoy to U937 cells. U937 cells were attached to the wells containing Bst2 decoy but not BSA.

Example 21

Plasma Half-life of Bst2 Decoy-Fc Fusions

FIG. 25 shows plasma half-life of Bst2 decoy or Fc fusions. The Bst2 decoy protein fused to various stabilizing IgG Fc regions demonstrated enhanced serum stability, as indicated by a representative pharmacokinetics plot for two Bst2 decoy-IgG1 fusions compared to Bst2 decoy alone.

To determine plasma half-life of Bst2 decoy or other Fc fusions, rats (Sprague-Dawley males) were surgically implanted with intravenous catheter. During subsequent sessions, the catheters were connected to an infusion pump. The protein sample was infused by hand over 1 min through catheters flushed with heparinized saline to reduce the risk of clotting. The end of the infusion was designated as time 0. Blood samples (0.4 ml) were withdrawn from the catheters at various time points. The plasma was separated by centrifugation and applied to a sandwich ELISA assay for determination of the plasma concentration of BST2 decoy or other Fc fusion proteins. The wells in a 96 well plate were coated with (100 μl/well) a 5 ug/ml solution of rabbit anti-BST2 polyclonal antibody in 50 mM carbonate buffer (pH 9.2) and blocked with 1% BSA/PBS. Each plasma sample diluted to fall into the linear range of the standard curve were incubated at 25° C. for 90 min. After PBS washing, the wells were incubated with horseradish peroxidase-labeled goat anti-Human IgG (1:50,000 dilution, Fc specific, Sigma, Cat. No. A-0170) at room temperature for 1 hour and then treated with TMB substrate (Pierce). The plates were read at 450 nm in a plate reader and the data were analyzed using the four-parameter curve-fitting program. For standard curve for each different protein, each purified protein standard was used in the solution of 1% BSA, 1% rat pre-immune serum with appropriate concentrations.

Example 22

Inhibition of Bst2 Decoy-Fc Fusions in the Binding Between Bst2 Decoy and Cells

Bst2 decoy-IgG Fc fusion proteins demonstrate a concentration-dependent inhibition of U937 cell binding to Bst2 decoy coated cell culture plates indicating that the Bst2 decoy-IgG Fc fusion proteins are functional.

Competitive inhibition of Fc fusion proteins in the binding between BST2 decoy and cells was measured as follows. Flat-bottomed 96-well plates were coated with Bst2 decoy (50 ug/ml) with sodium bicarbonate (100 mM, pH 9.5) for 2 hrs at 37° C. The plates were washed with PBS (pH 7.4) and incubated with 1% bovine serum albumin (BSA) at 25° C. After a rinse with PBS (pH 7.4) containing 1 mM $CaCl_2$ and 0.5 mM $MgCl_2$, U937 cells ($1\times10^6$/ml) were added to each Bst2-coated well. Before the addition, cells were pre-incubated with BST2 decoy-Fc fusion proteins for 2 hrs at 37° C. Bound cells were counted as described in Example 20.

Example 23

The Effect of Bst2 Decoy-Fc Fusions on a Mouse Model of Asthma

A mouse model of asthma was prepared as described in Example 8-1.

Figure 27:
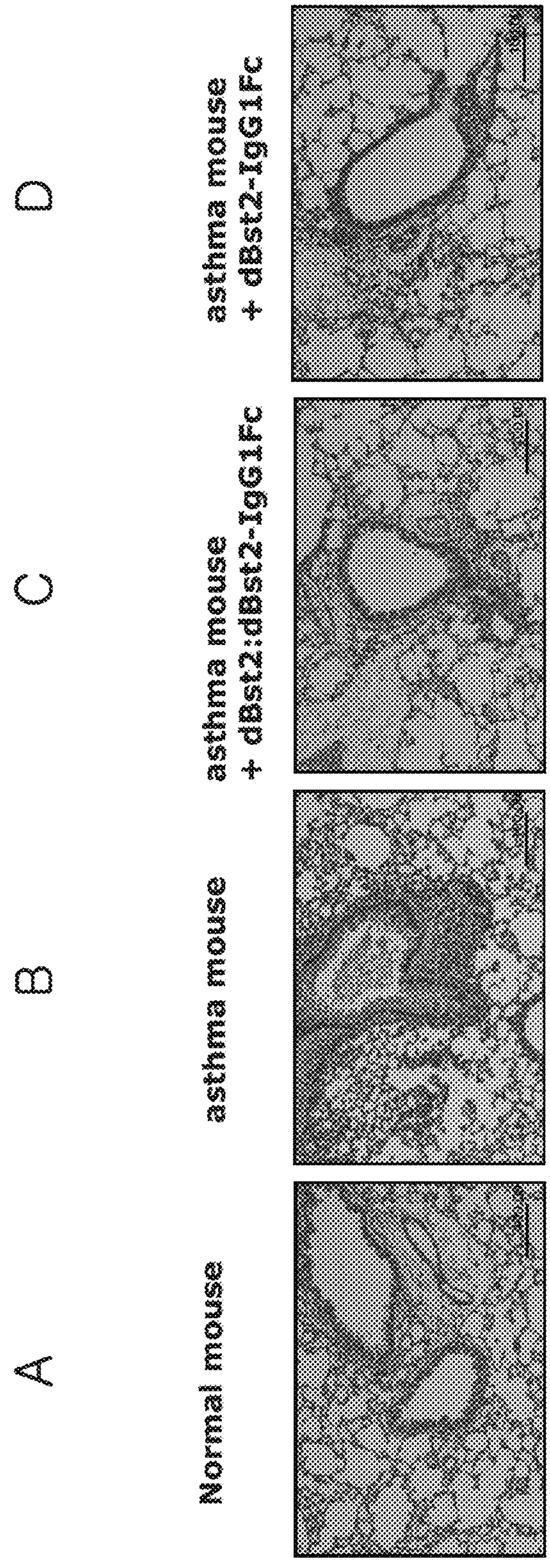

The effect of Bst2 decoy-Fc fusions on immune cell infiltration was assessed as described in Example 8-2. When ovalbumin-sensitized mice were treated with a Bst2 decoy, the total number of infiltrating cells was decreased and, especially, the number of neutrophils, eosinophils and lymphocytes except for macrophage was decreased in bronchoalveolar lavage (BAL) (FIG. 27).

Expression of 11-4, IL-5 and IL-13 was measured in the murine asthma model as described in Example 8-3 after injection with Bst2 decoy or Bst2 decoy Fc fusion proteins. The level of these cytokines was decreased suggesting that the Bst2 decoy proteins may have therapeutic effects on asthma (data not shown).

Example 24

Creation of Human-mouse Chimeric Bst2 Mice

A human-mouse chimeric BST2 mouse is made using the type of construct as exemplified in FIG. 28. The targeting vector which replaces the extra-cellular domain and C-terminus of mouse BST2 (DAMP-1) with the extra-cellular domain and C-terminus of human BST2 to be used for homologous recombination in mouse embryonic stem (ES) cells or other mouse cells is shown. Proper homologous recombination involves homologous recombination in the flanking arms shown (x) and cells with proper homologous recombination would be resistant to selection (e.g. Neomycin or G418 or other selection marker used). Cells with proper homologous recombination are selected by screening with either Southern blotting or PCR after selecting for the Neomycin (G418), which is an exemplified marker. Other selection markers may be used. To eliminate the Neomycin, or any other marker, in the targeting vector, one can either transfect recombined ES cells with an expression vector for Cre recombinase prior to making chimeric mice or one can mate the chimeric mice with a mouse expressing Cre recombinase. The chimeric mice can be generated using the recombined ES cells through standard techniques for generating knock-out, knock-in or other types of transgenic mice. Since the extracellular portion of the human-mouse chimeric BST2 is identical to the extracellular domain of human BST2, mice can be used to test human BST2 antibody in preclinical studies. Another option is to replace the entire coding region of mouse BST2 gene with the coding region of human BST2 gene, not just the coding region of the extracellular domain as it is shown in this figure, using the same strategy described here.

Example 25

Experimental Procedure for Combination Therapy in vitro

HUVECs were cultured in 12-well plates with or without transfection of Bst2 siRNA or control siRNA for 6 hr, then treated with or without IFNγ for 24 hr. In some experiments, cells were treated with crude media containing Bst2 decoy or mouse anti-human ICAM1 antibodies. After a wash with PBS (phosphate buffered saline), U937 cells were resuspended in serum free medium at $2\times10^6$ cells/ml. Assays were initiated by the addition of 200 ul U937 cells to HUVEC for a final volume of 1 ml. After 4 hr at 37° C., unbound U937 cells were removed by washing plates three times with PBS. Bound cells were fixed by the addition of 4% paraformaldehyde in PBS, and the bound cells were counted under microscopy in different fields. All statistical analyses were performed in Excel and statistical significance were evaluated with Student's t test. In some experiments, RNA samples were obtained from HUVECs after treatment with IFNγ and/or siRNAs, and real-time polymerase chain reaction (RT-PCR) analyses were performed.

Example 26

Results

Figure 29:
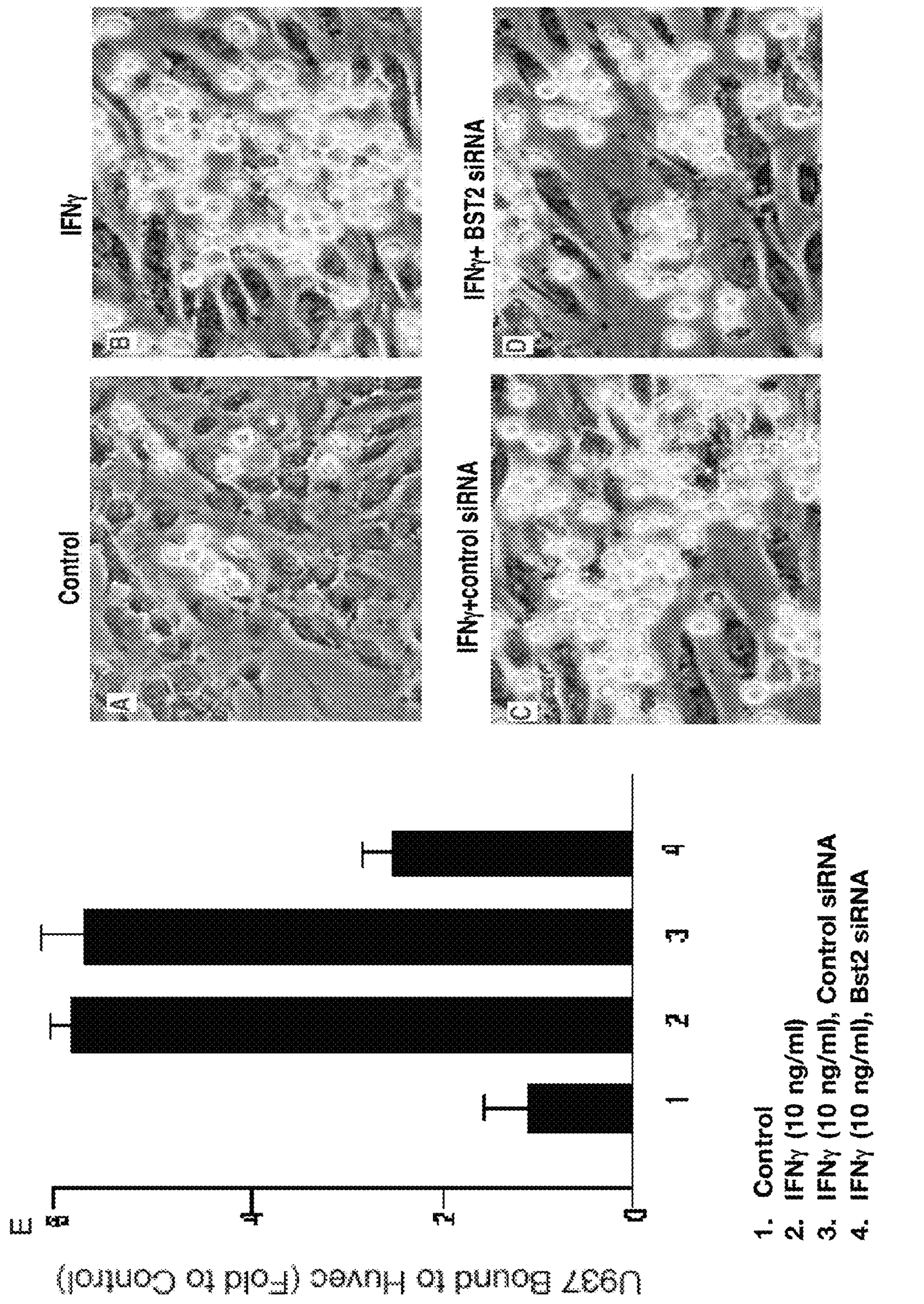

FIG. 29 shows that endogenous Bst2 is required for heterotypic aggregation between endothelial cells (HUVEC) and monocytic cells (U937) after stimulation with IFNγ. In order to show that the blockage of the endogenous Bst2 is important for inhibition of the heterotypic aggregation, HUVEC was treated with Bst2 siRNA to suppress endogenous expression of Bst2 prior to IFNγ treatment (10 ng/ml, 24 hr). FIG. 30 shows that Bst2 siRNA treatment or ICAM1 siRNA treatment does not affect ICAM1 expression or Bst2 expression in IFNγ-treated HUVEC, respectively. RT-PCR analyses were performed.

As shown in FIGS. 29 and 30, although both Bst2 and ICAM1 are considered to play a role in cellular adhesion, it is not known whether these two proteins cross-talk and function in an overlapping pathway or in independent, non-overlapping pathways. For combined anti-adhesion therapy, combined inhibition of two adhesion proteins that function in redundant pathways may be less effective than that with two proteins in non-overlapping pathways. When ICAM1 siRNA was added to the Bst2 siRNA reaction (B+I siRNA), ICAM1 siRNA did not result in further decrease in Bst2 expression, suggesting that ICAM1 is not required for Bst2 expression. Similarly, addition of the Bst2 siRNA to the ICAM1 siRNA-mediated reaction (I+B siRNA) did not cause any further reduction in ICAM1 expression, suggesting that Bst2 is not required for ICAM1 expression. These data indicate that Bst2 and ICAM1 may mediate cell adhesion via non-overlapping pathways.

Figure 31:
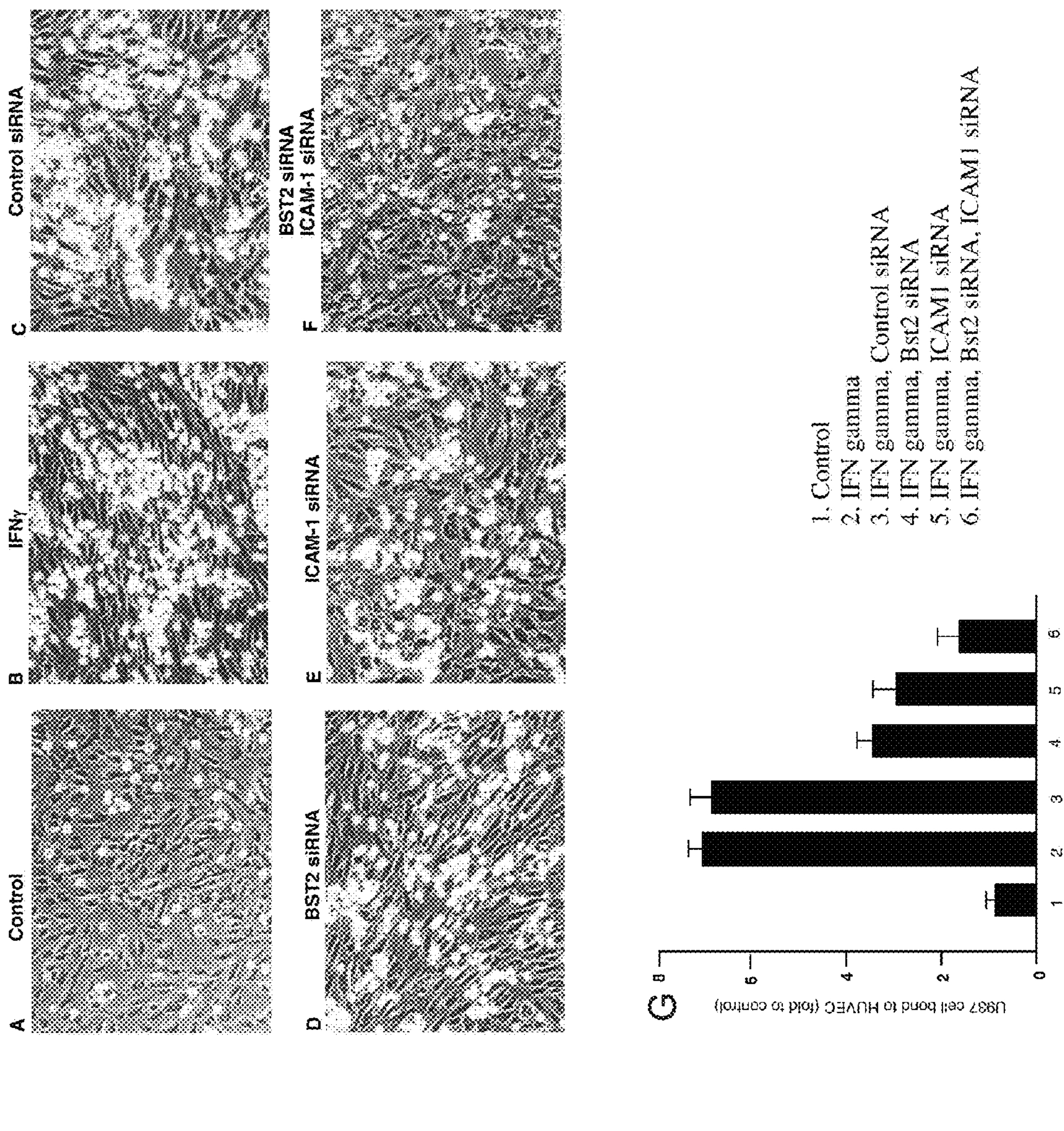
Figure 32:
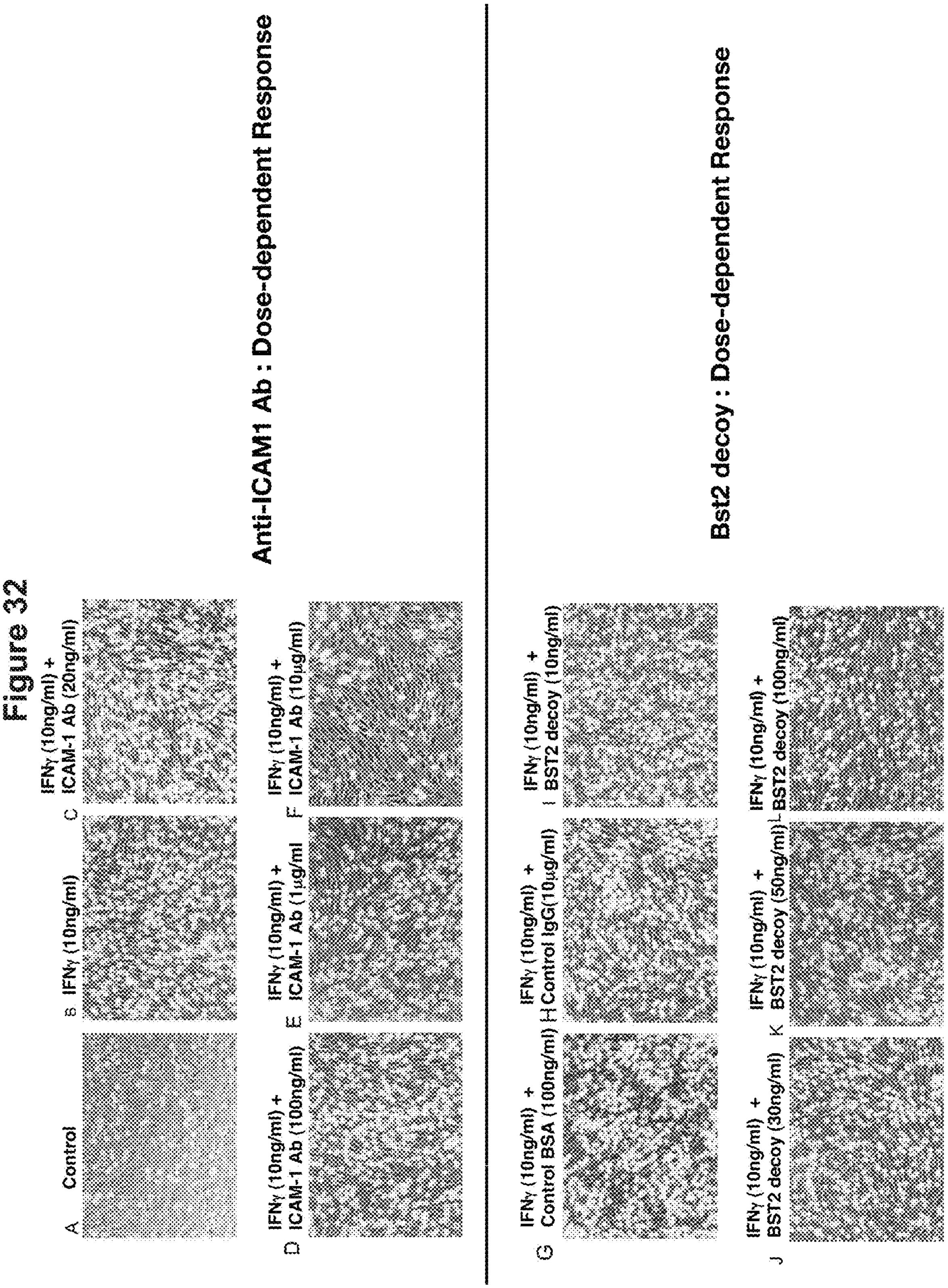
Figure 32:
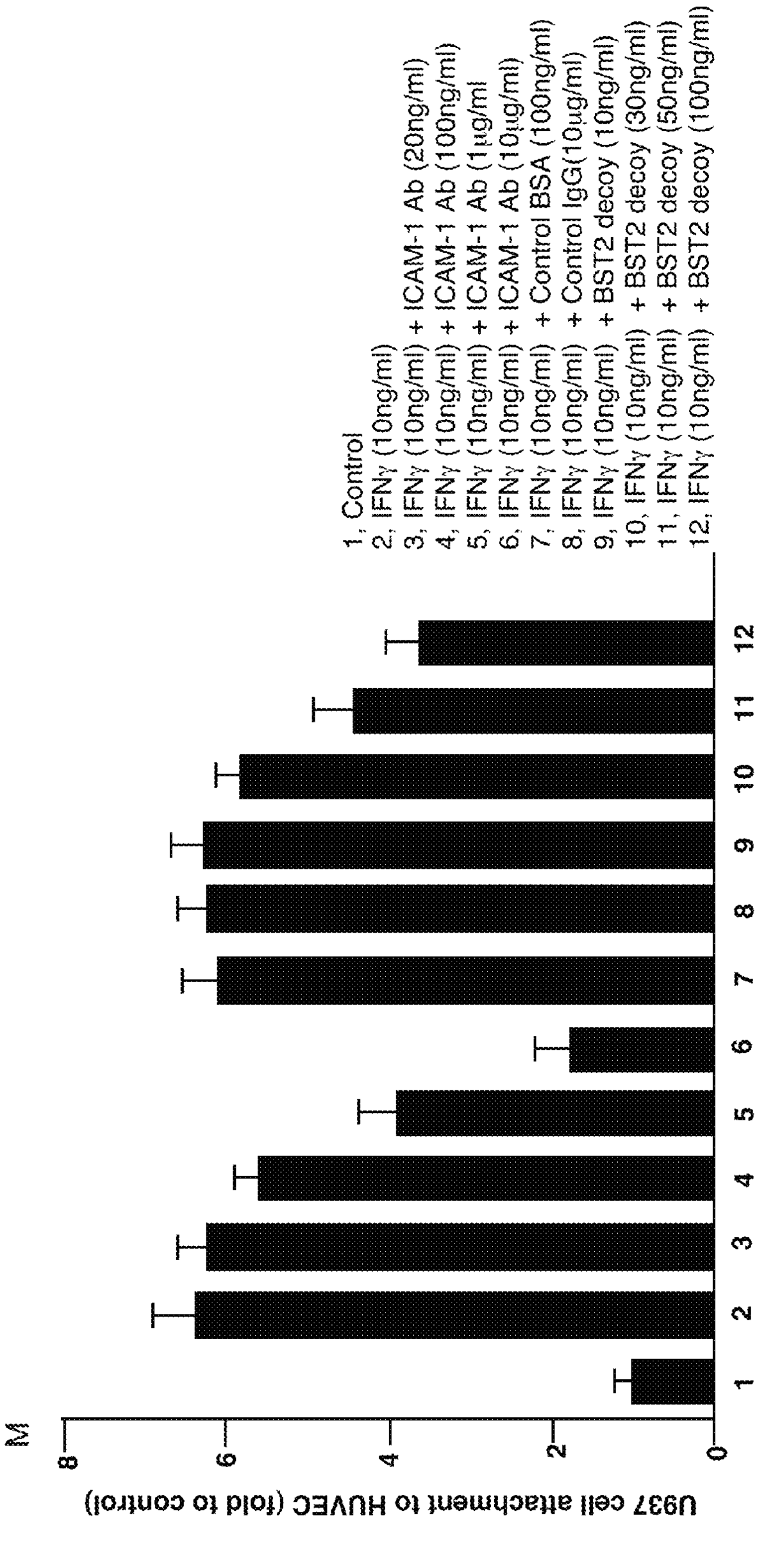

FIG. 31 shows that combination treatment of Bst2 siRNA and ICAM1 siRNA shows additive effects in heterotypic adhesion assay. And FIG. 32 shows the dose-dependent response of anti-ICAM1 or Bst2 decoy in heterotypic adhesion assay, and a quantitative analysis of the dose-dependent response of anti-ICAM1 and Bst2 decoy.

Based on the siRNA experiments in FIG. 31, cell adhesion assay was performed in the presence of mouse anti-human ICAM1 antibody or Bst2 decoy. Conditioned media containing Bst2 decoy was used. The amount of Bst2 decoy in the crude cell supernatant was roughly estimated by comparing the band intensities of the His-tagged Bst2 decoy and the protein standard after SDS-PAGE.

Figure 33:
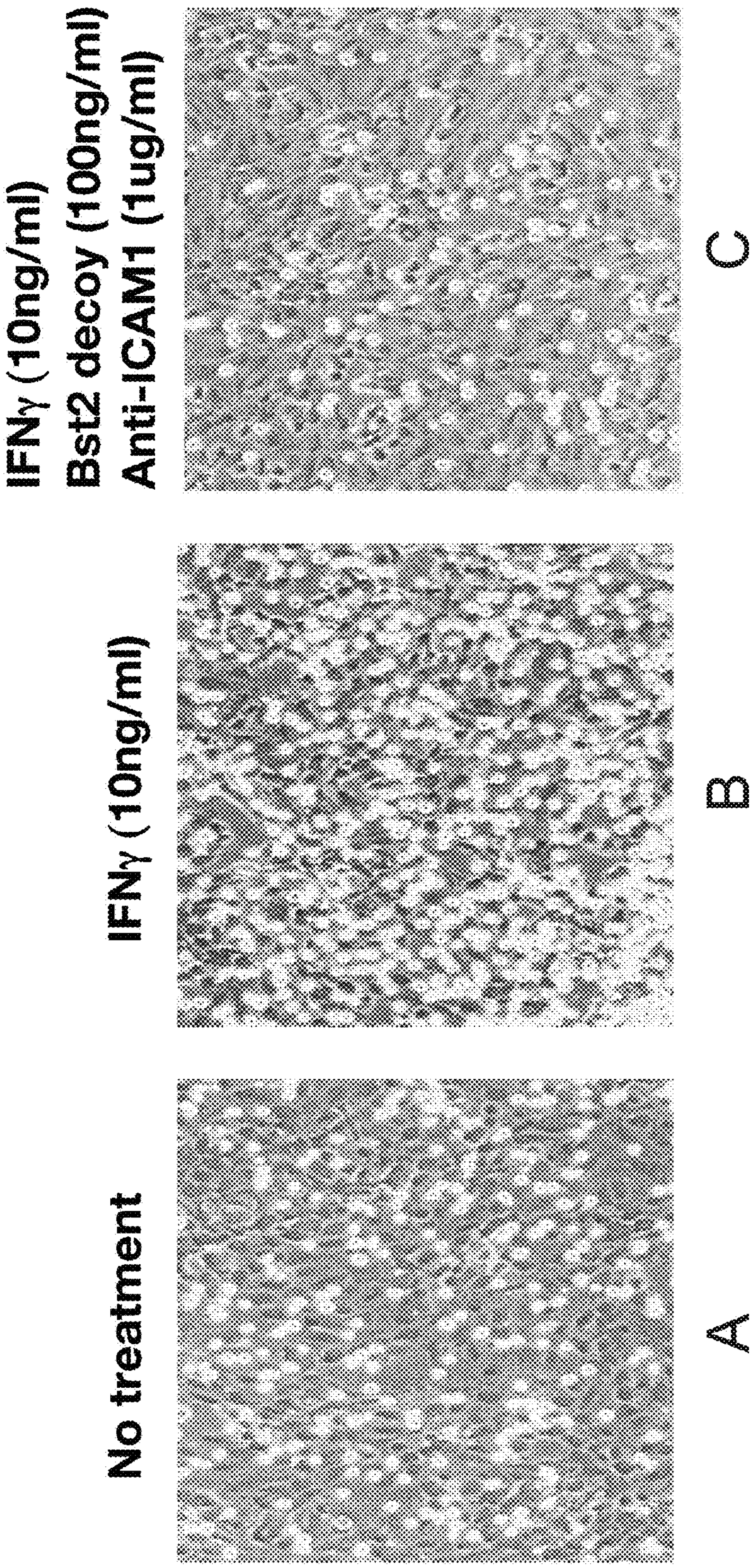

FIG. 33 shows that combination treatment of Bst2 decoy and anti-ICAM shows additive effects in cell adhesion. Sub-optimal doses of Bst2 decoy (100 ng/ml) and anti-ICAM1 (1 ug/ml) were used. Cell adhesion was completely inhibited to the control level when both Bst2 decoy and anti-ICAM1 were used.

The results shown in FIGS. 29-33 suggest that combined treatment of the Bst2 blockers and blockers of other immune, inflammatory mediators may be beneficial for treatment of many immune, inflammatory disorders. Such blockers that may be used with the Bst2 blockers include CTLA4-Ig or blockers of TNF alpha, IL6, IL1, LFA1, alpha 4 integrin, ICAM1 or VCAM1. In addition, combination treatment of the Bst2 decoy-Fc or anti-Bst2 with cyclosporine or glucocorticoid that suppress immune, inflammatory responses may be beneficial for transplantation conditions or many diseases that require corticosteroid treatment, respectively.

For preclinical studies in rat or mouse models, rat or mouse monoclonal antibodies against many of the rat or mouse proteins listed above (TNFR, IL6R, IL1R, LFA1, alpha 4 integrin, ICAM1, VCAM1) are commercially available (Abcam or other companies). CTLA4-Ig may have to be produced in-house. For the protein targets where monoclonal antibodies are not available or if it is not desirable to use monoclonal antibodies, soluble receptor decoy proteins of the corresponding protein targets, for example, TNFR-Fc (soluble TNFR1), could be used for combination therapy in animal models.

Example 27

The Possibility that Bst2 may be its Own Ligand

Bst2 is known to form a homodimer after activation. Consistent with this, it appears that Bst2 decoy is expressed as a dimer or higher multimers. This dimerization property of Bst2 suggests the possibility that Bst2 may serve as its own ligand in cell-cell interaction.

For testing this possibility, U937 cells are incubated with anti-Bst2 antibody, and the antibody-treated U937 cells are added to HUVECs after interferon treatment. In another experiment, U937 cells are treated with Bst2 siRNA or control siRNA, and the siRNA-treated U937 cells are added to HUVECs after interferon treatment.

If Bst2 on U937 cells is required for cell-cell interaction, U937 cells treated with anti-Bst2 or Bst2 siRNA would not bind to HUVECs. These results indicate that Bst2 on U937 cells interacts with Bst2 on HUVECs for adhesion identifying Bst2 as one of the possible Bst2 L proteins.

Example 28

Identification of Bst2 L using Genome Wide Full-Length cDNA (GFC) Arrays and Fluorometry Bst2 L may be screened using the GFC-Arrays (Genome Wide Full-Length cDNA Arrays) (OriGene Technologies, Rockville, Md.). GFC-Arrays are sets of transfection-ready cDNA plasmids in the mammalian expression vector pCMV-sport6 (GIBCO) arrayed in disposable 384 well plates. Each well contains 62.5 ng of a single lyophilized cDNA, a concentration optimized for reverse transfection into a variety of cells. The standard protocol for reverse transfection is appropriate for most commonly used cell types. The collection contains over 24,000 transfection-ready full-length human cDNA clones. GFC array also provides a subset of human gene arrays such as the arrays of Transmembrane Proteins and Druggable Genes (genes for enzymes/receptors to which drugs can be targeted). These two subset arrays (or the whole set arrays) may be screened for binding activity to Bst2 decoy Fc.

Briefly, by means of a high-throughput transfection methodology, individual genes are transfected into human cells such as 293T, CHO cells, COS cells or any other mammalian cells. To each well of 384-well plates containing 62.5 ng of a distinct cDNA is added 20 μl of serum-free medium containing FuGENE 6 (Roche). Forty microliters of 20% FBS DMEM media containing 293T, CHO cells, COS cells or other mammalian cells are plated in each well. After 48 h at 37° C. in 5% $CO_2$, optimized amount of Bst2 decoy Fc is added to each well and labeled with FITC labeled anti-Fc antibody. Fluorescence is analyzed using microplate fluorometry (384 well format). Each well that scores positive is retested on both Bst2 decoy Fc and control Fc. After screening with GFC-Arrays, each positive well is validated via standard transfection with the specific cDNA plasmid. All cDNAs in GFC-Arrays are available separately in OriGene (Rockville, Md.).

Example 29

Isolation of Bst2 L Via Expression Cloning

Expression cloning method requires identifying an abundant in vitro cell source for Bst2 L to construct a plasmid cDNA expression library. The cDNA expression library is then screened for Bst2 L using Bst2 decoy Fc or biotinylated Bst2 decoy with a panning technique.

Example 29-1

Identification of an Abundant in vitro Cell Source (Source Cell) for Bst2 L

Recombinant Bst2 decoy-Fc fusion protein is used to identify a putative cell line or primary cells expressing Bst2 L abundantly on the surface. Various cell lines and primary hematopoietic cells are screened. The possible cell sources for Bst2 L include but are not limited to, T cells, monocyte/macrophage cell lines such as human U937 cells, mouse RAW 264.7 cells, primary hematopoietic cells, B cells, dendritic cells, endothelial cells and fibroblasts. Mouse and rat cell lines are searched as well using rat Bst2 decoy-Fc fusion protein and mouse Damp1 decoy-Fc fusion protein, respectively.

Figure 15:
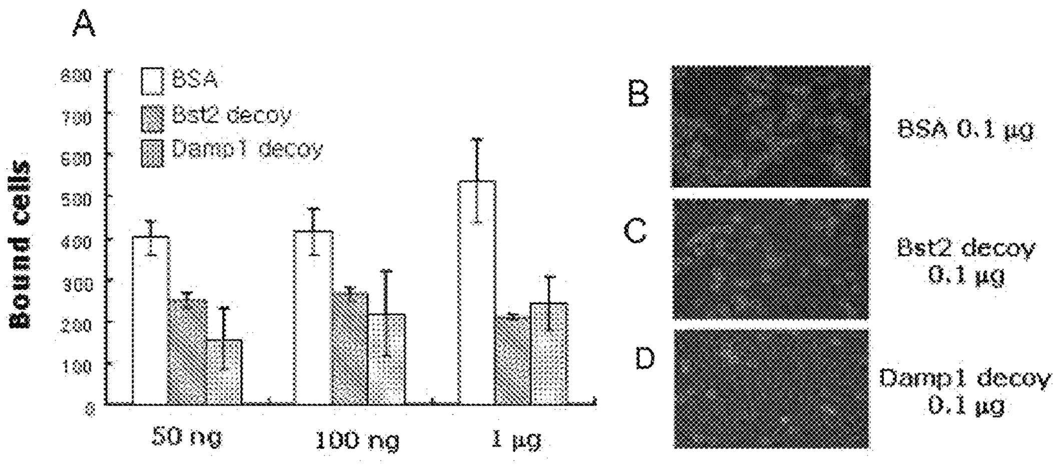
Figure 16:
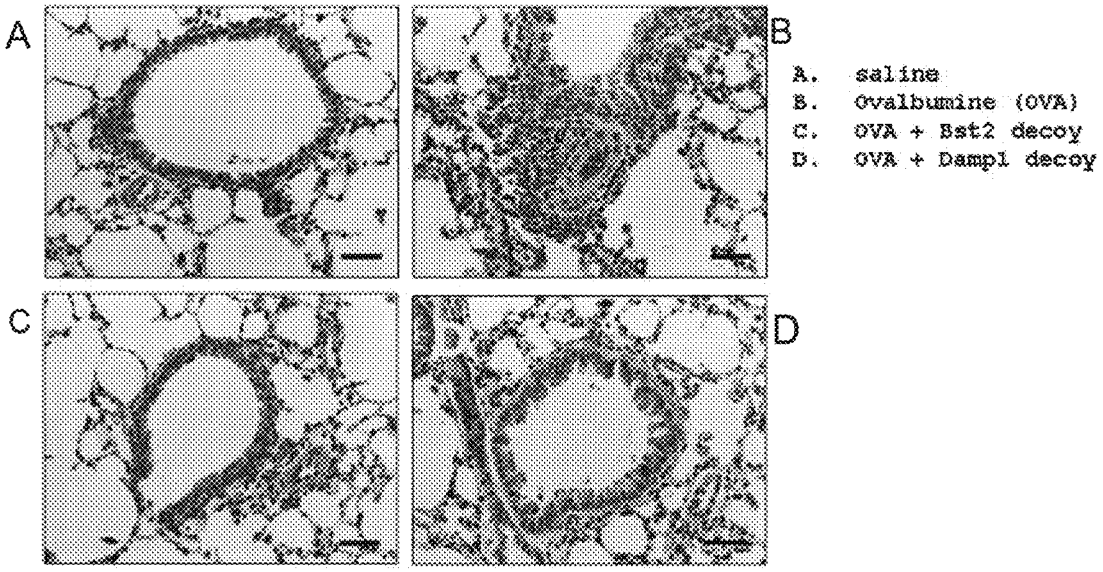

Because the human Bst2 decoy and the mouse Damp1 decoy function interchangeably in the cell adhesion assay and in the in vivo ovalbumin-induced asthma model as shown in FIGS. 15 and 27, the source cell line may be screened by both the mouse Damp1 decoy-Fc and human Bst2 decoy-Fc fusion proteins regardless of the species of the cell lines or primary cells used.

Cell lines or primary cells are screened for the presence of Bst2 L by indirect immunofluorescence or FACS (Fluorescence-activated cell sorter) analysis after staining with FITC-labeled human Bst2 decoy-Fc or mouse Damp1 decoy-Fc fusion proteins, followed by secondary antibody staining, for example, with goat F(ab') anti human IgG secondary antibody (Smith C A, Gruss H J, Davis T, Anderson D, et al. 1993, Cell 73, 1349-1360). The cells are then analyzed by FACS.

Example 29-2

Validation of the Bst2 L Source Cell Via FACS Analysis with FITC-labeled Bst2 Decoy-Fc The source cell line identified as above should show significant specific binding to FITC-labeled Bst2 decoy-Fc compared to the control Ig. Secondary antibody alone and purified human IgG Fc alone should not bind to the surface of the source cell line. These results indicate that binding of the Bst2 decoy-Fc is due to the Bst2 or Damp1 decoy moiety but not to the Fc portion of the probe. In order to further demonstrate the binding specificity, the binding should be inhibited by unconjugated Bst2 decoy but not by the unrelated control protein.

Example 29-3

Validation of the Bst2 L Source Cell Via Visualization of Bst2 L with $^{125}$I-Bst2 Decoy (Fc)

For validation, the source cells are incubated with $^{125}$I labeled-Bst2 decoy, or -Bst2 decoy Fc in the presence or absence of an excess amount of nonradioactive Bst2 decoy protein. Iodination by the lactoperoxidase method has been described (Urdal et al., 1988, J. Biol. Chem. 263:2870-2877). Cells are then incubated with crosslinker [bis(sulfosuccinimidyl)suberate]. Proteins are solubilized with 1% Triton X-100 cocktail, subjected to SDS-PAGE and visualized by autoradiography.

When the source cell line is found and validated as described (Example 29-1, 29-2 and 29-3), it may be possible to obtain a variant cell line that expresses an elevated number of the Bst2 L after many cycles of FACS analysis of the most brightly stained cell source.

Example 29-4

Construction of a Plasmid cDNA Expression Library from a Source Cell Line for Panning For isolation of Bst2 L, a cDNA expression library is constructed from the Bst2 L source cell identified and validated as above. A directional oligo-dT primed plasmid cDNA library is constructed from the source cell mRNA and ligated into the mammalian expression vectors (Invitrogen). The library is divided into pools of 1000 clones, and plasmid DNA of each pool is obtained. According to the method of Seed and Aruffo (Seed B, Arrufo A. Proc. Natl. Acad. Sci. USA, 1987, 84:3365) and its modification by Lacey et al. (Cell, 93:165, 1988), DNAs from individual pool are transfected into COS7 cells. After approximately 48-72 hr, cells are stained with human Bst2 decoy-Fc fusion for approximately 1 hr, washed and then fixed with paraformaldehyde or glutaraldehyde. Cultures are treated with enzyme-linked secondary antibodies such as alkaline-phosphatase conjugated goat anti-human IgG (Fc specific) antibody and immune complexes are detected by assaying for, for instance, alkaline phosphatase activity. One positive pool is selected, plasmid DNA is prepared for *E. coli* transformation. The *E. coli* transformants are used for the next cycle of enrichment. By repeating this cycle, the specific cDNA encoding the Bst2 L protein can be highly enriched yielding single cDNA clones.

The selected plasmid DNA is then transfected into COS7 cells and immunostained with either human IgG Fc domain, human Bst2 decoy-Fc fusion protein, or unrelated Fc fusion protein, followed by FITC-conjugated secondary antibody. At this stage, only the human Bst2-Fc fusion protein should bind to the source cell. These results then indicate that this source cell (or cell line) encodes Bst2 L and displays Bst2 L on its cell surface.

In an alternative approach, panning plates are coated with anti human IgG1 Fc polyclonal antibody (Jackson Immunoresearch) and then coated with Bst2 decoy-Fc. Blocking with bovine serum albumin may be necessary. COS7 cells transfected as described above are then added to the plates and adherent cells are suspended by treatment with EGTA and EDTA. The rest of the method for panning is similar as described above.

Example 29-5

Isolation of Bst2 L Via Expression Cloning using Biotinylated Bst2 Decoy as a Probe and Panning In an alternative approach, if the source cell contains a very high level of Bst2 L, Bst2 L may be isolated using biotinylated Bst2 decoy as a probe by following the method by Harada et al. (Proc. Natl. Acad. Sci. 1990, USA 87:857). In this method, biotinylated Bst2 decoy is crosslinked to cells expressing Bst2 L, and Bst2 L-expressing cells are enriched by panning on anti-biotin antibody-coated plates. It was reported that cross-linking is essential, for cells would not attach to the panning plate without it.

Construction of cDNA library and transient transfection to COS7 cells are performed as described above (see Example 29-4). After 48-72 hr, cells are detached by incubation with PBS containing 5 mM EDTA. Biotinylated Bst2 decoy is added and crossed-linked to cells. Cross-linked cells are added to the panning plate coated with anti-biotin antibody. Plasmid DNA is recovered from the cells attached to the plate and is used to transform *E. coli*. The amplified plasmid DNA is used for the next cycle of enrichment until it yields a single clone. COS7 cells transfected with one of these clones should then bind $^{125}$I-labeled Bst2 decoy specifically.

Example 29-6

Isolation of a Full-length cDNA of Bst2 L After Panning

As the DNA insert obtained after panning in expression cloning (see Examples 29-4 and 29-5) is likely to be a shorter truncated cDNA, a full-length cDNA cloning is necessary. Commercially available cDNA libraries (Clontech) is searched first using the short cDNA selected from the above procedures as a probe. The full-length cDNA of Bst2 L is obtained by screening a cDNA library from the source cell line using the short cDNA as a probe. Northern blot analysis of the mRNAs from the source cell line would show the Bst2 L transcript(s). Commercially available Northern blots (Clontech) may also be used to visualize the transcript.

After obtaining a full-length cDNA, nucleotide sequencing is performed. Sequences for a signal peptide, potential kinase domain, or any other interesting domains are searched.

If a signal peptide is detected in the nucleotide sequences, whether Bst2 L is released into media is tested. Bst2 L is epitope-tagged (for example, hemagglutinin) at the C-terminal and 293T cells are transfected with the expression vector for the Bst2 L-tag (HA). Western blot of cell extracts or conditioned media is probed with anti-tag (HA) antibody. If released into conditioned media, a smaller band than that observed in cell extracts are detected in the conditioned media. Affinity purification of the soluble protein and N-terminal sequence analysis of the soluble protein reveal the cleavage site.

Example 30

Direct Purification of the Rat Bst2 L or Damp1 L from an Abundant Animal Tissue Source (or Cell Line) and the Homologue Search for Human Bst2 L The direct purification method described here can be applied to human cell line membrane preparations if an abundant source cell line for the human Bst2 L is identified using the method described in Example 29-1. The cell line (or cell culture) sources, however, may not be convenient or too expensive to provide sufficient material for biochemical characterization and purification. Thus, alternate tissue sources from animals may be pursued. Animal Bst2 L such as rat-, dog-, rabbit-Bst2 L or Damp1 L could be identified first for subsequent human homologue search. Animal Bst2 L can be identified using direct purification methods after identifying an abundant tissue source in rats, dogs, rabbits, mice or other animals.

The first step for this method is to identify an abundant in vivo tissue source for Bst2 L in animals. Although any species of animals may be used, the methods described below are illustrated using rats.

The distribution of Bst2-specific binding activity in rat tissues is examined by uptake studies (Yang et al. J. Exp. Med. 174:515, 1991) of $^{125}$I-Bst2 decoy-BSA or RSA (rat serum albumin). The methods below, the modification of the method used for isolation of the receptor for advanced glycation end products (RAGE), are illustrated with $^{125}$I-Bst2 decoy-RSA as a binding probe. Once the uptake study demonstrates a major site of Bst2 L, direct purification including affinity purification steps using the Bst2 decoy-BSA Sepharose 4B column is performed using solubilized and fractionated membrane proteins. All column fractions are analyzed for binding activity by the solid-phase Bst2 decoy binding assay (see below). At the end of the purification step, the protein bands are excised and electro-eluted for amino acid sequencing analysis. The human homologue may be searched and cloned afterward.

Example 30-1

In vivo Tissue Distribution of BST2 Decoy Binding Activity

In vivo animal tissue source for Bst2 L can be identified by measuring the sequestration of $^{125}$I-labeled Bst2 decoy-RSA (rat serum albumin) or -BSA (bovine serum albumin). For tissue distribution studies, formaldehyde modified Bst2-RSA or Bst2-BSA is prepared as described in other studies (Horiuchi et al. J Biol Chem 261: 4962, 1986), by incubating RSA or BSA with formaldehyde. The protein is then radioiodinated. Similarly, normal RSA or BSA is iodinated to a comparable specific activity. Freshly drawn rat RBC are labeled with $^{51}$Cr to allow subsequent correction for tissue counts for blood-associated radioactivity.

The distribution of Bst2-specific binding activity in rat tissues is examined by uptake studies of $^{125}$I-Bst2-RSA (BSA). Either $^{125}$I-Bst2-RSA(BSA) or $^{125}$I-normal RSA (BSA) is injected intravenously into rats along with $^{51}$Cr-labeled RBC (red blood cell). Aliquots of blood are drawn at several time intervals, and various organs are removed and counted for radioactivity. The specificity of Bst2 ligand uptake in organs is assessed by injecting the animals with excess nonlabeled Bst2-RSA(BSA) before administration of the labeled Bst2. The RBC are lysed with water, and protein is precipitated with 20% TCA. The tissue-to-blood isotope ratio is calculated by the formula as described in Williamson et al. Diabetes 36:813 (1987). Whole organ counts are corrected for blood associated counts.

Tissue accumulation of Bst2-RSA(BSA) should not be affected by the prior injection of excess nonlabeled RSA (BSA), while pre-treatment of rats with excess nonlabeled Bst2-RSA(BSA) should decrease the accumulation of Bst2-RSA(BSA) in that organ. The uptake of Bst2-RSA(BSA) should remain low in all other major organs, with or without the nonlabeled competitor. When these criteria are met, the organ represents a potentially rich source for the isolation of the Bst2-binding proteins.

Example 30-2

Confirmation of the in vivo Tissue Source for Bst2 L via Solid-phase Binding Assay and Ligand Blotting Assay Once the uptake study demonstrates a major site of BST2 decoy protein sequestration and the potential tissue source for Bst2 L, membrane proteins of the tissue are prepared according to the standard protocols specific to the tissues or organs. The binding activity of tissue extracts can be demonstrated by solid phase binding assay and ligand blotting assay with $^{125}$I-Bst2 decoy as described below. These assays confirm and validate the in vivo tissue source for Bst2 L.

Solid-phase Binding Assay.

A solid-phase binding assay is required to facilitate the isolation of the Bst2 L from tissue. Detergent-solubilized membrane proteins are immobilized onto nitrocellulose and probed for ligand specific binding activity with $^{125}$I-Bst2 decoy-RSA or $^{125}$I-Bst2 decoy-Fc. The ligand should bind to the $^{125}$I-Bst2 decoy in a saturable and dose-dependent manner, and the binding should be blocked by antibody to Bst2 and/or by unlabeled Bst2 decoy-Fc or Bst2 decoy. Expression of Bst2 L in transfected cells should also allow the cells to bind $^{125}$I-Bst2 decoy in a saturable and dose-dependent manner. Using similar detergent-solubilized membrane preparations from other organs, the same solid phase Bst2 binding assay may be performed to confirm the in vivo source of the Bst2 L.

Ligand Blotting Assay to Visualize Bst2 L from the Identified Tissue Source.

Ligand blotting assay to visualize the Bst2 L band from the identified tissue source is carried out. Proteins obtained from the identified tissue source for Bst2 L are electrophoretically separated on SDS-PAGE and blotted onto nitrocellulose membranes, incubated with $^{125}$I-BST2-BSA (or Bst2 decoy Fc), and the ligand binding is evaluated by autoradiography.

Example 30-3

Direct Purification of Bst2 L from Solubilized Membrane Preparations of the in vivo Tissue Source After identification and confirmation of the in vivo tissue source of Bst2 L as described above, direct purification of Bst2 L can be performed using the solid-phase Bst2 decoy binding assay (see Example 30-2) as a means of monitoring Bst2 L activity. Membrane preparations from animal tissues (Example 30-1) or Bst2 L source cell lines (human or other species) (Example 29-1) are used.

Several purification steps including column chromatography and affinity chromatography can be used. It is desirable to employ Bst2 (Bst2 decoy)-BSA sepharose 4B column for affinity purification after one or two crude purification steps such as DEAE column or Sephadex column. The proteins bound to the affinity column are eluted, concentrated and analyzed for $^{125}$I-Bst2 (Bst2 decoy)-BSA binding activity. Preparative electrophoresis is then performed. The protein bands are excised and electro-eluted for N-terminal amino acid sequencing analysis.

Human homologue can be identified based on the rat, dog or rabbit Bst2 L sequences or mouse Damp1 L sequences.

Example 31

Isolation of Bst2 L Via Yeast Two Hybrid System

Bst2 L is isolated using the yeast two-hybrid system that relies on the reconstitution of the GAL4 transcriptional activator in the yeast *S. cerevisiae* (Fields S and Song O K, 1989, Nature 340:245-246). For example, commercially available library obtained from activated human T cells (Clontech) may be screened with the bait containing the extracellular domain of Bst2 using commercially available yeast two-hybrid kit.

Example 32

Validation of the Isolated Bst2 L Via in vitro Binding Assay

The Bst2 L isolated as above (Examples 28-31) should bind Bst2 (Bst2 decoy) specifically in vitro. The Bst2 (Bst2 decoy)-Bst2 L interaction can be determined in many different assays, and several examples of such assays are described below.

In one aspect, COS7 cells are transfected with the expression vector containing the full-length cDNA, and incubated with various concentrations of $^{125}$I-labeled Bst2 decoy-Fc in the presence or absence of unlabeled Bst2 decoy (Bst2 decoy-Fc) or unrelated protein (unrelated protein-Fc) in excess. Unlabeled Bst2 decoy (Bst2 decoy Fc) should completely block binding of radiolabeled Bst2 decoy-Fc. These results will indicate that Bst2 L specifically binds biologically active Bst2, Bst2 decoy or Bst2 decoy-Fc. The binding data are then analyzed to determine the affinity and number of sites per cell as described (Munson P J, Rodbard D, 1980, Anal. Biochem. 1 107:220-239).

In another aspect, Bst2-Bst2L interaction can be determined by FACS analysis. 293 cells, CHO cells or COS cells are transiently transfected with Bst2 L. After 24-48 hr, the cells are then incubated for 1 hr with a recombinant biotinylated Bst2 decoy Fc. The cells are further incubated for 30 minutes with phycoerythrin-conjugated streptavidin (Gibco BRL) and then analyzed by fluorescence activated cell sorting (FACS).

In another aspect, Bst2-Bst2 L interaction can be determined by co-immunoprecipitation assay. Purified Bst2 L is incubated with Bst2 decoy Fc and immunoprecipitated with protein A sepharose. Precipitates are resolved by SDS-PAGE and visualized by immunoblot with anti-Bst2 L.

In another aspect, a recombinant Bst2 L is produced, for example, in *E. coli*, and $^{125}$I-labeled Bst2 L is exposed to the wild-type, deletion mutants of Bst2, Bst2 decoy or Bst2 decoy-Fc, and control proteins immobilized to nylon filters after non-reducing SDS-PAGE. $^{125}$I-labeled Bst2 L should recognize the Bst2 proteins. This assay confirms the direct binding of Bst2-Bst2 L in vitro. When various deletion mutants of Bst2, Bst2 decoy or Bst2 decoy Fc proteins are employed, the binding domain of Bst2 that binds to Bst2 L can be also determined.

Example 33

In vitro Function of the Isolated Bst2 L

Cells treated with recombinant Bst2 L may elicit inflammatory responses. Cells including HUVECS are treated with recombinant Bst2 L, inflammatory cytokines such as interferon gamma, or combination of Bst2 L and cytokines. Cytokine production of these cells and U937 adhesion to these cells are measured. It is expected that Bst2 alone or in combination with inflammatory cytokines would enhance inflammatory responses and cell-cell adhesion. Bst2 decoy or Bst2 decoy-Fc should block these effects in vitro. Similarly, T cell activation and proliferation assays can be used to test the in vitro function of Bst2 L. These data indicate that Bst2 L directly mediates cell-cell interactions and Bst2 and Bst2 L are key regulators of immune, inflammatory responses. These assays can be repeated using rat or mouse cells to examine whether human Bst2 L functions in the rat or mouse system. These data indicate that Bst2 L directly mediates cell-cell interactions and that Bst2 and Bst2 L are key regulators of immune-inflammatory responses.

Example 34

In vivo Function of the Isolated Bst2 L

Mice or rats are injected with recombinant Bst2 L, Damp 1 L or rat Bst2 L. After injection, in vivo inflammatory parameters such as cytokine release are assessed. It is expected that Bst2 L (Damp1 L) injection would result in proinflammatory responses. These inflammatory responses should be blocked by the injection of Bst2 (Damp 1) decoy Fc or anti-Bst2 (Damp 1) antibodies. In another approach, anti-Bst2 L antibodies should also show anti-inflammatory effects. Such anti-Bst2 L antibodies can then be used as another therapeutic agent blocking the Bst2-Bst2 L interaction.

Example 35

Biochemical and Biological Characterization of Bst2 Ligand

Bst2 L isolated should meet the following biological criteria.

Measurement of the binding properties of the full-length Bst2 L protein. COS7 cells are transfected with the expression vector containing the full-length cDNA, and incubated with various concentrations of $^{125}$I-labeled Bst2 decoy-Fc and cell-bound radioactivity is measured. Competition with excess unlabeled Bst2 or Bst2 decoy-Fc, but not unrelated protein or unrelated protein-Fc, should completely block binding of radiolabeled Bst2 decoy-Fc. These results indicate that Bst2 L specifically binds biologically active Bst2, Bst2 decoy or Bst2 decoy-Fc. The binding data are analyzed to determine the affinity and number of sites per cell as described in Munson P J, Rodbard D, 1980, Anal. Biochem. 1 107:220-239.

Determination of the ligand-binding domain of Bst2 using $^{125}$I-labeled Bst2 L as a probe. A recombinant Bst2 L is produced, for example, in *E. coli*, and $^{125}$I labeled Bst2 L is exposed to the wild-type or deletion mutants of Bst2 or Bst2 decoy-Fc and control proteins immobilized to nylon filters after non-reducing SDS-PAGE as described in studies by Chen et al. (Chen et al., 1995; J. Biol. Chem. 270:2874-2878).

Example 36

Construction of Bst2/Damp1 Oriented Fab Library

Human Bst2-decoy or mouse Damp 1-decoy protein expressed in CHO cells was immunized into rabbits (New Zealand White) by the appropriate amount of injection with adjuvant (RIBI's or Freund's Incomplete/Complete) until the saturation of antibody titer specific to Bst2/Damp1 antigens. The antibody titer of immunized rabbits was determined by enzyme linked immunosorbent assay (ELISA) using horseradish peroxidase (HRP)-conjugated anti-His antibodies which recognize His tagged at C-termini of decoy proteins.

For preparation of Fab-display phage libraries, total RNA was prepared from bone marrow and spleen of the immunized rabbit using TRI reagent. First-strand cDNA was synthesized by using the Superscript II First-strand synthesis system with oligo (dT) priming (Invitrogen).

The first-strand cDNAs from each rabbit were subjected to first round PCR using Expand High Fidelity PCR System (Roche Molecular System) and 10 primer combinations for the amplification of rabbit $V_L$ coding sequence and 4 primer combinations for the amplification of rabbit VH coding sequences were used. Human Cκ and $C_H1$ coding sequences were amplified from Fab. The anti-sense primers consist of a hybrid rabbit/human sequences designed for the fusion of rabbit $V_L$ and $V_H$ coding sequences to human $C_k$ and CH1 coding sequences. In the second round of PCR, the first round variable region rabbit $V_H$ were overlapped with human constant CH1, and the first round variable region rabbit VL were overlapped with human constant Cκ. In the third round of PCR, the chimeric light chain products and chimeric heavy chain fragments were joined by an overlap extension PCR.

Example 36-1

The First Round PCR Primer Sets

* Vκ5' sense Primers (SEQ ID NO: 27)
RSCVK1 5' ggg ccc agg cgg ccg agc tcg tgm tga ccc aga ctc ca 3'

(SEQ ID NO: 28)
RSCVK2 5' ggg ccc agg cgg ccg agc tcg atm tga ccc aga ctc ca 3'

(SEQ ID NO: 29)
RSCVK3 5' ggg ccc agg cgg ccg agc tcg tga tga ccc aga ctg aa 3'

* Vκ3' reverse Primers

-continued (SEQ ID NO: 30)
RHybK1-B 5' aga tgg tgc agc cac agt tcg ttt gat ttc cac att ggt gcc 3'

(SEQ ID NO: 31)
RHybK2-B 5' aga tgg tgc agc cac agt tcg tag gat ctc cag ctc ggt ccc 3'

(SEQ ID NO: 32)
RHybK3-B 5' aga tgg tgc agc cac agt tcg ttt gac sac cac ctc ggt ccc 3'

* Vλ5' sense Primers (SEQ ID NO: 33)
RSCL1 5' ggg ccc agg cgg ccg agc tcg tgc tga ctc agt cgc cct c 3'

* Vλ3' reverse Primers (SEQ ID NO: 34)
RHybL-B 5' aga tgg tgc agc cac agt tcg gcc tgt gac ggt cag ctg ggt ccc 3'

* VH5' sense Primers (SEQ ID NO: 35)
RHyVH1 5' gct gcc caa cca gcc atg gcc cag tcg gtg gag gag tcc rgg 3'

(SEQ ID NO: 36)
RHyVH2 5' gct gcc caa caa gcc atg gcc cag tcg gtg aag gag tcc gag 3'

(SEQ ID NO: 37)
RHyVH3 5' gct gcc caa cca gcc atg gcc cag tcg ytg gag gag tcc ggg 3'

(SEQ ID NO: 38)
RHyVH4 5' gct gcc caa cca gcc atg gcc cag sag cag ctg rtg gag tcc gg 3'

* VH3' reverse Primers (SEQ ID NO: 39)
RHyIgGCH1-B 5' cga tgg gcc ctt ggt gga ggc tga rga gay ggt gac cag ggt gcc 3'

Primer for Amplification of the Human $C_K$ Region and the pelB Leader Sequence from a Cloned Human Fab (SEQ ID NO: 40)
HKC-F(sense) 5' cga act gtg gct gca cca tct gtc 3'

(SEQ ID NO: 41)
Lead-B(reverse) 5' ggc cat ggc tgg ttg ggc agc 3'

Primers for Amplification of the Human CH1 Chain from a Cloned Human Fab (SEQ ID NO: 42)
HIgGCH1-F(sense) 5' aga agc gta gtc cgg aac gtc 3'

(SEQ ID NO: 43)
dpseq(reverse) 5' aga agc gta gtc cgg aac gtc 3'

Example 36-2

The Second Round PCR Primer Sets

Primers for PCR Assembly of Rabbit VL Sequences with the Human CK PCR Product (SEQ ID NO: 44)
RSC-F(sense) 5' gag gag gag gag gag gag gcg ggg ccc agg cgg ccg agc tc 3'

(SEQ ID NO: 41)
Lead-B(reverse) 5' ggc cat ggc tgg ttg ggc agc 3'

Primers for PCR Assembly of Rabbit VH Sequences with the Human CH1 PCR Product (SEQ ID NO: 45)
lead VH(sense) 5' gct gcc caa cca gcc atg gcc 3'

-continued (SEQ ID NO: 46)
dpseq(reverse) 5' aga agc gta gtc cgg aac gtc 3'

Example 36-3

The Third Round PCR Primer Sets

Primers for PCR Assembly of Chimeric Light-chain Sequences with Chimeric Heavy-chain(Fd) Sequences (SEQ ID NO: 44)
RSC-F(sense) 5' gag gag gag gag gag gag gcg ggg ccc agg cgg ccg agc tc 3'

(SEQ ID NO: 47)
dp-EX(reverse) 5' gag gag gag gag gag gag aga agc gta gtc cgg aac gtc 3'

The resulting PCR products digested with SfiI were ligated into phagemid vector pComb3X (gene bank AF268281) and transformed into XL1-Blue/F'. The phage library was obtained from the overnight culture media after absorption of helper phage VSCM13, followed by the addition of PEG and NaCl.

Example 37

Panning of Fab Libraries for Anti-Bst2 or Anti-Damp1 Antibodies

A Total of four rounds of panning were performed. For high affinity antibody clone to Bst2 and Damp1, dynalbead (DYNAL, Cat. No. 143.01) panning method using obtained chimeric Fab phage library was used.

Dynalbeads M270, Epoxy were coated with Bst2 decoy, Damp1 decoy or bovine serum albumin (BSA) for 16~24 hr at 37° C. Bst2 decoy coated beads were washed with PBS (1.06 mM potassium phosphate monobasic, 155.17 mM sodium chloride, 2.97 mM sodium phosphate dibasic, pH 7.4) and 0.5% tween 20 in PBS and then suspended in 0.5% BSA in PBS. For removal of nonspecific binding, Bst2 phage library were preincubated with BSA coated beads. The pre-cleared phage pools were incubated with Bst2-beads for 2 h at room temperature and washed with 0.5% tween20 in PBS at several times by the magnetic separation method for removal of non-specific binding phages. Specific binding phage were eluted by the incubation of 0.1M sodium citrate (pH 3.0, 0.45 ml) for 10 min twice and neutralized with the addition of 1M Tris-HCl (pH 9.5, 0.1 ml). The eluted phages were infected to logarithmically growing XL1-Blue F' and amplified by helper phage VSCM13 for overnight. Phages were prepared by the precipitation with 4% PEG and 3% NaCl (w/v), and then suspended with 1% BSA and 0.02% NaN3 in PBS buffer. The output phage pool of each round was monitored by phage ELISA in using anti-HA-Horseradish peroxidase (Roche, Cat No 2 013 819). The Damp 1 decoy specific phage pools were selected as the same protocol as Bst2 specific ones described above.

Example 38

Screening of Fab Libraries for Antibodies Specific for Both Bst2 and Damp1

For selection of clones reactive to both Bst2 and Damp1, single phage clone was inoculated in 2xYT broth containing 30 μg/ml tetracyclin, 50 ug/ml carbenicillin, and 1% glucose and cultured at 37° C. overnight. Culture supernatant was sub-cultured in 2xYT broth containing 30 μg/ml tetracyclin, 50 μg/ml carbenicillin on a 96 deep-well plate and amplified in using helper phage VSCM13 and kanamycin. After over-night culture, the phage supernatant was obtained by centrifugation for 30 min at 3000 rpm and used in the Bst2/damp1 binding assay in an ELISA format.

Each well on a 96well maxi-sorp plate (Nunc) was coated with 1 μg of Bst2 decoy or Damp1 decoy at 4° C. overnight and blocked by incubation of 5% BSA in TBS (50 mM Tris-HCl, 150 mM NaCl, pH7.4) for 2 hr 37° C. Then, 100 μl of phage supernatant was subsequently added for 1 hr 37° C. Each well was washed with 0.05% Tween20 in TBS (7.4 pH) and added with 100 of horseradish peroxidase conjugated anti-HA antibody for 1 hr at 37° C. After washing as above, 200 μl OPD (o-Phenylenediamine dihydrochloride, 0.4 mg/ml, Sigma) solution was added, followed by the addition of 50 ul of 3M sulfuric acid (50 μl) as a stop solution. Results are shown in FIG. 36.

Example 39

Expression of Selected Antibodies

Positive phage clones obtained above were analyzed by DNA sequencing and chosen based on sequence alignment. See FIG. 37.

MAQSVKESEGRLVTPGTPLTLTCTVSGF-SLSNSGMSWVRQAPGKGLEWIGLIN-SYGTTYYASWAKGRFTISKTSTTVEL-KITSPTTEDTATYFCARGAGSSYGLWGQGTLVTVSSAS (SEQ ID NO:77) describes 2-15 heavy chain variable region amino acid sequence.

CDR1 of 2-15 heavy chain variable region amino acid sequence is NSGMS (SEQ ID NO:99)

CDR2 of 2-15 heavy chain variable region amino acid sequence is LINSYGTTYYASWAKG (SEQ ID NO:100)

CDR3 of 2-15 heavy chain variable region amino acid sequence is GAGSSYGL (SEQ ID NO:101)

MAQSVKESEGGLFKPTDTLTLTCTVSGF-SLSSYEMNWVRQAPGKGLEYIGIIRSDG-STYYASWAKSRSTITRNTNLNTVTLK-MTSLTAADTATYFCARDLGYSNDVWGPGTLVTVSSAST (SEQ ID NO:78) describes 2-14 heavy chain variable region amino acid sequence.

CDR1 of 2-14 heavy chain variable region amino acid sequence is SYEMN (SEQ ID NO:102)

CDR2 of 2-14 heavy chain variable region amino acid sequence is IIRSDGSTYYASWAKS (SEQ ID NO:103)

CDR3 of 2-14 heavy chain variable region amino acid sequence is DLGYSNDV (SEQ ID NO:104)

MAQSLEESGGRLVKPDETLTLTCTVS-GIDLSSYMIYWVRQAPGKGLEYIG-FIYGSGDTYYATWAKGRFTISRPST-TVDLKITSPTTGDTATYFCARSSGWGYGLDLWGPGTLVTISSAST (SEQ ID NO: 79) describes 2-10 heavy chain variable region amino acid sequence.

CDR1 of 2-10 heavy chain variable region amino acid sequence is SYMIY (SEQ ID NO:105)

CDR2 of 2-10 heavy chain variable region amino acid sequence is FIYGSGDTYYATWAKG (SEQ ID NO:106)

CDR3 of 2-10 heavy chain variable region amino acid sequence is SSGWGYGLDL (SEQ ID NO:107)

MAQQLVESGGRLVTPGGTLTLTCTAS-GIDLSSYHMQWVRQAPGKGLEYIG-FIDTVGSAYYASWAKGRFTISRTST-TVDLKMTSLTAADTATYFCAGDSGYSIGTLWGQGTLVTVSSAST (SEQ ID NO:80) describes 2-4 heavy chain variable region amino acid sequence.

CDR1 of 2-4 heavy chain variable region amino acid sequence is SYHMQ (SEQ ID NO:108)

CDR2 of 2-4 heavy chain variable region amino acid sequence is FIDTVGSAYYASWAKG (SEQ ID NO:109)

CDR3 of 2-4 heavy chain variable region amino acid sequence is DSGYSIGTL (SEQ ID NO:110)

MAQQQLVESGGGLVTPGTPLTLTCTVSG-FSLSSYAMIWVRQAPGKGLEYIGIIRSS-GNTYYASWAKGRFTISKTSTTVDL-KITSPTTEDTATYFCARDSGYSFGLWGQGTLVTVSSAST (SEQ ID NO:81) describes 2-5 heavy chain variable region amino acid sequence.

CDR1 of 2-5 heavy chain variable region amino acid sequence is SYAMI (SEQ ID NO:111)

CDR2 of 2-5 heavy chain variable region amino acid sequence is IIRSSGNTYYASWAKG (SEQ ID NO:112)

CDR3 of 2-5 heavy chain variable region amino acid sequence is DSGYSFGL (SEQ ID NO:113)

MAQSVKESEGGLFKPTDTLTLTCTVSGF-SLSSHEMNWVRQAPGNGLEYIGIINSY-ANTYYAGWAKSRSTITRNTNENTVTLT-MTSLTAADTATYFCVRDLGYSSDIWGPGTLVTISSAST (SEQ ID NO:82) describes 2-7 heavy chain variable region amino acid sequence.

CDR1 of 2-7 heavy chain variable region amino acid sequence is SHEMN (SEQ ID NO:114)

CDR2 of 2-7 heavy chain variable region amino acid sequence is IINSYANTYYAGWAKS (SEQ ID NO:115)

CDR3 of 2-7 heavy chain variable region amino acid sequence is DLGYSSDI (SEQ ID NO:116)

MAQSLEESGGRLVTPGTPLTLTCTVS-GIDLSSYEMSWVRQAPGKGLEYIG-FISTSGNTYYASWAKGRFTISKTST-

TVDLKITSPTIEDTAAYFCARGPAKSGYGTRLDLWGQGTLVTVSSAST (SEQ ID NO:83) describes 2-9 heavy chain variable region amino acid sequence.

CDR1 of 2-9 heavy chain variable region amino acid sequence is SYEMS (SEQ ID NO:117)

CDR2 of 2-9 heavy chain variable region amino acid sequence is FISTSGNTYYASWAKG (SEQ ID NO:118)

CDR3 of 2-9 heavy chain variable region amino acid sequence is GPAKSGYGTRLDL (SEQ ID NO:119)

MAQEQLMESGGGLVTPGGILSLTCTASG-FSISSYRMGWVRQAPGKGLEWIG-FINNYGSAYYASWAKSRSTITRNT-NLNTVTLKMTSLTAADTATYFCARESYSYGYAYDIWGPGTLVTVSSAST (SEQ ID NO:84) describes 2-11 heavy chain variable region amino acid sequence.

CDR1 of 2-11 heavy chain variable region amino acid sequence is SYRMG (SEQ ID NO:120)

CDR2 of 2-11 heavy chain variable region amino acid sequence is FINNYGSAYYASWAKS (SEQ ID NO:121)

CDR3 of 2-11 heavy chain variable region amino acid sequence is ESYSYGYAYDI (SEQ ID NO:122)

MAQEQLVESGGRLVTPGGSLTITCTVS-GIDLSGYAMGWVRQAPGKGLEYIGI-IGTSDTTYYASWAKGRFTISKTSST-TVDLKMTSLTTEDTATYFCVRSPGGSADLWGQGTLVTISSAST (SEQ ID NO:85) describes 2-13 heavy chain variable region amino acid sequence.

CDR1 of 2-13 heavy chain variable region amino acid sequence is GYAMG (SEQ ID NO:123)

CDR2 of 2-13 heavy chain variable region amino acid sequence is IIGTSDTTYYASWAKG (SEQ ID NO:124)

CDR3 of 2-13 heavy chain variable region amino acid sequence is SPGGSADL (SEQ ID NO:125)

MAQSVKESEGGLFKPTDTLTLTCTVSGF-SLSSYEMNWVRQAPGKGLEYIGIIRSDG-STYYASWAKSRSTITRNTNLNTVTLK-MTSLTAADTATYFCARDLGYSNDVWGPGTLVTISSAST (SEQ ID NO:86) describes 2-19 heavy chain variable region amino acid sequence.

CDR1 of 2-19 heavy chain variable region amino acid sequence is SYEMN (SEQ ID NO:126)

CDR2 of 2-19 heavy chain variable region amino acid sequence is IIRSDGSTYYASWAKS (SEQ ID NO:127)

CDR3 of 2-19 heavy chain variable region amino acid sequence is DLGYSNDV (SEQ ID NO:128)

MAQSVEESRGGLFKPTDTLTLTCTVSGF-SLSTYEMNWVRQAPGSGLEYIGIIN-SAGTTYYASWAKSRSTITRNT-NENTVTLKMTSLTAADTATYFCARDLGYSSDIWGPGTLVTVSSAST (SEQ ID NO:87) describes 2-24 heavy chain variable region amino acid sequence.

CDR1 of 2-24 heavy chain variable region amino acid sequence is TYEMN (SEQ ID NO:129)

CDR2 of 2-24 heavy chain variable region amino acid sequence is IINSAGTTYYASWAKS (SEQ ID NO:130)

CDR3 of 2-24 heavy chain variable region amino acid sequence is DLGYSSDI (SEQ ID NO:131)

QAAELVMTQTPSSTSTAVGDTVTIKC-QASQSIGSNLAWYQQKPGQPPKIL-IYSASNLASGVPSRFKGSGS-GTEYTLTISGVQREDAATYYCLGSDSSWDTVFGGGTELEILRTV (SEQ ID NO:88) describes 2-15 kappa chain variable region amino acid sequence.

CDR1 of 2-15 kappa chain variable region amino acid sequence is QASQSIGSNLA (SEQ ID NO:132)

CDR2 of 2-15 kappa chain variable region amino acid sequence is ASNLAS (SEQ ID NO:133)

CDR3 of 2-15 kappa chain variable region amino acid sequence is LGSDSSWDTV (SEQ ID NO:134)

QAAELDLTQTPSSTSTAVGGTVTINC-QASQNIGINLAWYQQKPGQPPKLLIW-YASDLASGVSSRFKGSGF-GTQFTLTISGVQREDAATYYCLGTYGSGDRAFGAGTNVEIKRTV (SEQ ID NO:89) describes 2-14 kappa chain variable region amino acid sequence.

CDR1 of 2-14 kappa chain variable region amino acid sequence is QASQNIGINLA (SEQ ID NO:135)

CDR2 of 2-14 kappa chain variable region amino acid sequence is ASDLAS (SEQ ID NO:136)

CDR3 of 2-14 kappa chain variable region amino acid sequence is LGTYGSGDRA (SEQ ID NO:137)

ELDLTQTPSSTSTAVGGTVTINCQASQS-INVWLSWYQQKPGQPPKLLIYQASKLAS-GVPSRFKGSGSGTQFTLTISGVQRED-VATYYCLGIYNDIDTAFGGGTEVVVKRTV (SEQ ID NO:90) describes 2-10 kappa chain variable region amino acid sequence.

CDR1 of 2-10 kappa chain variable region amino acid sequence is QASQSINVWLS (SEQ ID NO:138)

CDR2 of 2-10 kappa chain variable region amino acid sequence is ASKLAS (SEQ ID NO:139)

CDR3 of 2-10 kappa chain variable region amino acid sequence is LGIYNDIDTA (SEQ ID NO:140)

QAAELVLTQTPSSVSAAVGGTVTINC-QATQSIGINLAWYQQKPGQPPKLLIW-YASDLASGVPSRFKGSGFGTQFTLT-INGVQREDAATYYCLGSYGSGDRAFGAGTNVEIKRTV (SEQ ID NO:91) describes 2-4 kappa chain variable region amino acid sequence.

CDR1 of 2-4 kappa chain variable region amino acid sequence is QATQSIGINLA (SEQ ID NO:141)

CDR2 of 2-4 kappa chain variable region amino acid sequence is ASDLAS (SEQ ID NO:142)

CDR3 of 2-4 kappa chain variable region amino acid sequence is LGSYGSGDRA (SEQ ID NO:143)

QAAELVMTQTPSSVSAAVGGTVTINC-QASKNIGINLAWYQQKPGQPPKQLIW-YASDLASGVPSRFKGSGFGTQFTLT-INGVQREDAATYYCLGSYGSGDRAFGAGTNVEIKRTV (SEQ ID NO:92) describes 2-5 kappa chain variable region amino acid sequence.

CDR1 of 2-5 kappa chain variable region amino acid sequence is QASKNIGINLA (SEQ ID NO:144)

CDR2 of 2-5 kappa chain variable region amino acid sequence is ASDLAS (SEQ ID NO:145)

CDR3 of 2-5 kappa chain variable region amino acid sequence is LGSYGSGDRA (SEQ ID NO:146)

QAAELVMTQTPSSTSTAVGGTVTINC-QASQNIGINLAWYQQKPGQPPKLLIW-YASDLASGVPSRFKGSGF-GTQFTLTISGVQREDAATYYCLGSYGSGDRAFGAGTNVEIKRTV (SEQ ID NO:93) describes 2-7 kappa chain variable region amino acid sequence.

CDR1 of 2-7 kappa chain variable region amino acid sequence is QASQNIGINLA (SEQ ID NO:147)

CDR2 of 2-7 kappa chain variable region amino acid sequence is ASDLAS (SEQ ID NO:148)

CDR3 of 2-7 kappa chain variable region amino acid sequence is LGSYGSGDRA (SEQ ID NO:149)

QAAELDLTQTPSSTSTAVGGTVTINC-QASQNIGINLAWFQQKPGQPPKLLIW-YASDLASGVPSRFKGSGFGTQFTLTISN-

VEREDAATYYCLGTYGSGDRAFGAGTNVEIKRTV (SEQ ID NO:94) describes 2-9 kappa chain variable region amino acid sequence.

CDR1 of 2-9 kappa chain variable region amino acid sequence is QASQNIGINLA (SEQ ID NO:150)

CDR2 of 2-9 kappa chain variable region amino acid sequence is ASDLAS (SEQ ID NO:151)

CDR3 of 2-9 kappa chain variable region amino acid sequence is LGTYGSGDRA (SEQ ID NO:152)

ELDLTQTPSSTSTTVGGTVTINCRASQIIGINLAWYQQKPGQPPKLLIWYASDLASGVPSRFRGNVSGSQFTLTISGVQREDAATYYCLGTYGSGVRAFGAGTNVEIKRTV (SEQ ID NO:95) describes 2-11 kappa chain variable region amino acid sequence.

CDR1 of 2-11 kappa chain variable region amino acid sequence is RASQIIGINLA (SEQ ID NO:153)

CDR2 of 2-11 kappa chain variable region amino acid sequence is ASDLAS (SEQ ID NO:154)

CDR3 of 2-11 kappa chain variable region amino acid sequence is LGTYGSGVRA (SEQ ID NO:155)

QAAELDMTQTPSSTSTAVGGTVTMNCQASQNIGINLAWYQQKPGQPPKLLIWYASDLASGVPSRFKGSGFGTQFTLTISGMQREDAATYYCLGTYGSGVRAFGAGTNVEIKRTV (SEQ ID NO:96) describes 2-13 kappa chain variable region amino acid sequence.

CDR1 of 2-13 kappa chain variable region amino acid sequence is QASQNIGINLA (SEQ ID NO:156)

CDR2 of 2-13 kappa chain variable region amino acid sequence is ASDLAS (SEQ ID NO:157)

CDR3 of 2-13 kappa chain variable region amino acid sequence is LGTYGSGVRA (SEQ ID NO:158)

QAAELVLTQTPSSTSTAVGGTVTINCQASQNIGINLAWYQQKPGQPPKLLIWYTSDLASGVPSRFRGSGFGTQFTLTISAIQREDAATYYCLGTYGSGVRAFGAGTNVEIKRTV (SEQ ID NO:97) describes 2-19 kappa chain variable region amino acid sequence.

CDR1 of 2-19 kappa chain variable region amino acid sequence is QASQNIGINLA (SEQ ID NO:159)

CDR2 of 2-19 kappa chain variable region amino acid sequence is TSDLAS (SEQ ID NO:160)

CDR3 of 2-19 kappa chain variable region amino acid sequence is LGTYGSGVRA (SEQ ID NO:161)

QAAELVMTQTPSSTSTAVGGTVTINCQASQNIGINLAWYQQKPGQPPKLLIWYASDLASGAPSRFKGSGF-GTQFTLTISGVQREDAATYYCLGTYGSGDRAFGTGTNVEIKRTV (SEQ ID NO:98) describes 2-24 kappa chain variable region amino acid sequence.

CDR1 of 2-24 kappa chain variable region amino acid sequence is QASQNIGINLA (SEQ ID NO:162)

CDR2 of 2-24 kappa chain variable region amino acid sequence is ASDLAS (SEQ ID NO:163)

CDR3 of 2-24 kappa chain variable region amino acid sequence is LGTYGSGDRA (SEQ ID NO:164)

For expression in whole IgG1 form, each phage Fab DNA fragment was cloned into the expression vector, pCDH and pCDK, derived from pCDNA 3.1 (Invitrogen).

pCDH is an intermediate cloning vector for the expression of a full-length IgG heavy chain. The CH1-CH2-CH3 domains of an IgG heavy chain were PCR amplified from a whole pCDH is an intermediate cloning vector for the expression of a full-length IgG heavy chain. The CH1-CH2-CH3 domains of an IgG heavy chain was PCR amplified from a whole blood cell cDNA library (Clontech) using primers R1-CH1 and CH3-Not1 cloned into the EcoR1, Not1 site of pCDNA3.1 following EcoR1 and Not1 restriction digestion. A secretable full length IgG heavy chain was reconstructed by fusing the secretion signal for tPA 5' to the heavy chain variable region through overlap PCR cloning by first PCRing the tPA signal peptide with primers R1-tPA5 and tPA3 from the library used above and PCRing the variable region and CH1 from the phagemid used to express the Fab fragment with Heavy_CH1_Rev and the primer specific for the variable region (Ra_Hv_Fw1 through Ra_Hv_Fw9); these two PCR fragment were then fused through an overlap PCR reaction with primers R1-tPA5 and Heavy_CH1_Rev, digested with EcoR1 and Age1 and cloned into pCDH digested with the same enzymes.

pCDK is an intermediate vector for the expression of the IgG light chain made by PCR cloning the light chain with primers H3-light and light-Xba1, digesting the PCR product with HindIII and XbaI and cloning into pCDNA3.1 digested with the same enzymes. A secretable full length IgG light chain was reconstructed by fusing the secretion signal for tPA 5' to the light chain variable region through overlap PCR cloning by first PCRing the tPA signal peptide with primers H3-tPA5 and tPA3 from the library used above and PCRing the variable region and CK from the phagemid used to express the Fab fragment with specific primer pairs for the variable regions (Ra_Kp_F1 through 6 and Ra_Kp_Rva through d); these two PCR fragment were then fused through an overlap PCR reaction with primers H3-tPA5 and the specific light chain 3' primer, digested with HinDIII and BsiWI and cloned into pCDK digested with the same enzymes.

```
                                                    (SEQ ID NO: 48)
R1-CH1  5' cgcgaattcgcctccaccaagggcccatcg 3'

                                                    (SEQ ID NO: 49)
CH3-Not1 5' ggcggccgctcatttacccgggga 3'

                                                    (SEQ ID NO: 50)
R1-tPA5 5' cgcgaattcaggacctcaccatgggatgg 3'

                                                    (SEQ ID NO: 51)
tPA3 5' ggagtggacacctgtagct 3'

                                                    (SEQ ID NO: 52)
Heavy_CH1_Rev 5' ccacgctgctgagggagtagagtc 3'

                                                    (SEQ ID NO: 53)
Ra_Hv_F1: 5' gcaacagctacaggtgtccactcc cagcagcagctgatggag 3'
42 mer
```

-continued (SEQ ID NO: 54)
Ra_Hv_F2: 5' gcaacagctacaggtgtccactcc caggagcagctgatggagt 3'
43 mer (SEQ ID NO: 55)
Ra_Hv_F3: 5' gcaacagctacaggtgtccactcc caggagcagctggtggagt 3'
43 mer (SEQ ID NO: 56)
Ra_Hv_F4: 5' gcaacagctacaggtgtccactcc cagtcggtgaaggagtccg 3'
43 mer (SEQ ID NO: 57)
Ra_Hv_F5: 5' gcaacagctacaggtgtccactcc cagtcgttggaggagtccg 3'
43 mer (SEQ ID NO: 58)
Ra_Hv_F6: 5' gcaacagctacaggtgtccactcc cagtcggtggaggagtcc 3'
42 mer (SEQ ID NO: 59)
Ra_Hv_F7: 5' gcaacagctacaggtgtccactcc cagcggttggaggagtcc 3'
42 mer (SEQ ID NO: 60)
Ra_Hv_F8: 5' gcaacagctacaggtgtccactcc cagcagcagctggtggag 3'
42 mer (SEQ ID NO: 61)
Ra_Hv_F9: 5' gcaacagctacaggtgtccactcc cagtcgctggaggagtcc 3'
42 mer (SEQ ID NO: 62)
H3-light: 5' gcgaagcttcgaactgtggctgcaccatct 3'

(SEQ ID NO: 63)
light-Xba1: 5' gcgtctagattaacactctcccct 3'

(SEQ ID NO: 64)
H3-tPA5: 5' gcgaagcttaggacctcaccatgggatgg 3'

(SEQ ID NO: 65)
Ra_Kp_F1: 5' gcaacagctacaggtgtccactcc gagctcgatatgacccagac 3'
44 mer (SEQ ID NO: 66)
Ra_Kp_F2: 5' gcaacagctacaggtgtccactcc gagctcgtgctgaaccca 3'
42 mer (SEQ ID NO: 67)
Ra_Kp_F3: 5' gcaacagctacaggtgtccactcc gagctcgtgatgacccagac 3'
44 mer (SEQ ID NO: 68)
Ra_Kp_F4: 5' gcaacagctacaggtgtccactcc gagctcgatctgacccagac 3'
44 mer (SEQ ID NO: 69)
Ra_Kp_Rva: 5' cgccgtacg taggatctccagctcggtcc 3'
29 mer (SEQ ID NO: 70)
Ra_Kp_Rvb: 5' cgccgtacg tttgatttccacattggtgcc 3'
30 mer (SEQ ID NO: 71)
Ra_Kp_Rvc: 5' cgccgtacg tttgacgaccacctcggtc 3'
28 mer (SEQ ID NO: 72)
Ra_Kp_Rvd: 5' cgccgtacg taggatctccagctcggtccc 3'
30 mer For expression in whole IgG1 form, each phage Fab DNA fragment was cloned into the expression vector, pCDNA 3.1 (Invitrogen).

In order to express monoclonal antibodies (mAb, IgG1) selected above, a vector DNA was transiently or stably introduced into mammalian cells. Transient transfection was performed by calcium phosphate ($CaPO_4$) precipitation, as follows. One day before transfection, $7\times10^6$ cells of 293T (ATCC) were seeded and cultured onto a 150-mm cell culture plate. One hour before transfection, the culture medium was exchanged with IMDM medium (Cambrex) supplemented with 2% fetal bovine serum (GIBCO-BRL). TE buffer (1 mM Tris, 0.1 mM EDTA, pH 8.0) containing 75 μg of DNA and 250 mM calcium in a volume of 1.5 ml, was mixed with the equal volume of HEPES buffer (50 mM HEPES, 140 mM NaCl, 1.4 mM $Na_2HPO_4$, pH 7.05). The mixture was incubated for about 1 min at room temperature and was applied to the pre-cultured cells. The cells were incubated in a $CO_2$ incubator at 37° C. for 6 hrs. After the DNA/calcium solution was removed, the cells were added with serum-free medium and further cultured for 72 hrs or longer, and then the culture medium was harvested. Each mAb was purified from the culture media in using Protein A affinity chromatography (Amersham Biosciences, MabSelect). Culture media were loaded on protein A-packed column previously equilibrated with PBS buffer (1.06 mM potassium phosphate monobasic, 155.17 mM sodium chloride, 2.97 mM sodium phosphate dibasic, pH 7.4). The column was washed with PBS buffer for removing the contaminants about 20 column volumes. Bound antibodies were eluted by low pH buffer, such as 50 mM glycine-HCl using a step gradient and neutralized with the equal volume of 1M Tris (pH 8.0). The purified protein samples were subject to gel electrophoresis in 4-20% native PAGE (4-20% native PAGE, Invitrogen). See FIG. 38 for the purified proteins in gel.

Example 40

Competitive Binding Assay (in vitro)

Competitive inhibition of mAbs specific for Bst2 or Damp1 in the binding between BST2 decoy and cells was measured as described in Example 22.

Example 41

The Effect of mAbs on a Mouse Model of Asthma

A mouse model of asthma was prepared as described in Example 8-1. The effect of anti-Bst2/Damp1 antibodies on immune cell infiltration was assessed as described in Example 8-2. In mice sensitized with ovalbumin and treated with each mAb, the total number of infiltrating cells was decreased in bronchoalveolar lavage (BAL) (FIG. 39) after treatment with some anti-Bst2/Damp1 antibodies. The anti-Damp1 antibody 2-15 did not block immune cell infiltration significantly. One possibility is that the 2-15 monoclonal antibody may bind strongly to Damp1 decoy but may not accurately cover the potential Damp1 L binding site.

Example 42

Diagnostic Methods to Measure Inflammatory Status

Bst2 mRNA expression is increased in inflammatory condition. Measuring Bst2 mRNA level with quantitative PCR, real-time PCR or northern blot in cells and tissues isolated from a subject can yield useful information on the inflammation status of those cells and tissues. Measuring Bst2 protein levels by immunoblotting with antibody specific for Bst2 or alternatively with immunofluorescence microscopy and FACS (fluorescence activated cell sorter) using fluorescently-labeled antibody capable of binding to Bst2 on the cell membrane may also yield information regarding the inflammation status of those cells. Frequently, membrane proteins such as Bst2 can be cleaved to produce soluble Bst2 fragment which circulate in the body. Bst2 circulating in body fluids such as serum and urine, may be quantified with antibody specific for circulating Bst2 fragment, using commonly utilized methods such as radioimmunological assay (RIA) and ELISA. Quantification of circulating Bst2 fragment may reflect the inflammation status of the host and may be useful for diagnostic and therapeutic purposes.

Example 43

Evaluation of the Action of Bst2 Decoy in a TMA-induced Contact Hypersensitivity Model Evaluation of the action of Bst2 decoy in a mouse model of atopic dermatitis is shown in this Example.

Example 43-1

TMA-induced Contact Hypersensitivity

To evaluate efficacy of Bst2 decoy on allergic dermatitis, contact hypersensitivity was induced by repeated application of 2,4,6-trinitro-1-chlorobenzene (TNCB) in Balb/c mice. The mice were initially sensitized with 0.2 ml of 1% TNCB solution on day 0, Subsequent challenges of 0.2 ml of 0.2% TNCB solution was applied to the shaved backs of the animals 2-3 times per week from week 2 to week 6. By the end of week 6, all animal developed lesions on the dorsal skin treated with TNCB solution (FIGS. 40A-40C).

Example 43-2

Bst2 Decoy Markedly Enhanced Healing of TNCB-induced Skin Lesions

During week 7, 5 daily doses of Bst2 decoy were administered at 10 mg/kg to the animals by intravenous injection, and the animals were sacrificed for observation at the end of week 7. Although the animals that were treated with vehicle alone also exhibited some recovery form the TNCB treatment, animals that received Bst2 decoy recovered much quicker than the vehicle alone control group (FIGS. 41A-41C).

Example 43-3

The Effect of Bst2 Decoy on Tissue

H&E staining was performed on exposed skin sections. Animals treated with TNCB exhibited typical inflammation of the dermal layer including infiltration of multiple immune cells. Animals treated with Bst2 decoy exhibited near-normal morphology with little signs of inflammation (FIGS. 42A-42C).

Example 44

Evaluation of the Action of Bst2 Decoy in an OVA-based Atopic Model

Example 44-1

OVA-based Atopic Model

An experimental model of atopic dermatitis based on immunity against ovalbumin (OVA) was utilized to test Bst2 decoy for efficacy in atopic dermatitis. BALB/c mice were immunized at the beginning of weeks 1, 2, and 3 with intraperitoneal injections of OVA/ALUM. During week 4, an OVA-soaked patch was applied to the shaved backs of the animals. The patches were removed and 5 daily doses of Bst2 decoy was administered to the animal by intravenous injections of 10 mg/kg during week 5. OVA-soaked patches were applied again to the animals over week 6 and the animals were sacrificed for evaluation at the beginning of week 7 (FIG. 43). At the end of week 4 prior to administration of samples, all OVA-treated animals showed substantial formation on the treated lesions. And hematoxylin and eosin (H&E) staining of tissue sections showed that thickening and infiltration of immune cells in the dermal layer at the site of sensitization with OVA, but not negative control (FIGS. 44A-44B).

Example 44-2

Administration of Bst2 Decoy Substantially Reduced the Level of Lesion Formation At the end of week 6, animals receiving vehicle only injection exhibited little difference from the OVA patch control group. However, animals receiving Bst2 decoy showed little if any formation of lesions following a week long application of the OVA-soaked patch.

While H&E stained sections from the vehicle-treated animals showed little difference from the OVA-patch group at the end of week 4, sections from animals treated with Bst2 decoy demonstrated a marked decrease in inflammation to a level similar to the negative control group (FIGS. 45A-45B).

Example 44-3

Administration of Bst2 Decoy Leads to a Reduction in Serum Levels of Antigen-specific IgE Serum was prepared from blood sample collected from the sacrificed animals. OVA-specific IgE levels were determined by ELISA assays in which OVA was coated on the plate, OVA-specific immunoglobulin present in the serum samples allowed to blind, and IgE levels ascertained utilizing anti-IgE specific antibodies. Administration of Bst2 decoy led to a substantial reduction in OVA-specific IgE levels, strongly indicating the potential of Bst2 decoy in reduced and/or blocking allergic response driven dermatitis (FIG. 46).

Example 45

Sepsis Induction in Rats

Examples 45-48 show evaluation of the action of Bst2 decoy in a mouse model of sepsis. Sepsis can be induced in animals by cecal ligation and puncture (CLP). The CLP model of sepsis has been used extensively as a reliable model of the pathophysiologic and immunologic alterations in human sepsis. Bst2 decoy protein prevents the death by sepsis and reduces physiologic effect of sepsis such as altered cytokine release and tissue and organ damage.

A rat model of sepsis was induced through cecal ligation and puncture (CLP) as described previously (Wichterman K A, Baue A E, Chaudry I H: Sepsis and septic shock-a review of laboratory models and a proposal. J Surg Res 29:189-201, 1980). An incision was made along the midline of the abdomen on an anesthetized animal. The cecum was exteriorized, ligated and punctured with a stainless steel needle. An appropriate amount of fecal matter was then extruded. The gauge of the needle, number of punctures and amount of fecal matter extruded are all factors in determining the severity of sepsis and mortality. For these studies, a 16 G needle was used to create 2 one-sided punctures; just enough fecal material was extruded to demonstrate penetration through the cecal wall. The incision was sutured and appropriate post-operative care was administered. Sham-operated animals were subjected to similar laparotomy and intestinal manipulation, however, the cecum was neither ligated nor punctured. Immediately or 6 hours after the CLP procedure, animals were given intravenous injection of vehicle or a Bst2 decoy.

Example 46

Bst2 Decoy Enhanced Survival in a Dose Dependent Manner

Mortality of animals was monitored for up to 14 days after the procedure. Intravenous administration of various doses of Bst2 decoy had a positive effect on the overall survival of animal receiving CLP. 3, 10, and 30 mg/kg doses were administered immediately following the CLP procedure and daily survival monitored over the course of 14 days. While the CLP animals that received only vehicle showed a 14 day survival of 20%, animals receiving 3, 10 and 30 mg/kg of the Bst2 soluble fragment exhibited survival rates of 37.5%, 80% and 75%, respectively (FIG. 47A).

Administration of Bst2 decoy 6 hours post-CLP maintained a high level of survival. The 70% 14-day survival rate was very similar to the 80% observed when administered immediately following CLP, indicating that administration of Bst2 decoy can not only block the initiation of a strong systemic inflammatory response when given immediately after the inflammatory insult, but also exhibits therapeutic potential in cases where systemic inflammation has already been established (FIG. 47B).

Example 47

The Effect of Bst2 Decoy on Cytokine Production

Blood samples were collected at 1, 3, 6, 18 and 24 hours post-CLP. Plasma levels of representative inflammatory response proteins were measured using ELISA kits; TNF-alpha(BD Biosciences, San Diego, Calif.) and IL-6(BD Biosciences, San Diego, Calif.) at 1, 3, and 6 hours, HMGB-1 (Shino-Test Corp., Japan) at 18 and 24 hours. Typically, after CLP in rodents, TNF-alpha spikes at 3 hours and IL-6 spikes at 6 hours. In animals treated with the Bst2 soluble fragment, the TNF-alpha response was virtually absent, while the IL-6 spike was substantially suppressed, indicating that administration of Bst2 soluble fragment was capable of drastically reducing the systemic inflammation initiated by CLP (FIGS. 48A-48B). Also, measurements of HMGB-1 indicated that administration of Bst2 soluble fragment had the effect of reducing both the amount and rate of increase of this late indicator of inflammation (FIG. 48C).

Example 48

The Effect of Bst2 Decoy on Tissue/Organ Damage

Blood enzyme levels were measured at 6, 12, and 24 hours post-CLP (FIG. 49A-49D). Organ damage, as indicated by increased levels of alanine aminotransferase (ALT), aspartate aminotransferase (AST), blood urea nitrogen (BUN) and creatinine, was evident in all animals that underwent the CLP procedure. Animals that received the Bst2 soluble fragment maintained a near-normal level of these blood enzymes, evidently through the protective effects of the administered protein. Hematoxylin-eosin (H&E) staining of tissue sections of liver, kidney, and lung at 24 post-CLP also demonstrated the protective effects against organ damage caused by systemic inflammation typical of sepsis (FIG. 50).

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of reducing inflammation in a subject suffering from sepsis comprising administering a composition comprising a bone marrow stromal cell antigen 2 (Bst2) antagonist to a site of the inflammation, wherein said Bst2 antagonist comprises a soluble portion of Bst2, which comprises an extracellular portion of Bst2 or a fragment of the extracellular portion, in an amount effective to inhibit binding between a first leukocyte and a second leukocyte or an endothelial cell, wherein the extracellular portion is shown in amino acid positions 44 to 180 of SEQ ID NO:73.

2. The method according to claim 1, wherein the Bst2 antagonist is a Fc chimeric or fusion construct, an albumin chimeric or fusion construct, or linked to a non-proteinaceous polymer.

3. A method of treating sepsis in a subject comprising administering a composition comprising a bone marrow stromal cell antigen 2 (Bst2) antagonist to the person in need thereof, wherein said Bst2 antagonist comprises a soluble portion of Bst2, which comprises an extracellular portion of Bst2 or a fragment of the extracellular portion, in an amount effective to inhibit binding between a first leukocyte and a second leukocyte or an endothelial cell, wherein the extracellular portion is shown in amino acid positions 44 to 180 of SEQ ID NO:73.

4. The method according to claim 1, wherein the extracellular portion is shown in amino acid positions 44 to 159 of SEQ ID NO:73.

5. The method according to claim 1, wherein said first leukocyte and the second leukocyte or the endothelial cell are located either at a site of inflammation or at a site distant from inflammation but can transmit inflammatory and immune cytokines or other inflammatory signals to a site of inflammation.

6. The method according to claim 3, wherein the extracellular portion is shown in amino acid positions 44 to 159 of SEQ ID NO:73.

7. The method according to claim 3, wherein the Bst2 antagonist is a Fc chimeric or fusion construct, an albumin chimeric or fusion construct, or linked to a non-proteinaceous polymer.

8. The method according to claim 3, wherein said first leukocyte and the second leukocyte or the endothelial cell are located either at a site of inflammation or at a site distant from inflammation but can transmit inflammatory and immune cytokines or other inflammatory signals to a site of inflammation.

9. A method of inhibiting systemic inflammation in a subject suffering from sepsis comprising administering a composition comprising a bone marrow stromal cell antigen 2 (Bst2) antagonist to a site of the inflammation, wherein said Bst2 antagonist comprises a soluble portion of Bst2, which comprises an extracellular portion of Bst2 or a fragment of the extracellular portion, in an amount effective to inhibit binding between a first leukocyte and a second leukocyte or an endothelial cell, wherein the extracellular portion is shown in amino acid positions 44 to 180 of SEQ ID NO:73.

* * * * *

SEQUENCE LISTING

<160> NUMBER OF SEQ ID NOS: 164

<210> SEQ ID NO 1
<211> LENGTH: 116
<212> TYPE: PRT
<213> ORGANISM: Homo sapiens

<400> SEQUENCE: 1

```
Phe Thr Ile Lys Ala Asn Ser Glu Ala Cys Arg Asp Gly Leu Arg Ala
1               5                   10                  15

Val Met Glu Cys Arg Asn Val Thr His Leu Leu Gln Gln Glu Leu Thr
            20                  25                  30

Glu Ala Gln Lys Gly Phe Gln Asp Val Glu Ala Gln Ala Ala Thr Cys
        35                  40                  45

Asn His Thr Val Met Ala Leu Met Ala Ser Leu Asp Ala Glu Lys Ala
    50                  55                  60

Gln Gly Gln Lys Lys Val Glu Glu Leu Glu Gly Glu Ile Thr Thr Leu
65                  70                  75                  80

Asn His Lys Leu Gln Asp Ala Ser Ala Glu Val Glu Arg Leu Arg Arg
                85                  90                  95

Glu Asn Gln Val Leu Ser Val Arg Ile Ala Asp Lys Lys Tyr Tyr Pro
            100                 105                 110

Ser Ser Gln Asp
        115
```

<210> SEQ ID NO 2
<211> LENGTH: 104
<212> TYPE: PRT
<213> ORGANISM: Mus musculus

<400> SEQUENCE: 2

```
Phe Ala Val Thr Ala Asn Ser Val Ala Cys Arg Asp Gly Leu Arg Ala
1               5                   10                  15

Gln Ala Glu Cys Arg Asn Thr Thr His Leu Leu Gln Arg Gln Leu Thr
            20                  25                  30

Arg Thr Gln Asp Ser Leu Leu Gln Ala Glu Thr Gln Ala Asn Ser Cys
        35                  40                  45

Asn Leu Thr Val Val Thr Leu Gln Glu Ser Leu Glu Lys Lys Val Ser
    50                  55                  60

Gln Ala Leu Glu Gln Gln Ala Arg Ile Lys Glu Leu Glu Asn Glu Val
65                  70                  75                  80

Thr Lys Leu Asn Gln Glu Leu Glu Asn Leu Arg Ile Gln Lys Glu Thr
                85                  90                  95

Ser Ser Thr Val Gln Val Asn Ser
            100
```

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3

```
ttttctcttc tcagtctc                                                 18
```

<210> SEQ ID NO 4
<211> LENGTH: 18

-continued

<212> TYPE: DNA
<213> ORGANISM: Artificial Sequence
<220> FEATURE:
<223> OTHER INFORMATION: Primer

<400> SEQUENCE: 4
gcatctactt cgtatgac 18

<210> SEQ ID NO 5
<211> LENGTH: 21
<212> TYPE: DNA
<213> ORGANISM: Artificial Sequence
<220> FEATURE:
<223> OTHER INFORMATION: Target sequence

<400> SEQUENCE: 5
aagcgtgaga atcgcggaca a 21

<210> SEQ ID NO 6
<211> LENGTH: 21
<212> TYPE: DNA
<213> ORGANISM: Artificial Sequence
<220> FEATURE:
<223> OTHER INFORMATION: Sense oligomer

<400> SEQUENCE: 6
uuguccgcga uucucacgct t 21

<210> SEQ ID NO 7
<211> LENGTH: 21
<212> TYPE: DNA
<213> ORGANISM: Artificial Sequence
<220> FEATURE:
<223> OTHER INFORMATION: Antisense oligomer

<400> SEQUENCE: 7
gcgugagaau cgcggacaat t 21

<210> SEQ ID NO 8
<211> LENGTH: 24
<212> TYPE: DNA
<213> ORGANISM: Artificial Sequence
<220> FEATURE:
<223> OTHER INFORMATION: Primer

<400> SEQUENCE: 8
ctcccaggac gagcccaaat cttg 24

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ggcggccgct catttacccg ggga 24

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
ctcccaggac cgtacggtgg ctgc 24

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ggcggccgct taacactctc ccct 24

<210> SEQ ID NO 12
<211> LENGTH: 24
<212> TYPE: DNA
<213> ORGANISM: Artificial Sequence
<220> FEATURE:
<223> OTHER INFORMATION: Primer

<400> SEQUENCE: 12
ctcccaggac gcctccacca aggg 24

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ggcggccgct catttaccca gaga 24

<210> SEQ ID NO 14
<211> LENGTH: 24
<212> TYPE: DNA
<213> ORGANISM: Artificial Sequence
<220> FEATURE:
<223> OTHER INFORMATION: Primer

<400> SEQUENCE: 14
cgctcgagac agccatcatg gatg 24

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
ctcccaggac gagcccaaat cttg 24

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
ttgggctcgt cctgggagct gggg 24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
ggcggccgct catttacccg ggga 24

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
ctcccaggac cgtacggtgg ctgc 24

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19
accgtacggt cctgggagct gggg 24

<210> SEQ ID NO 20
<211> LENGTH: 24
<212> TYPE: DNA
<213> ORGANISM: Artificial Sequence
<220> FEATURE:
<223> OTHER INFORMATION: Primer

<400> SEQUENCE: 20
ggcggccgct taacactctc ccct 24

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
ctcccaggac gcctccacca aggg 24

<210> SEQ ID NO 22
<211> LENGTH: 24
<212> TYPE: DNA
<213> ORGANISM: Artificial Sequence
<220> FEATURE:
<223> OTHER INFORMATION: Primer

<400> SEQUENCE: 22
gtggaggcgt cctgggagct gggg 24

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
ggcggccgct catttaccca gaga 24

<210> SEQ ID NO 24
<211> LENGTH: 24

<212> TYPE: DNA
<213> ORGANISM: Artificial Sequence
<220> FEATURE:
<223> OTHER INFORMATION: Primer

<400> SEQUENCE: 24
catatttgga ctcgtcctgg gagc 24

<210> SEQ ID NO 25
<211> LENGTH: 28
<212> TYPE: DNA
<213> ORGANISM: Artificial Sequence
<220> FEATURE:
<223> OTHER INFORMATION: Primer

<400> SEQUENCE: 25
ctcccaggac gagtccaaat atggtccc 28

<210> SEQ ID NO 26
<211> LENGTH: 28
<212> TYPE: DNA
<213> ORGANISM: Artificial Sequence
<220> FEATURE:
<223> OTHER INFORMATION: Primer

<400> SEQUENCE: 26
ggcggccgct catttaccca gagacagg 28

<210> SEQ ID NO 27
<211> LENGTH: 38
<212> TYPE: DNA
<213> ORGANISM: Artificial Sequence
<220> FEATURE:
<223> OTHER INFORMATION: Primer

<400> SEQUENCE: 27
gggcccaggc ggccgagctc gtgmtgaccc agactcca 38

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28
gggcccaggc ggccgagctc gatmtgaccc agactcca 38

<210> SEQ ID NO 29
<211> LENGTH: 38
<212> TYPE: DNA
<213> ORGANISM: Artificial Sequence
<220> FEATURE:
<223> OTHER INFORMATION: Primer

<400> SEQUENCE: 29
gggcccaggc ggccgagctc gtgatgaccc agactgaa 38

<210> SEQ ID NO 30
<211> LENGTH: 42
<212> TYPE: DNA
<213> ORGANISM: Artificial Sequence
<220> FEATURE:
<223> OTHER INFORMATION: Primer

<400> SEQUENCE: 30
agatggtgca gccacagttc gtttgatttc cacattggtg cc 42

<210> SEQ ID NO 31
<211> LENGTH: 42
<212> TYPE: DNA
<213> ORGANISM: Artificial Sequence
<220> FEATURE:
<223> OTHER INFORMATION: Primer

<400> SEQUENCE: 31
agatggtgca gccacagttc gtaggatctc cagctcggtc cc 42

<210> SEQ ID NO 32
<211> LENGTH: 42
<212> TYPE: DNA
<213> ORGANISM: Artificial Sequence
<220> FEATURE:
<223> OTHER INFORMATION: Primer

<400> SEQUENCE: 32
agatggtgca gccacagttc gtttgacsac cacctcggtc cc 42

<210> SEQ ID NO 33
<211> LENGTH: 40
<212> TYPE: DNA
<213> ORGANISM: Artificial Sequence
<220> FEATURE:
<223> OTHER INFORMATION: Primer

<400> SEQUENCE: 33
gggcccaggc ggccgagctc gtgctgactc agtcgccctc 40

<210> SEQ ID NO 34
<211> LENGTH: 45
<212> TYPE: DNA
<213> ORGANISM: Artificial Sequence
<220> FEATURE:
<223> OTHER INFORMATION: Primer

<400> SEQUENCE: 34
agatggtgca gccacagttc ggcctgtgac ggtcagctgg gtccc 45

<210> SEQ ID NO 35
<211> LENGTH: 42
<212> TYPE: DNA
<213> ORGANISM: Artificial Sequence
<220> FEATURE:
<223> OTHER INFORMATION: Primer

<400> SEQUENCE: 35
gctgcccaac cagccatggc ccagtcggtg gaggagtccr gg 42

<210> SEQ ID NO 36
<211> LENGTH: 42
<212> TYPE: DNA
<213> ORGANISM: Artificial Sequence
<220> FEATURE:
<223> OTHER INFORMATION: Primer

<400> SEQUENCE: 36
gctgcccaac aagccatggc ccagtcggtg aaggagtccg ag 42

<210> SEQ ID NO 37
<211> LENGTH: 42
<212> TYPE: DNA
<213> ORGANISM: Artificial Sequence
<220> FEATURE:
<223> OTHER INFORMATION: Primer

<400> SEQUENCE: 37
gctgcccaac cagccatggc ccagtcgytg gaggagtccg gg 42

<210> SEQ ID NO 38
<211> LENGTH: 44
<212> TYPE: DNA
<213> ORGANISM: Artificial Sequence
<220> FEATURE:
<223> OTHER INFORMATION: Primer

<400> SEQUENCE: 38
gctgcccaac cagccatggc ccagsagcag ctgrtggagt ccgg 44

<210> SEQ ID NO 39
<211> LENGTH: 45
<212> TYPE: DNA
<213> ORGANISM: Artificial Sequence
<220> FEATURE:
<223> OTHER INFORMATION: Primer

<400> SEQUENCE: 39
cgatgggccc ttggtggagg ctgargagay ggtgaccagg gtgcc 45

<210> SEQ ID NO 40
<211> LENGTH: 24
<212> TYPE: DNA
<213> ORGANISM: Artificial Sequence
<220> FEATURE:
<223> OTHER INFORMATION: Primer

<400> SEQUENCE: 40
cgaactgtgg ctgcaccatc tgtc 24

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
ggccatggct ggttgggcag c 21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
agaagcgtag tccggaacgt c 21

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
agaagcgtag tccggaacgt c 21

<210> SEQ ID NO 44
<211> LENGTH: 41

<212> TYPE: DNA
<213> ORGANISM: Artificial Sequence
<220> FEATURE:
<223> OTHER INFORMATION: Primer

<400> SEQUENCE: 44
gaggaggagg aggaggaggc ggggcccagg cggccgagct c 41

<210> SEQ ID NO 45
<211> LENGTH: 21
<212> TYPE: DNA
<213> ORGANISM: Artificial Sequence
<220> FEATURE:
<223> OTHER INFORMATION: Primer

<400> SEQUENCE: 45
gctgcccaac cagccatggc c 21

<210> SEQ ID NO 46
<211> LENGTH: 21
<212> TYPE: DNA
<213> ORGANISM: Artificial Sequence
<220> FEATURE:
<223> OTHER INFORMATION: Primer

<400> SEQUENCE: 46
agaagcgtag tccggaacgt c 21

<210> SEQ ID NO 47
<211> LENGTH: 39
<212> TYPE: DNA
<213> ORGANISM: Artificial Sequence
<220> FEATURE:
<223> OTHER INFORMATION: Primer

<400> SEQUENCE: 47
gaggaggagg aggaggagag aagcgtagtc cggaacgtc 39

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
cgcgaattcg cctccaccaa gggcccatcg 30

<210> SEQ ID NO 49
<211> LENGTH: 24
<212> TYPE: DNA
<213> ORGANISM: Artificial Sequence
<220> FEATURE:
<223> OTHER INFORMATION: Primer

<400> SEQUENCE: 49
ggcggccgct catttacccg ggga 24

<210> SEQ ID NO 50
<211> LENGTH: 29
<212> TYPE: DNA
<213> ORGANISM: Artificial Sequence
<220> FEATURE:
<223> OTHER INFORMATION: Primer

<400> SEQUENCE: 50
cgcgaattca ggacctcacc atgggatgg 29

<210> SEQ ID NO 51
<211> LENGTH: 19
<212> TYPE: DNA
<213> ORGANISM: Artificial Sequence
<220> FEATURE:
<223> OTHER INFORMATION: Primer

<400> SEQUENCE: 51
ggagtggaca cctgtagct 19

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
ccacgctgct gagggagtag agtc 24

<210> SEQ ID NO 53
<211> LENGTH: 42
<212> TYPE: DNA
<213> ORGANISM: Artificial Sequence
<220> FEATURE:
<223> OTHER INFORMATION: Primer

<400> SEQUENCE: 53
gcaacagcta caggtgtcca ctcccagcag cagctgatgg ag 42

<210> SEQ ID NO 54
<211> LENGTH: 43
<212> TYPE: DNA
<213> ORGANISM: Artificial Sequence
<220> FEATURE:
<223> OTHER INFORMATION: Primer

<400> SEQUENCE: 54
gcaacagcta caggtgtcca ctcccaggag cagctgatgg agt 43

<210> SEQ ID NO 55
<211> LENGTH: 43
<212> TYPE: DNA
<213> ORGANISM: Artificial Sequence
<220> FEATURE:
<223> OTHER INFORMATION: Primer

<400> SEQUENCE: 55
gcaacagcta caggtgtcca ctcccaggag cagctggtgg agt 43

<210> SEQ ID NO 56
<211> LENGTH: 43
<212> TYPE: DNA
<213> ORGANISM: Artificial Sequence
<220> FEATURE:
<223> OTHER INFORMATION: Primer

<400> SEQUENCE: 56
gcaacagcta caggtgtcca ctcccagtcg gtgaaggagt ccg 43

<210> SEQ ID NO 57
<211> LENGTH: 43
<212> TYPE: DNA
<213> ORGANISM: Artificial Sequence
<220> FEATURE:
<223> OTHER INFORMATION: Primer

<400> SEQUENCE: 57
gcaacagcta caggtgtcca ctcccagtcg ttggaggagt ccg 43

<210> SEQ ID NO 58
<211> LENGTH: 42
<212> TYPE: DNA
<213> ORGANISM: Artificial Sequence
<220> FEATURE:
<223> OTHER INFORMATION: Primer

<400> SEQUENCE: 58
gcaacagcta caggtgtcca ctcccagtcg gtggaggagt cc 42

<210> SEQ ID NO 59
<211> LENGTH: 42
<212> TYPE: DNA
<213> ORGANISM: Artificial Sequence
<220> FEATURE:
<223> OTHER INFORMATION: Primer

<400> SEQUENCE: 59
gcaacagcta caggtgtcca ctcccagcgg ttggaggagt cc 42

<210> SEQ ID NO 60
<211> LENGTH: 42
<212> TYPE: DNA
<213> ORGANISM: Artificial Sequence
<220> FEATURE:
<223> OTHER INFORMATION: Primer

<400> SEQUENCE: 60
gcaacagcta caggtgtcca ctcccagcag cagctggtgg ag 42

<210> SEQ ID NO 61
<211> LENGTH: 42
<212> TYPE: DNA
<213> ORGANISM: Artificial Sequence
<220> FEATURE:
<223> OTHER INFORMATION: Primer

<400> SEQUENCE: 61
gcaacagcta caggtgtcca ctcccagtcg ctggaggagt cc 42

<210> SEQ ID NO 62
<211> LENGTH: 30
<212> TYPE: DNA
<213> ORGANISM: Artificial Sequence
<220> FEATURE:
<223> OTHER INFORMATION: Primer

<400> SEQUENCE: 62
gcgaagcttc gaactgtggc tgcaccatct 30

<210> SEQ ID NO 63
<211> LENGTH: 24
<212> TYPE: DNA
<213> ORGANISM: Artificial Sequence
<220> FEATURE:
<223> OTHER INFORMATION: Primer

<400> SEQUENCE: 63
gcgtctagat taacactctc ccct 24

<210> SEQ ID NO 64
<211> LENGTH: 29

<212> TYPE: DNA
<213> ORGANISM: Artificial Sequence
<220> FEATURE:
<223> OTHER INFORMATION: Primer

<400> SEQUENCE: 64
gcgaagctta ggacctcacc atgggatgg 29

<210> SEQ ID NO 65
<211> LENGTH: 44
<212> TYPE: DNA
<213> ORGANISM: Artificial Sequence
<220> FEATURE:
<223> OTHER INFORMATION: Primer

<400> SEQUENCE: 65
gcaacagcta caggtgtcca ctccgagctc gatatgaccc agac 44

<210> SEQ ID NO 66
<211> LENGTH: 42
<212> TYPE: DNA
<213> ORGANISM: Artificial Sequence
<220> FEATURE:
<223> OTHER INFORMATION: Primer

<400> SEQUENCE: 66
gcaacagcta caggtgtcca ctccgagctc gtgctgaacc ca 42

<210> SEQ ID NO 67
<211> LENGTH: 44
<212> TYPE: DNA
<213> ORGANISM: Artificial Sequence
<220> FEATURE:
<223> OTHER INFORMATION: Primer

<400> SEQUENCE: 67
gcaacagcta caggtgtcca ctccgagctc gtgatgaccc agac 44

<210> SEQ ID NO 68
<211> LENGTH: 44
<212> TYPE: DNA
<213> ORGANISM: Artificial Sequence
<220> FEATURE:
<223> OTHER INFORMATION: Primer

<400> SEQUENCE: 68
gcaacagcta caggtgtcca ctccgagctc gatctgaccc agac 44

<210> SEQ ID NO 69
<211> LENGTH: 29
<212> TYPE: DNA
<213> ORGANISM: Artificial Sequence
<220> FEATURE:
<223> OTHER INFORMATION: Primer

<400> SEQUENCE: 69
cgccgtacgt aggatctcca gctcggtcc 29

<210> SEQ ID NO 70
<211> LENGTH: 30
<212> TYPE: DNA
<213> ORGANISM: Artificial Sequence
<220> FEATURE:
<223> OTHER INFORMATION: Primer

<400> SEQUENCE: 70
cgccgtacgt ttgatttcca cattggtgcc 30

<210> SEQ ID NO 71
<211> LENGTH: 28
<212> TYPE: DNA
<213> ORGANISM: Artificial Sequence
<220> FEATURE:
<223> OTHER INFORMATION: Primer

<400> SEQUENCE: 71
cgccgtacgt ttgacgacca cctcggtc 28

<210> SEQ ID NO 72
<211> LENGTH: 30
<212> TYPE: DNA
<213> ORGANISM: Artificial Sequence
<220> FEATURE:
<223> OTHER INFORMATION: Primer

<400> SEQUENCE: 72
cgccgtacgt aggatctcca gctcggtccc 30

<210> SEQ ID NO 73
<211> LENGTH: 180
<212> TYPE: PRT
<213> ORGANISM: Homo sapiens

<400> SEQUENCE: 73

```
Met Ala Ser Thr Ser Tyr Asp Tyr Cys Arg Val Pro Met Glu Asp Gly
1               5                   10                  15

Asp Lys Arg Cys Lys Leu Leu Leu Gly Ile Gly Ile Leu Val Val Leu
            20                  25                  30

Ile Ile Val Ile Leu Gly Val Pro Leu Ile Ile Phe Thr Ile Lys Ala
        35                  40                  45

Asn Ser Glu Ala Cys Arg Asp Gly Leu Arg Ala Val Met Glu Cys Arg
    50                  55                  60

Asn Val Thr His Leu Leu Gln Gln Glu Leu Thr Glu Ala Gln Lys Gly
65                  70                  75                  80

Phe Gln Asp Val Glu Ala Gln Ala Ala Thr Cys Asn His Thr Val Met
                85                  90                  95

Ala Leu Met Ala Ser Leu Asp Ala Glu Lys Ala Gln Gly Gln Lys Lys
            100                 105                 110

Val Glu Glu Leu Glu Gly Glu Ile Thr Thr Leu Asn His Lys Leu Gln
        115                 120                 125

Asp Ala Ser Ala Glu Val Glu Arg Leu Arg Arg Glu Asn Gln Val Leu
    130                 135                 140

Ser Val Arg Ile Ala Asp Lys Lys Tyr Tyr Pro Ser Ser Gln Asp Ser
145                 150                 155                 160

Ser Ser Ala Ala Ala Pro Gln Leu Leu Ile Val Leu Leu Gly Leu Ser
                165                 170                 175

Ala Leu Leu Gln
            180
```

<210> SEQ ID NO 74
<211> LENGTH: 172
<212> TYPE: PRT
<213> ORGANISM: Mus musculus

<400> SEQUENCE: 74

```
Met Ala Pro Ser Phe Tyr His Tyr Leu Pro Val Pro Met Asp Glu Met
1               5                   10                  15
```

```
Gly Gly Lys Gln Gly Trp Gly Ser His Arg Gln Trp Leu Gly Ala Ala
            20                  25                  30

Ile Leu Val Val Leu Phe Gly Val Thr Leu Val Ile Leu Thr Ile Tyr
        35                  40                  45

Phe Ala Val Thr Ala Asn Ser Val Ala Cys Arg Asp Gly Leu Arg Ala
    50                  55                  60

Gln Ala Glu Cys Arg Asn Thr Thr His Leu Leu Gln Arg Gln Leu Thr
65                  70                  75                  80

Arg Thr Gln Asp Ser Leu Leu Gln Ala Glu Thr Gln Ala Asn Ser Cys
                85                  90                  95

Asn Leu Thr Val Val Thr Leu Gln Glu Ser Leu Glu Lys Lys Val Ser
            100                 105                 110

Gln Ala Leu Glu Gln Gln Ala Arg Ile Lys Glu Leu Glu Asn Glu Val
        115                 120                 125

Thr Lys Leu Asn Gln Glu Leu Glu Asn Leu Arg Ile Gln Lys Glu Thr
    130                 135                 140

Ser Ser Thr Val Gln Val Asn Ser Gly Ser Ser Met Val Val Ser Ser
145                 150                 155                 160

Leu Leu Val Leu Lys Val Ser Leu Phe Leu Leu Phe
                165                 170
```

<210> SEQ ID NO 75
<211> LENGTH: 41
<212> TYPE: DNA
<213> ORGANISM: Artificial Sequence
<220> FEATURE:
<223> OTHER INFORMATION: Primer

<400> SEQUENCE: 75
ttcacgctag ccccctttgc agatgaagaa acaggctcag a 41

<210> SEQ ID NO 76
<211> LENGTH: 39
<212> TYPE: DNA
<213> ORGANISM: Artificial Sequence
<220> FEATURE:
<223> OTHER INFORMATION: Primer

<400> SEQUENCE: 76
ttcacctcga ggcaggagat gggtgacatt gcgacactc 39

<210> SEQ ID NO 77
<211> LENGTH: 117
<212> TYPE: PRT
<213> ORGANISM: Artificial Sequence
<220> FEATURE:
<223> OTHER INFORMATION: 2-15 heavy chain variable region amino acid sequence

<400> SEQUENCE: 77

```
Met Ala Gln Ser Val Lys Glu Ser Glu Gly Arg Leu Val Thr Pro Gly
1               5                   10                  15

Thr Pro Leu Thr Leu Thr Cys Thr Val Ser Gly Phe Ser Leu Ser Asn
            20                  25                  30

Ser Gly Met Ser Trp Val Arg Gln Ala Pro Gly Lys Gly Leu Glu Trp
        35                  40                  45

Ile Gly Leu Ile Asn Ser Tyr Gly Thr Thr Tyr Tyr Ala Ser Trp Ala
    50                  55                  60

Lys Gly Arg Phe Thr Ile Ser Lys Thr Ser Thr Thr Val Glu Leu Lys
65                  70                  75                  80
```

```
Ile Thr Ser Pro Thr Thr Glu Asp Thr Ala Thr Tyr Phe Cys Ala Arg
                85                  90                  95

Gly Ala Gly Ser Ser Tyr Gly Leu Trp Gly Gln Gly Thr Leu Val Thr
            100                 105                 110

Val Ser Ser Ala Ser
        115


<210> SEQ ID NO 78
<211> LENGTH: 120
<212> TYPE: PRT
<213> ORGANISM: Artificial Sequence
<220> FEATURE:
<223> OTHER INFORMATION: 2-14 heavy chain variable region amino acid
      sequence

<400> SEQUENCE: 78

Met Ala Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Ser
            20                  25                  30

Tyr Glu Met Asn Trp Val Arg Gln Ala Pro Gly Lys Gly Leu Glu Tyr
        35                  40                  45

Ile Gly Ile Ile Arg Ser Asp Gly Ser Thr Tyr Tyr Ala Ser Trp Ala
    50                  55                  60

Lys Ser Arg Ser Thr Ile Thr Arg Asn Thr Asn Leu Asn Thr Val Thr
65                  70                  75                  80

Leu Lys Met Thr Ser Leu Thr Ala Ala Asp Thr Ala Thr Tyr Phe Cys
                85                  90                  95

Ala Arg Asp Leu Gly Tyr Ser Asn Asp Val Trp Gly Pro Gly Thr Leu
            100                 105                 110

Val Thr Val Ser Ser Ala Ser Thr
        115                 120


<210> SEQ ID NO 79
<211> LENGTH: 120
<212> TYPE: PRT
<213> ORGANISM: Artificial Sequence
<220> FEATURE:
<223> OTHER INFORMATION: 2-10 heavy chain variable region amino acid
      sequence

<400> SEQUENCE: 79

Met Ala Gln Ser Leu Glu Glu Ser Gly Gly Arg Leu Val Lys Pro Asp
1               5                   10                  15

Glu Thr Leu Thr Leu Thr Cys Thr Val Ser Gly Ile Asp Leu Ser Ser
            20                  25                  30

Tyr Met Ile Tyr Trp Val Arg Gln Ala Pro Gly Lys Gly Leu Glu Tyr
        35                  40                  45

Ile Gly Phe Ile Tyr Gly Ser Gly Asp Thr Tyr Tyr Ala Thr Trp Ala
    50                  55                  60

Lys Gly Arg Phe Thr Ile Ser Arg Pro Ser Thr Thr Val Asp Leu Lys
65                  70                  75                  80

Ile Thr Ser Pro Thr Thr Gly Asp Thr Ala Thr Tyr Phe Cys Ala Arg
                85                  90                  95

Ser Ser Gly Trp Gly Tyr Gly Leu Asp Leu Trp Gly Pro Gly Thr Leu
            100                 105                 110

Val Thr Ile Ser Ser Ala Ser Thr
        115                 120
```

<210> SEQ ID NO 80
<211> LENGTH: 119
<212> TYPE: PRT
<213> ORGANISM: Artificial Sequence
<220> FEATURE:
<223> OTHER INFORMATION: 2-4 heavy chain variable region amino acid sequence

<400> SEQUENCE: 80

```
Met Ala Gln Gln Leu Val Glu Ser Gly Gly Arg Leu Val Thr Pro Gly
1               5                   10                  15

Gly Thr Leu Thr Leu Thr Cys Thr Ala Ser Gly Ile Asp Leu Ser Ser
            20                  25                  30

Tyr His Met Gln Trp Val Arg Gln Ala Pro Gly Lys Gly Leu Glu Tyr
        35                  40                  45

Ile Gly Phe Ile Asp Thr Val Gly Ser Ala Tyr Tyr Ala Ser Trp Ala
    50                  55                  60

Lys Gly Arg Phe Thr Ile Ser Arg Thr Ser Thr Thr Val Asp Leu Lys
65                  70                  75                  80

Met Thr Ser Leu Thr Ala Ala Asp Thr Ala Thr Tyr Phe Cys Ala Gly
                85                  90                  95

Asp Ser Gly Tyr Ser Ile Gly Thr Leu Trp Gly Gln Gly Thr Leu Val
            100                 105                 110

Thr Val Ser Ser Ala Ser Thr
        115
```

<210> SEQ ID NO 81
<211> LENGTH: 119
<212> TYPE: PRT
<213> ORGANISM: Artificial Sequence
<220> FEATURE:
<223> OTHER INFORMATION: 2-5 heavy chain variable region amino acid sequence

<400> SEQUENCE: 81

```
Met Ala Gln Gln Gln Leu Val Glu Ser Gly Gly Gly Leu Val Thr Pro
1               5                   10                  15

Gly Thr Pro Leu Thr Leu Thr Cys Thr Val Ser Gly Phe Ser Leu Ser
            20                  25                  30

Ser Tyr Ala Met Ile Trp Val Arg Gln Ala Pro Gly Lys Gly Leu Glu
        35                  40                  45

Tyr Ile Gly Ile Ile Arg Ser Ser Gly Asn Thr Tyr Tyr Ala Ser Trp
    50                  55                  60

Ala Lys Gly Arg Phe Thr Ile Ser Lys Thr Ser Thr Thr Val Asp Leu
65                  70                  75                  80

Lys Ile Thr Ser Pro Thr Thr Glu Asp Thr Ala Thr Tyr Phe Cys Ala
                85                  90                  95

Arg Asp Ser Gly Tyr Ser Phe Gly Leu Trp Gly Gln Gly Thr Leu Val
            100                 105                 110

Thr Val Ser Ser Ala Ser Thr
        115
```

<210> SEQ ID NO 82
<211> LENGTH: 120
<212> TYPE: PRT
<213> ORGANISM: Artificial Sequence
<220> FEATURE:
<223> OTHER INFORMATION: 2-7 heavy chain variable region amino acid sequence

<400> SEQUENCE: 82

```
Met Ala Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Ser
            20                  25                  30

His Glu Met Asn Trp Val Arg Gln Ala Pro Gly Asn Gly Leu Glu Tyr
        35                  40                  45

Ile Gly Ile Ile Asn Ser Tyr Ala Asn Thr Tyr Tyr Ala Gly Trp Ala
    50                  55                  60

Lys Ser Arg Ser Thr Ile Thr Arg Asn Thr Asn Glu Asn Thr Val Thr
65                  70                  75                  80

Leu Thr Met Thr Ser Leu Thr Ala Ala Asp Thr Ala Thr Tyr Phe Cys
                85                  90                  95

Val Arg Asp Leu Gly Tyr Ser Ser Asp Ile Trp Gly Pro Gly Thr Leu
            100                 105                 110

Val Thr Ile Ser Ser Ala Ser Thr
        115                 120


<210> SEQ ID NO 83
<211> LENGTH: 123
<212> TYPE: PRT
<213> ORGANISM: Artificial Sequence
<220> FEATURE:
<223> OTHER INFORMATION: describes 2-9 heavy chain variable region
      amino acid sequence

<400> SEQUENCE: 83

Met Ala Gln Ser Leu Glu Glu Ser Gly Gly Arg Leu Val Thr Pro Gly
1               5                   10                  15

Thr Pro Leu Thr Leu Thr Cys Thr Val Ser Gly Ile Asp Leu Ser Ser
            20                  25                  30

Tyr Glu Met Ser Trp Val Arg Gln Ala Pro Gly Lys Gly Leu Glu Tyr
        35                  40                  45

Ile Gly Phe Ile Ser Thr Ser Gly Asn Thr Tyr Tyr Ala Ser Trp Ala
    50                  55                  60

Lys Gly Arg Phe Thr Ile Ser Lys Thr Ser Thr Thr Val Asp Leu Lys
65                  70                  75                  80

Ile Thr Ser Pro Thr Ile Glu Asp Thr Ala Ala Tyr Phe Cys Ala Arg
                85                  90                  95

Gly Pro Ala Lys Ser Gly Tyr Gly Thr Arg Leu Asp Leu Trp Gly Gln
            100                 105                 110

Gly Thr Leu Val Thr Val Ser Ser Ala Ser Thr
        115                 120


<210> SEQ ID NO 84
<211> LENGTH: 124
<212> TYPE: PRT
<213> ORGANISM: Artificial Sequence
<220> FEATURE:
<223> OTHER INFORMATION: 2-11 heavy chain variable region amino acid
      sequence

<400> SEQUENCE: 84

Met Ala Gln Glu Gln Leu Met Glu Ser Gly Gly Gly Leu Val Thr Pro
1               5                   10                  15

Gly Gly Ile Leu Ser Leu Thr Cys Thr Ala Ser Gly Phe Ser Ile Ser
            20                  25                  30

Ser Tyr Arg Met Gly Trp Val Arg Gln Ala Pro Gly Lys Gly Leu Glu
        35                  40                  45

Trp Ile Gly Phe Ile Asn Asn Tyr Gly Ser Ala Tyr Tyr Ala Ser Trp
```

```
    50                  55                  60

Ala Lys Ser Arg Ser Thr Ile Thr Arg Asn Thr Asn Leu Asn Thr Val
65                  70                  75                  80

Thr Leu Lys Met Thr Ser Leu Thr Ala Ala Asp Thr Ala Thr Tyr Phe
                85                  90                  95

Cys Ala Arg Glu Ser Tyr Ser Tyr Gly Tyr Ala Tyr Asp Ile Trp Gly
            100                 105                 110

Pro Gly Thr Leu Val Thr Val Ser Ser Ala Ser Thr
        115                 120


<210> SEQ ID NO 85
<211> LENGTH: 120
<212> TYPE: PRT
<213> ORGANISM: Artificial Sequence
<220> FEATURE:
<223> OTHER INFORMATION: 2-13 heavy chain variable region amino acid
      sequence

<400> SEQUENCE: 85

Met Ala Gln Glu Gln Leu Val Glu Ser Gly Gly Arg Leu Val Thr Pro
1               5                   10                  15

Gly Gly Ser Leu Thr Ile Thr Cys Thr Val Ser Gly Ile Asp Leu Ser
            20                  25                  30

Gly Tyr Ala Met Gly Trp Val Arg Gln Ala Pro Gly Lys Gly Leu Glu
        35                  40                  45

Tyr Ile Gly Ile Ile Gly Thr Ser Asp Thr Thr Tyr Tyr Ala Ser Trp
    50                  55                  60

Ala Lys Gly Arg Phe Thr Ile Ser Lys Thr Ser Ser Thr Thr Val Asp
65                  70                  75                  80

Leu Lys Met Thr Ser Leu Thr Thr Glu Asp Thr Ala Thr Tyr Phe Cys
                85                  90                  95

Val Arg Ser Pro Gly Gly Ser Ala Asp Leu Trp Gly Gln Gly Thr Leu
            100                 105                 110

Val Thr Ile Ser Ser Ala Ser Thr
        115                 120


<210> SEQ ID NO 86
<211> LENGTH: 120
<212> TYPE: PRT
<213> ORGANISM: Artificial Sequence
<220> FEATURE:
<223> OTHER INFORMATION: 2-19 heavy chain variable region amino acid
      sequence

<400> SEQUENCE: 86

Met Ala Gln Ser Val Lys Glu Ser Glu Gly Gly Leu Phe Lys Pro Thr
1               5                   10                  15

Asp Thr Leu Thr Leu Thr Cys Thr Val Ser Gly Phe Ser Leu Ser Ser
            20                  25                  30

Tyr Glu Met Asn Trp Val Arg Gln Ala Pro Gly Lys Gly Leu Glu Tyr
        35                  40                  45

Ile Gly Ile Ile Arg Ser Asp Gly Ser Thr Tyr Tyr Ala Ser Trp Ala
    50                  55                  60

Lys Ser Arg Ser Thr Ile Thr Arg Asn Thr Asn Leu Asn Thr Val Thr
65                  70                  75                  80

Leu Lys Met Thr Ser Leu Thr Ala Ala Asp Thr Ala Thr Tyr Phe Cys
                85                  90                  95

Ala Arg Asp Leu Gly Tyr Ser Asn Asp Val Trp Gly Pro Gly Thr Leu
            100                 105                 110
```

```
Val Thr Ile Ser Ser Ala Ser Thr
        115                 120


<210> SEQ ID NO 87
<211> LENGTH: 120
<212> TYPE: PRT
<213> ORGANISM: Artificial Sequence
<220> FEATURE:
<223> OTHER INFORMATION: 2-24 heavy chain variable region amino acid
      sequence

<400> SEQUENCE: 87

Met Ala Gln Ser Val Glu Glu Ser Arg Gly Gly Leu Phe Lys Pro Thr
1               5                   10                  15

Asp Thr Leu Thr Leu Thr Cys Thr Val Ser Gly Phe Ser Leu Ser Thr
            20                  25                  30

Tyr Glu Met Asn Trp Val Arg Gln Ala Pro Gly Ser Gly Leu Glu Tyr
        35                  40                  45

Ile Gly Ile Ile Asn Ser Ala Gly Thr Thr Tyr Tyr Ala Ser Trp Ala
    50                  55                  60

Lys Ser Arg Ser Thr Ile Thr Arg Asn Thr Asn Glu Asn Thr Val Thr
65                  70                  75                  80

Leu Lys Met Thr Ser Leu Thr Ala Ala Asp Thr Ala Thr Tyr Phe Cys
                85                  90                  95

Ala Arg Asp Leu Gly Tyr Ser Ser Asp Ile Trp Gly Pro Gly Thr Leu
            100                 105                 110

Val Thr Val Ser Ser Ala Ser Thr
        115                 120


<210> SEQ ID NO 88
<211> LENGTH: 114
<212> TYPE: PRT
<213> ORGANISM: Artificial Sequence
<220> FEATURE:
<223> OTHER INFORMATION: 2-15 kappa chain variable region amino acid
      sequence

<400> SEQUENCE: 88

Gln Ala Ala Glu Leu Val Met Thr Gln Thr Pro Ser Ser Thr Ser Thr
1               5                   10                  15

Ala Val Gly Asp Thr Val Thr Ile Lys Cys Gln Ala Ser Gln Ser Ile
            20                  25                  30

Gly Ser Asn Leu Ala Trp Tyr Gln Gln Lys Pro Gly Gln Pro Pro Lys
        35                  40                  45

Ile Leu Ile Tyr Ser Ala Ser Asn Leu Ala Ser Gly Val Pro Ser Arg
    50                  55                  60

Phe Lys Gly Ser Gly Ser Gly Thr Glu Tyr Thr Leu Thr Ile Ser Gly
65                  70                  75                  80

Val Gln Arg Glu Asp Ala Ala Thr Tyr Tyr Cys Leu Gly Ser Asp Ser
                85                  90                  95

Ser Trp Asp Thr Val Phe Gly Gly Gly Thr Glu Leu Glu Ile Leu Arg
            100                 105                 110

Thr Val


<210> SEQ ID NO 89
<211> LENGTH: 114
<212> TYPE: PRT
<213> ORGANISM: Artificial Sequence
<220> FEATURE:
<223> OTHER INFORMATION: 2-14 kappa chain variable region amino acid
```

sequence

<400> SEQUENCE: 89

Gln Ala Ala Glu Leu Asp Leu Thr Gln Thr Pro Ser Ser Thr Ser Thr
1 5 10 15

Ala Val Gly Gly Thr Val Thr Ile Asn Cys Gln Ala Ser Gln Asn Ile
20 25 30

Gly Ile Asn Leu Ala Trp Tyr Gln Gln Lys Pro Gly Gln Pro Pro Lys
35 40 45

Leu Leu Ile Trp Tyr Ala Ser Asp Leu Ala Ser Gly Val Ser Ser Arg
50 55 60

Phe Lys Gly Ser Gly Phe Gly Thr Gln Phe Thr Leu Thr Ile Ser Gly
65 70 75 80

Val Gln Arg Glu Asp Ala Ala Thr Tyr Tyr Cys Leu Gly Thr Tyr Gly
85 90 95

Ser Gly Asp Arg Ala Phe Gly Ala Gly Thr Asn Val Glu Ile Lys Arg
100 105 110

Thr Val

<210> SEQ ID NO 90
<211> LENGTH: 111
<212> TYPE: PRT
<213> ORGANISM: Artificial Sequence
<220> FEATURE:
<223> OTHER INFORMATION: 2-10 kappa chain variable region amino acid
sequence

<400> SEQUENCE: 90

Glu Leu Asp Leu Thr Gln Thr Pro Ser Ser Thr Ser Thr Ala Val Gly
1 5 10 15

Gly Thr Val Thr Ile Asn Cys Gln Ala Ser Gln Ser Ile Asn Val Trp
20 25 30

Leu Ser Trp Tyr Gln Gln Lys Pro Gly Gln Pro Pro Lys Leu Leu Ile
35 40 45

Tyr Gln Ala Ser Lys Leu Ala Ser Gly Val Pro Ser Arg Phe Lys Gly
50 55 60

Ser Gly Ser Gly Thr Gln Phe Thr Leu Thr Ile Ser Gly Val Gln Arg
65 70 75 80

Glu Asp Val Ala Thr Tyr Tyr Cys Leu Gly Ile Tyr Asn Asp Ile Asp
85 90 95

Thr Ala Phe Gly Gly Gly Thr Glu Val Val Val Lys Arg Thr Val
100 105 110

<210> SEQ ID NO 91
<211> LENGTH: 114
<212> TYPE: PRT
<213> ORGANISM: Artificial Sequence
<220> FEATURE:
<223> OTHER INFORMATION: 2-4 kappa chain variable region amino acid
sequence

<400> SEQUENCE: 91

Gln Ala Ala Glu Leu Val Leu Thr Gln Thr Pro Ser Ser Val Ser Ala
1 5 10 15

Ala Val Gly Gly Thr Val Thr Ile Asn Cys Gln Ala Thr Gln Ser Ile
20 25 30

Gly Ile Asn Leu Ala Trp Tyr Gln Gln Lys Pro Gly Gln Pro Pro Lys
35 40 45

Leu Leu Ile Trp Tyr Ala Ser Asp Leu Ala Ser Gly Val Pro Ser Arg

```
    50                  55                  60

Phe Lys Gly Ser Gly Phe Gly Thr Gln Phe Thr Leu Thr Ile Asn Gly
65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
            100                 105                 110

Thr Val


<210> SEQ ID NO 92
<211> LENGTH: 114
<212> TYPE: PRT
<213> ORGANISM: Artificial Sequence
<220> FEATURE:
<223> OTHER INFORMATION: 2-5 kappa chain variable region amino acid
      sequence

<400> SEQUENCE: 92

Gln Ala Ala Glu Leu Val Met Thr Gln Thr Pro Ser Ser Val Ser Ala
1               5                   10                  15

Ala Val Gly Gly Thr Val Thr Ile Asn Cys Gln Ala Ser Lys Asn Ile
            20                  25                  30

Gly Ile Asn Leu Ala Trp Tyr Gln Gln Lys Pro Gly Gln Pro Pro Lys
        35                  40                  45

Gln Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Asn Gly
65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
            100                 105                 110

Thr Val


<210> SEQ ID NO 93
<211> LENGTH: 114
<212> TYPE: PRT
<213> ORGANISM: Artificial Sequence
<220> FEATURE:
<223> OTHER INFORMATION: 2-7 kappa chain variable region amino acid
      sequence

<400> SEQUENCE: 93

Gln Ala Ala Glu Leu Val Met Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Ser Gly
65                  70                  75                  80

Val Gln Arg Glu Asp Ala Ala Thr Tyr Tyr Cys Leu Gly Ser Tyr Gly
                85                  90                  95

Ser Gly Asp Arg Ala Phe Gly Ala Gly Thr Asn Val Glu Ile Lys Arg
            100                 105                 110

Thr Val
```

<210> SEQ ID NO 94
<211> LENGTH: 114
<212> TYPE: PRT
<213> ORGANISM: Artificial Sequence
<220> FEATURE:
<223> OTHER INFORMATION: 2-9 kappa chain variable region amino acid sequence

<400> SEQUENCE: 94

```
Gln Ala Ala Glu Leu Asp Leu Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Phe Gln Gln Lys Pro Gly Gln Pro Pro Lys
        35                  40                  45

Leu Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Ser Asn
65                  70                  75                  80

Val Glu Arg Glu Asp Ala Ala Thr Tyr Tyr Cys Leu Gly Thr Tyr Gly
                85                  90                  95

Ser Gly Asp Arg Ala Phe Gly Ala Gly Thr Asn Val Glu Ile Lys Arg
            100                 105                 110

Thr Val
```

<210> SEQ ID NO 95
<211> LENGTH: 111
<212> TYPE: PRT
<213> ORGANISM: Artificial Sequence
<220> FEATURE:
<223> OTHER INFORMATION: 2-11 kappa chain variable region amino acid sequence

<400> SEQUENCE: 95

```
Glu Leu Asp Leu Thr Gln Thr Pro Ser Ser Thr Ser Thr Thr Val Gly
1               5                   10                  15

Gly Thr Val Thr Ile Asn Cys Arg Ala Ser Gln Ile Ile Gly Ile Asn
            20                  25                  30

Leu Ala Trp Tyr Gln Gln Lys Pro Gly Gln Pro Pro Lys Leu Leu Ile
        35                  40                  45

Trp Tyr Ala Ser Asp Leu Ala Ser Gly Val Pro Ser Arg Phe Arg Gly
    50                  55                  60

Asn Val Ser Gly Ser Gln Phe Thr Leu Thr Ile Ser Gly Val Gln Arg
65                  70                  75                  80

Glu Asp Ala Ala Thr Tyr Tyr Cys Leu Gly Thr Tyr Gly Ser Gly Val
                85                  90                  95

Arg Ala Phe Gly Ala Gly Thr Asn Val Glu Ile Lys Arg Thr Val
            100                 105                 110
```

<210> SEQ ID NO 96
<211> LENGTH: 114
<212> TYPE: PRT
<213> ORGANISM: Artificial Sequence
<220> FEATURE:
<223> OTHER INFORMATION: 2-13 kappa chain variable region amino acid sequence

<400> SEQUENCE: 96

```
Gln Ala Ala Glu Leu Asp Met Thr Gln Thr Pro Ser Ser Thr Ser Thr
1               5                   10                  15
```

```
Ala Val Gly Gly Thr Val Thr Met Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Val Pro Ser Arg
    50                  55                  60

Phe Lys Gly Ser Gly Phe Gly Thr Gln Phe Thr Leu Thr Ile Ser Gly
65                  70                  75                  80

Met Gln Arg Glu Asp Ala Ala Thr Tyr Tyr Cys Leu Gly Thr Tyr Gly
                85                  90                  95

Ser Gly Val Arg Ala Phe Gly Ala Gly Thr Asn Val Glu Ile Lys Arg
            100                 105                 110

Thr Val


<210> SEQ ID NO 97
<211> LENGTH: 114
<212> TYPE: PRT
<213> ORGANISM: Artificial Sequence
<220> FEATURE:
<223> OTHER INFORMATION: 2-19 kappa chain variable region amino acid
      sequence

<400> SEQUENCE: 97

Gln Ala Ala Glu Leu Val Leu Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Thr Ser Asp Leu Ala Ser Gly Val Pro Ser Arg
    50                  55                  60

Phe Arg Gly Ser Gly Phe Gly Thr Gln Phe Thr Leu Thr Ile Ser Ala
65                  70                  75                  80

Ile Gln Arg Glu Asp Ala Ala Thr Tyr Tyr Cys Leu Gly Thr Tyr Gly
                85                  90                  95

Ser Gly Val Arg Ala Phe Gly Ala Gly Thr Asn Val Glu Ile Lys Arg
            100                 105                 110

Thr Val


<210> SEQ ID NO 98
<211> LENGTH: 114
<212> TYPE: PRT
<213> ORGANISM: Artificial Sequence
<220> FEATURE:
<223> OTHER INFORMATION: 2-24 kappa chain variable region amino acid
      sequence

<400> SEQUENCE: 98

Gln Ala Ala Glu Leu Val Met Thr Gln Thr Pro Ser Ser Thr Ser Thr
1               5                   10                  15

Ala Val Gly Gly Thr Val Thr Ile Asn Cys Gln Ala Ser Gln Asn Ile
            20                  25                  30

Gly Ile Asn Leu Ala Trp Tyr Gln Gln Lys Pro Gly Gln Pro Pro Lys
        35                  40                  45

Leu Leu Ile Trp Tyr Ala Ser Asp Leu Ala Ser Gly Ala Pro Ser Arg
    50                  55                  60

Phe Lys Gly Ser Gly Phe Gly Thr Gln Phe Thr Leu Thr Ile Ser Gly
65                  70                  75                  80
```

```
Val Gln Arg Glu Asp Ala Ala Thr Tyr Tyr Cys Leu Gly Thr Tyr Gly
                85                  90                  95

Ser Gly Asp Arg Ala Phe Gly Thr Gly Thr Asn Val Glu Ile Lys Arg
            100                 105                 110

Thr Val


<210> SEQ ID NO 99
<211> LENGTH: 5
<212> TYPE: PRT
<213> ORGANISM: Artificial Sequence
<220> FEATURE:
<223> OTHER INFORMATION: CDR1 of 2-15 heavy chain variable region
      amino acid sequence

<400> SEQUENCE: 99

Asn Ser Gly Met Ser
1               5


<210> SEQ ID NO 100
<211> LENGTH: 16
<212> TYPE: PRT
<213> ORGANISM: Artificial Sequence
<220> FEATURE:
<223> OTHER INFORMATION: CDR2 of 2-15 heavy chain variable region
      amino acid sequence

<400> SEQUENCE: 100

Leu Ile Asn Ser Tyr Gly Thr Thr Tyr Tyr Ala Ser Trp Ala Lys Gly
1               5                   10                  15


<210> SEQ ID NO 101
<211> LENGTH: 8
<212> TYPE: PRT
<213> ORGANISM: Artificial Sequence
<220> FEATURE:
<223> OTHER INFORMATION: CDR3 of 2-15 heavy chain variable region
      amino acid sequence

<400> SEQUENCE: 101

Gly Ala Gly Ser Ser Tyr Gly Leu
1               5


<210> SEQ ID NO 102
<211> LENGTH: 5
<212> TYPE: PRT
<213> ORGANISM: Artificial Sequence
<220> FEATURE:
<223> OTHER INFORMATION: CDR1 of 2-14 heavy chain variable region
      amino acid sequence

<400> SEQUENCE: 102

Ser Tyr Glu Met Asn
1               5


<210> SEQ ID NO 103
<211> LENGTH: 16
<212> TYPE: PRT
<213> ORGANISM: Artificial Sequence
<220> FEATURE:
<223> OTHER INFORMATION: CDR2 of 2-14 heavy chain variable region
      amino acid sequence

<400> SEQUENCE: 103

Ile Ile Arg Ser Asp Gly Ser Thr Tyr Tyr Ala Ser Trp Ala Lys Ser
1               5                   10                  15
```

<210> SEQ ID NO 104
<211> LENGTH: 8
<212> TYPE: PRT
<213> ORGANISM: Artificial Sequence
<220> FEATURE:
<223> OTHER INFORMATION: CDR3 of 2-14 heavy chain variable region
amino acid sequence

<400> SEQUENCE: 104

Asp Leu Gly Tyr Ser Asn Asp Val
1 5

<210> SEQ ID NO 105
<211> LENGTH: 5
<212> TYPE: PRT
<213> ORGANISM: Artificial Sequence
<220> FEATURE:
<223> OTHER INFORMATION: CDR1 of 2-10 heavy chain variable region
amino acid sequence

<400> SEQUENCE: 105

Ser Tyr Met Ile Tyr
1 5

<210> SEQ ID NO 106
<211> LENGTH: 16
<212> TYPE: PRT
<213> ORGANISM: Artificial Sequence
<220> FEATURE:
<223> OTHER INFORMATION: CDR2 of 2-10 heavy chain variable region
amino acid sequence

<400> SEQUENCE: 106

Phe Ile Tyr Gly Ser Gly Asp Thr Tyr Tyr Ala Thr Trp Ala Lys Gly
1 5 10 15

<210> SEQ ID NO 107
<211> LENGTH: 10
<212> TYPE: PRT
<213> ORGANISM: Artificial Sequence
<220> FEATURE:
<223> OTHER INFORMATION: CDR3 of 2-10 heavy chain variable region
amino acid sequence

<400> SEQUENCE: 107

Ser Ser Gly Trp Gly Tyr Gly Leu Asp Leu
1 5 10

<210> SEQ ID NO 108
<211> LENGTH: 5
<212> TYPE: PRT
<213> ORGANISM: Artificial Sequence
<220> FEATURE:
<223> OTHER INFORMATION: CDR1 of 2-4 heavy chain variable region
amino acid sequence

<400> SEQUENCE: 108

Ser Tyr His Met Gln
1 5

<210> SEQ ID NO 109
<211> LENGTH: 16
<212> TYPE: PRT
<213> ORGANISM: Artificial Sequence
<220> FEATURE:
<223> OTHER INFORMATION: CDR2 of 2-4 heavy chain variable region
amino acid sequence

<400> SEQUENCE: 109

Phe Ile Asp Thr Val Gly Ser Ala Tyr Tyr Ala Ser Trp Ala Lys Gly
1 5 10 15

<210> SEQ ID NO 110
<211> LENGTH: 9
<212> TYPE: PRT
<213> ORGANISM: Artificial Sequence
<220> FEATURE:
<223> OTHER INFORMATION: CDR3 of 2-4 heavy chain variable region amino acid sequence

<400> SEQUENCE: 110

Asp Ser Gly Tyr Ser Ile Gly Thr Leu
1 5

<210> SEQ ID NO 111
<211> LENGTH: 5
<212> TYPE: PRT
<213> ORGANISM: Artificial Sequence
<220> FEATURE:
<223> OTHER INFORMATION: CDR1 of 2-5 heavy chain variable region amino acid sequence

<400> SEQUENCE: 111

Ser Tyr Ala Met Ile
1 5

<210> SEQ ID NO 112
<211> LENGTH: 16
<212> TYPE: PRT
<213> ORGANISM: Artificial Sequence
<220> FEATURE:
<223> OTHER INFORMATION: CDR2 of 2-5 heavy chain variable region amino acid sequence

<400> SEQUENCE: 112

Ile Ile Arg Ser Ser Gly Asn Thr Tyr Tyr Ala Ser Trp Ala Lys Gly
1 5 10 15

<210> SEQ ID NO 113
<211> LENGTH: 8
<212> TYPE: PRT
<213> ORGANISM: Artificial Sequence
<220> FEATURE:
<223> OTHER INFORMATION: CDR3 of 2-5 heavy chain variable region amino acid sequence

<400> SEQUENCE: 113

Asp Ser Gly Tyr Ser Phe Gly Leu
1 5

<210> SEQ ID NO 114
<211> LENGTH: 5
<212> TYPE: PRT
<213> ORGANISM: Artificial Sequence
<220> FEATURE:
<223> OTHER INFORMATION: CDR1 of 2-7 heavy chain variable region amino acid sequence

<400> SEQUENCE: 114

Ser His Glu Met Asn
1 5

<210> SEQ ID NO 115
<211> LENGTH: 16
<212> TYPE: PRT
<213> ORGANISM: Artificial Sequence
<220> FEATURE:
<223> OTHER INFORMATION: CDR2 of 2-7 heavy chain variable region amino acid sequence

<400> SEQUENCE: 115

Ile Ile Asn Ser Tyr Ala Asn Thr Tyr Tyr Ala Gly Trp Ala Lys Ser
1 5 10 15

<210> SEQ ID NO 116
<211> LENGTH: 8
<212> TYPE: PRT
<213> ORGANISM: Artificial Sequence
<220> FEATURE:
<223> OTHER INFORMATION: CDR3 of 2-7 heavy chain variable region amino acid sequence

<400> SEQUENCE: 116

Asp Leu Gly Tyr Ser Ser Asp Ile
1 5

<210> SEQ ID NO 117
<211> LENGTH: 5
<212> TYPE: PRT
<213> ORGANISM: Artificial Sequence
<220> FEATURE:
<223> OTHER INFORMATION: CDR1 of 2-9 heavy chain variable region amino acid sequence

<400> SEQUENCE: 117

Ser Tyr Glu Met Ser
1 5

<210> SEQ ID NO 118
<211> LENGTH: 16
<212> TYPE: PRT
<213> ORGANISM: Artificial Sequence
<220> FEATURE:
<223> OTHER INFORMATION: CDR2 of 2-9 heavy chain variable region amino acid sequence

<400> SEQUENCE: 118

Phe Ile Ser Thr Ser Gly Asn Thr Tyr Tyr Ala Ser Trp Ala Lys Gly
1 5 10 15

<210> SEQ ID NO 119
<211> LENGTH: 13
<212> TYPE: PRT
<213> ORGANISM: Artificial Sequence
<220> FEATURE:
<223> OTHER INFORMATION: CDR3 of 2-9 heavy chain variable region amino acid sequence

<400> SEQUENCE: 119

Gly Pro Ala Lys Ser Gly Tyr Gly Thr Arg Leu Asp Leu
1 5 10

<210> SEQ ID NO 120
<211> LENGTH: 5
<212> TYPE: PRT
<213> ORGANISM: Artificial Sequence
<220> FEATURE:
<223> OTHER INFORMATION: CDR1 of 2-11 heavy chain variable region amino acid sequence

<400> SEQUENCE: 120

Ser Tyr Arg Met Gly
1 5

<210> SEQ ID NO 121
<211> LENGTH: 16

<212> TYPE: PRT
<213> ORGANISM: Artificial Sequence
<220> FEATURE:
<223> OTHER INFORMATION: CDR2 of 2-11 heavy chain variable region
amino acid sequence

<400> SEQUENCE: 121

Phe Ile Asn Asn Tyr Gly Ser Ala Tyr Tyr Ala Ser Trp Ala Lys Ser
1 5 10 15

<210> SEQ ID NO 122
<211> LENGTH: 11
<212> TYPE: PRT
<213> ORGANISM: Artificial Sequence
<220> FEATURE:
<223> OTHER INFORMATION: CDR3 of 2-11 heavy chain variable region
amino acid sequence

<400> SEQUENCE: 122

Glu Ser Tyr Ser Tyr Gly Tyr Ala Tyr Asp Ile
1 5 10

<210> SEQ ID NO 123
<211> LENGTH: 5
<212> TYPE: PRT
<213> ORGANISM: Artificial Sequence
<220> FEATURE:
<223> OTHER INFORMATION: CDR1 of 2-13 heavy chain variable region
amino acid sequence

<400> SEQUENCE: 123

Gly Tyr Ala Met Gly
1 5

<210> SEQ ID NO 124
<211> LENGTH: 16
<212> TYPE: PRT
<213> ORGANISM: Artificial Sequence
<220> FEATURE:
<223> OTHER INFORMATION: CDR2 of 2-13 heavy chain variable region
amino acid sequence

<400> SEQUENCE: 124

Ile Ile Gly Thr Ser Asp Thr Thr Tyr Tyr Ala Ser Trp Ala Lys Gly
1 5 10 15

<210> SEQ ID NO 125
<211> LENGTH: 8
<212> TYPE: PRT
<213> ORGANISM: Artificial Sequence
<220> FEATURE:
<223> OTHER INFORMATION: CDR3 of 2-13 heavy chain variable region
amino acid sequence

<400> SEQUENCE: 125

Ser Pro Gly Gly Ser Ala Asp Leu
1 5

<210> SEQ ID NO 126
<211> LENGTH: 5
<212> TYPE: PRT
<213> ORGANISM: Artificial Sequence
<220> FEATURE:
<223> OTHER INFORMATION: CDR1 of 2-19 heavy chain variable region
amino acid sequence

<400> SEQUENCE: 126

Ser Tyr Glu Met Asn
1 5

<210> SEQ ID NO 127
<211> LENGTH: 16
<212> TYPE: PRT
<213> ORGANISM: Artificial Sequence
<220> FEATURE:
<223> OTHER INFORMATION: CDR2 of 2-19 heavy chain variable region amino acid sequence

<400> SEQUENCE: 127

```
Ile Ile Arg Ser Asp Gly Ser Thr Tyr Tyr Ala Ser Trp Ala Lys Ser
1               5                   10                  15
```

<210> SEQ ID NO 128
<211> LENGTH: 8
<212> TYPE: PRT
<213> ORGANISM: Artificial Sequence
<220> FEATURE:
<223> OTHER INFORMATION: CDR3 of 2-19 heavy chain variable region amino acid sequence

<400> SEQUENCE: 128

```
Asp Leu Gly Tyr Ser Asn Asp Val
1               5
```

<210> SEQ ID NO 129
<211> LENGTH: 5
<212> TYPE: PRT
<213> ORGANISM: Artificial Sequence
<220> FEATURE:
<223> OTHER INFORMATION: CDR1 of 2-24 heavy chain variable region amino acid sequence

<400> SEQUENCE: 129

```
Thr Tyr Glu Met Asn
1               5
```

<210> SEQ ID NO 130
<211> LENGTH: 16
<212> TYPE: PRT
<213> ORGANISM: Artificial Sequence
<220> FEATURE:
<223> OTHER INFORMATION: CDR2 of 2-24 heavy chain variable region amino acid sequence

<400> SEQUENCE: 130

```
Ile Ile Asn Ser Ala Gly Thr Thr Tyr Tyr Ala Ser Trp Ala Lys Ser
1               5                   10                  15
```

<210> SEQ ID NO 131
<211> LENGTH: 8
<212> TYPE: PRT
<213> ORGANISM: Artificial Sequence
<220> FEATURE:
<223> OTHER INFORMATION: CDR3 of 2-24 heavy chain variable region amino acid sequence

<400> SEQUENCE: 131

```
Asp Leu Gly Tyr Ser Ser Asp Ile
1               5
```

<210> SEQ ID NO 132
<211> LENGTH: 11
<212> TYPE: PRT
<213> ORGANISM: Artificial Sequence
<220> FEATURE:
<223> OTHER INFORMATION: CDR1 of 2-15 kappa chain variable region amino acid sequence

<400> SEQUENCE: 132

Gln Ala Ser Gln Ser Ile Gly Ser Asn Leu Ala
1 5 10

<210> SEQ ID NO 133
<211> LENGTH: 6
<212> TYPE: PRT
<213> ORGANISM: Artificial Sequence
<220> FEATURE:
<223> OTHER INFORMATION: CDR2 of 2-15 kappa chain variable region amino acid sequence

<400> SEQUENCE: 133

Ala Ser Asn Leu Ala Ser
1 5

<210> SEQ ID NO 134
<211> LENGTH: 10
<212> TYPE: PRT
<213> ORGANISM: Artificial Sequence
<220> FEATURE:
<223> OTHER INFORMATION: CDR3 of 2-15 kappa chain variable region amino acid sequence

<400> SEQUENCE: 134

Leu Gly Ser Asp Ser Ser Trp Asp Thr Val
1 5 10

<210> SEQ ID NO 135
<211> LENGTH: 11
<212> TYPE: PRT
<213> ORGANISM: Artificial Sequence
<220> FEATURE:
<223> OTHER INFORMATION: CDR1 of 2-14 kappa chain variable region amino acid sequence

<400> SEQUENCE: 135

Gln Ala Ser Gln Asn Ile Gly Ile Asn Leu Ala
1 5 10

<210> SEQ ID NO 136
<211> LENGTH: 6
<212> TYPE: PRT
<213> ORGANISM: Artificial Sequence
<220> FEATURE:
<223> OTHER INFORMATION: CDR2 of 2-14 kappa chain variable region amino acid sequence

<400> SEQUENCE: 136

Ala Ser Asp Leu Ala Ser
1 5

<210> SEQ ID NO 137
<211> LENGTH: 10
<212> TYPE: PRT
<213> ORGANISM: Artificial Sequence
<220> FEATURE:
<223> OTHER INFORMATION: CDR3 of 2-14 kappa chain variable region amino acid sequence

<400> SEQUENCE: 137

Leu Gly Thr Tyr Gly Ser Gly Asp Arg Ala
1 5 10

<210> SEQ ID NO 138
<211> LENGTH: 11
<212> TYPE: PRT
<213> ORGANISM: Artificial Sequence
<220> FEATURE:
<223> OTHER INFORMATION: CDR1 of 2-10 kappa chain variable region amino acid sequence

<400> SEQUENCE: 138

Gln Ala Ser Gln Ser Ile Asn Val Trp Leu Ser
1 5 10

<210> SEQ ID NO 139
<211> LENGTH: 6
<212> TYPE: PRT
<213> ORGANISM: Artificial Sequence
<220> FEATURE:
<223> OTHER INFORMATION: CDR2 of 2-10 kappa chain variable region amino acid sequence

<400> SEQUENCE: 139

Ala Ser Lys Leu Ala Ser
1 5

<210> SEQ ID NO 140
<211> LENGTH: 10
<212> TYPE: PRT
<213> ORGANISM: Artificial Sequence
<220> FEATURE:
<223> OTHER INFORMATION: CDR3 of 2-10 kappa chain variable region amino acid sequence

<400> SEQUENCE: 140

Leu Gly Ile Tyr Asn Asp Ile Asp Thr Ala
1 5 10

<210> SEQ ID NO 141
<211> LENGTH: 11
<212> TYPE: PRT
<213> ORGANISM: Artificial Sequence
<220> FEATURE:
<223> OTHER INFORMATION: CDR1 of 2-4 kappa chain variable region amino acid sequence

<400> SEQUENCE: 141

Gln Ala Thr Gln Ser Ile Gly Ile Asn Leu Ala
1 5 10

<210> SEQ ID NO 142
<211> LENGTH: 6
<212> TYPE: PRT
<213> ORGANISM: Artificial Sequence
<220> FEATURE:
<223> OTHER INFORMATION: CDR2 of 2-4 kappa chain variable region amino acid sequence

<400> SEQUENCE: 142

Ala Ser Asp Leu Ala Ser
1 5

<210> SEQ ID NO 143
<211> LENGTH: 10
<212> TYPE: PRT
<213> ORGANISM: Artificial Sequence
<220> FEATURE:
<223> OTHER INFORMATION: CDR3 of 2-4 kappa chain variable region amino acid sequence

<400> SEQUENCE: 143

Leu Gly Ser Tyr Gly Ser Gly Asp Arg Ala
1 5 10

<210> SEQ ID NO 144
<211> LENGTH: 11
<212> TYPE: PRT
<213> ORGANISM: Artificial Sequence
<220> FEATURE:
<223> OTHER INFORMATION: CDR1 of 2-5 kappa chain variable region amino acid sequence

<400> SEQUENCE: 144

Gln Ala Ser Lys Asn Ile Gly Ile Asn Leu Ala
1 5 10

<210> SEQ ID NO 145
<211> LENGTH: 6
<212> TYPE: PRT
<213> ORGANISM: Artificial Sequence
<220> FEATURE:
<223> OTHER INFORMATION: CDR2 of 2-5 kappa chain variable region amino acid sequence

<400> SEQUENCE: 145

Ala Ser Asp Leu Ala Ser
1 5

<210> SEQ ID NO 146
<211> LENGTH: 10
<212> TYPE: PRT
<213> ORGANISM: Artificial Sequence
<220> FEATURE:
<223> OTHER INFORMATION: CDR3 of 2-5 kappa chain variable region amino acid sequence

<400> SEQUENCE: 146

Leu Gly Ser Tyr Gly Ser Gly Asp Arg Ala
1 5 10

<210> SEQ ID NO 147
<211> LENGTH: 11
<212> TYPE: PRT
<213> ORGANISM: Artificial Sequence
<220> FEATURE:
<223> OTHER INFORMATION: CDR1 of 2-7 kappa chain variable region amino acid sequence

<400> SEQUENCE: 147

Gln Ala Ser Gln Asn Ile Gly Ile Asn Leu Ala
1 5 10

<210> SEQ ID NO 148
<211> LENGTH: 6
<212> TYPE: PRT
<213> ORGANISM: Artificial Sequence
<220> FEATURE:
<223> OTHER INFORMATION: CDR2 of 2-7 kappa chain variable region amino acid sequence

<400> SEQUENCE: 148

Ala Ser Asp Leu Ala Ser
1 5

<210> SEQ ID NO 149
<211> LENGTH: 10
<212> TYPE: PRT
<213> ORGANISM: Artificial Sequence
<220> FEATURE:
<223> OTHER INFORMATION: CDR3 of 2-7 kappa chain variable region amino acid sequence

<400> SEQUENCE: 149

```
Leu Gly Ser Tyr Gly Ser Gly Asp Arg Ala
1               5                   10


<210> SEQ ID NO 150
<211> LENGTH: 11
<212> TYPE: PRT
<213> ORGANISM: Artificial Sequence
<220> FEATURE:
<223> OTHER INFORMATION: CDR1 of 2-9 kappa chain variable region
      amino acid sequence

<400> SEQUENCE: 150

Gln Ala Ser Gln Asn Ile Gly Ile Asn Leu Ala
1               5                   10


<210> SEQ ID NO 151
<211> LENGTH: 6
<212> TYPE: PRT
<213> ORGANISM: Artificial Sequence
<220> FEATURE:
<223> OTHER INFORMATION: CDR2 of 2-9 kappa chain variable region
      amino acid sequence

<400> SEQUENCE: 151

Ala Ser Asp Leu Ala Ser
1               5


<210> SEQ ID NO 152
<211> LENGTH: 10
<212> TYPE: PRT
<213> ORGANISM: Artificial Sequence
<220> FEATURE:
<223> OTHER INFORMATION: CDR3 of 2-9 kappa chain variable region
      amino acid sequence

<400> SEQUENCE: 152

Leu Gly Thr Tyr Gly Ser Gly Asp Arg Ala
1               5                   10


<210> SEQ ID NO 153
<211> LENGTH: 11
<212> TYPE: PRT
<213> ORGANISM: Artificial Sequence
<220> FEATURE:
<223> OTHER INFORMATION: CDR1 of 2-11 kappa chain variable region
      amino acid sequence

<400> SEQUENCE: 153

Arg Ala Ser Gln Ile Ile Gly Ile Asn Leu Ala
1               5                   10


<210> SEQ ID NO 154
<211> LENGTH: 6
<212> TYPE: PRT
<213> ORGANISM: Artificial Sequence
<220> FEATURE:
<223> OTHER INFORMATION: CDR2 of 2-11 kappa chain variable region
      amino acid sequence

<400> SEQUENCE: 154

Ala Ser Asp Leu Ala Ser
1               5


<210> SEQ ID NO 155
<211> LENGTH: 10
<212> TYPE: PRT
<213> ORGANISM: Artificial Sequence
<220> FEATURE:
<223> OTHER INFORMATION: CDR3 of 2-11 kappa chain variable region
```

amino acid sequence

<400> SEQUENCE: 155

Leu Gly Thr Tyr Gly Ser Gly Val Arg Ala
1 5 10

<210> SEQ ID NO 156
<211> LENGTH: 11
<212> TYPE: PRT
<213> ORGANISM: Artificial Sequence
<220> FEATURE:
<223> OTHER INFORMATION: CDR1 of 2-13 kappa chain variable region amino acid sequence

<400> SEQUENCE: 156

Gln Ala Ser Gln Asn Ile Gly Ile Asn Leu Ala
1 5 10

<210> SEQ ID NO 157
<211> LENGTH: 6
<212> TYPE: PRT
<213> ORGANISM: Artificial Sequence
<220> FEATURE:
<223> OTHER INFORMATION: CDR2 of 2-13 kappa chain variable region amino acid sequence

<400> SEQUENCE: 157

Ala Ser Asp Leu Ala Ser
1 5

<210> SEQ ID NO 158
<211> LENGTH: 10
<212> TYPE: PRT
<213> ORGANISM: Artificial Sequence
<220> FEATURE:
<223> OTHER INFORMATION: CDR3 of 2-13 kappa chain variable region amino acid sequence

<400> SEQUENCE: 158

Leu Gly Thr Tyr Gly Ser Gly Val Arg Ala
1 5 10

<210> SEQ ID NO 159
<211> LENGTH: 11
<212> TYPE: PRT
<213> ORGANISM: Artificial Sequence
<220> FEATURE:
<223> OTHER INFORMATION: CDR1 of 2-19 kappa chain variable region amino acid sequence

<400> SEQUENCE: 159

Gln Ala Ser Gln Asn Ile Gly Ile Asn Leu Ala
1 5 10

<210> SEQ ID NO 160
<211> LENGTH: 6
<212> TYPE: PRT
<213> ORGANISM: Artificial Sequence
<220> FEATURE:
<223> OTHER INFORMATION: CDR2 of 2-19 kappa chain variable region amino acid sequence

<400> SEQUENCE: 160

Thr Ser Asp Leu Ala Ser
1 5

<210> SEQ ID NO 161
<211> LENGTH: 10

-continued

```
<212> TYPE: PRT
<213> ORGANISM: Artificial Sequence
<220> FEATURE:
<223> OTHER INFORMATION: CDR3 of 2-19 kappa chain variable region
      amino acid sequence

<400> SEQUENCE: 161

Leu Gly Thr Tyr Gly Ser Gly Val Arg Ala
1               5                   10


<210> SEQ ID NO 162
<211> LENGTH: 11
<212> TYPE: PRT
<213> ORGANISM: Artificial Sequence
<220> FEATURE:
<223> OTHER INFORMATION: CDR1 of 2-24 kappa chain variable region
      amino acid sequence

<400> SEQUENCE: 162

Gln Ala Ser Gln Asn Ile Gly Ile Asn Leu Ala
1               5                   10


<210> SEQ ID NO 163
<211> LENGTH: 6
<212> TYPE: PRT
<213> ORGANISM: Artificial Sequence
<220> FEATURE:
<223> OTHER INFORMATION: CDR2 of 2-24 kappa chain variable region
      amino acid sequence

<400> SEQUENCE: 163

Ala Ser Asp Leu Ala Ser
1               5


<210> SEQ ID NO 164
<211> LENGTH: 10
<212> TYPE: PRT
<213> ORGANISM: Artificial Sequence
<220> FEATURE:
<223> OTHER INFORMATION: CDR3 of 2-24 kappa chain variable region
      amino acid sequence

<400> SEQUENCE: 164

Leu Gly Thr Tyr Gly Ser Gly Asp Arg Ala
1               5                   10
```